US010755801B2

(12) United States Patent
Bremel et al.

(10) Patent No.: US 10,755,801 B2
(45) Date of Patent: Aug. 25, 2020

(54) IDENTIFYING PEPTIDES HAVING T-CELL-EXPOSED MOTIFS WITH KNOWN FREQUENCY OF OCCURRENCE IN A REFERENCE DATABASE

(71) Applicant: IOGENETICS, LLC, Madison, WI (US)

(72) Inventors: Robert D. Bremel, Hillpoint, WI (US); Jane Homan, Hillpoint, WI (US); Michael Imboden, Madison, WI (US)

(73) Assignee: IOGENETICS, LLC, Madison, WI (US)

(*) Notice: Subject to any disclaimer, the term of this patent is extended or adjusted under 35 U.S.C. 154(b) by 764 days.

(21) Appl. No.: 15/325,655

(22) PCT Filed: Jul. 10, 2015

(86) PCT No.: PCT/US2015/039969
§ 371 (c)(1),
(2) Date: Jan. 11, 2017

(87) PCT Pub. No.: WO2016/007870
PCT Pub. Date: Jan. 14, 2016

(65) Prior Publication Data

US 2017/0161430 A1 Jun. 8, 2017

Related U.S. Application Data

(60) Provisional application No. 62/023,212, filed on Jul. 11, 2014, provisional application No. 62/047,385, filed on Sep. 8, 2014, provisional application No. 62/085,792, filed on Dec. 1, 2014, provisional application No. 62/085,773, filed on Dec. 1, 2014.

(51) Int. Cl.

| | |
|---|---|
| ***G16B 30/00*** | (2019.01) |
| ***G16B 20/00*** | (2019.01) |
| ***G16B 50/00*** | (2019.01) |
| ***G01N 33/68*** | (2006.01) |

(52) U.S. Cl.
CPC ......... *G16B 30/00* (2019.02); *G01N 33/6854* (2013.01); *G01N 33/6878* (2013.01); *G16B 20/00* (2019.02); *G16B 50/00* (2019.02); *G01N 2800/24* (2013.01)

(58) Field of Classification Search
None
See application file for complete search history.

(56) References Cited

U.S. PATENT DOCUMENTS

| | | | |
|---|---|---|---|
| 2012/0289417 | A1 | 11/2012 | Carr et al. |
| 2013/0330335 | A1 | 12/2013 | Bremel et al. |

OTHER PUBLICATIONS

International Search Report and Written Opinion, International Patent Application No. PCT/US2015/039969, dated Dec. 29, 2015.
Calis, JJA et al. Degenerate T-Cell Recognition of Peptides on MHC Molecules Creates Large Holes in the T-Cell Repetoire, PLoS Comput. Biol. vol. 8, No. 3, e1002412, 11 pages (2012).
EP Search Report, EP Patent Application No. 15818218.8, dated Feb. 16, 2018.
King C. et al. Removing T-cell epitopes with computation protein design, Proceedings National Academy of Sciences, PNAS vol. 111, No. 23, May 19, 2014, pp. 8577-8582.
Patronov et al. T-cell epitope vaccine design by immunoinformatics, Journal of Medicinal Chemisty, vol. 42, No. 22, Jan. 3, 2013, pp. 4650-120139.

*Primary Examiner* — G Steven Vanni
(74) *Attorney, Agent, or Firm* — Cadimir Jones, S.C.; J. Mitchell Jones

(57) ABSTRACT

The present invention provides methods and systems for identifying and classifying epitopes and use of that information to analyze proteins and peptides within proteins, especially potential epitopes, and to use the information to design synthetic peptides and proteins, analyze biopharmaceutical proteins, and diagnose autoimmune conditions. Peptides which are bound in MHC grooves comprise two sets of amino acids: those that face inwards into the groove and determine the binding affinity to the MHC molecule (the groove exposed motifs or GEM) and those which do not interact with the groove but rather are on the obverse side exposed outwardly to the T-cells (the T-cell exposed Motifs or TCEM). The present invention utilizes information related to the identity and physiochemical characteristics of the GEM and TCEM.

7 Claims, 27 Drawing Sheets

Specification includes a Sequence Listing.

| Amino acid | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | | | | | | | | | | | | | | | |
| Pocket position | -3 | -2 | -1 | 1 | 2 | 3 | 4 | 5 | 6 | 7 | 8 | 9 | +1 | +2 | +3 |
| TCEM IIa | | | | | 2 | 3 | | 5 | | 7 | 8 | | | | |
| TCEM IIb | | | -1 | | | 3 | | 5 | | 7 | 8 | | | | |
| | | | | | | | | | | | | | | | |
| GEM IIa | -3 | -2 | -1 | 1 | | | 4 | | 6 | | | 9 | +1 | +2 | +3 |
| GEM IIb | -3 | -2 | | 1 | 2 | | 4 | | 6 | | | 9 | +1 | +2 | +3 |
| | | | | | | | | | | | | | | | |
| Pocket position | 1 | 2 | 3 | 4 | 5 | 6 | 7 | 8 | 9 | | | | | | |
| TCEM I | | | | 4 | 5 | 6 | 7 | 8 | | | | | | | |
| | | | | | | | | | | | | | | | |
| GEM I | 1 | 2 | 3 | | | | | | 9 | | | | | | |

FIG. 12

| peptide | Index aa | nDRB 1_010 1 | nDRB 1_030 1 | nDRB 1_040 1 | nDRB 1_040 4 | nDRB 1_040 5 | nDRB 1_070 1 | nDRB 1_080 2 | nDRB 1_090 1 | nDRB 1_110 1 | nDRB 1_120 1 | nDRB 1_130 2 | nDRB 1_150 1 | nDRB 3_010 1 | nDRB 3_020 2 | nDRB 4_010 1 | nDRB 5_010 1 |
|---|---|---|---|---|---|---|---|---|---|---|---|---|---|---|---|---|---|
| FAMERNAG SGIIISD (SEQ ID NO: 1) | 272 | -1.03 | 0.01 | -0.11 | -0.37 | 0.01 | -1.09 | -0.03 | -1.27 | 0.87 | 0.35 | -1.16 | -0.33 | -0.36 | -1.13 | 0.96 | -0.22 |
| **AMERNAG SGIIISDT** (SEQ ID NO: 4) | 273 | -0.39 | 0.73 | 0.91 | -0.02 | 0.81 | 0.42 | 0.73 | 0.30 | 1.72 | 0.62 | -0.12 | 0.80 | 0.94 | 0.26 | 1.92 | 0.97 |
| MERNAGSG IIISDTP (SEQ ID NO: 7) | 274 | 0.65 | 2.20 | 1.28 | 0.79 | 1.13 | 0.99 | 0.60 | 0.43 | 1.91 | 0.30 | 1.13 | 1.74 | 1.56 | 0.27 | 1.00 | 1.24 |
| ERNAGSGIII SDTPV (SEQ ID NO: 10) | 275 | 0.56 | 1.79 | 0.99 | 0.83 | 1.06 | 0.49 | 0.07 | 1.41 | 1.77 | 0.20 | 0.41 | 1.29 | 1.56 | 1.48 | -0.27 | 1.67 |
| RNAGSGIIIS DTPVH (SEQ ID NO: 13) | 276 | 0.22 | 1.82 | 0.47 | -0.03 | 0.93 | 0.20 | 0.23 | 0.38 | 1.31 | -0.07 | 0.85 | 0.77 | 0.86 | 0.65 | 1.51 | 1.06 |
| NAGSGIIISD TPVHD (SEQ ID NO: 443) | 277 | 0.00 | 0.88 | 1.01 | -1.31 | 0.31 | 0.57 | 0.89 | 0.33 | 0.80 | 0.15 | 1.24 | 0.00 | 1.24 | 0.70 | 1.41 | 0.88 |
| AGSGIIISDT PVHDC (SEQ ID NO: 501) | 278 | -0.53 | -0.36 | 0.81 | -0.68 | 0.55 | 0.10 | 0.81 | -1.37 | -0.09 | -0.40 | 0.54 | -0.47 | 0.68 | 0.73 | 1.09 | 0.42 |

FIG. 12 (cont'd)

| peptide | pos | nDPA1_0103-DPB1_0201 | nDPA1_0103-DPB1_0402 | nDPA1_0103-DPB1_0401 | nDPA1_0201-DPB1_0101 | nDPA1_0201-DPB1_0501 | nDPA1_0301-DPB1_0402 | nDQA1_0101-DQB1_0501 | nDQA1_0102-DQB1_0602 | nDQA1_0301-DQB1_0302 | nDQA1_0401-DQB1_0402 | nDQA1_0501-DQB1_0201 | nDQA1_0501-DQB1_0301 |
|---|---|---|---|---|---|---|---|---|---|---|---|---|---|
| FAMERNAGSGIIISD (SEQ ID NO: 1) | 272 | 0.65 | 0.21 | 0.37 | -0.03 | 0.19 | 0.05 | 1.12 | -1.20 | -0.73 | -0.55 | 0.28 | -1.22 |
| **AMERNAGSGIIISDT** (SEQ ID NO: 4) | 273 | 0.44 | 0.96 | -0.02 | -0.11 | 0.91 | -0.47 | 1.60 | -2.29 | -0.78 | -0.90 | 0.66 | -1.32 |
| MERNAGSGIIISDTP (SEQ ID NO: 7) | 274 | 0.32 | 1.70 | -0.30 | 0.23 | 0.80 | -0.13 | 0.80 | -1.86 | -0.98 | -0.89 | 0.23 | -1.37 |
| ERNAGSGIIISDTPV (SEQ ID NO: 10) | 275 | -0.07 | -0.57 | -0.46 | 0.16 | 0.58 | -0.63 | 0.43 | -1.33 | -1.44 | -1.16 | -0.11 | -1.45 |
| RNAGSGIIISDTPVH (SEQ ID NO: 13) | 276 | 0.76 | 0.44 | 0.23 | 1.62 | -0.03 | 0.83 | 1.39 | -0.24 | -0.38 | -0.42 | 0.22 | -0.78 |
| NAGSGIIISDTPVHD (SEQ ID NO: 443) | 277 | 0.79 | 0.31 | 0.85 | 1.78 | 0.56 | 0.91 | 0.81 | -0.58 | -1.24 | -1.26 | 0.19 | -1.07 |
| AGSGIIISDTPVHDC (SEQ ID NO: 501) | 278 | 0.04 | -1.42 | -0.11 | 0.43 | 1.61 | 0.52 | -0.46 | -0.49 | -1.45 | -1.08 | 0.44 | -1.29 |

FIG. 13

| gi | protein_id | pos | peptide | TCR II (2,3,5,7,8) | TCR I (3,4,5,6,7) | TCR II (-1,3,5,7,8) |
|---|---|---|---|---|---|---|
| F8VWT9 | F8VWT9_HUMAN Probable E3 ubiquitin-protein ligase | 4114 | TAVRAGLGSIIPLQL(SEQ ID NO: 489) | AG~G~II | VRAGL | V~~G~G~II |
| J3KPF0 | J3KPF0_HUMAN Probable E3 ubiquitin-protein ligase | 4088 | TAVRAGLGSIIPLQL(SEQ ID NO: 489) | AG~G~II | VRAGL | V~~G~G~II |
| K7EL53 | K7EL53_HUMAN Ubiquitin carboxyl-terminal hydrolase | 58 | ASETAGSGYIINTRR (SEQ ID NO: 490) | AG~G~II | ETAGS | E~~G~G~II |
| Q15149 | PLEC_HUMAN Plectin OS=Homo sapiens GN=PLEC PE=1 SV | 3195 | LEAQAGTGHIIDPAT(SEQ ID NO: 491) | AG~G~II | AQAGT | A~~G~G~II |
| Q15149-2 | PLEC_HUMAN Isoform 2 of Plectin OS=Homo sapiens GN | 3085 | LEAQAGTGHIIDPAT(SEQ ID NO: 491) | AG~G~II | AQAGT | A~~G~G~II |
| Q15149-3 | PLEC_HUMAN Isoform 3 of Plectin OS=Homo sapiens GN | 3081 | LEAQAGTGHIIDPAT(SEQ ID NO: 491) | AG~G~II | AQAGT | A~~G~G~II |
| Q15149-4 | PLEC_HUMAN Isoform 4 of Plectin OS=Homo sapiens GN | 3058 | LEAQAGTGHIIDPAT(SEQ ID NO: 491) | AG~G~II | AQAGT | A~~G~G~II |
| Q15149-5 | PLEC_HUMAN Isoform 5 of Plectin OS=Homo sapiens GN | 3058 | LEAQAGTGHIIDPAT(SEQ ID NO: 491) | AG~G~II | AQAGT | A~~G~G~II |
| Q15149-6 | PLEC_HUMAN Isoform 6 of Plectin OS=Homo sapiens GN | 3062 | LEAQAGTGHIIDPAT(SEQ ID NO: 491) | AG~G~II | AQAGT | A~~G~G~II |
| Q15149-7 | PLEC_HUMAN Isoform 7 of Plectin OS=Homo sapiens GN | 3026 | LEAQAGTGHIIDPAT(SEQ ID NO: 491) | AG~G~II | AQAGT | A~~G~G~II |
| Q15149-8 | PLEC_HUMAN Isoform 8 of Plectin OS=Homo sapiens GN | 3036 | LEAQAGTGHIIDPAT(SEQ ID NO: 491) | AG~G~II | AQAGT | A~~G~G~II |
| Q15149-9 | PLEC_HUMAN Isoform 9 of Plectin OS=Homo sapiens GN | 3044 | LEAQAGTGHIIDPAT(SEQ ID NO: 491) | AG~G~II | AQAGT | A~~G~G~II |
| Q5SQI0 | ATAT_HUMAN Alpha-tubulin N-acetyltransferase OS=Ho | 84 | SARPAGKGAIIGFIK(SEQ ID NO: 492) | AG~G~II | RPAGK | R~~G~G~II |
| Q5SQI0-2 | ATAT_HUMAN Isoform 2 of Alpha-tubulin N-acetyltran | 72 | SARPAGKGAIIGFIK(SEQ ID NO: 492) | AG~G~II | RPAGK | R~~G~G~II |
| Q5SQI0-3 | ATAT_HUMAN Isoform 3 of Alpha-tubulin N-acetyltran | 84 | SARPAGKGAIIGFIK(SEQ ID NO: 492) | AG~G~II | RPAGK | R~~G~G~II |
| Q5SQI0-4 | ATAT_HUMAN Isoform 4 of Alpha-tubulin N-acetyltran | 84 | SARPAGKGAIIGFIK(SEQ ID NO: 492) | AG~G~II | RPAGK | R~~G~G~II |
| Q5SQI0-5 | ATAT_HUMAN Isoform 5 of Alpha-tubulin N-acetyltran | 84 | SARPAGKGAIIGFIK(SEQ ID NO: 492) | AG~G~II | RPAGK | R~~G~G~II |
| Q5SQI0-6 | ATAT_HUMAN Isoform 6 of Alpha-tubulin N-acetyltran | 84 | SARPAGKGAIIGFIK(SEQ ID NO: 492) | AG~G~II | RPAGK | R~~G~G~II |
| Q5SQI0-7 | ATAT_HUMAN Isoform 7 of Alpha-tubulin N-acetyltran | 84 | SARPAGKGAIIGFIK(SEQ ID NO: 492) | AG~G~II | RPAGK | R~~G~G~II |
| Q8N7J2-2 | AMER2_HUMAN Isoform 2 of APC membrane recruitment | 256 | PRDPAGCGDIIADQE(SEQ ID NO: 493) | AG~G~II | DPAGC | D~~G~G~II |
| Q8NH79 | OR6X1_HUMAN Olfactory receptor 6X1 OS=Homo sapiens | 34 | ILTLAGNGLIIATVW(SEQ ID NO: 494) | AG~G~II | TLAGN | T~~G~G~II |
| Q92963 | RIT1_HUMAN GTP-binding protein Rit1 OS=Homo sapien | 88 | QYMRAGEGFIICYSI(SEQ ID NO: 495) | AG~G~II | MRAGE | M~~G~G~II |
| Q92963-2 | RIT1_HUMAN Isoform 2 of GTP-binding protein Rit1 O | 52 | QYMRAGEGFIICYSI(SEQ ID NO: 495) | AG~G~II | MRAGE | M~~G~G~II |
| Q92963-3 | RIT1_HUMAN Isoform 3 of GTP-binding protein Rit1 O | 105 | QYMRAGEGFIICYSI(SEQ ID NO: 495) | AG~G~II | MRAGE | M~~G~G~II |
| Q9Y4D8 | HECD4_HUMAN Probable E3 ubiquitin-protein ligase H | 3838 | TAVRAGLGSIIPLQL(SEQ ID NO: 489) | AG~G~II | VRAGL | V~~G~G~II |
| Q9Y4D8-4 | HECD4_HUMAN Isoform 4 of Probable E3 ubiquitin-pro | 3826 | TAVRAGLGSIIPLQL(SEQ ID NO: 489) | AG~G~II | VRAGL | V~~G~G~II |

FIG. 13 (cont'd)

| | | | | | | |
|---|---|---|---|---|---|---|
| C9JSD3 | C9JSD3_HUMAN Tubulin monoglycylase TTLL3 OS=Homo s | 202 | MGAPNAWSTIIVPGM(SEQ ID NO: 496) | NA~S~II | APNAW | A~~A~S~II |
| E9PGH5 | E9PGH5_HUMAN Cytochrome P450 2U1 OS=Homo sapiens G | 13 | SIISNAVSNIICSLC(SEQ ID NO: 497) | NA~S~II | ISNAV | I~~A~S~II |
| H0Y5E3 | H0Y5E3_HUMAN Tubulin monoglycylase TTLL3 (Fragment | 352 | MGAPNAWSTIIVPGM(SEQ ID NO: 496) | NA~S~II | APNAW | A~~A~S~II |
| H0YCJ5 | H0YCJ5_HUMAN Baculoviral IAP repeat-containing pro | 156 | PGDENAESSIIHFEP(SEQ ID NO: 498) | NA~S~II | DENAE | D~~A~S~II |
| H0YGU3 | H0YGU3_HUMAN All-trans-retinol 13 | 115 | QQGENATSNIILTLA(SEQ ID NO: 499) | NA~S~II | GENAT | G~~A~S~II |
| H3BLT7 | H3BLT7_HUMAN Tubulin monoglycylase TTLL3 (Fragment | 370 | MGAPNAWSTIIVPGM(SEQ ID NO: 496) | NA~S~II | APNAW | A~~A~S~II |
| J3KQB2 | J3KQB2_HUMAN Tubulin monoglycylase TTLL3 OS=Homo s | 557 | MGAPNAWSTIIVPGM(SEQ ID NO: 496) | NA~S~II | APNAW | A~~A~S~II |
| P51589 | CP2J2_HUMAN Cytochrome P450 2J2 OS=Homo sapiens GN | 182 | FKINNAVSNIICSIT(SEQ ID NO: 500) | NA~S~II | INNAV | I~~A~S~II |
| P59998-2 | ARPC4_HUMAN Isoform 2 of Actin-related protein 2/3 | 475 | MGAPNAWSTIIVPGM(SEQ ID NO: 496) | NA~S~II | APNAW | A~~A~S~II |
| Q13489 | BIRC3_HUMAN Baculoviral IAP repeat-containing prot | 352 | PGDENAESSIIHFEP(SEQ ID NO: 498) | NA~S~II | DENAE | D~~A~S~II |
| Q7Z449 | CP2U1_HUMAN Cytochrome P450 2U1 OS=Homo sapiens GN | 222 | SIISNAVSNIICSLC(SEQ ID NO: 497) | NA~S~II | ISNAV | I~~A~S~II |
| Q9Y4R7 | TTLL3_HUMAN Tubulin monoglycylase TTLL3 OS=Homo sa | 414 | MGAPNAWSTIIVPGM(SEQ ID NO: 496) | NA~S~II | APNAW | A~~A~S~II |
| Q9Y4R7-2 | TTLL3_HUMAN Isoform 2 of Tubulin monoglycylase TTL | 202 | MGAPNAWSTIIVPGM(SEQ ID NO: 496) | NA~S~II | APNAW | A~~A~S~II |
| Q9Y4R7-5 | TTLL3_HUMAN Isoform 3 of Tubulin monoglycylase TTL | 202 | MGAPNAWSTIIVPGM(SEQ ID NO: 496) | NA~S~II | APNAW | A~~A~S~II |
| Q9Y4R7-6 | TTLL3_HUMAN Isoform 4 of Tubulin monoglycylase TTL | 142 | MGAPNAWSTIIVPGM(SEQ ID NO: 496) | NA~S~II | APNAW | A~~A~S~II |

FIG. 19

| pos | peptide (15-mer) | TCR II (2,3,5,7,8) | TCR II (-1,3,5,7,8) | TCR I (4,5,6,7,8) | FC TCR II... | FC TCR II... | FC TCR I... | Suppressive... | Suppressive... | Suppressive... | motif group... | motif group... | motif group... |
|---|---|---|---|---|---|---|---|---|---|---|---|---|---|
| 27 | AAGIGILTVILG | | | | | | | | | | ~ | ~ | ~ |
| 28 | AGIGILTVILGV | | | | | | | | | | ~ | ~ | ~ |
| 29 | GIGILTVILGVL | LT~I~GV | G~~T~I~GV | ~~~ILTVI~ | | 15 | | | [illegible] | | ~ | Mutated | ~ |
| 30 | IGILTVILGVLLL | | | | | | | | | | ~ | ~ | ~ |
| 31 | GILTVILGVLLLI | VI~G~LL | L~~I~G~LL | ~~~TVILG~ | 16 | | | [illegible] | | | Mutated | ~ | ~ |
| 32 | ILTVILGVLLLIG | | | | | | | | | | ~ | ~ | ~ |
| 33 | LTVILGVLLLIG | LG~L~LI | V~~G~L~LI | ~~~ILGVL~ | 16 | | 15 | [illegible] | | [illegible] | Mutated | ~ | Mutated |
| 34 | TVILGVLLLIGC | | | | | | | | | | ~ | ~ | ~ |
| 35 | VILGVLLLIGC | VL~L~GC | L~~L~L~GC | ~~~GVLLL~ | | | 15 | | | [illegible] | ~ | ~ | Mutated |
| 36 | ILGVLLLIGCW | | | | | | | | | | ~ | ~ | ~ |
| 37 | LGVLLLIGCWY | LL~G~WY | V~~L~G~WY | ~~~LLLIG~ | 15 | 15 | | [illegible] | [illegible] | | Mutated | Mutated | ~ |
| 38 | GVLLLIGCWY | | | | | | | | | | ~ | ~ | ~ |
| 39 | VLLLIGCWYC | | | | | | | | | | ~ | ~ | ~ |

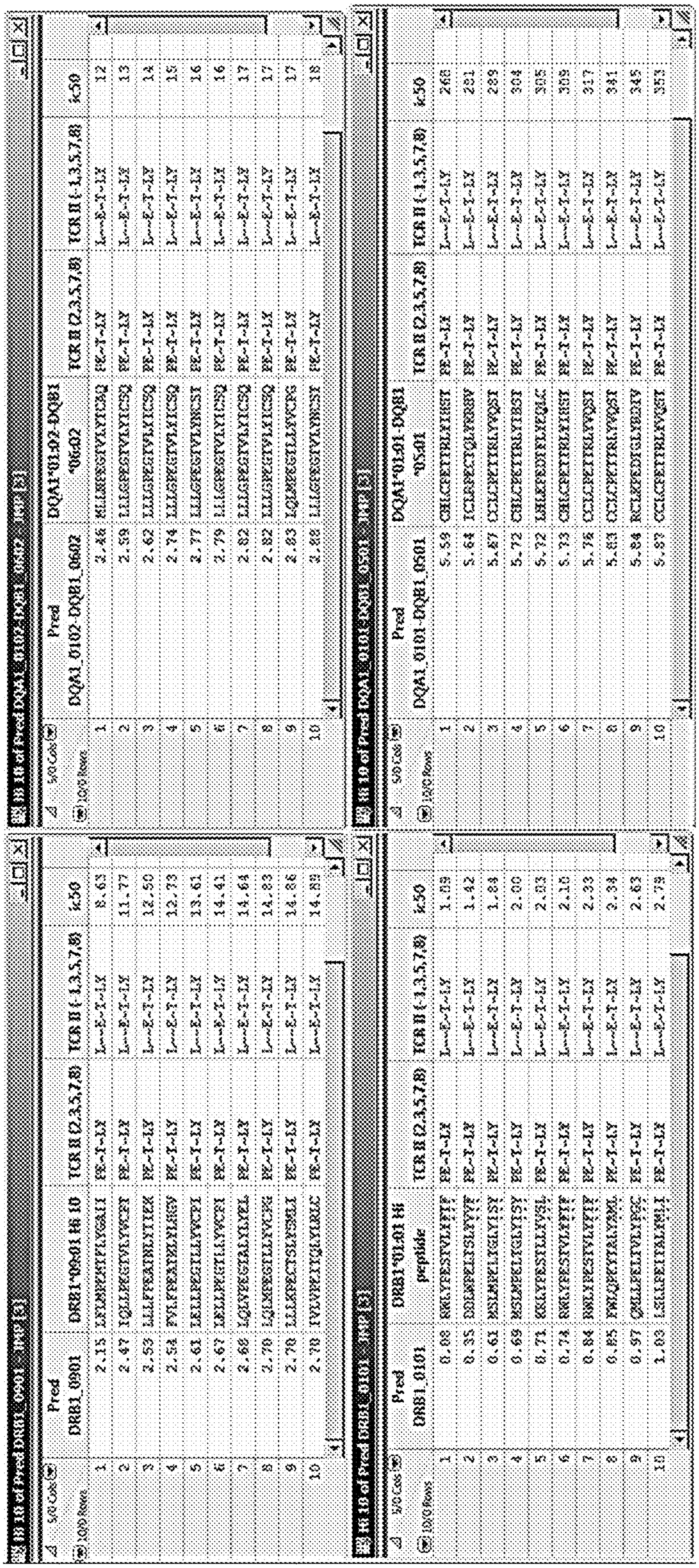

FIG. 27

Hi 10 of Pred DRB1_0901_H4F [$]

| | Pred DRB1_0901 | DRB1*09:01 Hi 10 | TCR II (2,3,5,7,8) | TCR II (-1,3,5,7,8) | ic50 |
|---|---|---|---|---|---|
| 1 | 2.15 | LKLMRFKHFYLYGAII | FE-T-LY | L--E-T-LY | 8.63 |
| 2 | 2.47 | IQLLPEGTVLYLYCPI | FE-T-LY | L--E-T-LY | 11.77 |
| 3 | 2.53 | LLLFFEATHLYIEK | FE-T-LY | L--E-T-LY | 12.50 |
| 4 | 2.54 | FVLFPEATHLHGW | FE-T-LY | L--E-T-LY | 12.73 |
| 5 | 2.61 | LELLPEGILLYWCPI | FE-T-LY | L--E-T-LY | 13.61 |
| 6 | 2.67 | LELLPEGTLLYWCPI | FE-T-LY | L--E-T-LY | 14.41 |
| 7 | 2.68 | LQVTPEGIALYLYPL | FE-T-LY | L--E-T-LY | 14.64 |
| 8 | 2.70 | LQLMPEGILLYWCPG | FE-T-LY | L--E-T-LY | 14.83 |
| 9 | 2.70 | LLLKPECTSLYSMLI | FE-T-LY | L--E-T-LY | 14.86 |
| 10 | 2.70 | FVLVPFITQLYLRLC | FE-T-LY | L--E-T-LY | 14.89 |

Hi 10 of Pred DQA1_0102-DQB1_0602_H4F [$]

| | Pred DQA1_0102-DQB1_0602 | DQA1*01:02-DQB1 *06:02 | TCR II (2,3,5,7,8) | TCR II (-1,3,5,7,8) | ic50 |
|---|---|---|---|---|---|
| 1 | 2.46 | MLLMPEGTVLYLTCSQ | FE-T-LY | L--E-T-LY | 12 |
| 2 | 2.59 | LLLGPEGTVLYICSQ | FE-T-LY | L--E-T-LY | 13 |
| 3 | 2.62 | LLLGPEGTVLYICSQ | FE-T-LY | L--E-T-LY | 14 |
| 4 | 2.74 | LLLGPEGTVLYICSQ | FE-T-LY | L--E-T-LY | 15 |
| 5 | 2.77 | LLLGPEGTVLYNSI | FE-T-LY | L--E-T-LY | 16 |
| 6 | 2.79 | LLLGPEGTVLYICSQ | FE-T-LY | L--E-T-LY | 16 |
| 7 | 2.82 | LLLGPEGTVLYICSQ | FE-T-LY | L--E-T-LY | 17 |
| 8 | 2.82 | LLLMPEGILLYWCPG | FE-T-LY | L--E-T-LY | 17 |
| 9 | 2.83 | LQLMPEGILLYWCPG | FE-T-LY | L--E-T-LY | 17 |
| 10 | 2.88 | LLLGPEGTVLYWCSI | FE-T-LY | L--E-T-LY | 18 |

Hi 10 of Pred DRB1_0101_H4F [$]

| | Pred DRB1_0101 | DRB1*01:01 H peptide | TCR II (2,3,5,7,8) | TCR II (-1,3,5,7,8) | ic50 |
|---|---|---|---|---|---|
| 1 | 0.08 | RWLYPESTVLFTP | FE-T-LY | L--E-T-LY | 1.09 |
| 2 | 0.35 | DDLMPELTSLAYYF | FE-T-LY | L--E-T-LY | 1.42 |
| 3 | 0.61 | MSLMPELTSLYISY | FE-T-LY | L--E-T-LY | 1.84 |
| 4 | 0.69 | MSLMPELTGLYISY | FE-T-LY | L--E-T-LY | 2.00 |
| 5 | 0.71 | KKLYPESTILLYSL | FE-T-LY | L--E-T-LY | 2.03 |
| 6 | 0.74 | RWLYPESTVLFTY | FE-T-LY | L--E-T-LY | 2.10 |
| 7 | 0.84 | RWLWRESTVLFTF | FE-T-LY | L--E-T-LY | 2.33 |
| 8 | 0.85 | FWLQPEYTALYXML | FE-T-LY | L--E-T-LY | 2.38 |
| 9 | 0.97 | CHLLFELTVLMFGC | FE-T-LY | L--E-T-LY | 2.63 |
| 10 | 1.03 | LSLLPEITALYMLI | FE-T-LY | L--E-T-LY | 2.79 |

Hi 10 of Pred DQA1_0101-DQB1_0501_H4F [$]

| | Pred DQA1_0101-DQB1_0501 | DQA1*01:01-DQB1 *05:01 | TCR II (2,3,5,7,8) | TCR II (-1,3,5,7,8) | ic50 |
|---|---|---|---|---|---|
| 1 | 5.58 | CHLCPETTRLYIHST | FE-T-LY | L--E-T-LY | 268 |
| 2 | 5.64 | ICLRPECTQLFRHSV | FE-T-LY | L--E-T-LY | 281 |
| 3 | 5.67 | CCLKPETIRLYIQSI | FE-T-LY | L--E-T-LY | 289 |
| 4 | 5.72 | CHLCPETTRLYIBSI | FE-T-LY | L--E-T-LY | 304 |
| 5 | 5.72 | LHLKPEDTRLYPELC | FE-T-LY | L--E-T-LY | 305 |
| 6 | 5.73 | CHLCPETTRLYIHST | FE-T-LY | L--E-T-LY | 309 |
| 7 | 5.78 | CCLKPETTRLYQSI | FE-T-LY | L--E-T-LY | 327 |
| 8 | 5.83 | CCLKPETTRLYYQSI | FE-T-LY | L--E-T-LY | 341 |
| 9 | 5.84 | RCLKPEDTGLYKDNV | FE-T-LY | L--E-T-LY | 345 |
| 10 | 5.97 | CCLCPETTRLYVGSI | FE-T-LY | L--E-T-LY | 375 |

IDENTIFYING PEPTIDES HAVING T-CELL-EXPOSED MOTIFS WITH KNOWN FREQUENCY OF OCCURRENCE IN A REFERENCE DATABASE

BACKGROUND OF THE INVENTION

The adaptive immune system is comprised of antibodies, generated by B-cells, and cell mediated immunity which depends on the recognition by T-cells of peptides bound in the major histocompatibility molecules and presented on the surface of antigen presenting cells (APCs). Many cell types may serve as APCs, but primarily they comprise dendritic cells, macrophages, and B-cells (the so called "professional" APCs). While each B-cell becomes dedicated to the production of one antibody sequence, that sequence is derived as the product of somatic hypermutation (SHM) of the genes in that B-cell that encode the immunoglobulin variable region. The presentation of peptides bound in MHC molecules is a function of cleavage of polypeptides by various endosomal peptidases, including but not limited to cathepsins, and the competitive binding of peptides to genetically defined MHC molecules. Hence, the presentation to antigens by the immune system is the combination of stochastic, innate, and genetically determined events.

The primary function of the adaptive immune system is to differentiate self from not-self and to allow the body to mount an appropriate response to molecules, once identified as self or as not-self. When a familiar self-antigen is recognized, the desired outcome is down-regulation of the immune response or tolerance. When an unfamiliar non-self-antigen is encountered, the appropriate outcome is usually a robust up-regulation to yield an immune response in which cytokine responses enlist additional cellular responses to remove the foreign stimulus and protect the integrity of the host.

The discrimination between self and not-self is largely dependent on the T-cell responses and is the combination of the host's genetically determined MHC molecules in combination with motifs comprised in peptides which are bound by MHC molecules and exposed to T-cells in the context of the MHC molecules.

There is a need to be able to predict peptide sequences which comprise motifs that are likely to be recognized by T-cells, and to identify those motifs which are likely to give rise to down-regulation or suppression of the immune response (sometimes termed "Tregitopes" [1]) and those which are likely to result in up-regulation or activation of the immune response (T-helper activity). Having the ability to identify T cell epitopes most likely to upregulate or downregulate an immune response then enables the design of a number of interventions including the design of vaccines with improved properties and the ability to specifically target T cell populations and to reduce or eliminate such populations.

SUMMARY OF THE INVENTION

The present invention provides methods and systems for identifying and classifying epitopes and use of that information to analyze proteins and peptides within proteins, especially potential epitopes, and to use the information to design synthetic peptides and proteins, analyze biopharmaceutical proteins, and diagnose autoimmune conditions. Peptides which are bound in MHC grooves comprise two sets of amino acids: those that face inwards into the groove and determine the binding affinity to the MHC molecule (the groove exposed motifs or GEM) and those which do not interact with the groove but rather are on the obverse side exposed outwardly to the T-cells (the T-cell exposed Motifs or TCEM). The present invention utilizes information related to the identity and physiochemical characteristics of the GEM and TCEM as described in more detail below.

Using the methods described herein, it is possible to categorize any set of peptides, irrespective of whether their source is from antibody molecules, molecules from pathogens, or from biotherapeutic molecules, or any other protein of interest. Whether a peptide bound within a pMHC will be an up-regulating or down-regulating epitope, is a product of (a) its binding affinity (and hence dwell time) in the context of the host MHC allele, and (b) the frequency with which T-cells have been previously exposed to that motif. Common TCEMs with high affinity GEMs would be expected to overstimulate and lead to down-regulation, immunosuppression, or tolerance. By combining predictions of pMHC binding affinities and endosomal processing with databases of TCEM motif frequencies based on amino acid sequence, it is possible to create databases to cross reference molecules from different origins in order to make predictions as to their immunogenic potential as components of vaccines, and the role of the motifs as possible sources of auto-immune responses or allergic responses, or as suppressive T-cell responses.

Accordingly, the present invention provides methods for evaluating peptides derived from any source protein and for ranking peptides based on their likelihood of upregulating or downregulating the cellular and humoral immune response. It further provides compositions of peptides designed to elicit a particular immune response and also a means of specifically targeting T cells.

In some embodiments the application of the methods described herein provides a scoring system for ranking peptides based on their frequency of occurrence in a large reference database of peptide motifs. In some embodiments the reference database is that derived from immunoglobulin variable regions including both the germline and somatically hypermutated variable region sequences. Immunoglobulin constant regions provide another source of reference proteins. In yet other embodiments the reference database is that derived from the human proteome other than immunoglobulins. In alternative embodiments the reference database is made up of T cell receptor sequences. The present invention provides a method of categorizing TCEMs in target proteins by identifying TCEMS in such proteins by means of application of a computer algorithm and then categorizing such TCEMs relative to their frequency of occurrence in a reference database of the immunoglobulins or proteome. Another application is to categorize the TCEMs in target proteins relative to their frequency of occurrence in a database of comparable target proteins. Accordingly the invention provides for application of computer algorithms to categorize TCEMs relative to databases of allergens and microorganisms (including but not limited to pathogens and the commensal human microbiome and including but not limited to bacteria, viruses, fungi and parasites). The categorization approach allows for scoring of frequency of occurrence and determination of common and rare TCEMs. This scoring system provides an indicator of whether a given amino acid TCEM motif, when encountered in a protein of interest, is likely to give rise to upregulation or downregulation of the immune response provided certain other conditions are fulfilled. A preferred condition is whether the peptide has a high probability of being bound with high affinity to the MHC molecule of the alleles of the given host and in the competitive context of its protein of origin while at the same time displaying a specific motif for recognition by a T-cell (helper or Treg). A further preferred condition is whether the peptide of interest is likely to be excised by an endosomal peptidase to allow it to be bound by an MHC molecule. As a TCEM is the product of binding of a peptide in the groove of either an MHC I or MHC II molecule, it follows that the present invention provides a means of categorizing peptides and TCEMs bound to either type of MHC and thus resulting in binding to either CD4+ or CD8+ T cells. As the amino acid positions of peptides bound in MHC I and MHC II molecules are different, the invention provides for evaluation of TCEMs comprising different amino acid positions determined by the binding positions in the MHC molecular groove, including but not limited to those described by Rudolph et al, as described in further detail below. In particular embodiments the invention provides for scoring based on frequency classes, and metrics for determining the relative frequency of occurrence of any particular TCEM with respect to the reference database of interest.

Every TCEM has a complimentary groove exposed motif or GEM which determines the binding affinity of the peptide to the MHC. In another embodiment therefore the present invention allows determination of the binding affinity of the peptide for a particular MHC allele or set of alleles and hence addresses another key factor in determining the dwell time of the peptide in conjunction with the MHC. Having identified both GEM and TCEM motifs, it follows that the present invention enables manipulation of either.

By application of the scoring system for TCEMs, described herein, in a further embodiment, the invention provides a ranking system to identify immunosuppressive epitopes (sometimes called Tregitopes). In further embodiments, a set of T-cell exposed motifs (TCEM) are identified which occur with high frequency in immunoglobulin variable regions of both germline and mutated immunoglobulin variable regions. These are discontinuous amino acid motifs representing the positions exposed to T-cells when a peptide is bound in an MHC groove. These are motifs, which because of the frequency of their occurrence, in combination with their affinity, are likely to give rise to immunosuppressive responses when they are also bound by MHC molecules. In specific embodiments described herein, a number of peptides may be identified which are high frequency occurrences, and which also have a high frequency of high affinity binding across a broad array of MHC molecules and thus are examples of probable down-regulatory or suppressive epitopes. Some of these TCEM arise in immunoglobulin germline sequences. Yet other TCEM arise in high frequency in mutated immunoglobulin sequences. Within this group it is possible to further categorize into those most frequently found associated with GEMS that are of high, medium, or lower binding affinity for a permuted population of 65 MHC alleles.

In yet further embodiments, the invention described herein provides a method to apply the ranking system to identify epitopes which have a high probability of stimulating the immune response because they are rare in occurrence and which, provided the other conditions of MHC binding affinity and endopeptidase cleavage are fulfilled, have a high likelihood of generating a stimulatory rather than suppressive immune response.

In additional embodiments the invention provides for design and expression of synthetic proteins in which modifications are made to the TCEM by means of changing one or more amino acids to alter the frequency categorization of the TCEM, or similarly the changing of the affinity of MHC binding by changing of amino acids in the GEMs. A further modification which may be made in the course of designing and expressing a synthetic protein is to alter the amino acids flanking the MHC binding peptide which carries the TCEM, in order to provide a greater probability of excision by cathepsin necessary to allow presentation of the TCEM of interest by an antigen presenting cell. By these means the embodiments include introduction of amino acid sequences which do not normally occur in conjunction with a particular TCEM but which result in a particularly desired outcome.

A further source of TCEMs exposed to the immune response is the immunoglobulin constant region. Each class or isotype of immunoglobulin constant region (IgM, IgA, IgD, IgE, IgG and the subclasses thereof) comprises a different sequence and hence a different set of TCEM motifs. Within each class the sequences, and hence motifs, are highly conserved. As shown herein, the repertoire of motifs found in the constant regions are different from those found in the variable region. It appears therefore that motifs in the constant region are excluded from use in the variable region. Constant region motifs—as they are indeed constant—are the most frequent class of TCEM motifs derived from immunoglobulins. It follows therefore that when these motifs are also high binding affinity they may stimulate Tregulatory or suppressor responses. In one embodiment, therefore, the present invention enables identification of constant region TCEM motifs which have high predicted binding affinity to various MHC alleles and are predicted to have a Tregulatory function when bound by these MHC alleles.

In particular embodiments the invention provides for the construction of a non transitory computer readable medium in which the database developed to categorize TCEMs is stored and the application of computer algorithms and code to the manipulation of said database to compare the frequency of TCEMs in a target protein of interest. The invention similarly provides a system for analysis of target proteins by application of a process and memory into which target protein sequences are entered and algorithms executed to identify TCEMs and compare the frequency of these with the frequency of occurrence in a reference database of reference proteins. As described above, it follows that the databases of interest include immunoglobulins of both germline and mutated origin, immunoglobulin constant regions and human proteome proteins, and databases of target proteins including but not limited to allergens, microorganisms and indeed any group of target proteins of interest. The aforesaid algorithms provide means to analyze peptides binding to either MHC I or MHC II and the corresponding populations of binding T cells.

The terms upregulation and downregulation are used herein to describe the outcome of a T-cell pMHC-Interaction, because any interaction between a T-cell and a pMHC that results in binding may be considered "immunostimulation". However, not all such events result in an active cascade of cytokines and cellular responses leading to up-regulation of the immune system and leading towards destruction of the target. Some binding interactions result in a cytokine response which diminishes the immune response and shutdown of the cellular responses or down-regulation; this appears to occur most when such immunostimulation is too frequent or too prolonged. Hence, when confronted with a self-protein the appropriate outcome is likely down-regulation (avoidance of self-destruction). An adverse reaction to a self-protein may therefore be by inappropriate upregulation or by the removal of down regulation. Furthermore, the presence in pathogen proteins of motifs which occur in high frequency in self proteins and which bind with high affinity in the protein of interest will tend to have a down regulating effect.

Autoimmune responses can arise when T-cell responses are stimulated by amino acid motifs occurring in pathogens and other environmental or "non self" or exogenous sources and result in the direction of the immune response to the same T-cell motifs where they also occur in self proteins, leading to a disequilibrium in the normal response to that self-protein. A further embodiment of the present invention is thus to provide a method of identifying motifs in non-self-proteins and scanning self-proteins to identify matching TCEM motifs which may become the target of autoimmune responses. This has application, including but not limited to, in the diagnosis and management of autoimmune diseases. In yet further embodiments, this also provides for a method to apply an important evaluative step to biotherapeutic and vaccine proteins to assist in avoidance of adverse reactions. In a further embodiment, therefore, the invention addresses the identification of epitope mimics which can give rise to adverse reactions including but not limited to autoimmune disease.

In a further embodiment of the present invention, characteristic patterns of T-cell motifs found in immunoglobulins are determined. In comparison with the pattern of frequency found in normal immunoglobulin variable regions, patterns of motif frequency are also identified which are associated with specific immunopathologies. In B-cell pathologies, the normal patterns of somatic hypermutation are disrupted and the balance of common and rare TCEM motifs changes. Hence, the application of the methods described herein, when applied to analyze the immunoglobulins of a patient, can provide assistance in the diagnosis of immunopathologies. Examples include, but are not limited to, immunopathologies such as lymphomas, leukemias, lupus erythematosus, multiple sclerosis and others. Further by identifying the mechanism in which the immunopathology arises, the analytical methods provided herein facilitate the design of interventions.

Overall therefore the invention described herein provides a means to collate and categorize the discontinuous amino acid motifs exposed to T-cells which may result in regulation and direction of the cellular immune response. Like the immune system itself, the methods described herein draw on the vast variety of motifs found in immunoglobulin variable regions as a reference database of motif frequency. In one particular embodiment therefore the invention provides for the assembly of databases which may be used as references for categorizing TCEMs and GEMs by extraction of such motifs from immunoglobulins, proteins of the proteome or groups of target proteins of interest, through the application of computer algorithms and assembly of a computer readable database.

The invention further provides for the design and expression of synthetic peptides and polypeptides which embody particular features in their TCEMs and GEMs and flanking cathepsin cleavage sites that add desired functionality and specificity of binding affinity or cleavage. Such features are determined by applications of the invention and used to design peptides and poly peptides for expression. In yet further embodiments the invention applied such properties to modify and design synthetic peptides which embody TCEMs identified in certain target proteins. In particular examples of these the target proteins of interest are tumor associated proteins, including but not limited to those associated with melanoma such as MART, MAGE and PMEL. Other proteins of interest in which TCEMs are identified and may be incorporated into synthetic peptides or polypeptides in which GEMs or flanking cathepsin cleavage sites have been modified to provide functionality, include myelin basic protein and the core protein of hepatitis B virus. Also in particular embodiments the modified synthetic peptides and poly peptides may be applied to patients to upregulate or down regulate the immune response to the TCEM of interest.

A further embodiment of the present invention is the application of peptides comprising TCEMs of determined characteristics in conjunction with synthetic MHC molecules linked to a further peptide of particular functionality. Thus a TCEM can be designed to bind to a given population of T cells and facilitate delivery of a toxin or a cytokine to such T cells. In a yet further embodiment the combination of chosen TCEM, MHC molecule and a further peptide enables the attachment of a pMHC combination as a means of binding a T cell population to a substrate such as but not limited to a purification matrix, a tissue culture plate or bead or to a cell or liposome.

In some embodiments the production of synthetic proteins comprising TCEMs comprising certain desired features is limited to a single TCEM. In yet other embodiments, the synthetic protein may comprise a multiplicity of TCEMs. In particular embodiments, the many TCEMs may be linked by linker sequences which may provide for the inclusion of cathepsin cleavage sites of particular functionality.

In a particular embodiment the production of synthetic polypeptides comprising TCEMs is directed to the production of compositions made up of only a limited number of amino acids. In yet further embodiments such synthetic polypeptides may be applied to the treatment of autoimmune diseases including but not limited to multiple sclerosis, systemic lupus erythematosis, myasthenia gravis, rheumatoid arthritis, Alzheimer's disease, diabetes, and Parkinson's disease. In such instances the synthetic polypeptide delivers TCEMs to the patient designed to down regulate the immune response or tolerize.

A number of biopharmaceutical products have been developed which have the ability to reduce the count of T-regulatory T cells. One example is ipilimumab, which binds to the CTLA4 receptors on T cells and inhibits T-regulatory T cell function. The effect is, however, directed to all Treg cells and does not discriminate those which are tumor specific. The invention described herein identifies Treg binding peptides which are specific to tumor proteins. In one example described above, these are TCEM motifs identified in HPV oncoproteins. In another embodiment, the TCEM motifs are MART or HBV associated motifs. However, it should be understood that these examples are non-limiting and the same approach applies to any oncoprotein in which a TCEM of interest is identified.

In some embodiments, the combination of a MHC molecule and a TCEM bearing peptide can preferably be configured as a target ("bait") to specifically bind to T-cells and allow their elimination by a cytotoxin or targeted energy. In some embodiments, suitable TCEMs are selected based on the analysis of high frequency motifs in a protein of interest, and by reference to a database of TCEM frequencies, as probable Tregs. In other preferred embodiments, the TCEMs are TCEMs which elicit a strong immunostimulatory upregulation. In some preferred embodiments, a MHC and TCEM-bearing peptide combination which results in the specific reduction of upregulating T cell responses, for instance in autoimmunity, is provided.

Accordingly, in some embodiments, the present invention provides a MHC-TCEM bearing peptide complex. In some preferred embodiments, the complex is attached to or includes a cytotoxin, for example radionuclide or positron emitter. The cytotoxin may be attached to, or included in, either the MHC molecule or the peptide which will be presented to a patient's T-cells bound as a pMHC so that the cytotoxin (e.g. radionuclide or positron emitter) will inflict lethal damage to the specifically binding T-cell. The following examples of substances with may be linked to the peptide or MHC to damage the T-cell should not be considered limiting. In some preferred embodiments, an alpha emitter or Auger electron emitter may be attached to or included in the peptide. Among the radionuclides of particular interest are alpha emitters, including but not limited to, Bismuth 213, Actinium 225 and Lead 212. Alpha emitters produce a high ionization density radiation with a short pathway length suitable to target single cells. Another non-limiting example is emitters of Auger particles such as Gadolinium-67, Technicium-99, Indium-111, Iodine-123, Iodine-125, and Tellurium-201. These examples, which are considered non-limiting, are appropriate because such low energy emissions result in a short distance of travel and thus confine cell damage to the immediate vicinity of the radiolabel, enabling targeting to a specific T cell. Incorporation of the radionuclide may be by inclusion in the peptide itself (e.g., iodine bound to tyrosine) or by addition of tags to the terminal amino acids of the peptide.

In yet further embodiments, the peptide or MHC may be labelled or tagged by a positron emitter. Among non-limiting examples of positron emitters which may be used to label peptides, and their half-lives, are Carbon-11 (20.4 minutes), Nitrogen 13 (10 minutes), Fluorine 18 (110 minutes), Iron 52 (8.3 hours), Iodine 124 (4.3 days), Yttrium86 (14.7 hours), Gadolium68 (68 minutes) and Arsenic 72 (26 hours).

In further embodiments, the peptide of interest may be labeled with a metallic particle such as gold or ferritin. When mounted in the MHC corresponding to the HLA of a patient and administered in vivo, the metallic particle may be targeted by an electromagnetic field as a means of destruction of the bound T cell.

In alternative embodiments, instead of a radionuclide, a non-radioactive cytotoxin is attached to the MHC molecule or to the peptide bearing the TCEM of interest. Among examples of such non-radioactive cytotoxins are RNAses, phospholipase, membrane active peptides such as cercropin, and diphtheria toxin.

In a particularly preferred embodiment, a cytotoxin or radionuclide tagged peptide which comprises a TCEM of high frequency, selected by reference to a reference database, is mutated to obtain a higher affinity of binding for a particular MHC. Such a mutated peptide is preferably assembled into a MHC molecule corresponding to the HLA allele of a specific patient and administered to that patient to bring about a desired reduction of a specific T cell population.

In further embodiments, a peptide of interest bearing a TCEM-bearing peptide is labeled with a radionuclide or with a non-radioactive label, such as but not limited to, colorimetric tags such as streptavidin or fluorescein. When assembled as a pMHC with MHC molecules corresponding to those of a specific patient the addition in vitro of PBMCs from that patient to the tagged pMHC can serve as an index or enumerator of the specific T cells in that patient. A preferred embodiment of this method comprises monitoring the presence of specific Tregs in a patient as an index of growth or metastasis of a tumor.

The production of soluble MHC molecules is known to those skilled in the art. In preferred embodiments, the MHC molecules are provided in a form suitable for patient administration. In some embodiments, soluble MHC are expressed in CHO cells as described herein.

In particularly preferred embodiments, secreted HLA molecules are constructed with the alpha or beta chain as a fusion with an immunoglobulin Fc region. The Fc region may be derived from IgG or IgA or IgM. In some embodiments, the cysteine cross bridges are removed to prevent assembly of the Fc regions as dimers. The presence of the Fc region enables detection using standard immunoassays (e.g., using an anti-human Fc detection antibody), it further provides a site for addition of tags, cytotoxins, and labels as described above.

Accordingly, the present invention provides methods for evaluating peptides derived from any source protein and for ranking the peptides within those proteins based on their likelihood of up-regulating or down-regulating the cellular immune response and various applications of such methods, including, but not limited to, in the evaluation of biopharmaceuticals, design of vaccines or immunotherapeutics, identification of epitope mimics, identification of autoimmune reactions and diagnosis of immunopathologies. It further provides compositions of peptides comprising characteristics most likely to result in various immunological outcomes, including those likely to lead to an immunosuppressive response. As a consequence the present invention provides for the modification of proteins of interest to remove immunosuppressive motifs or motifs predicted to cause excessive upregulation of the immune response. In yet further embodiments the present invention provides for the design of synthetic polypeptide and protein sequences which provide for interventions in a number of disease conditions.

In some embodiments, the present invention provides methods of designing an immunogen, comprising: categorizing the T-cell exposed motifs in a protein of interest according to their frequency of occurrence in reference to a reference database of reference proteins; determining the binding affinity of groove exposed motifs in the protein of interest and identifying those which have high binding affinity; identifying potential immunosuppressive peptides in the protein of interest; and synthesizing a synthetic isoform of the protein of interest in which the immunosuppressive peptide epitopes have been removed or modified by an amino acid substitution, deletion or other mutation to provide the immunogen. In some preferred, but not limiting, embodiments the protein of interest is an influenza protein or an Ebolavirus protein. In some embodiments, the Ebolavirus is selected from the group consisting of Zaire Ebolavirus, Sudan Ebolavirus, Cote D'Ivoire Ebolavirus, Lake Victoria Marburg virus, and Guinea-Sierra Leone Ebolaviruses of 2014. In some embodiments, the Ebolavirus protein is selected from the group consisting of envelope glycoprotein, small secreted glycoprotein, VP24, and VP40 of an Ebolavirus. In some embodiments, the immunogen comprises a peptide of from 20-40 amino acids in length selected from the protein of interest. In some embodiments, the immunogen comprises less than 15% of the amino acids of the wild type protein of interest. In some embodiments, the protein of interest is the Ebolavirus GP2 protein and said immunogen comprises a polypeptide of from 100 to 175 amino acids derived from said protein of interest. In some preferred embodiments, the protein of interest is an influenza hemagglutinin protein. In yet other embodiments the immunogen may be from another microbial pathogen, whether viral bacterial fungal or parasitic in origin, or a tumor related protein.

In some embodiments, the present invention provides a fusion protein. In some preferred embodiments the fusion protein comprises an Ebolavirus immunogen as described above. In some embodiments, the fusion protein comprises at least a portion of an immunoglobulin. In some embodiments, the fusion protein comprises a first polypeptide comprising a peptide of 20-40 amino acids derived from the protein of interest operatively linked to the N terminal of a portion of an immunoglobulin molecule. In some embodiments, the at least a portion of an immunoglobulin is linked to said immunogen peptide by a linker. In some embodiments, a first polypeptide comprising the immunogenic polypeptide derived from the protein of interest is operatively linked to the N terminal of an immunoglobulin heavy chain and a second polypeptide comprising the immunogenic polypeptide derived from the protein of interest is operatively linked to the N terminal of an immunoglobulin light chain. In some embodiments, three copies of a first polypeptide comprising the immunogenic polypeptide derived from said protein of interest are sequentially linked by a linker and the C terminal of the third copy of said immunogenic polypeptide is linked by a linker to the N terminal of an immunoglobulin heavy chain. In some embodiments, the linker comprises a plurality of glycines and serine residues. In some embodiments, the linker is from 4-10 amino acids in length. In some embodiments, the linker comprises a plurality of glycine and serine residues and is from 16-28 amino acids in length. In some embodiments, the linker is encoded by SEQ ID NO:435 or 436. In some embodiments, the immunoglobulin is murine immunoglobulin. In some embodiments, the immunoglobulin is human immunoglobulin. In some preferred embodiments, the fusion protein is encoded by a sequence selected from the group consisting of SEQ ID NOs:405 to 434. In yet other embodiments the fusion protein encodes a sequence derived from another microorganism of interest or a tumor related protein.

In some embodiments, the present invention provides a host cell expressing immunogen or fusion protein as described above.

In some embodiments, the present invention provides methods of making an immunotherapeutic comprising immunizing an animal with an immunogen or fusion protein as described above; harvesting cells and making hybridomas; extracting immunoglobulin variable region sequences from the hybridomas and constructing a murine-human chimeric antibody; and expressing the antibody in a host cell. The immunogen may be derived from a microorganism of interest including from the group comprising viruses, bacteria, fungi or parasites. In some embodiments, the present invention provides an immunotherapeutic made by the foregoing method. In some embodiments, the recombinant antibody is operatively linked to a microbiocide. In some embodiments, the microbiocide is virucidal. In some embodiments, the microbiocide is selected from the group consisting of defensins, cathelicidins, and phospolipases. In some embodiments, the immunotherapeutic neutralizes Ebola virus, in other cases the immunotherapeutic neutralizes another microorganism including from the group comprising viruses, bacteria, fungi or parasites.

In some embodiments, the present invention provides methods of treating a subject suspected of being infected with Ebolavirus by administering an immunotherapeutic as described above. In yet other embodiments the invention provides a method for treating a subject infected by another microorganism.

In some embodiments, the present invention provides a vaccine comprising an Ebolavirus immunogen or fusion protein as described above.

In some embodiments, the present invention provides a method of providing protection to a subject from infection by a microorganism, by immunization with a vaccine comprising an immunogen or fusion protein as described above. In some preferred embodiments the method is applied to protect the subject from Ebolavirus infection or influenza infection. In yet other embodiments protection is provided against infection by other microorganisms. In yet another embodiment the method provides a therapeutic benefit to an individual who is already infected by a microorganism or who is affected by cancer.

In some particularly preferred embodiments, the immunogen is from an influenza hemagglutinin. In some cases the T cell exposed motif in said influenza hemagglutinin is identified as occurring with high frequency in a reference database of reference proteins and the methods further comprise: identifying an alternate T-cell exposed motif in other similar hemagglutinins of the same hemagglutinin class wherein said alternate T cell exposed occurs with a low frequency in a reference database of reference proteins and substituting the high frequency motif with the low frequency motif. In some embodiments, the reference database of reference proteins comprises human immunoglobulin heavy and light chain variable regions. In some embodiments, the influenza hemagglutinin is from the group comprising H1, H2, H3, H5, and H7. In some embodiments, the alternate motif that is substituted occurs with a frequency of from 16 to 64-fold less frequently in the reference database of reference proteins as the motif which it substitutes. In some embodiments, the hemagglutinin with one or more substituted motifs is incorporated into a vaccine. In some embodiments, the hemagglutinin with one or more substituted motifs is expressed in a host cell. In some embodiments, the hemagglutinin with one or more substituted motifs is expressed in a host cell as a fusion peptide operatively linked with part or all of an immunoglobulin.

In some embodiments, the present invention provides methods to predict immune response to a peptide in a target protein comprising: establishing a reference database of T cell exposed motifs by assembling a database of reference proteins, extracting peptide sequences from the reference proteins, identifying T-cell exposed motifs in the peptide sequences by a computer implemented algorithm; and categorizing the T-cell exposed motifs based on the frequency of occurrence of the T-cell exposed motifs in the reference database of reference proteins; extracting peptide sequences from the target protein, identifying T-cell exposed motifs in the peptide sequences from the target protein by a computer implemented algorithm; and comparing T cell exposed motifs from the target protein to the frequency of occurrence of the same T cell motifs in the reference database.

In some embodiments, the database of reference proteins is selected from the group consisting of immunoglobulin variable regions, immunoglobulin constant regions, T cell receptor molecules, proteins of the human proteome other than immunoglobulins, allergens and microorganism proteins. In some embodiments, the database of reference proteins comprises at least 300 proteins. In some embodiments, the database of reference proteins comprises at least 5000 immunoglobulin variable region sequences. In some embodiments, the database of reference proteins comprising immunoglobulin variable regions comprises representatives of at least three immunoglobulin germline gene families. In some embodiments, the sequences in the database of reference proteins comprising immunoglobulin variable regions are identified as originating from germline or somatic mutated origin. In some embodiments, the sequences in the database of reference proteins comprising immunoglobulin variable regions are identified as originating from heavy chain or light chain origin.

In some embodiments, the configuration of amino acids in the T-cell exposed motifs comprise the 2, 3, 5, 7, 8 positions of a 15 amino acid peptide binding in a MHC-II groove which is numbered from −3 to +3. In some embodiments, the configuration of amino acids in the T-cell exposed motifs comprise the −1, 3, 5, 7, 8 positions of a 15 amino acid peptide binding in a MHC-II groove which is numbered from −3 to +3. In some embodiments, the configuration of amino acids in the T-cell exposed motifs comprise the 4, 5, 6, 7, 8 positions of a 9 amino acid peptide binding in a MHC-I groove.

In some embodiments, the categorizing further comprises determining whether the T-cell exposed motifs in the target protein occur with a frequency of greater than 1 in 8 in the reference database. In some embodiments, the categorizing further comprises determining whether the T-cell exposed motifs in the target protein occur with a frequency of greater than 1 in 64 in the reference database. In some embodiments, the categorizing further comprises determining whether the T-cell exposed motifs in the target protein occur with a frequency of greater than 1 in 1024 in the reference database. In some embodiments, the categorizing further comprises determining whether the T-cell exposed motifs in the target protein occur with a frequency of less than 1 in 1024 in the reference database. In some embodiments, the categorizing further comprises determining whether the T-cell exposed motifs in the target protein occur with a frequency of greater than the mean frequency of occurrence in the reference database. In some embodiments, the categorizing further comprises determining whether the T-cell exposed motifs in the target protein occur with a frequency of less than the mean frequency of occurrence in the reference database.

In some embodiments, the methods further comprise the step of characterizing the overall immunogenicity of the target protein by ranking of the frequency of occurrence of a plurality of the T-cell exposed motifs in the target protein. In some embodiments, the methods further comprise determining the predicted MHC binding affinity of the peptide sequences comprising the T-cell exposed motifs derived from the target protein by determining the MHC allele-specific binding of the groove exposed motifs corresponding to each T-cell exposed motif. In some embodiments, the methods further comprise identifying the peptide sequences within the target protein which have T-cell exposed motifs with a high frequency of occurrence in a reference database of immunoglobulin variable regions and which have groove exposed motifs associated with the T-cell exposed motifs that have a predicted high binding affinity to one or more MHC alleles. In some embodiments, the methods further comprise peptide sequences within the target protein that are predicted immunosuppressive T-cell epitopes. In some embodiments, the methods further comprise identifying the peptide sequences within the target protein which have T-cell exposed motifs with a low frequency of occurrence in a reference database immunoglobulin variable regions and which have groove exposed motifs associated with the T-cell exposed motifs that have a high predicted binding affinity. In some embodiments, the methods further comprise identifying the peptide sequences within the target protein that lead to upregulation of the immune response. In some embodiments, the methods further comprise designing modifications in a peptide selected from the target protein wherein the modifications are selected to produce a result selected from the group consisting of (a) a lower or higher frequency of representation as compared to the reference database of reference proteins, and (b) increased or decreased MHC binding affinity of the selected peptide, and expressing a synthetic polypeptide comprising the modified peptide and purifying the synthetic polypeptide. In some embodiments, the methods further comprise selecting one or more peptide sequences having a desired frequency of T-cell exposed motif representation as compared to the reference database of reference proteins from the target protein and synthesizing a nucleic acid construct comprising the one or more peptide sequences in operable association with one or more sequences that do not naturally occur with the one or more peptide sequences. In some embodiments, the methods further comprise expressing the protein product of the nucleic acid construct. In some embodiments, the methods further comprise purifying the protein encoded by the nucleic acid construct.

In some embodiments, the present invention provides methods to predict cross reaction of T-cell binding comprising: establishing a reference database of T cell exposed motifs by assembling a multiplicity of databases of reference proteins, extracting peptide sequences from the reference proteins, and identifying T-cell exposed motifs in the peptide sequences by a computer implemented algorithm; categorizing the T-cell exposed motifs based on the frequency of occurrence of the T-cell exposed motifs in the multiplicity of databases of reference proteins, and comparing the frequency of occurrence of the T cell exposed motifs in more than one of the multiplicity of databases of reference proteins.

In some embodiments, the present invention provides a non-transitory computer readable medium comprising: a database of peptides comprising T-cell exposed motifs categorized based on the frequency of occurrence of the T-cell exposed motifs in a reference database of reference proteins, wherein the database retains the identity of the peptide from which the T cell exposed motif is obtained in the reference database of reference proteins; computer executable code that upon execution allows entry of target protein sequences; computer executable code that upon execution extracts target peptide sequences from the target protein sequences and identifies T-cell exposed motifs in the target peptide sequences; and computer executable code that compares the T-cell exposed motifs in the target peptide sequences to the database of T-cell exposed motifs to determine the frequency of representation of the T-cell exposed motifs in the target peptide sequences as compared to the reference database of reference proteins.

In some embodiments, the database of reference proteins is selected from the group consisting of immunoglobulin variable regions, immunoglobulin constant regions, T cell receptor molecules, proteins of the human proteome other than immunoglobulins, allergens and microorganism proteins. In some embodiments, the reference database of reference proteins comprises at least 300 proteins. In some embodiments, the reference database of reference proteins comprises at least 5000 immunoglobulin variable region sequences. In some embodiments, the reference database of reference proteins comprising immunoglobulin variable regions comprises representatives of at least three immunoglobulin germline gene families. In some embodiments, the sequences in the reference database of reference proteins comprising immunoglobulin variable regions are identified as originating from germline or somatic mutated origin. In some embodiments, the sequences in the reference database of reference proteins comprising immunoglobulin variable regions are identified as originating from heavy or light chains. In some embodiments, the database of peptides comprising T cell exposed motifs is further categorized according to the probability of the peptide from which the T cell exposed motif is derived binding to a MHC allele. In some embodiments, the database of peptides comprising T cell exposed motifs is further categorized according to the predicted MHC binding affinity of the groove exposed motif comprised within the peptide from which the T cell exposed motif is derived.

In some embodiments, the configuration of amino acids in the T-cell exposed motifs comprise the 2, 3, 5, 7, 8 positions of a 15 amino acid peptide binding in a MHC-II groove which is numbered from −3 to +3. In some embodiments, the configuration of amino acids in the T-cell exposed motifs comprise the −1, 3, 5, 7, 8 positions of a 15 amino acid peptide binding in a MHC-II groove which is numbered from −3 to +3. In some embodiments, the configuration of amino acids in the T-cell exposed motifs comprise the 4, 5, 6, 7, 8 positions of a 9 amino acid peptide binding in a MHC-I groove.

In some embodiments, the target protein sequences are biopharmaceutical protein sequences. In some embodiments, the target protein sequences are microbial protein sequences. In some embodiments, the target protein sequences are mammalian protein sequences. In some embodiments, the target protein sequences are selected from the group consisting of non-mammalian protein sequences, arthropod protein sequences, and plant protein sequences.

In some embodiments, the present invention provides systems for analysis of target proteins comprising: a processor and memory, wherein the processor and memory are configured to (i) assemble a reference database of reference proteins, extract peptide sequences from the reference proteins; identify T-cell exposed motifs in the peptide sequences by a computer implemented algorithm; and categorize the T-cell exposed motifs based on the frequency of occurrence of the T-cell exposed motifs in the reference database of reference proteins so as to establish a database of peptides categorized by their constituent T cell exposed motif frequency; (ii) extract target peptide sequences from a target protein of interest; (iii) identify T-cell exposed motifs in the target peptide sequences from the target protein of interest by a computer implemented algorithm; and (iv) compare the T-cell exposed motifs in the target peptide sequences to the database of T-cell exposed motifs categorized based on the frequency of occurrence of the T-cell exposed motifs in the reference database of reference proteins to determine the frequency of representation of the T-cell exposed motifs in the target peptide sequences as compared to the reference database of reference proteins.

In some embodiments, the target protein sequences are selected from the group consisting of biopharmaceutical protein sequences, microbial protein sequences, mammalian protein sequences, non-mammalian protein sequences, arthropod protein sequences, and plant protein sequences. In some embodiments, the processor and memory are further configured to determine the affinity of binding of the target peptide sequences to one or more MHC alleles.

In some embodiments, the configuration of amino acids in the T-cell exposed motifs comprise the 2, 3, 5, 7, 8 positions of a 15 amino acid peptide binding in a MHC-II groove which is numbered from −3 to +3. In some embodiments, the configuration of amino acids in the T-cell exposed motifs comprise the −1, 3, 5, 7, 8 positions of a 15 amino acid peptide binding in a MHC-II groove which is numbered from −3 to +3. In some embodiments, the configuration of amino acids in the T-cell exposed motifs comprise the 4, 5, 6, 7, 8 positions of a 9 amino acid peptide binding in a MHC-I groove.

In some embodiments, the reference database of reference proteins is selected from the group consisting of immunoglobulin variable regions, immunoglobulin constant regions, T cell receptor molecules, proteins of the human proteome other than immunoglobulins, allergens and microorganism proteins. In some embodiments, the reference database of reference proteins comprises at least 300 proteins. In some embodiments, the reference database of reference proteins comprises at least 5000 immunoglobulin variable region sequences. In some embodiments, the reference database of reference proteins comprising immunoglobulin variable regions comprises representatives of at least three immunoglobulin germline gene families. In some embodiments, the database of reference proteins comprising immunoglobulin variable regions comprises sequences that are identified as originating from germline or somatic mutated origin. In some embodiments, the reference database of reference proteins comprising immunoglobulin variable regions comprises sequences that are identified as originating from heavy or light chain origin.

In some embodiments, the present invention provides methods of evaluating a target protein for peptide sequences with motifs that may induce adverse immune responses comprising: identifying T-cell exposed motifs in target peptide sequences in the target protein and determining the frequency of occurrence of the T-cell exposed motifs by comparison with a reference database of T-cell exposed motifs; identifying groove exposed motifs associated with T-cell exposed motifs in target peptide sequences in the target protein based on the frequency of representation in the reference database; determining the predicted binding affinity of the target peptide sequences comprising the groove exposed motifs and identifying MHC binding based on the predicted binding affinity to the target peptide sequences comprising the groove exposed motifs; and evaluating the combination of frequency and binding affinity as an indicator of potential to cause an adverse immune response.

In some embodiments, the peptide sequences in the target protein comprise a combination selected from the group consisting of (a) a T-cell exposed motif with a high frequency of representation in the reference database and a high predicted binding affinity to an MHC allele likely to induce immunosuppression, and (b) a T-cell exposed motif with low frequency of representation in the reference database and a high predicted binding affinity to an MHC allele likely to induce a strong upregulation of the immune response. In some embodiments, the target protein is selected from the group consisting of biopharmaceutical proteins and vaccines.

In some embodiments, the present invention provides methods of modifying the immune response to a protein of interest comprising applying the method of claim 55 to identify a protein comprising peptides with potential adverse motifs and modifying the protein of interest by changing one or more amino acids in the potential adverse motifs and further expressing the modified protein as a synthetic protein product.

In some embodiments, the present invention provides methods of identifying a potential epitope mimic in a protein of interest comprising: identifying the T-cell exposed motifs in target peptide sequences in a first protein of interest and determining the frequency of occurrence of the T-cell exposed motifs in a reference database to identify T-cell exposed motifs which are present at high frequency in the reference database; identifying groove exposed motifs associated with the T-cell exposed motifs in the first protein of interest that have a high frequency of representation in the reference database; determining the predicted binding affinity of the target peptide sequences from the first protein of interest comprising the groove exposed motifs; and repeating the foregoing steps on a second protein of interest to identify identical T-cell exposed motifs associated with a same or different groove exposed motif; wherein the first protein is an exogenous protein and the second protein is an endogenous or self-protein and wherein exposure to the first protein results in an adverse immune response directed to the second protein.

In some embodiments, the present invention provides methods of modifying the immune response to a protein of interest comprising applying the method described above to identify peptides which are potential epitope mimics based on the T-cell exposed motif and/or groove exposed motif compositions and modifying the motifs by changing one or more amino acids in the motifs in the protein of interest. In some embodiments, the epitope mimic is identified as an autoimmune disease target. In some embodiments, the methods further comprise using information from the process to inform a diagnosis for an autoimmune disease.

In some embodiments, the present invention provides methods of diagnosing an immunopathology comprising: obtaining a blood sample from a subject suspected of being affected by an immunopathology; determining the sequence of a multiplicity of immunoglobulin sequences in the blood sample; determining a frequency distribution pattern of T-cell exposed motifs in the immunoglobulins in the blood sample; comparing the frequency distribution of T cell exposed motifs with a reference frequency distribution characteristic an immunopathology; and providing a diagnosis based on the comparison. In some embodiments, the immunopathology is selected from the group consisting of lymphoma, leukemia, lupus erythematosus, and multiple sclerosis. In some embodiments, the reference database is compiled from immunoglobulins sequenced from individuals with an immunopathology.

In some embodiments, the present invention provides a synthetic polypeptide comprising a T-cell exposed motif that occurs with a desired frequency of representation as compared to the frequency of occurrence in a reference database of reference proteins and wherein the amino acids in the counterpart groove exposed motif of the T cell exposed motif are selected to provide a desired profile of binding affinity to at least one selected MHC allele. In some embodiments, the present invention provides a synthetic polypeptide comprising a T-cell exposed motif that occurs with a desired frequency of representation as compared to a reference database of reference proteins and wherein the amino acids in the counterpart groove exposed motif are selected to provide high affinity binding to at least one selected MHC allele. In some embodiments, the present invention provides a synthetic polypeptide comprising a T-cell exposed motif that occurs with a desired frequency of representation as compared to a reference database of reference proteins and wherein the amino acids in the counterpart groove exposed motif are selected to provide low affinity binding to at least one selected MHC allele. In some embodiments, the present invention provides a synthetic polypeptide comprising a first peptide of 9-23 amino acids which comprises a T-cell exposed motif that occurs with a desired frequency in a reference database of reference proteins and wherein the first peptide containing a T-cell exposed motif is flanked on both sides by flanking peptide sequences selected to provide probability of >0.5 of excision of the first peptide by endosomal peptidases.

In some preferred embodiments, the synthetic polypeptide is operably associated with an exogenous sequence.

In some embodiments, the configuration of amino acids in the T-cell exposed motif comprises the 2, 3, 5, 7, 8 positions of a 15 amino acid peptide binding in a MHC-II groove which is numbered from −3 to +3. In some embodiments, the configuration of amino acids in the T-cell exposed motifs comprise the −1, 3, 5, 7, 8 positions of a 15 amino acid peptide binding in a MHC-II groove which is numbered from −3 to +3. In some embodiments, the configuration of amino acids in the T-cell exposed motifs comprise the 4, 5, 6, 7, 8 positions of a 9 amino acid peptide binding in a MHC-I groove. In some embodiments, the synthetic polypeptide has one or more mutations in a T cell exposed motif or groove exposed motif as compared to the corresponding wild-type T cell motif. In some embodiments, the one or more mutations is at a site selected from the group consisting of the 2, 3, 5, 7, 8 positions of a 15 amino acid peptide binding in a MHC-II groove which is numbered from −3 to +3, the −1, 3, 5, 7, 8 positions of a 15 amino acid peptide binding in a MHC-II groove which is numbered from −3 to +3, the 4, 5, 6, 7, 8 positions of a 9 amino acid peptide binding in a MHC-I groove, the −3, 2, −1, 1, 4, 6, 9, +1, +2, +3 positions of a 15 amino acid peptide binding in a MHC-II groove which is numbered from −3 to +3, the −3, 2, 1, 2, 4, 6, 9, +1, +2, +3 positions of a 15 amino acid peptide binding in a MHC-II groove which is numbered from −3 to +3, and the 1, 2, 3, 9 positions of a 9 amino acid peptide binding in a MHC-I groove.

In some embodiments, the reference database of reference proteins is selected from the group consisting of immunoglobulin variable regions, immunoglobulin constant regions, T cell receptor molecules, proteins of the human proteome other than immunoglobulins, allergens and microorganism proteins. In some embodiments, the desired frequency of T-cell exposed motif occurrence in the reference database is greater than 1 in 1024 T-cell exposed motifs and the database comprises at least 5000 proteins. In some embodiments, the desired frequency of T-cell exposed motif occurrence is greater than the mean frequency in the reference database. In some embodiments, the desired frequency of T-cell exposed motif occurrence is less than the mean frequency in the reference database. In some embodiments, the binding to at least one selected MHC allele is to more than 4 alleles. In some embodiments, the flanking sequences comprise 4-10 amino acids.

In some embodiments, the synthetic polypeptide is immunosuppressive. In some embodiments, the synthetic polypeptide upregulates the immune response.

In some embodiments, the T-cell exposed motif is derived from a reference database of tumor associated antigens. In some embodiments, the tumor associated antigen is from the group comprising MART, MAGE antigens, PMEL. In some embodiments, the peptide comprising the T-cell exposed motif is selected from the group consisting of SEQ ID NOs: 119, 121, 123, 124, 126, 128, 130, 132 and 134, and wherein X represents any amino acid. In some embodiments, the peptide comprising the T-cell exposed motif is selected from the group consisting of SEQ ID NOs: 118, 120, 122, 125, 127, 129, 131 and 133.

In some embodiments, the T-cell exposed motif is derived from a viral protein. In some embodiments, the protein is selected from the group of viral proteins consisting hepatitis B core protein, and human papilloma virus proteins E6 and E7. In some embodiments, the peptide comprising the T-cell exposed motif is selected from the group consisting of SEQ ID NOs:237-285, and wherein X represents any amino acid. In some embodiments, the peptide comprising the T-cell exposed motif is selected from the group consisting of SEQ ID NOs: 259-278 and 467.

In some embodiments, the T cell exposed motif is derived from myelin basic protein. In some embodiments, the peptide comprising the T-cell exposed motif is selected from the group consisting of SEQ ID NOs: 136, 138 and 140, wherein X represents any amino acid. In some embodiments, the peptide comprising the T-cell exposed motif is selected from the group consisting of SEQ ID NOs: 135, 137 and 139.

In some embodiments, the present invention provides a purified biopharmaceutical protein preparation comprising a synthetic polypeptide as described above.

In some embodiments, the present invention provides a vaccine comprising a synthetic polypeptide as described above.

In some embodiments, the present invention provides methods of designing a synthetic polypeptide encoding an immunogen comprising: categorizing the T-cell exposed motifs in a protein of interest according to their frequency of occurrence in reference to a reference database of reference proteins; determining the binding affinity of groove exposed motifs in the protein of interest and identifying those which have high binding affinity; identifying potential immunosuppressive peptides in the protein of interest; and synthesizing a synthetic polypeptide comprising an isoform of the protein of interest in which the immunosuppressive peptide epitopes have been removed or modified by an amino acid substitution, deletion or other mutation.

In some embodiments, the potential immunosuppressive epitopes have been modified to reduce their immunosuppressive function by a modification selected from the group consisting of changing one or more amino acids in the groove exposed motif to reduce the binding affinity, changing one or more T-cell exposed motif amino acids to prevent binding to T cells, and changing one or more amino acids flanking within 4 amino acids of either side of the peptide to reduce the probability of excision. In some embodiments, a peptide sequence containing an immunosuppressive T-cell exposed motif is removed from the synthetic polypeptide comprising an isoform of the protein.

In some embodiments, the reference database of reference proteins is selected from the group consisting of immunoglobulin variable regions, immunoglobulin constant regions, T cell receptor molecules, proteins of the human proteome other than immunoglobulins, allergens and microorganism proteins.

In some embodiments, the immunogen is a component of a vaccine. In some embodiments, the immunogen comprises a peptide of from 20-40 amino acids in length selected from the protein of interest. In some embodiments, the immunogen comprises less than 15% of the amino acids of the wild type protein of interest. In some embodiments, the protein of interest is a tumor associated antigen. In some embodiments, the tumor associated antigen is from the group comprising MART, MAGE antigens, PMEL. In some embodiments, the protein of interest is a viral protein. In some embodiments, the viral protein is from the group comprising hepatitis B and human papillomavirus. In some embodiments, the potential immunosuppressive peptides in the protein of interest are selected from the group consisting of SEQ ID NOs: 119, 121, 123, 124, 126, 128, 130, 132, 134 and 237 to 285. In some embodiments, the protein of interest is an influenza hemagglutinin protein. In some embodiments, the T cell exposed motif in the influenza hemagglutinin is identified as occurring with high frequency in a reference database of reference proteins and further comprising: identifying an alternate T-cell exposed motif in other similar hemagglutinins of the same hemagglutinin class wherein the alternate T cell exposed occurs with a low frequency in a reference database of reference proteins; and substituting the high frequency motif with the low frequency motif. In some embodiments, the influenza hemagglutinin is from the group comprising H1, H2, H3, H5, and H7. In some embodiments, the alternate motif that is substituted occurs with a frequency of from 16 to 64-fold less frequently in the reference database of reference proteins as the motif which it substitutes. In some embodiments, the protein of interest is an Ebolavirus protein. In some embodiments, the Ebolavirus is selected from the group consisting of Zaire Ebolavirus, Sudan Ebolavirus, Cote D'Ivoire Ebolavirus, Lake Victoria Marburg virus, and Guinea-Sierra Leone Ebolaviruses of 2014. In some embodiments, the Ebolavirus protein is selected from the group consisting of envelope glycoprotein, small secreted glycoprotein, VP24, and VP40 of an Ebolavirus. In some embodiments, the protein of interest is the Ebolavirus GP2 protein and the immunogen comprises a polypeptide of from 100 to 175 amino acids derived from the protein of interest.

In some embodiments, the present invention provides a synthetic polypeptide encoding an immunogen produced by the methods described above.

In some embodiments, the present invention provides a fusion protein comprising the synthetic polypeptide encoding an immunogen as described above. In preferred embodiments, the synthetic polypeptide is placed in fame or in operable association with a peptide sequence not naturally associated with the synthetic polypeptide.

In some embodiments, the fusion protein comprises at least a portion of an immunoglobulin. In some embodiments, the fusion protein comprises a first polypeptide comprising a peptide of 20-40 amino acids derived from the protein of interest operatively linked to the N terminal of a portion of an immunoglobulin molecule. In some embodiments, the at least a portion of an immunoglobulin is linked to the immunogen peptide by a linker. In some embodiments, a first polypeptide comprising the immunogenic polypeptide derived from the protein of interest is operatively linked to the N terminal of an immunoglobulin heavy chain and a second polypeptide comprising the immunogenic polypeptide derived from the protein of interest is operatively linked to the N terminal of an immunoglobulin light chain. In some embodiments, three copies of a first polypeptide comprising the immunogenic polypeptide derived from the protein of interest are sequentially linked by a linker and the C terminal of the third copy of the immunogenic polypeptide is linked by a linker to the N terminal of an immunoglobulin heavy chain. In some embodiments, the linker comprises a plurality of glycine and serine residues. In some embodiments, the linker is from 4-10 amino acids in length. In some embodiments, the linker comprises a plurality of glycine and serine residues and is from 16-28 amino acids in length. In some embodiments, the linker is encoded by SEQ ID NO:435 or 436.

In some embodiments, the present invention provides a vaccine comprising a fusion protein as described above.

In some embodiments, the fusion protein is encoded by a sequence selected from the group consisting of SEQ ID NOs:405-434.

In some embodiments, the present invention provides methods of providing protection to a subject from infection by Ebolavirus by immunization with a vaccine comprising an immunogen or fusion protein as defined above.

In some embodiments, the present invention provides a host cell expressing a synthetic polypeptide or fusion protein as described above.

In some embodiments, the present invention provides methods of making an immunotherapeutic comprising immunizing an animal with the synthetic polypeptide encoding an immunogen or fusion protein as defined above, the method comprising harvesting cells and making hybridomas; extracting immunoglobulin variable region sequences from the hybridomas and constructing a humanized or murine-human chimeric antibody; and expressing the antibody in a host cell.

In some embodiments, the present invention provides an immunotherapeutic made by the foregoing method. In some embodiments, the recombinant antibody is operatively linked to a microbiocide. In some embodiments, the microbiocide is virucidal. In some embodiments, the microbiocide is selected from the group consisting of defensins, cathelicidins, and phospholipases. In some embodiments, the immunotherapeutic neutralizes Ebola virus. In some embodiments, the present invention provides a method of treating a subject suspected of being infected with Ebolavirus by administering the immunotherapeutic.

In some embodiments, the present invention provides a synthetic polypeptide which is an isoform of a protein of interest in which one or more immunosuppressive epitopes have been identified and functionally eliminated by the method described above. In some embodiments, the potential immunosuppressive epitopes have been modified to preclude their immunosuppressive function by a modification selected from the group consisting of changing one or more amino acids in the groove exposed motif to reduce the binding affinity; changing one or more T cell exposed motif amino acids to prevent binding to T cells; and changing one or more amino acids flanking within 4 amino acids of either side of the peptide to reduce the probability of excision. In some embodiments, an immunosuppressive epitope peptide identified in the natural isoform has been identified and excluded from the sequence of the synthetic isoform. In some embodiments, the present invention provides a vaccine comprising the synthetic polypeptide as described above.

In some embodiments, the present invention provides a polypeptide composition comprising a first synthetic peptide comprising a T-cell exposed motif that occurs with a desired frequency of representation compared to a reference database of reference proteins and a second peptide or polypeptide comprising a MHC molecule subunit in operable association with a third peptide or polypeptide which does not naturally occur with the second peptide and wherein the first synthetic peptide comprises a groove exposed motif that binds to the MHC molecule of the second peptide or polypeptide with high affinity. In some embodiments, the present invention provides a polypeptide composition comprising a first synthetic peptide comprising a MHC molecule subunit and a second peptide or polypeptide comprising a T-cell exposed motif that occurs with a desired frequency of representation compared to a reference database of reference proteins in operable association with a third molecule which does not naturally occur with the second peptide and wherein the second synthetic peptide comprises a groove exposed motif that binds to the MHC molecule of the second peptide or polypeptide with high affinity.

In some embodiments, the predetermined frequency of T-cell exposed motif occurrence in the reference database is greater than 1 in 64 T-cell exposed motifs and the database comprises at least 5000 proteins. In some embodiments, the predetermined frequency of T-cell exposed motif occurrence in the reference database is greater than or equal to 1 in 1024 T-cell exposed motifs and the database comprises at least 5000 proteins. In some embodiments, the predetermined frequency of T-cell exposed motif occurrence in the reference database is from 1 in 1024 to 1 in 16000 T-cell exposed motifs and the database comprises at least 5000 proteins. In some embodiments, the predetermined frequency of T-cell exposed motif occurrence in the reference database is less than 1 in 16000 T-cell exposed motifs and the database comprises at least 5000 proteins. In some embodiments, the T-cell exposed motif is selected from a reference database selected from the group consisting of T-cell exposed motifs found reference database of reference proteins is selected from the group consisting of immunoglobulin variable regions, immunoglobulin constant regions, T cell receptor molecules, proteins of the human proteome other than immunoglobulins, allergens and microorganism proteins. In some embodiments, the third molecule comprises a cytotoxin. In some embodiments, the third molecule comprises a radionuclide molecule. In some embodiments, the radionuclide is an alpha emitter. In some embodiments, the radionuclide is an Auger electron emitter. In some embodiments, the third molecule comprises a positron emitter.

In some embodiments, the second peptide or polypeptide comprising a T cell exposed motif is derived from an oncoprotein or a tumor associated protein. In some embodiments, the oncoprotein is a viral protein from the group comprising papillomavirus, polyomaviruses, adenoviruses, herpesviruses, and retroviruses. In some embodiments, the second peptide or polypeptide comprising a T cell exposed motif is derived from the synthetic polypeptides or fusion polypeptides described above.

In some embodiments, the third peptide or polypeptide is a non-radioactive cytotoxin or cytocide. In some embodiments, the third peptide or polypeptide is a label peptide or an anchor peptide.

In some embodiments, the MHC molecule is selected based on the alleles of a patient. In some embodiments, the MHC molecule subunit is an alpha chain subunit. In some embodiments, the MHC molecule subunit is a beta chain subunit. In some embodiments, the MHC molecule subunit is from an MHC I. In some embodiments, the MHC molecule subunit is from an MHC II.

In some embodiments, the present invention provides a method of suppressing an immune response in a patient by administration to a subject of a polypeptide composition as described above.

In some embodiments, the present invention provides a method of enumerating the T cells in a patient which bind to a specific T cell exposed motif comprising contacting patient T cells with a composition as described above and enumerating the percentage that bind to the composition. In some embodiments, the patient is a cancer patient.

In some embodiments, the present invention provides a synthetic polypeptide comprising a multiplicity of T cell exposed motifs in operable association, wherein the T-cell exposed motifs are selected from a reference database of T cell exposed motifs assembled from a group selected from the group consisting of T-cell exposed motifs found in germline immunoglobulin variable region sequences, T-cell exposed motifs found in somatically mutated immunoglobulin variable region sequences, T-cell exposed motifs found in immunoglobulin constant chains and T-cell exposed motifs found in T-cell receptor molecules, and wherein each of the T-cell exposed motifs in the multiplicity of T-cell exposed motifs have a desired frequency of representation in the reference database.

In some embodiments, the desired frequency of T-cell exposed motif representation in the reference database is greater than 1 in 64 T-cell exposed motifs and the database comprises at least 5000 proteins. In some embodiments, the desired frequency of T-cell exposed motif representation in the reference database is greater than 1 in 512 T-cell exposed motifs and the database comprises at least 5000 proteins. In some embodiments, the desired frequency of T-cell exposed motif representation in the reference database is from 1 in 512 to 1 in 16000 T-cell exposed motifs and the database comprises at least 5000 proteins. In some embodiments, the desired frequency of T-cell exposed motif representation in the reference database is less than 1 in 16000 T-cell exposed motifs and the database comprises at least 5000 proteins.

In some embodiments, the synthetic polypeptide further comprises a peptide linker sequence between each T-cell exposed motif. In some embodiments, the linker sequences each comprise 2-15 amino acids. In some embodiments, the linker sequences comprise endosomal peptidase cleavage sites with a probability of cleavage of >0.5. In some embodiments, the T-cell exposed motif is also categorized in a database comprising proteins from the groups consisting of the human proteome other than immunoglobulins, allergens, and microorganisms. In some embodiments, the multiplicity of T-cell exposed motifS comprise 2-10 different T-cell exposed motifs. In some embodiments, the multiplicity of T-cell exposed motifs comprise repetition of the same T-cell exposed motif. In some embodiments, the polypeptide is from 30 to 150 amino acids in length. In some embodiments, the polypeptide comprises less than 5 different amino acids. In some embodiments, the polypeptide comprises less than 10 different amino acids.

In some embodiments, the present invention provides a method of generating an immunosuppressive response by administration of the synthetic polypeptide as described above to a subject. In some embodiments, the subject has an autoimmune disease. In some embodiments, the autoimmune disease is from the group comprising multiple sclerosis, systemic lupus erythematosis, myasthenia gravis, rheumatoid arthritis, Alzheimers disease, diabetes, and Parkinsons disease.

In some embodiments, the present invention provides a polypeptide composition comprising a first synthetic polypeptide comprising a MHC beta chain and a second synthetic polypeptide comprising a MHC subunit chain operably linked to a third synthetic polypeptide which does not normally occur in association with the MHC alpha chain. In some embodiments, the third synthetic polypeptide is an immunoglobulin sequence. In some embodiments, the immunoglobulin sequence is a constant region sequence. In some embodiments, the cysteine residue forming the hinge cross link is substituted. In some embodiments, the third synthetic polypeptide is operably linked to a cytotoxin. In some embodiments, the third synthetic polypeptide incorporates a radionuclide. In some embodiments, the MHC subunit chain is an alpha chain. In some embodiments, the MHC subunit chain is a beta chain. In some embodiments, the MHC is a Type II MHC from the group comprising DR, DP and DQ. In some embodiments, the MHC is a Type I MHC from the group comprising MHC IA and MHC IB.

In some embodiments, the present invention provides a host cell expressing the polypeptide composition described above.

DESCRIPTION OF THE FIGURES

FIG. 5: Positional frequencies of unique T-cell exposed motifs are shown for TCEM IIa, TCEM IIb, and TCEM I for IGHV3. The center of each of the TCEM are plotted against the $log_2$ of the number of different motifs at the particular location in the IGHV. The upper panel shows IGHV3 germline sequences and the lower panel is from the entire SHM 40K data set that has 22,458 different IGHV3 proteins. A quantile density contouring algorithm was used to generate the color gradation contours. The highlighted colors show that the majority of the unique germline motifs are found in CDR 1 and CDR 2 whereas the majority of mutated motifs are found in CDR 3 (which is not found in the germline. Note that FW3 also has a substantial number of unique motifs. Figure shows output for IGHV3; other germline families are very similar.

FIG. 12: Shows the predicted binding affinity of nDQA1_0102-DQB1_0602 in hemagglutinin of Influenza A 2009 California far exceeds that of other alleles at position 273-276.

FIG. 13: Shows the proteins in the human proteome containing the two motifs of interest, AG˜G˜II and NA˜S˜II which are predicted to bind to DQA1*01:02/DQB1*06:02 DQ.

FIG. 19: Shows the peptides from MART-1 for which there are corresponding motifs in the IGHV database. The frequency TCEM motifs are shown for TCEMI and the two TCEM II and frequency classes are shown for each. In the right hand side of the panel the TCEMs are categorized as matching germline or mutated IGHV sequences. The high binding affinity of the peptide indexed at amino acid position 37 makes it a predicted immunosuppressive Treg for all alleles and at position 33 for TCEM I.

FIG. 27: Tabulation of the affinities (ln(ic50)) of the up to ten highest affinity peptides generated for each allele of interest

DEFINITIONS

Figures 1, 2:
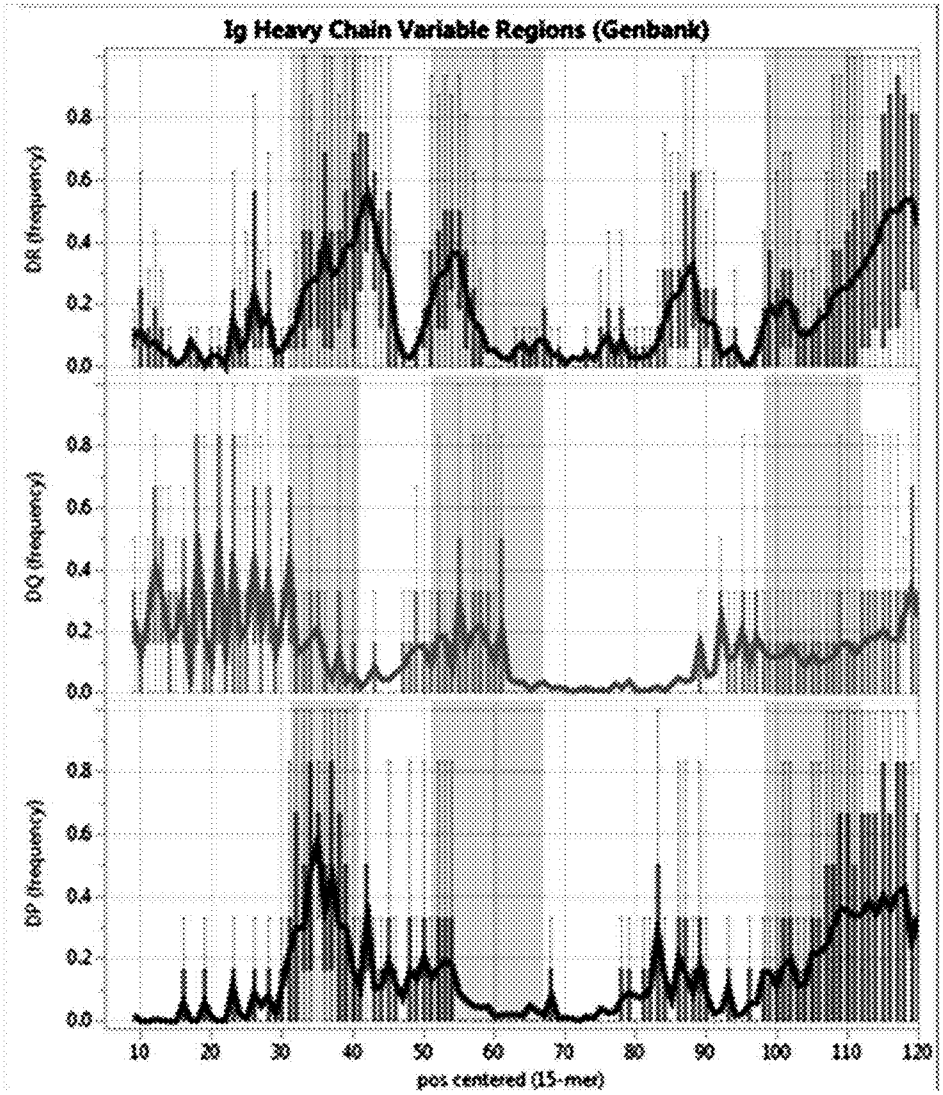
FIG. 1: Discontinuous sets of amino acids in peptides were placed into categorical groups based on the structural analysis of amino acid contact points in pMHC:T-cell receptor complexes (Rudolph et al [2]). The positions of the amino acids used in the classification scheme are shown. For MHC-II, T-cell exposed motifs are related to pocket positions in a 15-mer, with a conventional 9-mer core flanked by 3 amino acids on each end. A 9-mer is shown for MHC-I. Two types of class II T-cell exposed motifs, TCEM IIa and TCEM IIb are considered. They are discontinuous and occupy the register positions shown. TCEM IIa comprises amino acids 2, 3, 5, 7, 8 and TCEM IIb comprises −1, 3, 5, 7, 8. The obverse face of the 15-mer comprises the corresponding groove exposed motifs, GEM IIA and GEM IIb, which are primarily involved in peptide binding to the MHC. The class I motif is a continuous series of amino acids occupying amino acid positions 4, 5, 6, 7, 8 in a conventional MHC-I pocket. The GEM I, amino acids 1, 2, 3, 9 are those amino acids primarily responsible for binding the peptide in the MHC-I.
FIG. 2: Predicted MHC binding affinity of all sequential peptides derived from a subset of ten thousand IGHV3-origin variable regions. A: DR, B: DP, C: DQ alleles MHC II (15-mers). The binding affinity is expressed as the fraction of alleles binding the peptide centered at the indicated position, where the binding affinity of the peptide to an allele is predicted more than 1 standard deviation below the mean for that allele within the particular protein. The solid line represents the average and the extensions show the 10% and 90% points. Thus, a predicted affinity as seen for DR centered at aa 38 of 0.62 indicates that on average 10 of the 16 DR alleles for which predictions are made are predicted to bind this peptide with an affinity in excess of 1 standard deviation below the mean. As shown by the extensions some peptides in are bound by essentially all MHC II alleles evaluated. The grey shaded background indicates the approximate location of the three CDRs.

As used herein, the term "genome" refers to the genetic material (e.g., chromosomes) of an organism or a host cell.

As used herein, the term "proteome" refers to the entire set of proteins expressed by a genome, cell, tissue or organism. A "partial proteome" refers to a subset the entire set of proteins expressed by a genome, cell, tissue or organism. Examples of "partial proteomes" include, but are not limited to, transmembrane proteins, secreted proteins, and proteins with a membrane motif. Human proteome refers to all the proteins comprised in a human being. Multiple such sets of proteins have been sequenced and are accessible at the InterPro international repository (www.ebi.ac.uk/interpro). Human proteome is also understood to include those proteins and antigens thereof which may be over-expressed in certain pathologies, or expressed in a different isoforms in certain pathologies. Hence, as used herein, tumor associated antigens are considered part of the human proteome.

As used herein, the terms "protein," "polypeptide," and "peptide" refer to a molecule comprising amino acids joined via peptide bonds. In general "peptide" is used to refer to a sequence of 20 or less amino acids and “polypeptide” is used to refer to a sequence of greater than 20 amino acids.

As used herein, the term, “synthetic polypeptide,” “synthetic peptide” and “synthetic protein” refer to peptides, polypeptides, and proteins that are produced by a recombinant process (i.e., expression of exogenous nucleic acid encoding the peptide, polypeptide or protein in an organism, host cell, or cell-free system) or by chemical synthesis.

As used herein, the term “protein of interest” refers to a protein encoded by a nucleic acid of interest. It may be applied to any protein to which further analysis is applied or the properties of which are tested or examined. Similarly, as used herein, “target protein” may be used to describe a protein of interest that is subject to further analysis.

As used herein “peptidase” refers to an enzyme which cleaves a protein or peptide. The term peptidase may be used interchangeably with protease, proteinases, oligopeptidases, and proteolytic enzymes. Peptidases may be endopeptidases (endoproteases), or exopeptidases (exoproteases). Similarly the term peptidase inhibitor may be used interchangeably with protease inhibitor or inhibitor of any of the other alternate terms for peptidase.

As used herein, the term “exopeptidase” refers to a peptidase that requires a free N-terminal amino group, C-terminal carboxyl group or both, and hydrolyses a bond not more than three residues from the terminus. The exopeptidases are further divided into aminopeptidases, carboxypeptidases, dipeptidyl-peptidases, peptidyl-dipeptidases, tripeptidyl-peptidases and dipeptidases.

As used herein, the term “endopeptidase” refers to a peptidase that hydrolyses internal, alpha-peptide bonds in a polypeptide chain, tending to act away from the N-terminus or C-terminus. Examples of endopeptidases are chymotrypsin, pepsin, papain and cathepsins. A very few endopeptidases act a fixed distance from one terminus of the substrate, an example being mitochondrial intermediate peptidase. Some endopeptidases act only on substrates smaller than proteins, and these are termed oligopeptidases. An example of an oligopeptidase is thimet oligopeptidase. Endopeptidases initiate the digestion of food proteins, generating new N- and C-termini that are substrates for the exopeptidases that complete the process. Endopeptidases also process proteins by limited proteolysis. Examples are the removal of signal peptides from secreted proteins (e.g. signal peptidase I) and the maturation of precursor proteins (e.g. enteropeptidase, furin). In the nomenclature of the Nomenclature Committee of the International Union of Biochemistry and Molecular Biology (NC-IUBMB) endopeptidases are allocated to sub-subclasses EC 3.4.21, EC 3.4.22, EC 3.4.23, EC 3.4.24 and EC 3.4.25 for serine-, cysteine-, aspartic-, metallo- and threonine-type endopeptidases, respectively. Endopeptidases of particular interest are the cathepsins, and especially cathepsin B, L and S known to be active in antigen presenting cells.

As used herein, the term “immunogen” refers to a molecule which stimulates a response from the adaptive immune system, which may include responses drawn from the group comprising an antibody response, a cytotoxic T cell response, a T helper response, and a T cell memory. An immunogen may stimulate an upregulation of the immune response with a resultant inflammatory response, or may result in down regulation or immunosuppression. Thus the T-cell response may be a T regulatory response. An immunogen also may stimulate a B-cell response and lead to an increase in antibody titer.

As used herein, the term “native” (or wild type) when used in reference to a protein refers to proteins encoded by the genome of a cell, tissue, or organism, other than one manipulated to produce synthetic proteins.

As used herein the term “epitope” refers to a peptide sequence which elicits an immune response, from either T cells or B cells or antibody As used herein, the term “B-cell epitope” refers to a polypeptide sequence that is recognized and bound by a B-cell receptor. A B-cell epitope may be a linear peptide or may comprise several discontinuous sequences which together are folded to form a structural epitope. Such component sequences which together make up a B-cell epitope are referred to herein as B-cell epitope sequences. Hence, a B-cell epitope may comprise one or more B-cell epitope sequences. Hence, a B cell epitope may comprise one or more B-cell epitope sequences. A linear B-cell epitope may comprise as few as 2-4 amino acids or more amino acids.

As used herein, the term “predicted B-cell epitope” refers to a polypeptide sequence that is predicted to bind to a B-cell receptor by a computer program, for example, as described in PCT US2011/029192, PCT US2012/055038, and US2014/014523, each of which is incorporated herein by reference, and in addition by Bepipred (Larsen, et al., Immunome Research 2:2, 2006.) and others as referenced by Larsen et al (ibid) (Hopp T et al PNAS 78:3824-3828, 1981; Parker J et al, Biochem. 25:5425-5432, 1986). A predicted B-cell epitope may refer to the identification of B-cell epitope sequences forming part of a structural B-cell epitope or to a complete B-cell epitope.

As used herein, the term “T-cell epitope” refers to a polypeptide sequence which when bound to a major histocompatibility protein molecule provides a configuration recognized by a T-cell receptor. Typically, T-cell epitopes are presented bound to a MHC molecule on the surface of an antigen-presenting cell.

As used herein, the term “predicted T-cell epitope” refers to a polypeptide sequence that is predicted to bind to a major histocompatibility protein molecule by the neural network algorithms described herein, by other computerized methods, or as determined experimentally.

As used herein, the term “major histocompatibility complex (MHC)” refers to the MHC Class I and MHC Class II genes and the proteins encoded thereby. Molecules of the MHC bind small peptides and present them on the surface of cells for recognition by T-cell receptor-bearing T-cells. The MHC-Is both polygenic (there are several MHC class I and MHC class II genes) and polyallelic or polymorphic (there are multiple alleles of each gene). The terms MHC-I, MHC-II, MHC-1 and MHC-2 are variously used herein to indicate these classes of molecules. Included are both classical and nonclassical MHC molecules. An MHC molecule is made up of multiple chains (alpha and beta chains) which associate to form a molecule. The MHC molecule contains a cleft or groove which forms a binding site for peptides. Peptides bound in the cleft or groove may then be presented to T-cell receptors. The term “MHC binding region” refers to the groove region of the MHC molecule where peptide binding occurs.

As used herein, a “MHC II binding groove” refers to the structure of an MHC molecule that binds to a peptide. The peptide that binds to the MHC II binding groove may be from about 11 amino acids to about 23 amino acids in length, but typically comprises a 15-mer. The amino acid positions in the peptide that binds to the groove are numbered based on a central core of 9 amino acids numbered 1-9, and positions outside the 9 amino acid core numbered as negative (N terminal) or positive (C terminal). Hence, in a 15mer the amino acid binding positions are numbered from −3 to +3 or as follows: −3, −2, −1, 1, 2, 3, 4, 5, 6, 7, 8, 9, +1, +2, +3.

As used herein, the term "haplotype" refers to the HLA alleles found on one chromosome and the proteins encoded thereby. Haplotype may also refer to the allele present at any one locus within the MHC. Each class of MHC-Is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein. HLA alleles are listed at hla.alleles.org/nomenclature/naming.html, which is incorporated herein by reference.

The MHCs exhibit extreme polymorphism: within the human population there are, at each genetic locus, a great number of haplotypes comprising distinct alleles—the IMGT/HLA database release (February 2010) lists 948 class I and 633 class II molecules, many of which are represented at high frequency (>1%). MHC alleles may differ by as many as 30-aa substitutions. Different polymorphic MHC alleles, of both class I and class II, have different peptide specificities: each allele encodes proteins that bind peptides exhibiting particular sequence patterns.

The naming of new HLA genes and allele sequences and their quality control is the responsibility of the WHO Nomenclature Committee for Factors of the HLA System, which first met in 1968, and laid down the criteria for successive meetings. This committee meets regularly to discuss issues of nomenclature and has published 19 major reports documenting firstly the HLA antigens and more recently the genes and alleles. The standardization of HLA antigenic specifications has been controlled by the exchange of typing reagents and cells in the International Histocompatibility Workshops. The IMGT/HLA Database collects both new and confirmatory sequences, which are then expertly analyzed and curated before been named by the Nomenclature Committee. The resulting sequences are then included in the tools and files made available from both the IMGT/HLA Database and at hla.alleles.org.

Each HLA allele name has a unique number corresponding to up to four sets of digits separated by colons. See e.g., hla.alleles.org/nomenclature/naming.html which provides a description of standard HLA nomenclature and Marsh et al., Nomenclature for Factors of the HLA System, 2010 Tissue Antigens 2010 75:291-455. HLA-DRB1*13:01 and HLA-DRB1*13:01:01:02 are examples of standard HLA nomenclature. The length of the allele designation is dependent on the sequence of the allele and that of its nearest relative. All alleles receive at least a four digit name, which corresponds to the first two sets of digits, longer names are only assigned when necessary.

The digits before the first colon describe the type, which often corresponds to the serological antigen carried by an allotype. The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns or in the 5' or 3' untranslated regions that flank the exons and introns are distinguished by the use of the fourth set of digits. In addition to the unique allele number there are additional optional suffixes that may be added to an allele to indicate its expression status. Alleles that have been shown not to be expressed, 'Null' alleles have been given the suffix 'N'. Those alleles which have been shown to be alternatively expressed may have the suffix 'L', 'S', 'C', 'A' or 'Q'. The suffix 'L' is used to indicate an allele which has been shown to have 'Low' cell surface expression when compared to normal levels. The 'S' suffix is used to denote an allele specifying a protein which is expressed as a soluble 'Secreted' molecule but is not present on the cell surface. A 'C' suffix to indicate an allele product which is present in the 'Cytoplasm' but not on the cell surface. An 'A' suffix to indicate 'Aberrant' expression where there is some doubt as to whether a protein is expressed. A 'Q' suffix when the expression of an allele is 'Questionable' given that the mutation seen in the allele has previously been shown to affect normal expression levels.

In some instances, the HLA designations used herein may differ from the standard HLA nomenclature just described due to limitations in entering characters in the databases described herein. As an example, DRB1_0104, DRB1*0104, and DRB1-0104 are equivalent to the standard nomenclature of DRB1*01:04. In most instances, the asterisk is replaced with an underscore or dash and the semicolon between the two digit sets is omitted.

As used herein, the term "polypeptide sequence that binds to at least one major histocompatibility complex (MHC) binding region" refers to a polypeptide sequence that is recognized and bound by one or more particular MHC binding regions as predicted by the neural network algorithms described herein or as determined experimentally.

As used herein the terms "canonical" and "non-canonical" are used to refer to the orientation of an amino acid sequence. Canonical refers to an amino acid sequence presented or read in the N terminal to C terminal order; non-canonical is used to describe an amino acid sequence presented in the inverted or C terminal to N terminal order.

As used herein, the term "allergen" refers to an antigenic substance capable of producing immediate hypersensitivity and includes both synthetic as well as natural immunostimulant peptides and proteins. Allergen includes but is not limited to any protein or peptide catalogued in the Structural Database of Allergenic Proteins database http://fermi.utmb.edu/SDAP/index.html As used herein, the term "transmembrane protein" refers to proteins that span a biological membrane. There are two basic types of transmembrane proteins. Alpha-helical proteins are present in the inner membranes of bacterial cells or the plasma membrane of eukaryotes, and sometimes in the outer membranes. Beta-barrel proteins are found only in outer membranes of Gram-negative bacteria, cell wall of Gram-positive bacteria, and outer membranes of mitochondria and chloroplasts.

As used herein, the term "consensus protease cleavage site" refers to an amino acid sequence that is recognized by a protease such as trypsin or pepsin.

As used herein, the term "affinity" refers to a measure of the strength of binding between two members of a binding pair, for example, an antibody and an epitope and an epitope and a MHC-I or II haplotype. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT\ LN(K)$ where R=gas constant and temperature is in degrees Kelvin. Affinity may be determined experimentally, for example by surface plasmon resonance (SPR) using commercially available Biacore SPR units (GE Healthcare) or in silico by methods such as those described herein in detail. Affinity may also be expressed as the ic50 or inhibitory concentration 50, that concentration at which 50% of the peptide is displaced. Likewise ln(ic50) refers to the natural log of the ic50.

The term "$K_{off}$", as used herein, is intended to refer to the off rate constant, for example, for dissociation of an antibody from the antibody/antigen complex, or for dissociation of an epitope from an MHC haplotype.

The term "$K_d$", as used herein, is intended to refer to the dissociation constant (the reciprocal of the affinity constant "Ka"), for example, for a particular antibody-antigen interaction or interaction between an epitope and an MHC haplotype.

As used herein, the terms "strong binder" and "strong binding" and "High binder" and "high binding" or "high affinity" refer to a binding pair or describe a binding pair that have an affinity of greater than $2\times10^7 M^{-1}$ (equivalent to a dissociation constant of 50 nM Kd)

As used herein, the term "moderate binder" and "moderate binding" and "moderate affinity" refer to a binding pair or describe a binding pair that have an affinity of from $2\times10^7 M^{-1}$ to $2\times10^6 M^{-1}$.

As used herein, the terms "weak binder" and "weak binding" and "low affinity" refer to a binding pair or describe a binding pair that have an affinity of less than $2\times10^6 M^{-1}$ (equivalent to a dissociation constant of 500 nM Kd)

Binding affinity may also be expressed by the standard deviation from the mean binding found in the peptides making up a protein. Hence a binding affinity may be expressed as "$-1\sigma$" or $<-1\sigma$, where this refers to a binding affinity of 1 or more standard deviations below the mean. A common mathematical transformation used in statistical analysis is a process called standardization wherein the distribution is transformed from its standard units to standard deviation units where the distribution has a mean of zero and a variance (and standard deviation) of 1. Because each protein comprises unique distributions for the different MHC alleles standardization of the affinity data to zero mean and unit variance provides a numerical scale where different alleles and different proteins can be compared. Analysis of a wide range of experimental results suggest that a criterion of standard deviation units can be used to discriminate between potential immunological responses and non-responses. An affinity of 1 standard deviation below the mean was found to be a useful threshold in this regard and thus approximately 15% (16.2% to be exact) of the peptides found in any protein will fall into this category.

The terms "specific binding" or "specifically binding" when used in reference to the interaction of an antibody and a protein or peptide or an epitope and an MHC haplotype means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the term "antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein "immunoglobulin" means the distinct antibody molecule secreted by a clonal line of B cells; hence when the term "100 immunoglobulins" is used it conveys the distinct products of 100 different B-cell clones and their lineages.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "support vector machine" refers to a set of related supervised learning methods used for classification and regression. Given a set of training examples, each marked as belonging to one of two categories, an SVM training algorithm builds a model that predicts whether a new example falls into one category or the other.

As used herein, the term "classifier" when used in relation to statistical processes refers to processes such as neural nets and support vector machines.

As used herein "neural net", which is used interchangeably with "neural network" and sometimes abbreviated as NN, refers to various configurations of classifiers used in machine learning, including multilayered perceptrons with one or more hidden layer, support vector machines and dynamic Bayesian networks. These methods share in common the ability to be trained, the quality of their training evaluated, and their ability to make either categorical classifications of non numeric data or to generate equations for predictions of continuous numbers in a regression mode. Perceptron as used herein is a classifier which maps its input x to an output value which is a function of x, or a graphical representation thereof.

As used herein, the term "principal component analysis", or as abbreviated PCA, refers to a mathematical process which reduces the dimensionality of a set of data (Wold, S., Sjorstrom, M., and Eriksson, L., Chemometrics and Intelligent Laboratory Systems 2001. 58: 109-130.; Multivariate and Megavariate Data Analysis Basic Principles and Applications (Parts I&II) by L. Eriksson, E. Johansson, N. Kettaneh-Wold, and J. Trygg, 2006 $2^{nd}$ Edit. Umetrics Academy). Derivation of principal components is a linear transformation that locates directions of maximum variance in the original input data, and rotates the data along these axes. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Further, the principal components are scale-independent in that they can be developed from different types of measurements. The application of PCA generates numerical coefficients (descriptors). The coefficients are effectively proxy variables whose numerical values are seen to be related to underlying physical properties of the molecules. A description of the application of PCA to generate descriptors of amino acids and by combination thereof peptides is provided in PCT U52011/029192 incorporated herein by reference, Unlike neural nets PCA do not have any predictive capability. PCA is deductive not inductive.

As used herein, the term "vector" when used in relation to a computer algorithm or the present invention, refers to the mathematical properties of the amino acid sequence.

As used herein, the term "vector," when used in relation to recombinant DNA technology, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

As used herein, the terms "biocide" or "biocides" or "microbiocides" refer to at least a portion of a naturally occurring or synthetic molecule (e.g., peptides or enzymes) that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the terms "protein biocide" and "protein biocides" or "protein microbiocides" refer to at least a portion of a naturally occurring or synthetic peptide molecule or enzyme that directly kills or promotes the death and/or attenuation of (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

As used herein, the term "neutralization," "pathogen neutralization," refer to destruction or inactivation (e.g., loss of virulence) of a "pathogen" (e.g., bacterium, parasite, virus, fungus, mold, prion, and the like) thus preventing the pathogen's ability to initiate a disease state in a subject.

As used herein, the term "microorganism targeting molecule" refers to any molecule (e.g., protein) that interacts with a microorganism. In preferred embodiments, the microorganism targeting molecule specifically interacts with microorganisms at the exclusion of non-microorganism host cells. Preferred microorganism targeting molecules interact with broad classes of microorganism (e.g., all bacteria or all gram positive or negative bacteria). However, the present invention also contemplates microorganism targeting molecules that interact with a specific species or sub-species of microorganism. In some preferred embodiments, microorganism targeting molecules interact with "Pathogen Associated Molecular Patterns (PAMPS)". In some embodiments, microorganism targeting molecules are recognition molecules that are known to interact with or bind to PAMPS (e.g., including, but not limited to, as CD14, lipopolysaccharide binding protein (LBP), surfactant protein D (SP-D), and Mannan binding lectin (MBL)). In other embodiments, microorganism targeting molecules are antibodies (e.g., monoclonal antibodies directed towards PAMPS or monoclonal antibodies directed to specific organisms or serotype specific epitopes).

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "subject" is an animal such as vertebrate, preferably a mammal such as a human, a bird, or a fish. Mammals are understood to include, but are not limited to, murines, simians, humans, bovines, ovines, cervids, equines, porcines, canines, felines etc.).

An "effective amount" is an amount sufficient to effect beneficial or desired results. An effective amount can be administered in one or more administrations.

As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The terms "bacteria" and "bacterium" refer to prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause product degradation or spoilage.

"Strain" as used herein in reference to a microorganism describes an isolate of a microorganism (e.g., bacteria, virus, fungus, parasite) considered to be of the same species but with a unique genome and, if nucleotide changes are non-synonymous, a unique proteome differing from other strains of the same organism. Typically strains may be the result of isolation from a different host or at a different location and time but multiple strains of the same organism may be isolated from the same host.

As used herein "Complementarity Determining Regions" (CDRs) are those parts of the immunoglobulin variable chains which determine how these molecules bind to their specific antigen. Each immunoglobulin variable region typically comprises three CDRs and these are the most highly variable regions of the molecule.

As used herein, the term "motif" refers to a characteristic sequence of amino acids forming a distinctive pattern.

The term "Groove Exposed Motif" (GEM) as used herein refers to a subset of amino acids within a peptide that binds to an MHC molecule; the GEM comprises those amino acids which are turned inward towards the groove formed by the MHC molecule and which play a significant role in determining the binding affinity. In the case of human MHC-I the GEM amino acids are typically (1, 2, 3, 9). In the case of MHC-II molecules two formats of GEM are most common comprising amino acids (−3, 2, −1, 1, 4, 6, 9, +1, +2, +3) and (−3, 2, 1, 2, 4, 6, 9, +1, +2, +3) based on a 15-mer peptide with a central core of 9 amino acids numbered 1-9 and positions outside the core numbered as negative (N terminal) or positive (C terminal).

"Immunoglobulin germline" is used herein to refer to the variable region sequences encoded in the inherited germline genes and which have not yet undergone any somatic hypermutation. Each individual carries and expresses multiple copies of germline genes for the variable regions of heavy and light chains. These undergo somatic hypermutation during affinity maturation. Information on the germline sequences of immunoglobulins is collated and referenced by The International Immunogenetics Information System [3]. "Germline family" as used herein refers to the 7 main gene groups, catalogued at IMGT, which share similarity in their sequences and which are further subdivided into subfamilies.

"Affinity maturation" is the molecular evolution that occurs during somatic hypermutation during which unique variable region sequences generated that are the best at targeting and neutralizing and antigen become clonally expanded and dominate the responding cell populations.

"Germline motif" as used herein describes the amino acid subsets that are found in germline immunoglobulins. Germline motifs comprise both GEM and TCEM motifs found in the variable regions of immunoglobulins which have not yet undergone somatic hypermutation.

"Immunopathology" when used herein describes an abnormality of the immune system. An immunopathology may affect B-cells and their lineage causing qualitative or quantitative changes in the production of immunoglobulins. Immunopathologies may alternatively affect T-cells and result in abnormal T-cell responses. Immunopathologies may also affect the antigen presenting cells. Immunopathologies may be the result of neoplasias of the cells of the immune system. Immunopathology is also used to describe diseases mediated by the immune system such as autoimmune diseases. Illustrative examples of immunopathologies include, but are not limited to, B-cell lymphoma, T-cell lymphomas, Systemic Lupus Erythematosus (SLE), allergies, hypersensitivities, immunodeficiency syndromes, radiation exposure or chronic fatigue syndrome.

"Obverse" as used herein describes the outward directed face or the side facing outwards. Hence, in the context of a pMHC complex, the obverse side is that face presented to the T-cell receptor and comprises the space-shape made up of the TCEM and the contiguous and surrounding outward facing components of the MHC molecule that will be different for each different MHC allele.

"pMHC" Is used to describe a complex of a peptide bound to an MHC molecule. In many instances a peptide bound to an MHC-I will be a 9-mer or 10-mer however other sizes of 7-11 amino acids may be thus bound. Similarly MHC-II molecules may form pMHC complexes with peptides of 15 amino acids or with peptides of other sizes from 11-23 amino acids. The term pMHC is thus understood to include any short peptide bound to a corresponding MHC.

"Somatic hypermutation" (SHM), as used herein refers to the process by which variability in the immunoglobulin variable region is generated during the proliferation of individual B-cells responding to an immune stimulus. SHM occurs in the complementarity determining regions.

"T-cell exposed motif" (TCEM), as used herein, refers to the sub set of amino acids in a peptide bound in a MHC molecule which are directed outwards and exposed to a T-cell binding to the pMHC complex. A T-cell binds to a complex molecular space-shape made up of the outer surface MHC of the particular HLA allele and the exposed amino acids of the peptide bound within the MHC. Hence any T-cell recognizes a space shape or receptor which is specific to the combination of HLA and peptide. The amino acids which comprise the TCEM in an MHC-I binding peptide typically comprise positions 4, 5, 6, 7, 8 of a 9-mer. The amino acids which comprise the TCEM in an MHC-II binding peptide typically comprise 2, 3, 5, 7, 8 or −1, 3, 5, 7, 8 based on a 15-mer peptide with a central core of 9 amino acids numbered 1-9 and positions outside the core numbered as negative (N terminal) or positive (C terminal). As indicated under pMHC, the peptide bound to a MHC may be of other lengths and thus the numbering system here is considered a non-exclusive example of the instances of 9-mer and 15 mer peptides.

"Regulatory T-cell" or "Treg" as used herein, refers to a T-cell which has an immunosuppressive or down-regulatory function. Regulatory T-cells were formerly known as suppressor T-cells. Regulatory T-cells come in many forms but typically are characterized by expression CD4+, CD25, and Foxp3. Tregs are involved in shutting down immune responses after they have successfully eliminated invading organisms, and also in preventing immune responses to self-antigens or autoimmunity.

"Tregitope" as used herein describes an epitope to which a Treg or regulatory T-cell binds.

"uTOPE™ analysis" as used herein refers to the computer assisted processes for predicting binding of peptides to MHC and predicting cathepsin cleavage, described in PCT US2011/029192, PCT US2012/055038, and US2014/01452, each of which is incorporated herein by reference.

"Framework region" as used herein refers to the amino acid sequences within an immunoglobulin variable region which do not undergo somatic hypermutation.

"Isotype" as used herein refers to the related proteins of particular gene family. Immunoglobulin isotype refers to the distinct forms of heavy and light chains in the immunoglobulins. In heavy chains there are five heavy chain isotypes (alpha, delta, gamma, epsilon, and mu, leading to the formation of IgA, IgD, IgG, IgE and IgM respectively) and light chains have two isotypes (kappa and lambda). Isotype when applied to immunoglobulins herein is used interchangeably with immunoglobulin "class".

"Isoform" as used herein refers to different forms of a protein which differ in a small number of amino acids. The isoform may be a full length protein (i.e., by reference to a reference wild-type protein or isoform) or a modified form of a partial protein, i.e., be shorter in length than a reference wild-type protein or isoform.

"Class switch recombination" (CSR) as used herein refers to the change from one isotype of immunoglobulin to another in an activated B cell, wherein the constant region associated with a specific variable region is changed, typically from IgM to IgG or other isotypes.

"Immunostimulation" as used herein refers to the signaling that leads to activation of an immune response, whether said immune response is characterized by a recruitment of cells or the release of cytokines which lead to suppression of the immune response. Thus immunostimulation refers to both upregulation or down regulation.

"Up-regulation" as used herein refers to an immunostimulation which leads to cytokine release and cell recruitment tending to eliminate a non self or exogenous epitope. Such responses include recruitment of T cells, including effectors such as cytotoxic T cells, and inflammation. In an adverse reaction upregulation may be directed to a self-epitope.

"Down regulation" as used herein refers to an immunostimulation which leads to cytokine release that tends to dampen or eliminate a cell response. In some instances such elimination may include apoptosis of the responding T cells.

"Frequency class" or "frequency classification" as used herein is used to describe the counts of TCEM motifs found in a given dataset of peptides. A logarithmic (log base 2) frequency categorization scheme was developed to describe the distribution of motifs in a dataset. As the cellular interactions between T-cells and antigen presenting cells displaying the motifs in MHC molecules on their surfaces are the ultimate result of the molecular interactions, using a log base 2 system implies that each adjacent frequency class would double or halve the cellular interactions with that motif. Thus using such a frequency categorization scheme makes it possible to characterize subtle differences in motif usage as well as providing a comprehensible way of visualizing the cellular interaction dynamics with the different motifs. Hence a Frequency Class 2, or FC 2 means 1 in 4, a Frequency class 10 or FC 10 means 1 in $2^{10}$ or 1 in 1024.

"40K set" as used herein refers to the database of 40,000 IGHV assembled from Genbank as described in Example 1

"IGHV" as used herein is an abbreviation for immunoglobulin heavy chain variable regions "IGLV" as used herein is an abbreviation for immunoglobulin light chain variable regions "Adverse immune response" as used herein may refer to (a) the induction of immunosuppression when the appropriate response is an active immune response to eliminate a pathogen or tumor or (b) the induction of an upregulated active immune response to a self-antigen or (c) an excessive up-regulation unbalanced by any suppression, as may occur for instance in an allergic response.

As used herein "epitope mimic" or "TCEM mimic" is used to describe a peptide which has an identical or overlapping TCEM, but may have a different GEM. Such a mimic occurring in one protein may induce an immune response directed towards another protein which carries the same TCEM motif. This may give rise to autoimmunity or inappropriate responses to the second protein.

As used herein "MART" refers to melanoma associated antigen recognized by T cells As used herein "PMEL" refers to Melanocyte protein As used herein "MAGE" refers to the protein product of any member of the melanoma-associated antigen gene family "Anchor peptide", as used herein, refers to peptides or polypeptides which allow binding to a substrate to facilitate purification or which facilitate attachment to a solid medium such as a bead or plastic dish or are capable of insertion into a membrane of a cell or liposome or virus like particle. Among the examples of anchor peptides are the following, which are considered non limiting, his tags, immunoglobulins, Fc region of immunoglobulin, G coupled protein, receptor ligand, biotin, and FLAG tags "Cytotoxin" or "cytocide" as used herein refers to a peptide or polypeptide which is toxic to cells and which causes cell death. Among the non-limiting examples of such polypeptides are RNAses, phospholipase, membrane active peptides such as cercropin, and diphtheria toxin. Cytotoxin also includes radionuclides which are cytotoxic.

"Cytokine" as used herein refers to a protein which is active in cell signaling and may include, among other examples, chemokines, interferons, interleukins, lymphokines, granulocyte colony-stimulating factor tumor necrosis factor and programmed death proteins.

As used herein the term "Alpha emitter" refers to a radioisotope which emits alpha radiation. Examples of alpha emitters which may be suitable for clinical use include Astatine-211, Bismuth-212, Bismuth-213, Actinium-225 Radium-223, Terbium-149, Fermium-255

As used herein "Auger particles" refers to the low energy electrons emitted by radionuclides such as but not limited to, Gadolinium-67, Technicium-99, Indium-111, Iodine-123, Iodine-125, Tellurium-201. Auger electrons are advantageous as they have a short path of transit through tissue.

As used herein "oncoprotein" means a protein encoded by an oncogene which can cause the transformation of a cell into a tumor cell if introduced into it. Examples of oncoproteins include but are not limited to the early proteins of papillomaviruses, polyomaviruses, adenoviruses and herpesviruses, however oncoproteins are not necessarily of viral origin.

"Label peptide" as used herein refers to a peptide or polypeptide which provides, either directly or by a ligated residue, a colorimetric, fluorescent, radiation emitting, light emitting, metallic or radiopaque signal which can be used to identify the location of said peptide. Among the non-limiting examples of such label peptides are streptavidin, fluorescein, luciferase, gold, ferritin, tritium.

"MHC subunit chain" as used herein refers to the alpha and beta subunits of MHC molecules. A MHC II molecule is made up of an alpha chain which is constant among each of the DR, DP, and DQ variants and a beta chain which varies by allele. The MHC I molecule is made up of a constant beta macroglobulin and a variable MHC A, B or C chain.

DESCRIPTION OF THE INVENTION

The present invention provides methods and systems for identifying and classifying epitopes and use of that information to analyze proteins and peptides within proteins, especially potential epitopes, and to use the information to design synthetic peptides and proteins, analyze biopharmaceutical and other proteins, and diagnose autoimmune conditions and immunopathologies.

Any protein taken up by an antigen presenting cell (APC) can be processed to lead to stimulation of an immune response. Proteins may be derived from endogenous sources, such as cellular proteins and antibodies or from exogenous sources, including but not limited to pathogens, environmental and microbiome microorganisms, allergens and other environmental proteins. Antigen presenting cells include, but are not limited to, dendritic cells, B-cells and macrophages. Peptides may be presented on the surface of any cell bound to MHC molecules. Each cell carries MHC molecules encoded in various gene loci and heterozygous copies thereof. Each allele of each MHC locus has a unique binding groove which engages peptides released by enzyme action from proteins. The endopeptidase cleavage to release peptides and the binding reaction between short peptides and the MHC molecules has been well studied and modelled (see, e.g., PCT US2011/029192, PCT US2012/055038, US2014/014523, and PCT US2014/041525, each of which is incorporated herein by reference). The present invention addresses characterization of the interaction between a T-cell receptor and the complex of a peptide bound in a MHC molecular groove.

The peptides which binding MHC grooves are typically a 9-mer binding an MHC-I and a 15-mer binding in a MHC-II groove. In a preferred embodiment therefore these peptide sizes are used throughout the analyses presented herein. However these peptide lengths should not be considered limiting and the same processes can be implemented and used as the basis for analysis of peptides of 7-11 amino acids in the case of MHC-I molecules and peptides of 11-23 amino acids for MHC-II alleles.

Peptides which are bound in MHC grooves comprise two sets of amino acids: those that face inwards into the groove and determine the binding affinity to the MHC molecule (the groove exposed motifs or GEM) and those which do not interact with the groove, but rather are on the obverse side exposed outwardly to the T-cells (the T-cell exposed motifs or TCEM). In the case of MHC-I, molecules the central amino acids 4, 5, 6, 7, 8 of the typical nonamer peptide bound form the T-cell exposed motif or TCEM, while the binding affinity to the groove is determined by amino acids 1, 2, 3, 9, the groove exposed motif or GEM. It has been recognized that two sets of amino acid positions may form these configurations for MHC-II presentation (Rudolph et al How TCRs bind MHCs, peptides, and coreceptors. Ann Rev Immunol (2006) 24:419-466 [2]). In the context of a MHC-II binding groove defined as a 15 amino acid chain:

TCEM IIa exposes amino acids in pocket positions (2, 3, 5, 7, 8) with the corresponding GEM IIa amino acids as (−3, 2, −1, 1, 4, 6, 9, +1, +2, +3)

TCEM IIb exposes (−1, 3, 5, 7, 8) with the corresponding GEM IIb (−3, 2, 1, 2, 4, 6, 9, +1, +2, +3)

FIG. 1 illustrates the amino acid and MHC pocket position numbering scheme used herein.

It should be understood that any given peptide may comprise both TCEM which are formed by binding in MHC-I grooves and TCEM which are formed by binding in MHC-II molecule grooves; and indeed that a single peptide may comprise not only MHC-I and MHC-II TCEMs, but also can fulfill the criteria of both TCEM IIa and TCEM IIb as described above. Furthermore any peptide may be arranged in an MHC groove in a canonical or non-canonical position and hence a TCEM may be exposed to a T cell in either orientation.

Any given TCEM may be combined with many different GEM to make up the entire MHC binding peptide. Which amino acids are found in the GEM positions is a function of the protein of origin, whether self or non-self. It follows that a GEM may be designed or engineered to provide a desired binding affinity. The GEM amino acids will determine binding affinity on an MHC allele and locus specific basis. Thus binding to MHC-IA and MHC-IB, and to MHC-II DR, DQ and DP alleles of MHCII all can result in higher or lower binding affinity GEMS. Such binding is also competitive relative to other excised peptides from the same protein or otherwise found in the same cellular location.

Based on these structural considerations of which amino acids determine pMHC binding affinity and which amino acids are exposed to T-cells as the obverse face of a pMHC complex, it is possible to categorize any set of peptides, irrespective of whether their source is from antibody molecules, molecules from pathogens, or from biotherapeutic molecules or any other protein. Whether a pMHC will be an upregulating or downregulating epitope, is a product of both its binding affinity (and hence dwell time) in the context of the host MHC alleles and the frequency with which T-cells have been previously exposed to that motif.

By combining predictions of pMHC binding affinities and endosomal processing with databases of TCEM motif frequencies, it is possible to create databases to cross reference molecules from different origins in order to make predictions as to their immunogenic potential as components of vaccines, and their role as possible sources of auto-immune responses or allergic responses, or as regulatory T-cell responses. One embodiment of the present invention is therefore to provide methods to quantify the frequency of TCEM motifs and to categorize them as frequent or rare with respect to a particular reference database of reference proteins. By so doing it becomes possible to predict whether a given TCEM, when combined with a GEM which provides more or less binding affinity in a host of a specific immunogenetic composition will contribute to up or down regulation of the adaptive immune response. Further, in one preferred embodiment, it enables the design of proteins which embody immunogens with desired properties.

The primary function of the adaptive immune system is to differentiate self from not-self and to allow the body to mount an appropriate response to molecules, once identified as self or as not-self. This may require that there is no response to a self-antigen (tolerization) and at the other extreme a very vigorous and rapid cellular, antibody and cytokine response to an invading pathogen. Calibration of the response according to the recognition of the antigen is the product of several layers of recognition and the balance of qualitative, quantitative, and temporal stimuli.

Qualitative stimuli include the characteristics of the TCEM motifs as presented in the context of the binding MHC molecule. Quantitative stimuli are determined by the GEM which determines the MHC binding affinity d, and hence dwell time of the peptide in the MHC, the number of T cells responding, as a function of the frequency of the TCEM motif, and the binding affinity between the T cell receptor and the pMHC complex.

One source of variation and diversity in peptide sequences that are exposed to the immune system is the generation of unique immunoglobulin variable region sequences as the result of somatic hypermutation. Each of the many germline immunoglobulin sequences an individual host carries may give rise to many different mutated sequences. The light chain and heavy chain variable regions, denoted IGHV and IGLV, are the parts of the molecule that undergo this molecular evolution to enable them to specifically recognize antigens. The specific, mutated sequences are found in both the B-cell receptors (BCR) and secreted immunoglobulin (Ig) molecules. After molecular evolution of the variable region sequences of the BCR the Ig molecules undergo class-switch recombination (CSR) and are secreted as immunoglobulin molecules, one unique sequence per cell clonal line. Thus, as the result of the somatic hypermutation, the immunoglobulin variable regions are a vast source of peptide variation. This is in addition to the background repertoire of peptides found within the un-mutated germline sequences.

Not only do the mutated immunoglobulin sequences become presented on B-cell surfaces as B-cell receptors and secreted as antibodies, but the same sequences, and those of germline sequences, are also processed by the endosomal enzymes of B-cells so that fragments of the sequences become presented on the surface of B-cells bound in the grooves of the MHC molecules [4,5]. B-cells therefore display peptide fragments of immunoglobulin variable regions as both MHC-I and MHC-II complexes with bound peptides (pMHC). The pMHC are recognized by contacting T-cells and based on such recognition may give rise to secondary cellular responses. Hence, immunoglobulin variable regions form an important source of education of the T-cell repertoire in the genetically defined context of the individual's MHC molecules.

T-cells are exposed in the thymus to self-antigens and certain clones of T-cell precursors are deleted. Further education of T-cells occurs through on going exposure to self-antigens. An additional tier of T-cell stimulation is then provided on a continuous basis by exposure to the diversity of motifs generated through antibody hypermutation. This allows T-cells to be exposed to motifs which are common and those which are rare. Those which are common motifs, if they are also associated with a long dwell time in the MHC due to a high biding affinity, tend to down regulate T-cells.

In one embodiment, the present invention identifies a set of TCEM sequences which are common and which are likely to result in down-regulation. While occasional reports of such Tregs have been recorded [6], the present invention provides a comprehensive and systematic way to identify high frequency down regulatory motifs on an allele specific basis. It further provides sequence identification of such high frequency motifs.

A further source of TCEMs exposed to the immune response is the immunoglobulin constant region. Each isotype or class of immunoglobulin (IgM, IgA, IgD, IgE, IgG and the subclasses thereof) comprises a different sequence and hence a different set of TCEM motifs. Within each isotype the sequences and hence motifs are highly conserved. As we show, the repertoire of motifs found in the constant regions are different from those found in the variable region. It appears therefore that motifs in the constant region are excluded from the "vocabulary" of motifs used in the variable region in naturally derived immunoglobulins. Constant region motifs—as they are indeed constant—are the most frequent class of TCEM motifs derived from immunoglobulins. It follows therefore that when these motifs are also high binding affinity they may stimulate Tregulatory or suppressor responses. In one embodiment therefore the present invention identifies constant regions TCEM motifs which have high predicted binding affinity to various MHC alleles and are predicted to have a T-regulatory function when bound by these MHC alleles.

A further source of TCEMs which lead to modulation of the T cell repertoire is the proteins of the microbiome, whether this be the skin, mucosal, or gastrointestinal microbiome. In addition, the pathogens, environmental proteins and allergens to which an individual is exposed during their lifetime will further mold their T cell repertoire. In another set of embodiments therefore databases comprising the proteomes of microorganisms, or allergens are assembled and the TCEMs therein examined and categorized according to the frequency distribution of the TCEMs in constituent peptides and the predicted binding affinity of the intercalated GEM motifs. This enables not only the better design of vaccines but understanding of mechanisms of immune evasion. This may arise when microorganisms evolve to utilize immunoglobulin or human proteome like motifs. Differing patterns of motif usage may be detected in bacterial pathogens with chronic intracellular habitats and viruses characterized by latent infection as compared to those which have a rapid infectious course. By understanding the patterns of evasion based on TCEM usage more effective methods of intervention in infectious disease may be developed.

In further embodiments, this invention provides a method to evaluate biopharmaceutical proteins to determine the probability that they will cause an adverse immune response. In another embodiment the method can be applied to evaluate a vaccine candidate both for the presence of unique TCEMs likely to lead to a protective or therapeutic immune response and to determine the presence of down regulating TCEMs which will tend to negate a protective response.

As high speed and deep sequencing capabilities increase the number of antibody variable regions available for analysis will increase exponentially, hence the capability described herein will find increasing importance in analysis of immunoglobulin hypervariable regions as a database of TCEMs. In parallel, as sequencing of other proteomes and, in particular, as increased accessibility of individual human proteomes is available, the methods described herein provide a systematic approach to matching TCEMs identified in pathogens, antibodies and other environmental immune stimuli to the TCEMs found in the human proteome, and hence enabling recognition of potential mimics which can give rise to autoimmune responses. Further, as protein therapeutics are the fastest growing class of drugs, it becomes increasingly important to understand whether these are likely to provoke adverse immunogenicity or autoimmune responses.

Autoimmune diseases, in which the immune response is directed against self-epitopes constitute a very large and serious group of diseases. Autoimmune diseases include an array of dysregulations or imbalances of self-recognition. Adverse immune responses may arise through up-regulation (for instance when an infectious agent provides an epitope mimic) or conversely by loss of self-tolerance. By being able to identify epitope mimics which can give rise to autoimmune responses, the present invention also offers a means to design interventions to mitigate autoimmune responses. This may be approached by administration of motifs to upregulate or down regulate the response the mimic and either to induce immunity or to repair tolerance. Such intervention would require the approach provided by the present invention to identify the epitope motif and categorize its ability to upregulate or downregulate in the context of the specific host HLA.

Among the diseases recognized to be the result of autoimmunity, or to have an autoimmune component, are celiac disease, narcolepsy, rheumatoid arthritis and multiple sclerosis (Jones, E. Y. et al, 2006. Nat. Rev. Immunol. 6:271-282.). Other autoimmune diseases include but are not limited to Ankylosing Spondylitis, Atopic allergy, Atopic Dermatitis, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Bullous Pemphigoid, Castleman's disease, Celiac disease, Cogan syndrome, Cold agglutinin disease, Crohn's Disease, Dermatomyositis, Diabetes mellitus type 1, Eosinophilic fasciitis, Gastrointestinal pemphigoid, Goodpasture's syndrome, Graves' disease, Guillain-Barré syndrome, Anti-ganglioside Hashimoto's encephalitis, Hashimoto's thyroiditis, Systemic Lupus erythematosus, Miller-Fisher syndrome, Mixed Connective Tissue Disease, Myasthenia gravis, Pemphigus vulgaris, Polymyositis, Primary biliary cirrhosis, Psoriasis, Psoriatic Arthritis, Relapsing polychondritis, Rheumatoid arthritis, Sjögren's syndrome, Temporal arteritis, Ulcerative Colitis, Vasculitis, and Wegener's granulomatosis.

In a number of other instances microbial infections are known to lead to a subsequent autoimmune reaction, including, for example but not limited to, in Lyme Disease, Streptococcal infections, and chronic respiratory infections (Hildenbrand, P. et al, 2009. Am. J. Neuroradiol. 30:1079-1087; Lee, J. L. et al, Autoimmun. Rev. 10.1016.2009; Leidinger, P. et al Respir. Res. 10:20, 2009), Guillan Barre (Yuki N (2001) *Lancet Infect Dis* 1 (1): 29-37, Yuki N (2005) *Curr Opin Immunol* 17 (6): 577-582; Kieseier B C et al, (2004) *Muscle Nerve* 30 (2): 131-156), rheumatoid arthritis (Rashid T et al (2007) *Clin Exp Rheumatol* 25 (2): 259-267), rheumatic fever (Guilherme L, Kalil J (2009) *J Clin Immunol*). In one embodiment the computer based analysis system described herein allows characterization of TCEMs which are epitope mimics and can be applied to a variety of potential mimic substrates, including but not limited to vaccines, biotherapeutic drugs, food ingredients and the like, to enable prediction of whether an adverse reaction could arise through exposure of an individual to a molecular mimic and which individuals (i.e. comprising which HLA haplotypes) may be most at risk.

The development of vaccines can result in a large population of subjects being exposed to a novel array of epitope motifs. A number of situations have arisen in which adverse immune responses to vaccines have resulted through autoimmune reactions. As one non-limiting example, Influenza vaccination has been associated with Guillan Barre disease (Vellozzi Clin Infect Dis 2014) and with narcolepsy ((Ahmed et al 2015 [7]). The present invention therefore provides methods to evaluate vaccines and identify potential mimics and the individuals in which such autoimmune responses may occur. It further provides a means of pharmacovigilance for reacting to reports of adverse reactions as vaccines are applied to a wider population.

Certain pathologies of B-cells result in the production of abnormal antibodies and the disruption of normal patterns of SHM. Examples of such diseases include lymphomas, leukemias, lupus erythematosus; such examples should not be considered limiting. B-cell lymphomas may arise as the result of infection as in Burkett's lymphoma or be the product of other causes of mutagenesis. Among the B-cell lymphomas are diffuse large B-cell lymphoma, Follicular lymphoma Mucosa-Associated Lymphatic Tissue lymphoma, Small cell lymphocytic lymphoma, Mantle cell lymphoma, Burkett's lymphoma, Mediastinal large B-cell lymphoma, Waldenström macroglobulinemia, Nodal marginal zone B-cell lymphoma, Splenic marginal zone lymphoma), Intravascular large B-cell lymphoma, Primary effusion lymphoma, and Lymphomatoid granulomatosis. B-cell leukemias include B-cell chronic lymphocytic leukemia/ small lymphocytic lymphoma, Acute lymphoblastic leukemia, B-cell prolymphocytic leukemia, Precursor B lymphoblastic leukemia and Hairy cell leukemia. In each of these immunopathologies the characteristics of the epitope motif frequencies, including the TCEM, found in the immunoglobulins produced, is changed as immunoglobulin synthesis is disrupted or maturation is changed. A further embodiment of the present invention is to characterize the patterns of TCEM found in such abnormal antibodies. In one application of this capability the invention enables diagnosis of abnormalities of immunoglobulins and the underlying immunopathologies. In a further embodiment, the invention offers a means of motif characterization needed to design interventions for some B-cell pathologies, whether by introduction of up regulatory or down regulatory stimuli.

Personalized medicine approaches are of increasing interest to the health sector. FDA published a Guidance (2013 Paving the Way for Personalized Medicine FDA's Role in a New Era of Medical Product Development U.S. Department Of Health And Human Services U.S. Food And Drug Administration) in which it notes that paradigmatic developments in science and technology offer new promise for developing targeted therapeutics and tools for predicting who will respond to a medical therapy or who will suffer ill effects. The present invention offers just such a development in that it allows better understanding of the interaction between individual immunogenetics and protein immunogens and the development of biotherapeutics and vaccines specifically targeted to an individual patient or immunogenetic subgroup.

The design of clinical trials to evaluate new protein drug products and vaccines can be enhanced by a better understanding of the role of immunogenetics. More efficient use of enrollees can be made if the trial is designed with reference to the immunogenetics of the patients. An embodiment of the present invention is therefore to identify similarities in the response of patients to protein drugs and vaccines based on the patient HLA and to stratify the trial accordingly. This is because the individual HLA will affect both binding affinity of GEM and the context of presentation of TCEM. A particular embodiment of the invention is to anticipate potential effects of TCEM that are found in the drug product tested based on potential autoimmune mimics and the stratification of the MHC binding affinity of the corresponding GEMs.

The methods provided herein also allow analysis of the epitopes associated with cancer. Tumor associated proteins may be analyzed to identify regions of predicted high affinity MHC binding and antibody targets. Among the epitopes are those which have TCEMs that are also found at high frequency and in germline and mutated immunoglobulin sequences. This tends to give rise to immunosuppression. Furthermore, tolerance to tumor surface antigens tends to inhibit an aggressive immune response from attacking and destroying cancer cells. Tolerance may arise as the result of excessive stimulation by a particular TCEM over time resulting in down regulation. By defining the TCEMs found in tumor associated antigen proteins it becomes possible to design interventions to upregulate or downregulate the anti-tumor responses by introduction of peptides with matching TCEMs but different levels of MHC binding affinity reflected in their GEM sequences. The ability to identify TCEM and to use them in conjunction with modified GEMs to alter the dwell time in contact with a MHC, and hence whether they lead to up or down regulation, is one approach to modulation of a T-cell response.

In some embodiments the discovery of immunosuppressive epitopes can be a step in the process of designing immunomodulatory interventions. A protein comprises some epitopes which up-regulate the CD4+ and CD8+ immune responses and some epitope peptides which result in a down-regulation or T-regulatory response to the tumor associated antigen. The balance of upregulation and down regulation is essential to the outcome of the overall immune response. As previously described, the function of a TCEM as an upregulator or down regulator will depend not only on the frequency of prior exposure to the TCEM motif but also to the affinity of binding and hence the MHC dwell time of the peptide of interest. In one embodiment of the present invention tumor associated antigens are examined to determine the position of both upregulating and down regulating epitopes. The design of vaccinal peptides will be guided by those peptides which are upregulating, but which also are not compromised by downregulating peptides, either in the immediate proximity or in the same protein.

The present invention also offers a means of designing patient-specific cancer interventions. In some embodiments, analysis of the balance between upregulating and downregulating epitopes can assist in understanding the progression of cancer. Tumor associated antigen proteins comprise both up and down regulating epitopes based on the combination of exposed TCEM motifs and the affinity of GEM binding. In some embodiments the present invention enables analysis that demonstrates that different isoforms or splice variants of tumor associated antigens differ in the presence and location of T regulatory down regulating epitopes which may depend on the immunogenetic makeup of the host. In yet other embodiment examination of a tumor associated antigen using the methods described herein identifies a T regulatory epitope which may impede the development of a protective response to a vaccine. The tumor associated antigens which may be thus analyzed include, but are not limited to those which arise from mutation, tumor antigens that are shared between many tumors, differentiation antigens and antigens that are over expressed in tumors. Such tumor antigens are compiled in several databases including cancerimmunity.org. In some particular embodiments analysis is applied to tumor associated antigens including: abnormal spindle-like microcephaly associated splice variant 1, abnormal spindle-like microcephaly-associated protein isoform 2, ATPase family AAA domain-containing protein 2, Carbonic anhydrase 9, Carcinoembryonic antigen-related cell adhesion molecule 5, cyclin-dependent kinase 1 isoform 1, cytochrome b-c1 complex subunit 7 isoform 1, Endoplasmin, IQGAP3, kinesin-like protein KIF2C, Kinetochore protein Nuf2, Late secretory pathway protein AVL9 homolog, lipid phosphate phosphohydrolase 2 isoform 1, macrophage-stimulating protein receptor isoform 1 preproprotein, Matrix metalloproteinase 3, Melanocyte protein PM EL, MART Melanoma antigen recognized by T-cells 1, melanoma associated antigens (MAGE), Mucin-1, Mucin-6, Nuclear transcription factor Y subunit PROM1, protein prostate-specific antigen, Prostatic acid phosphatase, Receptor tyrosine-protein kinase erbB-2, receptor tyrosine-protein kinase erbB-3 isoform 1, serine threonine-protein kinase PLK4 isoform 1, Siah2 protein, soluble MET variant 6, Stromelysin-3 structural maintenance of chromosomes protein, tyrosinase, Tyrosine-protein kinase ABL1, ubiquitin carboxyl-terminal hydrolase L5. In one preferred embodiment the tumor associated antigen analyzed is expressed in melanoma and includes but is not limited, to MART, PMEL, MAGE antigens. In yet further embodiments, analysis is applied to characterize the neoantigens which arise spontaneously through mutation and which may give rise to cancer. Such progression is critically linked to the individual's immunogenetics and this may be the determining factor in whether progression to neoplasia results from any given mutation.

Having identified a peptide which carries a Treg motif opens the way to design interventions in which the down regulation of the immune response can be manipulated, to reduce or eliminate the down regulation. Hence limitations on an otherwise protective or upregulated immune response to a cancer associated protein or tumor associated antigen can be removed.

Another approach, enabled by the methods presented herein, is to use TCEM to target additional molecules to T-cells. Among these additional molecules, but not limited to them, are agents which are toxic to T-cells. Hence a cytotoxin or cytocide could be directed specifically to a T-cell by fusing it to, or expressing as a fusion with, a MHC molecule which binds to a peptide which has been selected based on its TCEM and with a GEM selected to give a high binding affinity to the MHC. Thus when a T-cell specifically binds to said TCEM it will be exposed to the cytotoxin or cytocide. In some embodiments, where a peptide motif that induces a T regulatory response is identified, that motif can be used to bind to an MHC and serve as a trap or binder for the specific corresponding T-cell. When said peptide motif is bound to an MHC molecule further linked to a cytotoxin, the TCEM motif can serve as a "poison pill" to very selectively trap and kill T-cells that bind to the particular peptide MHC complex. In some embodiments this can be used as a means of enhancing the response to a therapeutic vaccine by eliminating downregulating T cell responses. The present invention thus offers a means of identifying the peptide motifs which can be used to selectively eliminate certain adverse T-cell populations. Such adverse T-cells may play a role in the immune response to tumors, to infectious agents or in autoimmunity.

In an alternate example the MHC molecule is expressed in association with or fused to a cytokine so that when bound to a selected TCEM the cytokine cell signaling activates the T cell response, inflammatory response or alternatively downregulates it. In this case the GEM counterpart to the selected TCEM can be adjusted by changing amino acids to ensure a tight binding to the MHC molecule. A broad array of cytokines may be utilized and are well known to those skilled in the art but include among many other examples, interferons, interleukins, granulocyte stimulating factors and programmed death proteins.

A further application of a TCEM bound by a selected GEM to a tagged MHC molecule is a configuration which can assist in capturing the T cells of interest in vitro. In this application a MHC molecule is fused to, or expressed with, a second peptide of choice such as a His tag, Fc component of immunoglobulin, Flag tag or other tag which enables binding to a substrate such as a tissue culture dish, bead, or purification matrix. Similarly a suitable tag can be added to enable insertion into a cell membrane or a virus like particle or liposome to "decorate" such carriers with the pMHC with a desired TCEM, necessary to attract and bind certain T cells of interest in vitro or in vivo.

Underlying the ability to categorize TCEM as common or rare is the development of reference databases of TCEM and the peptides of which they form a part. The present invention in one embodiment provides methods to generate such reference databases and to enable the extraction and ranking of TCEM and GEM motifs. This method of extraction may be applied to sequences assembled from public or private repositories of immunoglobulin sequences, including but not limited to Genbank and IMGT, but also to human proteome sequence databases. In some embodiments the relevant databases are of T cell receptor proteins. In yet further embodiments the source database repository is of microbes or allergens, such as PATRIC (the Pathosystems Resource Integration Center), VIPR (Virus Pathogen Database and Analysis Resource), allergen (Structural Database of Allergenic Proteins (Maintained at the University of Texas Medical Branch)) microbiome (NIH Human Microbiome project) and biopharmaceuticals (IMGT.org). The extraction of the discontinuous motifs are an essential step to allowing identification of matching motifs in proteins of different sources and in the reference databases. The present invention teaches the importance of such motif extraction and provides methods for performing extraction. This capability is expected to have great utility as the accessibility of high throughput deep sequencing increases.

The administration of peptide mixtures which are shown to have an immunosuppressive effect is known to the art [8]. One specific example of this is the administration of an empirically derived mixture polymers of four amino acids to make Glatirimer acetate. The present invention offers a means to proactively design an immunosuppressive peptide mixture rather than depending on empirical experimentation.

In some particular embodiments the present invention allows the identification of TCEM motifs that are particularly likely to be immunosuppressive. A TCEM motif that occurs in IGHV more frequently than 1 in 4000, corresponding to occurrence in up to and including frequency class 12, and especially those occurring more often than 1 in 1000 corresponding to frequency class 10, whether of germline or somatically mutated origin would be likely to be recognized as self. This is also the case for TCEM motifs occurring in immunoglobulin constant regions of any isotype. If TCEMS of either source (constant or variable chain) also comprise a high affinity GEM, then they would be likely to generate a T regulatory response. In some particular embodiments therefore, the present invention enables the design of synthetic peptides and synthetic polypeptide compositions which would bind to MHC II and invoke an immunosuppressive response. Such peptides may include a single TCEM motif. In yet other embodiments a synthetic polypeptide may be generated which includes multiple TCEM motifs each derived from FC 1-12 of immunoglobulin variable region origin or constant region and each capable of contributing a suppressive effect. In some embodiments it may be desired to modulate the immunosuppressive effect by inclusion only of TCEM motifs from FC 6-12, to reduce the overall weight of immunosuppressive stimuli. In yet other embodiments an immunosuppressive motif or motifs may be selected with a particular specific antigen target of immunosuppression in mind; in others the intent may be to generate a non-specific immunosuppression.

In other embodiments identifying patterns of TCEM in microorganisms can aid understanding of strategies of immune evasion adopted by various organisms. In these circumstances understanding whether a TCEM is used commonly or rarely within the proteome of a specific organism may be important to assess immune response.

In some embodiments particular configurations of the immunosuppressive TCEMs may be selected. As examples, which are non-limiting, a polypeptide comprising the TCEM may be comprised of a limited number of amino acids. In some preferred embodiments this may be only 3 or 4 or 5 amino acids, or some other subset, while in other embodiments it may be the full repertoire of 20 amino acids. In yet other embodiments the TCEM with immunosuppressive properties may be bound to an MHC molecule which is linked to a cytokine in order to generate an immunosuppressive cytokine response in the proximity of T cells that bind to the protein of interest in a specific manner.

In some embodiments such immunosuppressive peptides and polypeptides may be administered to subjects as an intervention for the management of autoimmune diseases. Such autoimmune diseases are many, but include multiple sclerosis, lupus erythematosus, rheumatoid arthritis and others as are listed elsewhere in this specification.

It will be further understood that in the development of a vaccine to protect against an infectious microorganism (virus, bacteria, mycoplasma, fungus, parasite, etc.) the key challenges are to identify immunogens which will confer protective immunity, whether by generation of neutralizing antibody or by a cytotoxic cellular response. In this process it is important to understand which potential epitopes for vaccine inclusion will provide an upregulation of T-helper cells and T-effecter cells and stimulate antibody production. It is equally important to understand which epitopes may lead to immunosuppression or to the generation of an antibody response which does not generate any immune memory enabling recall. In some situations this evaluation must be constantly updated in light of the obtaining of new field isolates of an organism so as to determine if a proposed or approved vaccine is still relevant to current field isolates.

In the face of the recent epidemic of Ebolavirus (EBOV) disease this situation arises, where a number of reference strains of the virus, some dating from as long as 40 years ago, must be compared to current day isolates. In one particular embodiment therefore the present invention enables the conduct of immunovigilance to compare the presence of immunostimulatory epitopes and immunosuppressive epitopes in multiple strains of a virus. The examination of current strains also enables the design of a vaccine in which specific upregulatory epitope motifs are identified and then further selected based on the absence of probable immunosuppressive motifs. Such probable T-suppressive motifs are identified by reference to a reference database of T-cell exposed motifs. While EBOV is cited as a topical example, this example should not be considered limiting and the same strategy may be applied to diseases of other infectious microbial etiology. In a further non-limiting example the same strategy is applied to influenza. The characteristics which enable design of a good vaccine also can be applied to develop a good immunogen for the generation of antibodies in an animal model, thereby facilitating the preparation of hybridomas which serve as the basis for developing antibody based immunotherapies, providing a yet further embodiment of the invention.

Although these examples pertain to two viral diseases the same approach is equally applicable to development of vaccines and evaluation of epitope changes in bacterial, fungal and parasite microorganisms.

EXAMPLES

Example 1: Assembly of Motifs in Immunoglobulin Variable Regions as a Reference Database As of December 2013, Genbank contained approximately 45,000 sequences identified as immunoglobulin heavy variable regions (IGHV) and for which the repository metadata records did not contain indications that they were derived from individuals with immunopathology. Some sequences were submitted in conjunction with specific publications; others were direct submissions. The majority do not indicate a source molecule isotype. Genbank does not provide a means to identify and link sequence submissions in the database for heavy and light chain immunoglobulins from the same molecule. In some cases these can be deduced from accession numbers.

Approximately 45,000 heavy chain variable regions were retrieved from NCBI Protein resource with a search argument "(immunoglobulin heavy chain variable region) AND (*Homo sapiens*)". The numbers of IGHV greatly outnumber the number of light chain sequences. In addition, because of the way proteins are deposited and annotated the heavy chain and light chain variable region pairs are not explicitly connected. Therefore only IGHV sequences were used in this analysis. Restrictive combinations of search arguments were used to create non-redundant subsets of this larger set that were either immunoglobulin class-defined or for which the metadata attached to the accession indicated that they were associated with an immunopathology. Additionally, manual curation was used to remove sequences that were obviously not immunoglobulins. The final dataset thus included approximately 40,000 (n=39,957) non-class-defined immunoglobulins. As the resulting dataset comprises many different accession groups from studies carried out over a considerable period of time it can be considered a representative sample of the gamut of "natural" human immunoglobulins.

Accessions with signal peptides were identified and removed from the input sequences using the combined signal peptide and transmembrane predictor Phobius (phobius.sbc.su.se). IGHV were included in the final set if they contained at least 80 amino acids, a value approximating the shortest germline equivalent sequence. All sequences longer than 130 amino acids were truncated at that point.

Class-defined IGHV sets of IgG (n=1630), IgE (n=667), and IgM (n=537) were derived similarly by adding additional key words to the search arguments. There are inevitable biases in the class-defined datasets. For example the sources of nearly all of the IgE sequences were from cohorts of asthmatics [9-11] and either did not include or identify the sequences of non-asthmatics in the cohorts. Likewise the IgG sequences were derived from an HIV study [12]. Germline IGHV (n=161) were obtained from the IMGT repository (www.imgt.org), and immunoglobulin heavy chain constant regions (IGHC) class reference sequences from Genbank. Additional database collections were assembled including 163 commercial biotherapeutic sequences (IMGT.org repository). Ig sequences where the secondary annotations specified derivation from an immunopathology were assembled by a Genbank query. These numbered approximately 4000.

The human proteome, exclusive of immunoglobulins, was downloaded from The Universal Protein Resource (UniProt) comprising approximately 81,000 proteins which includes multiple isoforms of some proteins.

These datasets, together with additional datasets described in subsequent Examples, were used as reference series for comparison of the binding patterns, determination of motif frequencies, and comparison of proteins of interest.

Example 2: Extraction and Scoring of Motifs

For each of the analyses described below each sequence in the derived databases was broken into 15-mers and 9-mers, each offset by a single amino acid. Thus, the combined set of 40,000 IGHV sequences resulted in approximately $4.2\times10^6$ peptides.

The same manipulations were subsequently carried out with the IGHV germline sequences, immunoglobulin constant regions, immunoglobulin light chain variable regions, and the human proteome and T cell receptor sequences.

For each derived 9-mer and 15-mer peptide, the predicted binding affinity to 37 MHC I and 28 MHC II alleles was determined. This was done using methods previously described [13]. Briefly, the principal components of physical properties of each amino acid were derived from a large set of published data. The first three principal components account for approximately 90% of the variability. For a peptide a matrix is constructed consisting of the descriptors for each of the constituent amino acids. Binding affinity datasets for the MHC I and MHC II alleles were obtained from IEDB (The Immune Epitope Database) and used as training sets for neural network development (NN). Amino acid sequences of the peptides were converted to principal component matrices and a bootstrap aggregation "bagging" process was used with the training sets to produce ensembles of NN equations for each of the alleles [14,15]. The ensemble approach enables the computation of a predicted mean and variance of affinity for each component peptide. Predictions for each MHC for each protein will exhibit a unique distribution binding affinities. Thus for computations consisting of either binding affinities for a number of alleles or a number of different proteins the predicted mean affinities for each allele are standardized to zero mean and unit variance. This standardization is done within protein using a Johnson Sb algorithm (JMP platform) and the predictions for the protein reported in standard deviation units.

The probability of cleavage of each protein by human cathepsin B, L, or S was determined using methods previously described. Briefly, matrices of the amino acid principal components were derived as outlined above for a cleavage site octomer (CSO). By convention the scissile bond is between amino acids 4 and 5 of the CSO and is described as P1P1'. Large proteomic data sets of cleavage by the three cathepsins were used to produce the input cleavage training sets for development of a NN binary classifiers [16-18]. Bagging was used to create the ensemble predictors and the median of the probabilities of the predictive equation ensembles is used as the probability of scissile bond cleavage of a CSO. The accuracy of the predictors varies for the different cathepsins and for different P1P1' dipeptides. The overall median AROC for the classifiers is 0.87. Using this process a probability of cleavage by the each of cathepsins was computed for all possible octomers indexed by single amino acids from each immunoglobulin.

It should be noted that there is a substantial cellular tropism to cathepsin expression and not all APC have the same profile of cathepsins; B cells do not express cathepsin L. We have examined and have found a good overall concordance across a variety of published endosomal cleavage datasets such as CLIP processing [19] and display of self-peptides [20].

We extracted datasets of T-cell exposed motifs (TCEM) and groove exposed motifs (GEM) motifs from all 40,000 curated IGHV proteins. This was done by creating sets of 15-mer motifs, and then the corresponding sets of TCEM for MHC-I TCEM and MHC-II TCEMa and TCEMb, in which the different relevant TCEM positions are given their amino acid, while non-TCEM positions were replaced by a standard non-amino acid code ("¯") or an X. TCEM positions are shown in FIG. 1. In this way it is possible using standard relational algebra of sets to extract replicated TCEMs as well as determining their frequencies of occurrence and their affiliated GEM binding affinity characteristics. Hence 15-mers with their associated TCEM and GEM were generated from all downloaded sequences.

We initially applied uTOPE™ MHC Binding affinity prediction analysis (see, e.g., PCT US2011/029192, PCT U52012/055038, U52014/01452, and U52014/041525, each of which is incorporated herein by reference) to a subset of the IGHV sequences. Because of computational resource limitations we initially did a full MHC binding prediction predictions on approximately a third of the 40K set (14 K sequences). Some figures provided herein are based on this initial subset. Having now completed the processing of the complete dataset no significant differences are seen in the figures, or in the conclusions drawn from the subset vs the whole dataset.

Motif Extraction

Each of the mature somatic hypermutated (SHM) IGHV sequences comprise approximately 120 amino acids (without signal peptides) and thus produce approximately 110 motifs. Thus, the 40,000 IGHV proteins produced about $4.4\times10^6$ peptides each having 3 different potential TCEM configurations. As any one discontinuous pentamer motif can have $20^5$ different configurations, or 3.2 million, 9.6 million total potential motifs exist in the following three possible configurations (as seen in FIG. 1):

1. MCH IIA (2, 3, 5, 7, 8) as 15-mer
2. MHC IIB (−1, 3, 5, 7, 8) as 15-mer
3. MHC I (4, 5, 6, 7, 8) as 9-mer We observed that there is a high level of motif re-use within the IGHV. Each of the 3 sets consisted of only approximately 275,000 unique motif sequences and thus there was significant motif re-use in different molecules. The motif usage frequencies were found to follow a power law (Pareto) distribution characteristic of network ensembles, as shown in Table 1.

TABLE 1

| FC TCR II (−1, 3, 5, 7, 8) | N Rows | Mean (N TCR II (−1, 3, 5, 7, 8), Germline) | Mean (N TCR II (−1, 3, 5, 7, 8), Mutated) |
|---|---|---|---|
| 1 | 8 | 25,710 | |
| 2 | 56 | 15,205 | 13,919 |
| 3 | 43 | 6,453 | 6,022 |
| 4 | 140 | 3,683 | 3,417 |
| 5 | 215 | 1,715 | 1,639 |
| 6 | 500 | 908 | 878 |
| 7 | 571 | 451 | 430 |
| 8 | 1,136 | 225 | 215 |
| 9 | 1,853 | 115 | 110 |
| 10 | 3,146 | 61 | 54 |
| 11 | 6,372 | 29 | 27 |
| 12 | 12,592 | 14 | 13 |
| 13 | 24,279 | 7 | 6 |
| 14 | 34,571 | 4 | 3 |
| 15 | 55,298 | 2 | 2 |
| 16 | 135,960 | 1 | 1 |

Motifs of germline origin were processed in the same manner as the non-germline somatically hypermutated set above. The pattern of usage of germline-origin motif sequences were found to follow a similar distribution pattern. Pareto distributions are found in a wide variety of physical and biological systems and tend to exhibit linear behavior over many orders of magnitude. As is common when dealing with systems displaying this distribution pattern a logarithmic (log base 2) frequency categorization scheme was developed. As the cellular interactions between T-cells and antigen presenting cells displaying the motifs in MHC molecules on their surfaces are the ultimate result of the molecular interactions, using a log base 2 system implies that each adjacent frequency class would double or halve the cellular interactions with that motif. Thus using such a frequency categorization scheme makes it possible to characterize subtle differences in motif usage as well as providing a comprehensible way of visualizing the cellular interaction dynamics with the different motifs. Overall, the variable regions were found to comprise approximately equal numbers of germline-origin and somatic hypermutated sequences.

When both the SHM and Germline motif sets were extracted, each of the TCEMs were assigned unique identifier keys which indicated their genetic origin and frequency classification. The identifier keys are essential for carrying out the set algebra manipulations to identify and characterize the TCEMs in different protein molecules.

Thus, relational set algebra manipulation of the combined SHM and germline TCEMs using the keys assigned in combination with a protein sequence of any origin can be used to characterize all of the motifs in a particular protein into three groups as being of SHM-origin, of germline-origin, or of neither. In addition, the frequency classification scheme provides insights into how T-cells will react to sequences in the proteins of interest.

The 40K database of immunoglobulin heavy chain variable region is taken to represent the "normal" situation, but in this database the depositors of the sequences did not identify (or may not have known) the isotype origin of the antibody molecule. However in some cases the depositors included additional metadata with the Genbank sequence accession. Thus, a further set of databases were created using metadata in the accession records of the Genbank sequences. In particular, two broad categories of sequences were identified: one set comprised antibody molecules that were isotype identified (IgG, IgE, IgM) and a second set comprised antibody molecules associated with several different immunopathologies. Immunopathologies such as rheumatoid arthritis, lupus erythematosus, leukemia, lymphoma, multiple sclerosis and the like are generally characterized by abnormal T-cell and B-cell interactions. The metadata was further curated to create unique, non-redundant sets of molecules. Subsets were created for IgG, IgE, IgM, lupus erythematosus (SLE), rheumatoid arthritis, chronic lymphocytic leukemia, lymphoma, and multiple sclerosis. Further curation was necessary because the original Genbank metadata sometimes associated more than one immunopathology with a particular antibody molecule. In total, these further curated subsets comprised approximately 8,000 molecules with individual subsets ranging from 200 molecules to 3000 IGHV sequences. These sequences were categorized for motifs as described above.

The human proteome database comprised approximately 81,000 proteins. This includes multiple isoforms of many proteins, hence the 81,000 exceeds the total proteome of any one human being by approximately 4 fold. The proteome consists of about twice as many proteins as the IGHV database, but their average size is considerably larger than that of the IGHV. When decomposed into their composite 15-mer peptides each indexed by one amino acid this resulted a total of 33 million peptides. When processed similarly to described above this produced about 2.42 million unique motifs, comprising about 7.5 million unique motif sequences in aggregate for the three motif configurations. As expected, IGHV-origin motifs were found in the proteome. The 275,000 motifs of IGHV-origin were found to match approximately 10% of the human proteome motifs. Thus, a database of IGHV sequences ten times the size of the current should provide complete coverage for all motifs in the human proteome. The total B-cell clones in a human exceed $10^7$ and thus the full B-cell population provides full coverage of the human proteome. In addition, it was found that about 15% of the IGHV-origin motifs had no matches in the human proteome thus giving credence to the concept that the IGHV provides a broad training of the immune system even for proteins foreign to the body.

Database Assembly

The datasets resulting from the above processes were designed to be analyzed and manipulated within JMP® (SAS Inc., Raleigh N.C.) using tools that combine relational set algebra with statistical analysis. In particular, the sets were created so that a set JOIN operation with any protein or group of proteins (for example a virus, a bacteria, a biotherapeutic) would enable the identification of matching motifs between the sets.

For Example:

JOIN-ing the motif sequences from influenza H1N1 with the 40K IGHV motif sequence dataset identified a set of motif sequences present in both the virus and the antibody molecules and which had a characteristic binding pattern with a clinically relevant MHC HLA.

A further JOIN with the human proteome identified a specific subset of proteins that also contained the same motif and further identifies motifs from other human proteins of non-immunoglobulin origin that likewise share motifs with the virus.

Although JMP® is used in this Example, this is not considered limiting and alternative computer programs may be used to derive and process the datasets.

Categorization Based on GEM Motifs

From the same database of downloaded sequences as in Example 1, we then identified the GEM motifs based on the following peptide positions and as shown in FIG. 1:

| | |
|---|---|
| GEM | MHC-IIA as (−3, 2, −1, 1, 4, 6, 9, +1, +2, +3) as 15-mer |
| GEM | MHC-IIB ((−3, 2, 1, 2, 4, 6, 9, +1, +2, +3) as 15-mer |
| GEM | MHC-I (1, 2, 3, 9) as 9-mer |

These motifs were categorized based on the frequency of their association with any given TCEM. MHC groove binding affinities were calculated as described in PCT US2011/029192, incorporated herein by reference.

The GEM motifs were then categorized into 3 groups based on the average binding affinities found in association with given TCEMS. This allows us to identify combinations of TCEM frequency and GEM affinity found in the IGHV databases.

Figure 3:
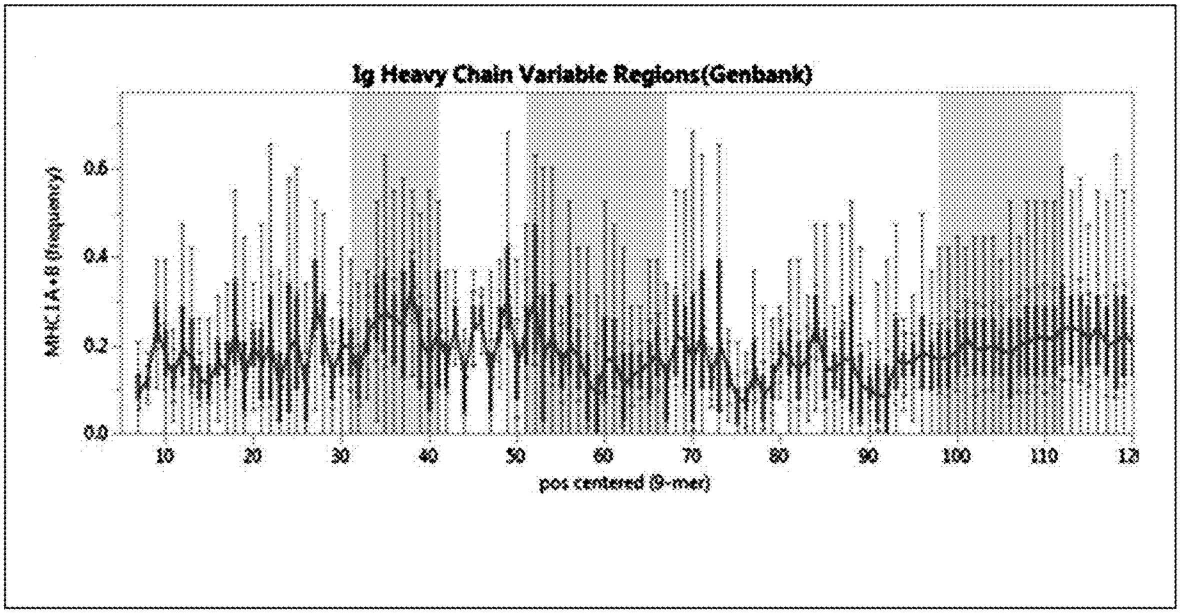
FIG. 3: Predicted binding affinity of MHC I A and B alleles (9-mers). In contrast to MHC-II the distribution of MHC-I binding is fairly uniform throughout the IGHV region. As for FIG. 1, peptides are centered at the amino acid position shown and the Y axis shows the fraction of alleles which bind with an affinity of more than one standard deviation below the mean of all alleles at that position.

When any other protein is examined, for example a pathogen protein, TCEMs may be identified which are also found in high or low frequency in IGHV, however in the new protein of interest these will be associated with a variety of different GEMs which provide for lower or higher binding affinity on an allele specific basis. The joint classification of TCEM frequency/GEM affinity allows a comparative index of the likelihood of interface with a T-cell that recognizes the same motif in the context of the same MHC allele Example 3: Characteristics of Motifs Observed in IGHV Each of the seven IGHV germline families designated IGHV1-IGHV7 exhibit distinct patterns. Sequences from all seven families were processed and graphics generated. To simplify the description of the multi-dimensional patterns, we will refer primarily to sequences of IGHV3 germline origin subsets which is the largest family, derived from the larger datasets [3]. The pattern of MHC-II binding in approximately ten thousand IGHV3 molecules (isotype undefined) is shown in FIG. 2. The shaded areas in FIG. 2 show the approximate the locations of the CDRs. There are several regions where peptides generated by SHM result in GEM with predicted high affinities for a range of MHC-II alleles, for example ranging widely from 0-16 different DRB alleles. In other regions the peptides have uniformly low predicted binding affinities. The predicted binding affinities of DP and DR alleles have similar patterns, but differ from the DQ alleles. In particular, the DQ alleles have a preference for peptides in Framework region 1. Interestingly, the patterns of predicted pMHC binding affinity before (in the germlines), and after SHM are similar. In the regions with predicted high affinity pMHC binding, it would be expected that the roles of the different pMHC types would be different: germline-origin motifs would maintain their TCEM and provide a suppressive or down regulatory function, whereas SHM-motifs would stimulate CD4+ helper activity. FIG. 3 shows the corresponding MHC-I binding affinity pattern.

Figure 4:
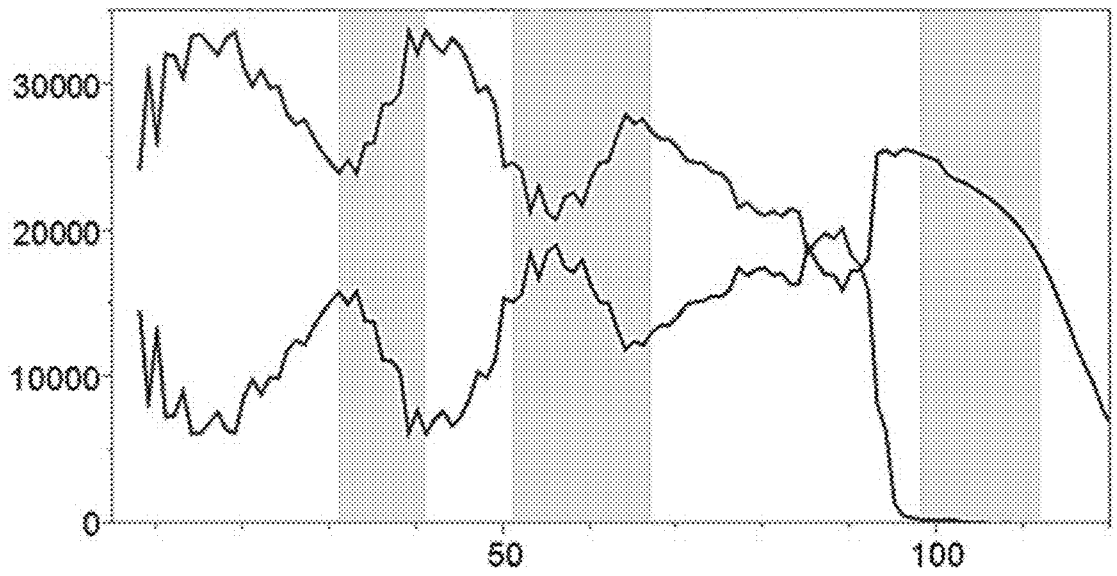
FIG. 4: Frequency of unique motifs as a function of amino acid centered location for the entire 40K dataset. The red line plots the number of unique germline-origin motifs and the blue line the unique motifs generated by SHM.
Figure 5:
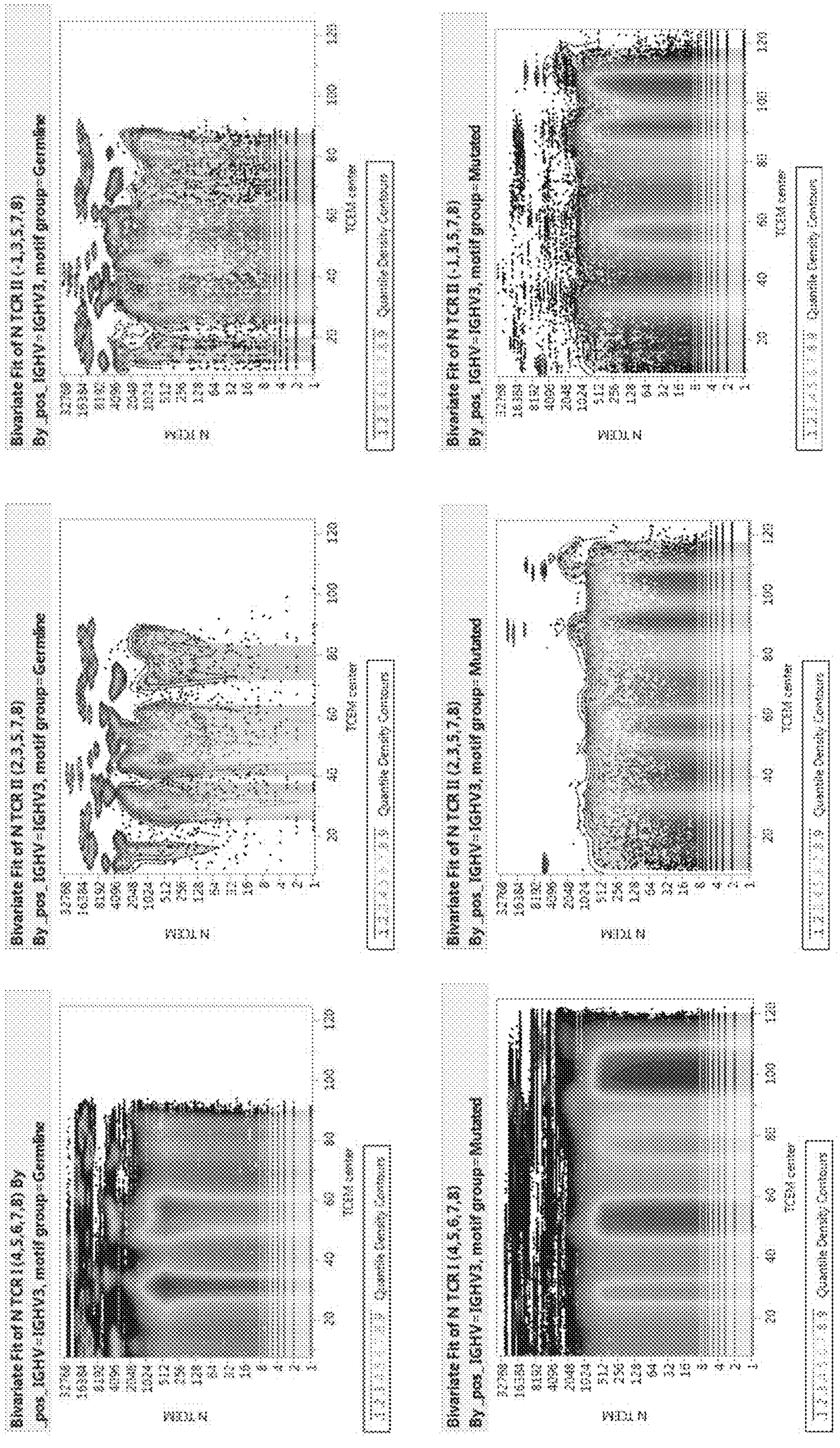

The patterns of repeated motifs are shown in FIGS. 4 and 5. A total of 61 germline motifs are found un-mutated in approximately 25% of the molecules (i.e., 10,000 of 40,000 IGHV). While the germline-origin TCEM motifs are conserved in mature antibodies, such antibodies typically have a wide range of pMHC affinities due to somatic hypermutation affecting the GEM amino acids. There are also several regions which show a high degree of repetition in the SHM TCEM. The two highest repeated zones are at centered at approximately at aa 90 and at about aa 105, which correspond to the N- and C-terminal sides of the CDR3. Taken together with the data in FIG. 2, it is clear that regions of high motif repeats are also regions where predicted high affinity pMHC binding is found. Thus, there are repeated, high affinity pMHC with the same TCEM, but with different GEM.

Frequency Scoring System

Examination of the patterns in FIG. 5 indicate a gradation of TCEM repeats. We therefore devised a numerical system to classify the motifs based on their characteristic frequency of occurrence. We use log base 2 categories as a convenient classification which also provides a system in which the two-fold difference in motif frequencies in adjacent categories indicates a two-fold difference in the frequency of T-cell: B-cell encounters. With a total of about 40,000 total IGHV under consideration, a log base 2 system with a range of 16 categories provides an appropriate range for categorizing from high frequency motifs to those that occur as singletons. ($1/2^1$-$1/2^{16}$ corresponds to the occurrence in 1/2 to 1/65,536 cells). This scaling system provides a system for handling increasing size of database as well. As more sequences accumulate it is unlikely that frequency of motifs will change their categories significantly. Thus, the frequency categories are expected to be relatively constant and the scoring system can accommodate databases of various sizes. For example, doubling the repository from 40K to 80K is likely to add more singletons but a singleton 1/40,000 is most likely to only another identical motif (2/80,000 is the same frequency). Only 40,000 unique IGHV sequences could be assembled from Genbank but the frequency distributions show that at this size the cumulative distribution it approaching the upper asymptote; increasing the database size would not alter the fact that >90% occur in FC1-15. This is confirmed by analysis the non-redundant immunoglobulin class-defined subsets.

The result was therefore a 16 category classification in which a class FC1 (1/2), FC3 (1/8) etc. represent common motifs and FC11-FC16 are very rare motifs (1/65,536). It should be noted that certain synthetic antibodies contain TCEMs which occur in yet rarer frequencies (>FC16), as discussed below.

Figure 6:
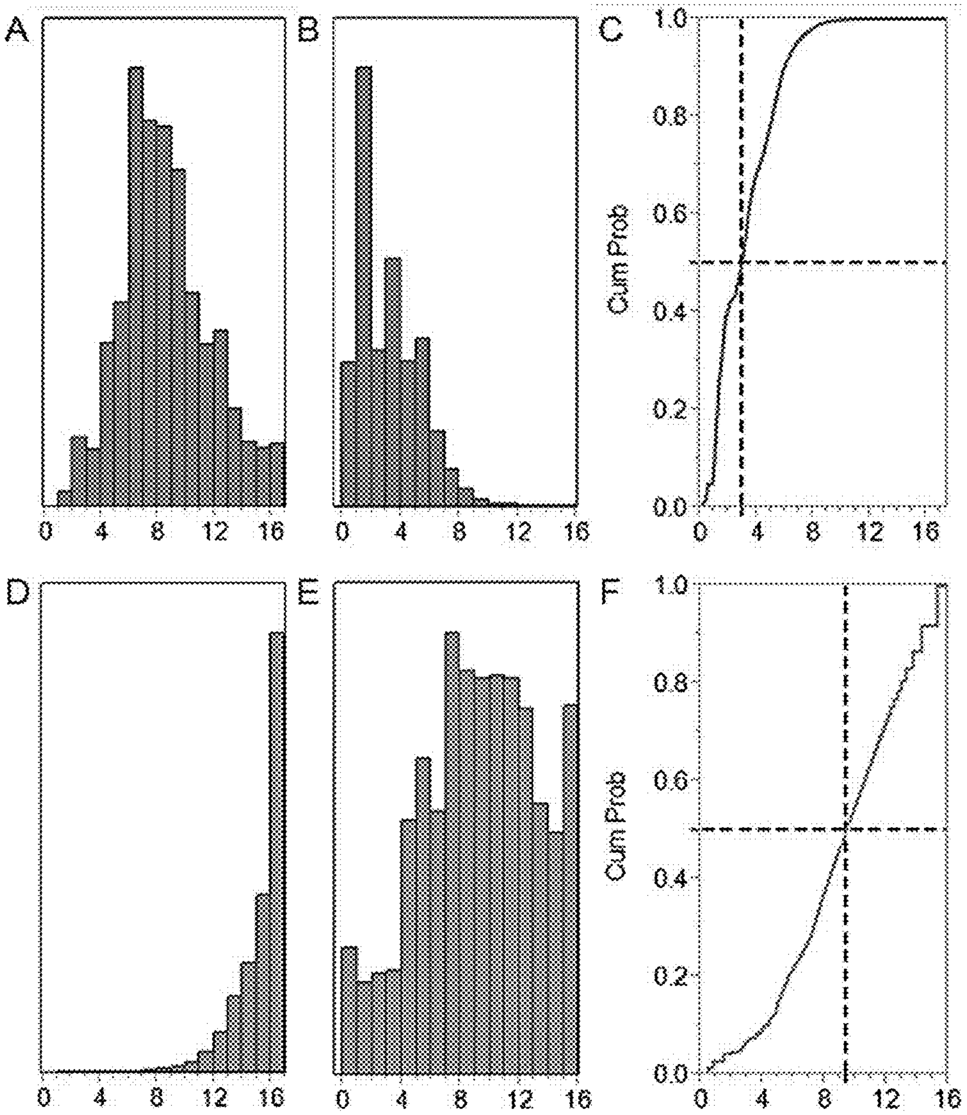
FIG. 6: Frequency distributions of unique T-cell exposed motifs in IGHV3. Frequency distributions of unique TCEM IIa motifs found in 22,458 IGHV3-origin sequences, comprising a total of $2.2\times10^6$ possible motifs. Panels A-C show germline-origin motifs and Panels D-F show SHM-origin motifs. Panels A and D: histogram of frequency of occurrence (histogram bins as $-\log_2$). Panels Band E: frequency weighted histogram. Panels C and F: cumulative distribution frequency of B and E. The dashed lines depict the frequency distribution midpoint.

FIG. 6 shows the frequency distributions of MHC-II TCEMs found in IGHV germline sequences, and in IGHV sequences which have undergone somatic hypermutation. FIG. 6 shows plots for TCEM IIa; very similar patterns were observed for TCEM II and TCEM I.

Germline sequences show a large number of commonly repeated TCEMs whereas mutated TCEMs have a spike in rare TCEMs. Approximately 11% of the TCEMs in mutated IGHV are found only once in the database; conversely 89% of the motifs are used repeatedly. As each variable region has about 100 motifs, each molecule will have roughly 10 unique motifs.

Patterns of TCEM in Specific Subsets of IGHV

Germline:

Each IGHV germline origin family has a unique set of motifs and thus exhibits its own characteristic motif repeat patterns. The patterns in FIG. 6C show that the 80% of the germline sequences are found in the commonest frequency categories (FC) 1, 2 and 3. In contrast in FIG. 6F the cumulative frequency distribution of IGHV which have undergone SHM is sigmoid on a log axis reflective of a log-normal distribution and shows that 50% of the cumulative motifs found in SHM regions occur by FC 10 and below with most occurring between FC 5 and FC 10 corresponding to $1/2^5$-$1/2^{10}$ or about 1/32 to 1/1024 clonal-origin cells. The spike in category FC3 in the SHM group is the result of motifs in the sequences found bordering CDR3 as seen in FIGS. 4 and 5. These results imply that multiple, high affinity, repeated TCEM are found in a relatively high proportion of the clonal lines.

TABLE 2

Rare and common TCEM motifs from germline and mutated sequences. Each motif is characterized by a specific frequency in the database. An inverse log base 2 classification scheme was developed to provide a convenient number of classification groups. A total of 16 frequency classes are used for the database of 40,000 unique motifs. A motif found exactly 10,000 times would be given a frequency class of 2 ($½^2$ = ¼). However, motifs are not found at precise frequencies and thus the frequency class designation is rounded to the next highest integer. For example, a motif found 10,500 times would also be assigned to frequency class 3, whereas a motif found 9,500 times would also be classified as frequency class 4.

| | | Frequency class |
|---|---|---|
| Germline Antibody Variable Regions | | |
| Very Common | >1 in 4 | FC 1 and FC2 |
| Common | >1 in 16 | FC3 and FC4 |
| Mature Mutated Antibody variable regions | | |
| Very Common | >1 in 64 | FC1 to FC6 |
| Common | >1 in 512 | FC 7 to FC9 |
| Very rare | >1 in 65,536 | FC16 |
| Rare | <1 in 32,768 | FC15 |

When the cumulative frequencies for each of the motif patterns (TCEM IIa and TCEM IIb) are combined the summary of the frequencies is shown in Table 1; hence a very common germline motif is found in ¼ of all germline sequences and a very rare motif is found only in 1/40,000 variable region sequences.

Immunoglobulin Class

Figure 7:
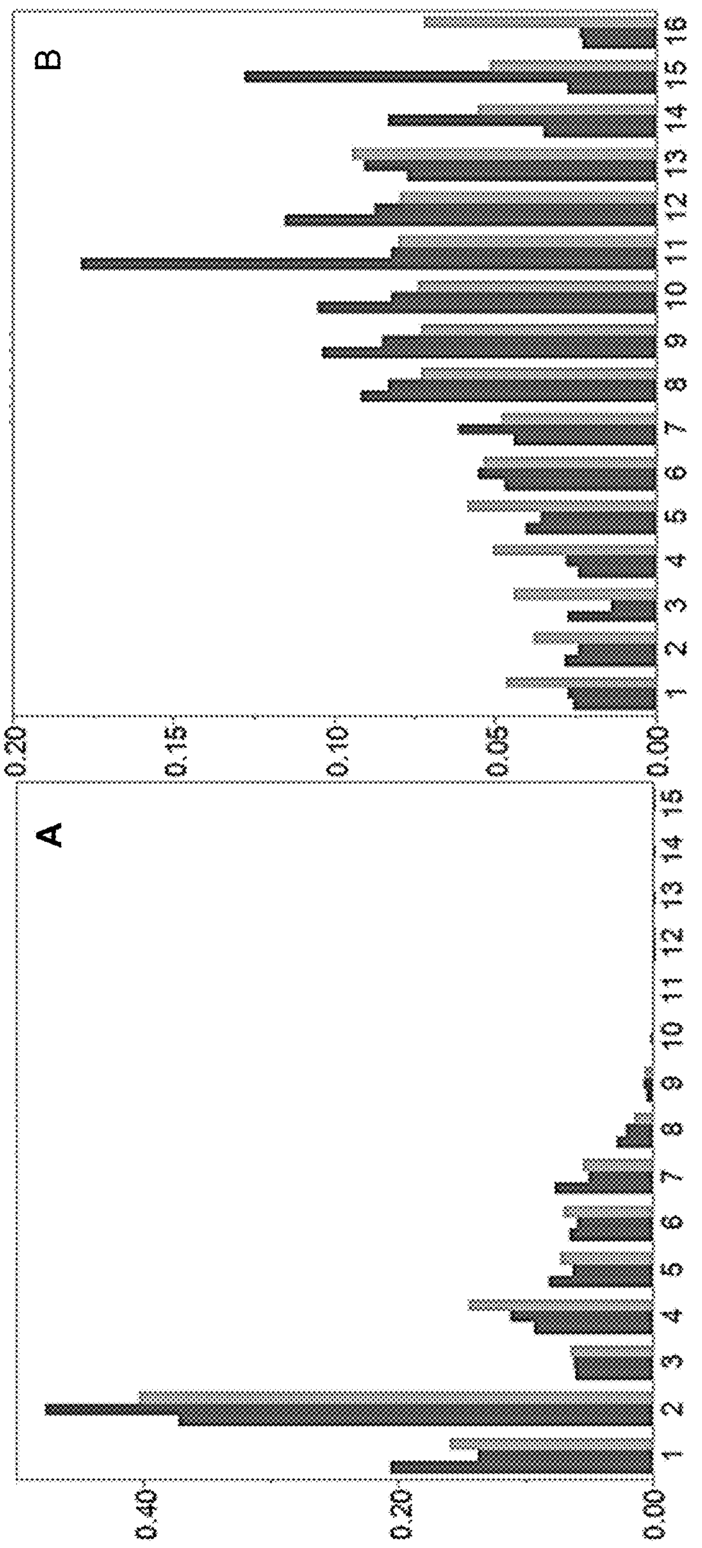
FIG. 7A-B: Distributions of T-cell exposed motif by frequency class for immunoglobulin class-defined IGHV. Histograms of distributions of TCEM IIa by frequency class for immunoglobulin class-defined IGHV. Panel A: germline-origin sequences and Panel B: SHM-origin motifs. IgG: red, IgM: green, and IgE: blue. A frequency classification for each motif was created by binning motifs based on the frequency in the 40K database on a $-\log_2$ scale. For the Ig class-defined datasets shown here the TCEMs in each successive peptide indexed by a single amino acid in the IGHV were then assigned to a frequency class from the main database.

FIG. 7 shows the Frequency Class (FC) patterns for three different groups of isotype-defined or class defined IGHV3, IgG, IgM and IgE. The patterns show that for IgG and IgE there is a shift towards more low frequency (FC>10) motifs; this is expected as SHM progresses from an IgM starting germline. The spike in FC 16 corresponds to singletons with a cellular clonal frequencies in the range of $1/2^{15}$-$1/2^{16}$ (approximately 1/50,000). There is a clear up-tic in the FC patterns for the singletons. For the large dataset used to derive the FC distribution patterns, singletons comprised 9.7% of the total motifs. The pattern for IgE, which like IgG has undergone a class switch, has a peak at FC 11 & 12 and then tails off dramatically to be less than IgM for FC 14-16. While different from IgG, it is unclear whether this is a characteristic of IgE generally or might be due to bias arising from the inclusion in the database of a large number of samples are from a study of asthmatic children [9]. In either case the differences in T-help activity associated with TCEM could be of relevance.

Biotherapeutics and Synthetics:

Examination of 163 commercial biotherapeutic antibodies cataloged in IMGT.org shows that while many motifs follow the same general distribution within frequency categories found in germline and the Genbank origin naturally derived mutated sequence database, these antibodies also have a large number of completely unique motifs unrecognized in naturally occurring antibodies.

Figure 8:
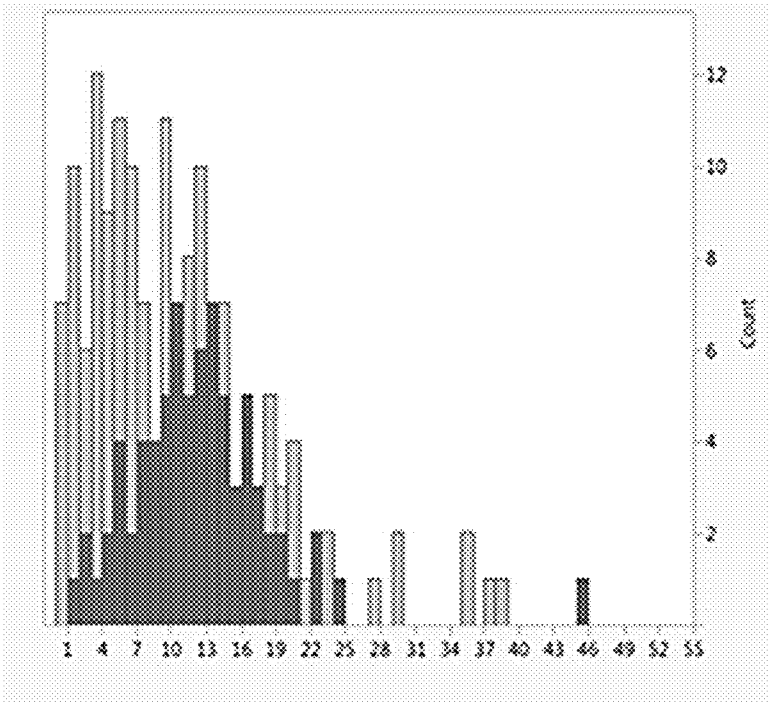
FIG. 8: Count shown in pale green of rare motifs in 163 biotherapeutic antibody products. These are motifs that are not found in the FC1-FC16 group. The majority thus have 7-10 rare motifs, 46 have one rare motif. When the humanized subset is selected (dark green) it is seen that this group of products have a greater variety of very rare motifs (mean=12).
Figure 9:
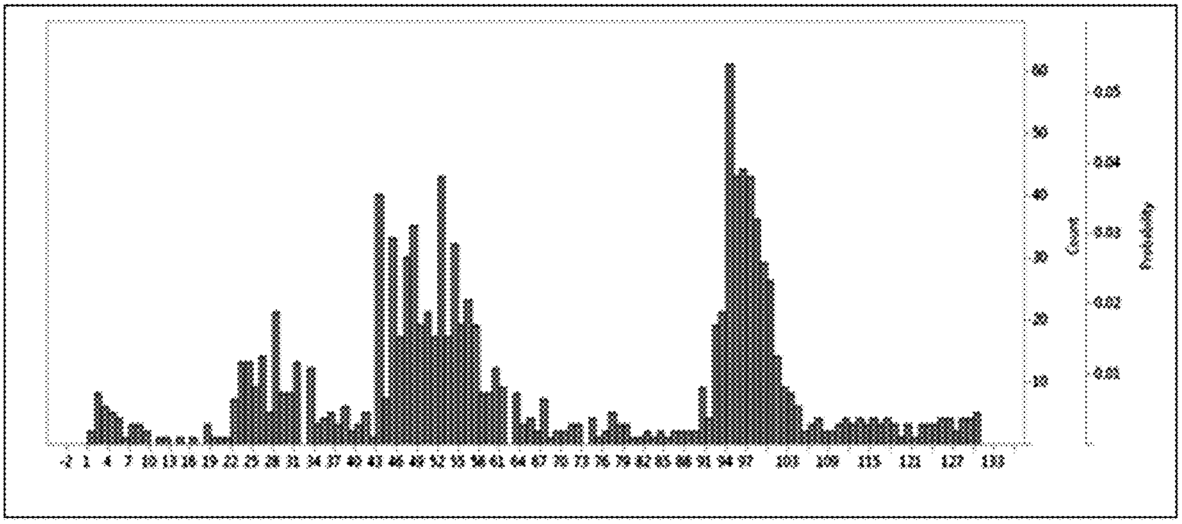
FIG. 9: Shows the distribution of rare motifs found in commercial antibodies across the variable region. The counts are aligned with the index amino acid of the TCEM. It is seen that more rare motifs occur in the CD3 region. Motifs found in the FC1-16 are excluded from this plot.

FIG. 8 and FIG. 9 shows the pattern of such rare TCEM in the 163 commercial biotherapeutic antibodies. These motifs are not found at all in the 40 thousand "normal" antibodies in our Genbank derived database used as the basis for motif frequency categorization; i.e., they do not fall within our categories of FC 1-16. Nor are the motifs found in either the isotype-defined groups downloaded from Genbank. The highlighted group are humanized molecules that have an average of 12 rare motifs. The remainder of the molecules are fully human (derived from phage display or humanized mice) or chimerics in which the IGHV would be entirely of murine origin. There is broad overlap in the occurrence of rare motifs between all of these sources.

Example 4: Immunoglobulin Constant Regions

Figure 10:
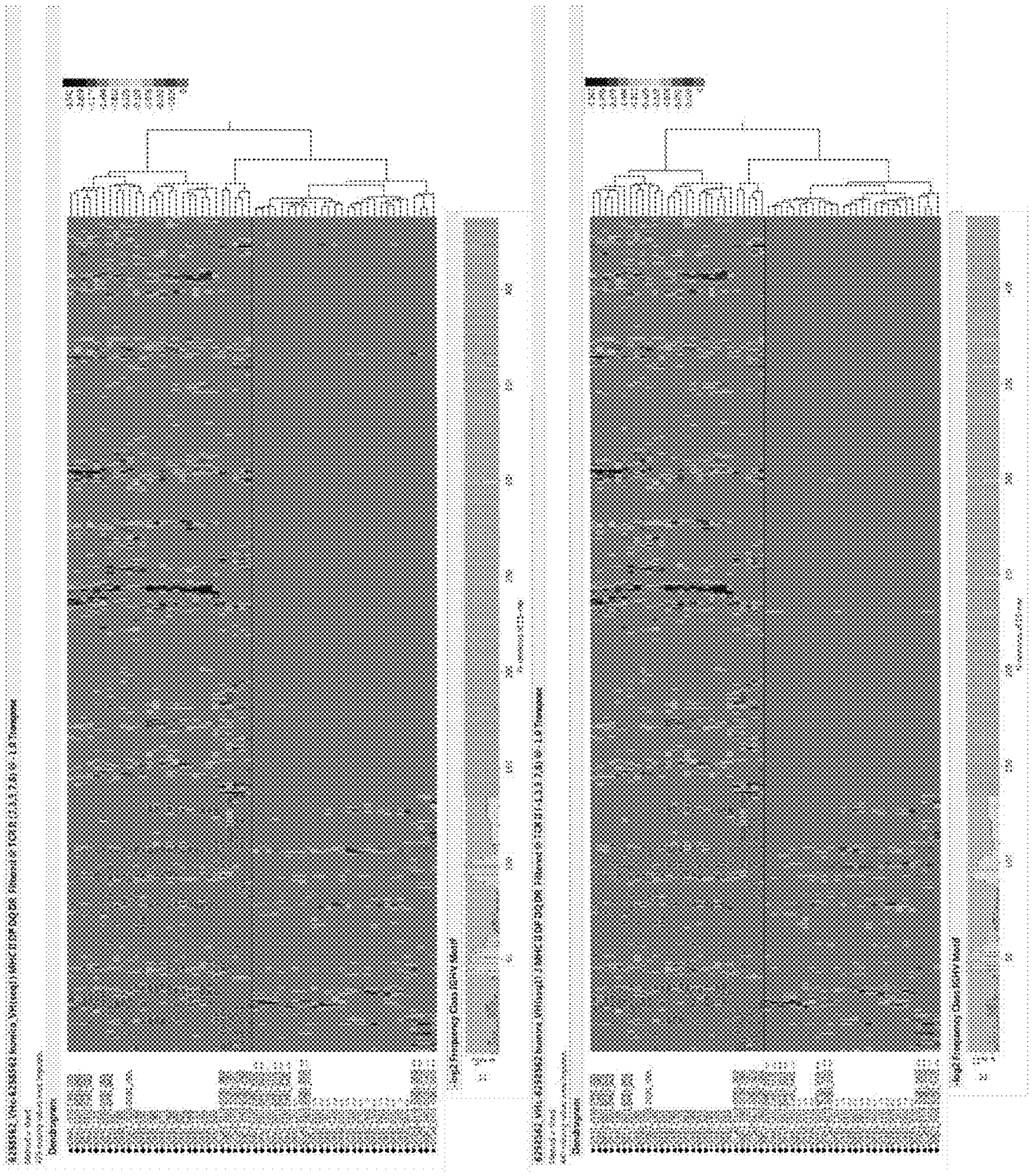
FIG. 10: Shows the differential usage of motifs between heavy chain variable and constant region. Example shown is a full length heavy chain (from U.S. Pat. No. 6,258,562). Top Panel shows TCEM IIA, Bottom panel shows TCEM IIB motifs. In the bottom bar on each panel, motifs derived from germline HVIG are shown in green, motifs found in mutated HVIG database are shown in cream; in both cases the height of the bar shows the frequency group as indicated on the Y axis of the bottom bar. Motifs shown in red motif are not found in HVIG database. The initial 134 amino acid index positions correspond to the variable region. It is noted that the constant region comprises almost totally motifs not present in the 40K HVIG motif database.

Examination of the peptide motifs in the constant regions of each isotype of immunoglobulin revealed that the TCEM motifs used in constant regions are distinct from those used in immunoglobulin variable regions. FIG. 10 shows the clear distinction between motif use in constant and variable regions.

Motifs used in the immunoglobulin constant region are excluded from use in normal immunoglobulin variable regions. This may reflect the effect of central or early tolerance to these motifs. Essentially the TCEM motifs found in the constant region correspond to the commonest frequency class as they are present in all immunoglobulins of that isotype. It follows that when they also comprise GEM motifs which give rise to high binding affinity they are motifs with a high probability of serving as T regulatory stimulators for individuals carrying the corresponding MHC allele.

The constant region motifs which have binding affinity in excess of 2 standard deviations below the mean were determined; these are very strong binders likely to have along dwell time in the MHC groove and consequently are most likely to have an immune suppressive effect.

Example 5: Immunoglobulin Light Chain Variable Region and T-Cell Receptor Databases Human immunoglobulin light chain variable regions (IGLV) were downloaded from Genbank using the argument "(immunoglobulin light chain variable region) AND (*Homo sapiens*)".

As of June 2014 approximately 16,000 sequences were available comprising 4,022 kappa and 4,921 lambda and 7419 variants. Various restrictive combinations of search arguments were used to create non-redundant subsets of this larger set that were either immunoglobulin class-defined or for which the metadata attached to the accession indicated that they were associated with an immunopathology. Additionally, manual curation was used to remove sequences that were obviously not immunoglobulins or not light chains. IGLV were included in the final set if they contained at least 80 amino acids, a value approximating the shortest germline equivalent sequence. All sequences longer than 130 amino acids were truncated at that point. For Germline IGLV 108 sequences comprising 72 kappa germlines+36 lambda germlines were obtained from the IMGT repository (www.imgt.org), and immunoglobulin light chain constant regions (IGLC) class reference sequences from Genbank.

TCEM and GEM motifs were extracted, scored, and categorized as described in Example 2 and 3. A total of 2106 Germline and 106,325 mutated unique TCEM IIA motifs, 2125 Germline and 106,845 mutated TCEM IIb motifs, and 2040 Germline and 104,879 mutated TCEM I motifs were found in IGLV. TCEM motifs extracted from IGLV were compared with those extracted previously from IGHV. Overall there is an overlap of approximately 60 IGLV unique: 45 IGHV+IGLV shared for all TCEM frames. Where a motif occurred in both datasets it was reclassified to the dataset in which it has the highest frequency of occurrence. Hence a motif previously identified as an IGHV FC8 which appears with a higher frequency in the IGLV dataset in 1 in 64 light chains was reclassified as a FC6 etc.

New algorithms were written to incorporate the IHLV dataset into the reference datasets and to reference motifs found in other proteins of interest according to whether they correspond to an IGHV or IGLV frequency category.

T-Cell Receptor Motifs

T-cell receptor germline and naturally occurring mutated sequences were downloaded from IMGT and from Genbank using (T-cell receptor) AND (*Homo sapiens*) as a search argument. Sequences that were found to be from unrelated sources or were derived from pathological conditions were removed. The resulting data set comprised 121 germline and 7338 human TCRs. Alpha, beta, gamma, and delta sequences were deduced by the Germline motif content, where these categories were not indicated in the Genbank annotations. The 121 germline sequences comprised 47 alpha, 60 beta, 11 gamma, 3 delta sequences.

Having curated the Genbank set as described for light chains, the remaining dataset comprised 7,338 molecules which in turn comprises 472,274 total TCEM motifs. The Genbank set includes some each of the alpha, beta, delta and gamma derivatives but also many unspecified sequences, in which the origin was deduced retrospectively by the motif distribution.

We evaluated the overlap of motif distribution with that in the IGHV and IGLV complex. Among the 472,274 total TCEM motifs in the TCR set, 5,009/6,863 (72.98%) germline and 33,300/48,090 (69.24%) mutated sequence origin motifs were unique to the TCR set.

Only 8,292 of 280,000 were shared with the IGHV motifs (~3%) and approximately the same with the light chain motifs. Overall 3,243 found in the TCR set were found in both light and heavy chain variable region motif sets, ~1%. These numbers are consistent with the level of sharing previously observed between proteome light chain and heavy chain.

Tables 3a-c show the degree of overlap among the TCR and immunoglobulin variable region motifs.

TABLE 3a

Overlaps between TCR and between immunoglobulin motifs for Type 1 motifs

| motif group (4, 5, 6, 7, 8) TCR | motif group (4, 5, 6, 7, 8) LC | motif group (4, 5, 6, 7, 8) HC | N Rows |
|---|---|---|---|
| Germline TCR | | | 4,627 |
| Germline TCR | | Germline_HC | 2 |
| Germline TCR | | Mutated_HC | 944 |
| Germline TCR | Germline_LC | | 16 |
| Germline TCR | Germline_LC | Mutated_HC | 60 |
| Germline TCR | Mutated_LC | | 533 |
| Germline TCR | Mutated_LC | Germline_HC | 23 |
| Germline TCR | Mutated_LC | Mutated_HC | 524 |
| Total | | | 6,729 |
| Mutated TCR | | | 29,177 |
| Mutated TCR | | Germline_HC | 15 |
| Mutated TCR | | Mutated_HC | 8,325 |
| Mutated TCR | Germline_LC | | 29 |
| Mutated TCR | Germline_LC | Germline_HC | 7 |
| Mutated TCR | Germline_LC | Mutated_HC | 195 |
| Mutated TCR | Mutated_LC | | 2,281 |
| Mutated TCR | Mutated_LC | Germline_HC | 233 |
| Mutated TCR | Mutated_LC | Mutated_HC | 3,305 |
| Total | | | 43,567 |

TABLE 3b

Overlaps between TCR and between immunoglobulin motifs for Type IIA motifs

| motif group (2, 3, 5, 7, 8) TCR | motif group (2, 3, 5, 7, 8) LC | motif group (2, 3, 5, 7, 8) HC | N Rows |
|---|---|---|---|
| | | Germline_HC | 333 |
| | | Mutated_HC | 219,131 |
| | Germline_LC | | 727 |
| | Germline_LC | Germline_HC | 8 |
| | Germline_LC | Mutated_HC | 1,107 |
| | Mutated_LC | | 55,651 |
| | Mutated_LC | Germline_HC | 1,500 |
| | Mutated_LC | Mutated_HC | 42,031 |
| Germline TCR | | | 4,846 |
| Germline TCR | | Mutated_HC | 864 |
| Germline TCR | Germline_LC | | 11 |
| Germline TCR | Germline_LC | Germline_HC | 4 |
| Germline TCR | Germline_LC | Mutated_HC | 39 |
| Germline TCR | Mutated_LC | | 551 |
| Germline TCR | Mutated_LC | Germline_HC | 25 |
| Germline TCR | Mutated_LC | Mutated_HC | 482 |
| Total | | | 6,822 |
| Mutated TCR | | | 32,164 |
| Mutated TCR | | Germline_HC | 16 |
| Mutated TCR | | Mutated_HC | 7,880 |
| Mutated TCR | Germline_LC | | 29 |
| Mutated TCR | Germline_LC | Germline_HC | 5 |
| Mutated TCR | Germline_LC | Mutated_HC | 176 |
| Mutated TCR | Mutated_LC | | 2,622 |
| Mutated TCR | Mutated_LC | Germline | 238 |
| Mutated TCR | Mutated_LC | Mutated | 3,225 |
| Total | | | 46,355 |

TABLE 3c

Overlaps between TCR and between immunoglobulin motifs for Type IIB motifs

| motif group (−1, 3, 5, 7, 8) TCR | motif group (−1, 3, 5, 7, 8) LC | motif group (−1, 3, 5, 7, 8) HC | N Rows |
|---|---|---|---|
| | | Germline_HC | 338 |
| | | Mutated_HC | 218,888 |
| | Germline_LC | | 757 |
| | Germline_LC | Germline_HC | 18 |
| | Germline_LC | Mutated_HC | 1,089 |
| | Mutated_LC | | 56,418 |
| | Mutated_LC | Germline_HC | 1,508 |
| | Mutated_LC | Mutated_HC | 41,647 |
| Germline TCR | | | 5,009 |
| Germline TCR | | Germline_HC | 4 |
| Germline TCR | | Mutated_HC | 796 |
| Germline TCR | Germline_LC | | 9 |
| Germline TCR | Germline_LC | Germline_HC | 4 |
| Germline TCR | Germline_LC | Mutated_HC | 40 |
| Germline TCR | Mutated_LC | | 522 |
| Germline TCR | Mutated_LC | Germline_HC | 24 |
| Germline TCR | Mutated_LC | Mutated_HC | 455 |
| Total | | | 6,863 |
| Mutated TCR | | | 33,300 |
| Mutated TCR | | Germline_HC | 19 |
| Mutated TCR | | Mutated_HC | 8,292 |
| Mutated TCR | Germline_LC | | 44 |
| Mutated TCR | Germline_LC | Germline_HC | 10 |
| Mutated TCR | Germline_LC | Mutated_HC | 154 |
| Mutated TCR | Mutated_LC | | 2,817 |
| Mutated TCR | Mutated_LC | Germline_HC | 220 |
| Mutated TCR | Mutated_LC | Mutated_HC | 3,234 |
| Total | | | 48,090 |

Example 6 Microbial Database Assembly

To establish a reference database enabling the determination of frequency of use of T cell exposed motifs in microorganisms two groups of bacteria were utilized. This database is an example of the approach in determining T cell exposed motif use in microbes and is not considered limiting with respect to the bacteria included nor to the class of microorganisms.

The first group of bacteria comprises 38 species in 67 genera from the gastrointestinal microbiome. The second group comprises up to five proteomes each of 28 species in 12 genera of pathogenic bacteria. We characterized the patterns of TCEM usage within each proteome dataset, and compared them to each other, and to the repertoire of motifs in immunoglobulin variable regions.

a. Gastrointestinal microbiome bacteria (Microbiome) The proteomes were assembled from the NIH Human Microbiome Project Reference Genomes database (www.hmpdacc.org/HMRGD) and included 67 species in 35 genera (listed in Table 4). This set comprised, a total of 378,061 proteins with an average length of 290 amino acids. This is not a set of fully annotated proteomes and may include some partial proteomes. The final set comprised $1.09\times10^8$ total TCEM in each of the three reading frames and is thus of a comparable total size to the bacterial pathogen set.

b. Exemplary bacterial pathogens (Pathogens) comprising 28 species each represented by up to 5 proteomes (132 in all) selected at random from the complete proteomes available at PATRIC (www.patricbrc.org) [21]. The genera included were: *Bordetella, Brucella, Burkholderia, Chlamydia, Clostridium, Coxiella, Francisella, Mycobacterium, Neisseria, Staphylococcus, Streptococcus*, and *Ureaplasma*. Species and strains are shown in Table 4. Proteomes ranged in size from approximately 6000 proteins (*Burkholderia*) to 689 (*Ureaplasma*). Overall 427,906 proteins were included in the analysis. The final pathogen dataset comprised $1.16\times10^8$ TCEM in each of the three TCEM reading frames.

To construct the TCEM sets, concatenated amino acid FASTA files of each of the proteomes were assembled, wherein each protein in the proteome was then decomposed into sets of 9-mer and 15-mer peptides, each offset by a single amino acid and placed in successive rows of a JMP® data table. Three different TCEM reading frames were constructed from each peptide in corresponding columns using column formulas of JMP®. These were TCEM I comprising amino acids (4, 5, 6, 7, 8) of a core MHC-I 9-mer, and TCEM IIa and TCEM IIb comprising amino acids corresponding to amino acids (2, 3, 5, 7, 8) and (−1, 3, 5, 7, 8) of the central 9-mer core of a 15-mer [2,22]. The groove exposed motifs (GEM) responsible for the binding interactions were assembled as the intercalated set of non-TCEM amino acids in each peptide. The unique identifier of each protein, the peptide, and the N terminal positions of each peptide in the parent protein within the proteome were retained with each TCEM. In this way TCEM sets were hyperlinked to the parental proteins by JMP® so that the parental proteins could be readily retrieved for other analyses. Three sets of tables, one for each TCEM reading frame, were constructed for each protein set.

TABLE 4

Pathogen and Gastrointestinal Microbiome proteomes included in analysis
Compete proteomes of the following organisms were downloaded from PATRIC. Isolate identifications shown are as listed in PATRIC. Gastrointestinal microbiome bacterial proteomes were assembled from the NIH Human Microbiome Project Reference Genomes database (www.hmpdacc.org/HMRGD).

| Pathogens | GI microbiome |
|---|---|
| *Bordetella bronchiseptica* 2371640 | *Anaerobaculum hydrogeniformans* ATCC BAA-1850 |
| *Bordetella bronchiseptica* 253 | *Anaerostipes caccae* DSM 14662 |
| *Bordetella bronchiseptica* D445 | *Anaerostipes* sp. 3 2 56FAA |
| *Bordetella bronchiseptica* RB50 | *Bacteroides cellulosilyticus* DSM 14838 |
| *Bordetella bronchiseptica* SEAT0006 | *Bacteroides clarus* YIT 12056 |
| *Bordetella pertussis* B1920 | *Bacteroides eggerthii* DSM 20697 |
| *Bordetella pertussis* Bp H897 | *Bacteroides* sp. 3 1 19 |
| *Bordetella pertussis* Bp SEAT 0004 | *Bacteroides sp. D22* |
| *Bordetella pertussis* CHLA15 | *Bacteroides xylanisolvens* SD CC 1b |
| *Bordetella pertussis* Tohama I | *Bacteroides xylanisolvens* SD CC 2a |
| *Brucella melitensis* 043 | *Bifidobacterium breve* DSM 20213 = JCM 1192 |
| *Brucella melitensis* ATCC 23457 | *Bifidobacterium* sp. 12 1 47BFAA |
| *Brucella melitensis* B115 | *Citrobacter youngae* ATCC 29220 |
| *Brucella melitensis* M5 | Clostridiales butyrate-prod |
| *Brucella melitensis* S66 | Clostridiales butyrate-producing bacter |
| *Burkholderia cenocepacia* AU 1054 | Clostridiales butyrate-producing bacterium SS |
| *Burkholderia cenocepacia* H111 | Clostridiales butyrate-producing bacterium SSC/2 |
| *Burkholderia cenocepacia* KC-01 | *Clostridium* sp. M62/1 |
| *Burkholderia cepacia* ATCC 25416 | *Clostridium* sp. SS2/1 |
| *Burkholderia cepacia* Bu72 | *Coprobacillus* sp. 8 2 54BFAA |
| *Burkholderia mallei* ATCC 10399 | *Coprococcus* sp. HPP0074 |
| *Burkholderia mallei* ATCC 23344 | *Corynebacterium* sp. HFH0082 |
| *Burkholderia mallei* FMH | *Edwardsiella tarda* ATCC 23685 |
| *Burkholderia mallei* JHU | *Enterobacter cancero* genus ATCC 35316 |
| *Burkholderia mallei* NCTC 10247 | *Enterococcus faecalis* TX2134 |
| *Burkholderia pseudomallei* 1026b | Erysipelotrichaceae bacterium 21 3 |
| *Burkholderia pseudomallei* 1106a | *Escherichia coli* 4 1 47FAA |
| *Burkholderia pseudomallei* 1106b | *Escherichia coli* MS 60-1 |
| *Burkholderia pseudomallei* K96243 | *Escherichia coli* MS 69-1 |
| *Burkholderia pseudomallei* MSHR305 | *Escherichia coli* MS 78-1 |
| *Chlamydia trachomatis* A363 | *Escherichia coli* MS 84-1 |
| *Chlamydia trachomatis* Ds2923 | *Eubacterium rectale* M104/1 |
| *Chlamydia trachomatis* FSW5 | *Faecalibacterium prausnitzii* M21/2 |
| *Chlamydia trachomatis* Jali20 | *Fusobacterium mortiferum* ATCC 9817 |
| *Chlamydia trachomatis* Sweden2 | *Fusobacterium varium* ATCC 27725 |
| *Clostridium difficile* ATCC 43255 | *Hafnia alvei* ATCC 51873 |
| *Clostridium difficile* ATCC 9689 | *Helicobacter pylori* GAM101Biv |
| *Clostridium difficile* CD165 | *Helicobacter pylori* GAM246Ai |
| *Clostridium difficile* DA00212 | *Helicobacter pylori* GAM252T |
| *Clostridium difficile* Y270 | *Helicobacter pylori* GAM83Bi |
| *Clostridium perfringens* ATCC 13124 | *Helicobacter pylori* GAM93Bi |
| *Clostridium perfringens* CPE str F4969 | *Helicobacter pylori* GAM96Ai |
| *Clostridium perfringens* E str JGS1987 | *Helicobacter pylori* HP116Bi |

TABLE 4-continued

Pathogen and Gastrointestinal Microbiome proteomes included in analysis
Compete proteomes of the following organisms were downloaded from PATRIC. Isolate identifications shown are as listed in PATRIC. Gastrointestinal microbiome bacterial proteomes were assembled from the NIH Human Microbiome Project Reference Genomes database (www.hmpdacc.org/HMRGD).

| Pathogens | GI microbiome |
|---|---|
| *Clostridium perfringens* JJC | *Helicobacter pylori* HP250BFiii |
| *Clostridium perfringens* str 13 | *Helicobacter pylori* HP250BSi |
| *Coxiella burnetii* Cb185 | *Klebsiella pneumoniae* subsp. *pneumoniae* WGLW3 |
| *Coxiella burnetii* Dugway 5J108-111 | Lachnospiraceae bacterium 2 1 58FAA |
| *Coxiella burnetii* RSA 331 | Lachnospiraceae bacterium 3 1 57FAA CT1 |
| *Coxiella burnetii* RSA 493 | Lachnospiraceae bacterium 5 1 57FAA |
| *Coxiella burnetii* Z3055 | Lachnospiraceae bacterium 5 1 63FAA |
| *Francisella novicida* FTE | Lachnospiraceae bacterium 7 1 58FAA |
| *Francisella novicida* FTG | *Lactobacillus reuteri* MM4-1A |
| *Francisella novicida* GA99-3548 | *Lactobacillus reuteri* SD2112 |
| *Francisella novicida* GA99-3549 | *Listeria innocua* ATCC 33091 |
| *Francisella novicida* U112 | *Megamonas hypermegale* ART12/1 |
| *Francisella tularensis* subsp *holarctica* | *Methanobrevibacter smithii* DSM 2375 |
| *Francisella tularensis* subsp *holarctica* 257 | *Paraprevotella xylaniphila* YIT 11841 |
| *Francisella tularensis* subsp *holarctica* F92 | *Phascolarctobacterium succinatutens* YIT 12067 |
| *Francisella tularensis* subsp *holarctica* FSC022 | *Prevotella oralis* HGA0225 |
| *Francisella tularensis* subsp *holarctica* FSC200 | *Roseburia intestinalis* M50/1 |
| *Francisella tularensis* subsp *tularensis* FSC033 | *Roseburia intestinalis* XB684 |
| *Francisella tularensis* subsp *tularensis* FSC198 | *Ruminococcus obeum* A2-162 |
| *Francisella tularensis* subsp *tularensis* MA00-2987 | *Ruminococcus torques* L2-14 |
| *Francisella tularensis* subsp *tularensis* NE061598 | *Succinatimonas hippei* YIT 12066 |
| *Francisella tularensis* subsp *tularensis* SCHU S4 | *Sutterella wadsworthensis* 2 1 59BFAA |
| *Mycobacterium abscessus* 4S-0303 | *Veillonella* sp. 6 1 27 |
| *Mycobacterium abscessus* 5S-1212 | *Weissella paramesenteroides* ATCC 33313 |
| *Mycobacterium abscessus* 6G-0212 | |
| *Mycobacterium abscessus* M156 | |
| *Mycobacterium abscessus* V06705 | |
| *Mycobacterium bovis* BCG str ATCC 35733 | |
| *Mycobacterium bovis* BCG str TCC 35740 | |
| *Mycobacterium bovis* BCG str ATCC 35743 | |
| *Mycobacterium bovis* BCG str Glaxo | |
| *Mycobacterium bovis* BCG str Pasteur 1173P2 | |
| *Mycobacterium leprae* Br4923 | |
| *Mycobacterium leprae* TN | |
| *Mycobacterium tuberculosis* H37Ra | |
| *Mycobacterium tuberculosis* H37RvAE | |
| *Mycobacterium tuberculosis* H37RvCO | |
| *Mycobacterium tuberculosis* H37RvHA | |
| *Mycobacterium tuberculosis* H37RvJO | |
| *Neisseria gonorrhoeae* 1291 | |
| *Neisseria gonorrhoeae* DGI2 | |
| *Neisseria gonorrhoeae* FA 1090 | |
| *Neisseria gonorrhoeae* PID18 | |
| *Neisseria gonorrhoeae* SK-93-1035 | |
| *Neisseria meningitidis* 2003022 | |
| *Neisseria meningitidis* 2004032 | |
| *Neisseria meningitidis* 64182 | |
| *Neisseria meningitidis* 93003 | |
| *Neisseria meningitidis* NM3222 | |
| *Staphylococcus aureus* subsp *aureus* ATCC 51811 | |
| *Staphylococcus aureus* subsp *aureus* ATCC BAA-39 | |
| *Staphylococcus aureus* subsp *aureus* COL | |
| *Staphylococcus aureus* subsp *aureus* MRSA131 | |
| *Staphylococcus aureus* subsp *aureus* USA300 TCH1516 | |
| *Staphylococcus epidermidis* NIH051668 | |
| *Staphylococcus epidermidis* VCU120 | |
| *Staphylococcus epidermidis* VCU139 | |
| *Staphylococcus epidermidis* W23144 | |
| *Staphylococcus epidermidis* WI05 | |
| *Streptococcus agalactiae* A909 | |
| *Streptococcus agalactiae* CCUG 24810 | |
| *Streptococcus agalactiae* GB00247 | |
| *Streptococcus agalactiae* GB00951 | |
| *Streptococcus agalactiae* ILRI005 | |

TABLE 4-continued

Pathogen and Gastrointestinal Microbiome proteomes included in analysis
Compete proteomes of the following organisms were downloaded from PATRIC. Isolate identifications
shown are as listed in PATRIC. Gastrointestinal microbiome bacterial proteomes were assembled from
the NIH Human Microbiome Project Reference Genomes database (www.hmpdacc.org/HMRGD).

| Pathogens | GI microbiome |
|---|---|
| *Streptococcus dysgalactiae* subsp *dysgalactiae* ATCC 27957 | |
| *Streptococcus dysgalactiae* subsp *equisimilis* 167 | |
| *Streptococcus dysgalactiae* subsp *equisimilis* ATCC 12394 | |
| *Streptococcus dysgalactiae* subsp *equisimilis* GGS 124 | |
| *Streptococcus dysgalactiae* subsp *equisimilis* RE378 | |
| *Streptococcus mutans* TCI-110 | |
| *Streptococcus mutans* TCI-149 | |
| *Streptococcus mutans* TCI-223 | |
| *Streptococcus mutans* TCI-400 | |
| *Streptococcus mutans* TCI-92 | |
| *Streptococcus pneumoniae* ATCC 700669 | |
| *Streptococcus pneumoniae* Hungary19A-6 | |
| *Streptococcus pneumoniae* SP195 | |
| *Streptococcus pneumoniae* Taiwan19F-14 | |
| *Streptococcus pneumoniae* TCH843119A | |
| *Streptococcus pyogenes* GA03805 | |
| *Streptococcus pyogenes* GA16797 | |
| *Streptococcus pyogenes* GA19681 | |
| *Streptococcus pyogenes* MGAS2096 | |
| *Streptococcus pyogenes* UTMEM-1 | |
| *Ureaplasma urealyticum* 2608 | |
| *Ureaplasma urealyticum* serovar 11 str ATCC 33695 | |
| *Ureaplasma urealyticum* serovar 2 str ATCC 27814 | |
| *Ureaplasma urealyticum* serovar 7 str ATCC 27819 | |
| *Ureaplasma urealyticum* serovar 9 str ATCC 33175 | |

Example 7: Analysis of Specific Epitopes

Influenza A 2009 H1N1 California

Figure 11:
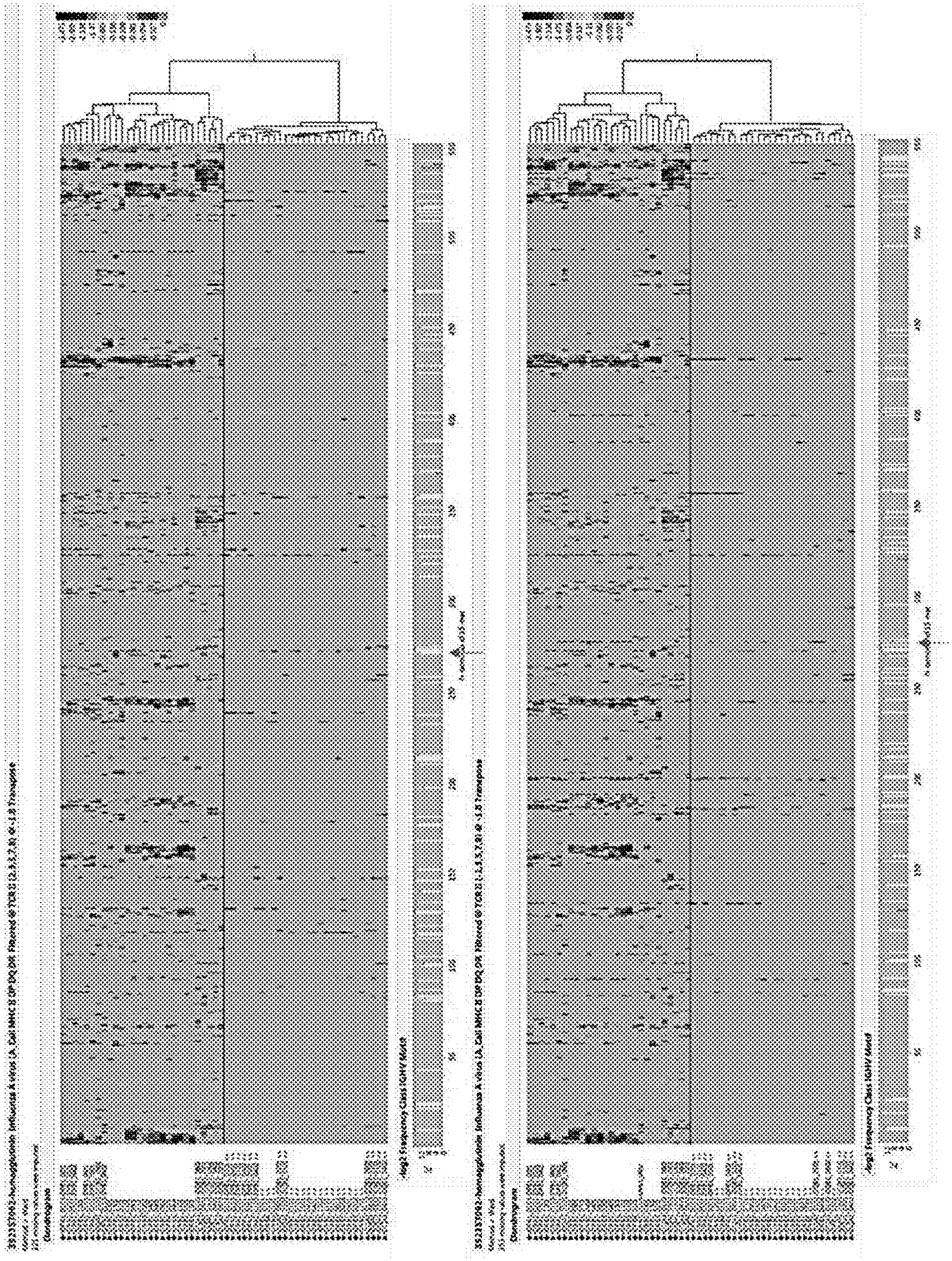
FIG. 11: Shows TCEM identified in hemagglutinin of Influenza A 2009 California. Arrows in the lower tier of each diagram indicate that in both TCEM IIa and TCEM IIb several alleles have peptides with motifs found in IGHV with a binding affinity exceeds −1 standard deviation at position 273-276; the top tier of each diagram shows the peptides which have binding affinity in excess of −1 standard deviation to the indicated alleles. Simultaneous peptide affinity threshold mapping of TCEM containing peptides in a target protein and in IGHV database. Horizontal axis is the amino acid position of the N-terminal amino acid of the peptide (9-mer for MHC I and 15-mer for MHC II) containing the matching TCEM. Allele identification is shown on the left portion of the panel. Allele designations without a suffix are the TCEM in the target protein and those with a "< >" suffix indicate the TCEM in the IGHV database. For both the target protein and the IGHV peptides that exceed the standardized affinity threshold are color coded as indicated by the thermometer. For the TCEM in the IGHV the threshold is the overall mean standardized affinity of binding for all the peptides containing the particular TCEM (ranges from singletons to thousands). Any TCEM can be found in association with a wide range of groove exposed motifs which confer a potential wide range of affinities for the peptides. The boxed-X peptides in the panel represent peptides in the target protein for which the threshold was exceeded in the IGHV. It should be noted that the peptides that exceed the threshold in the IGHV might or might not exceed that threshold in the target protein. For consistency they are designated with a boxed-X in either case. The number of peptides that contain a particular TCEM are shown by their frequency classification FC (FC=−log 2 frequency) in the lower graphic pane. Thus a FC 12 implies the TCEM is found in $1/2^{12}=1/4096$ and a FC $8=1/2^8=1/256$ frequency in IGHV clones.

Type 1 narcolepsy has been described as an autoimmune disorder found almost exclusively in individuals carrying a DQA1*01:02/DQB1*06:02 allele [23,24]. In 2010 following the spread of H1N1 influenza a cluster of diagnoses narcolepsy cases following influenza infection was described [25]. Simultaneously cases of narcolepsy in Europe were linked to vaccination with the Pandermix® influenza vaccine containing the California 2009 H1N1 hemagglutinin protein (Influenza A virus (A/California/07/2009(H1N1) gi 392357062) [26]. A recent publication identified a possible key CD4+ epitope at amino acid positions 275-287 in the California 2009 hemagglutinin. We examined the binding affinity of CD4+ alleles across the sequence of interest and identified DQA1*01:02/DQB1*06:02 allele showing a predicted binding affinity of −2.29 standard deviations below the mean for the 15 mer index position 273 an extraordinarily high binding affinity and −1.86 and −1.33 in positions 274 and 275 respectively, (FIGS. 11 and 12). DQA1*01:02/DQB1*06:02 is the only MHC-II allele which has a binding affinity significantly below the mean, hence the only allele of 28 tested that is likely to bind tightly in this region. Furthermore when we examined the TCEM in this region we find several motifs with a high frequency in IGHV. These include the following shown in Table 5:

| peptide | 15mer index position | TCEMIIa | TCEMIIb | Mutated FC class |
|---|---|---|---|---|
| FAMERNAGSGIIISD (SEQ ID NO: 1) | 272 | RN~G~GI (SEQ ID NO: 2) | M~~N~G~GI (SEQ ID NO: 3) | 13 |
| AMERNAGSGIIISDT (SEQ ID NO: 4) | 273 | **NA~S~II** (SEQ ID NO: 5) | E~~A~S~II (SEQ ID NO: 6) | 16 |
| MERNAGSGIIISDTP (SEQ ID NO: 7) | 274 | **AG~G~II** (SEQ ID NO: 8) | R~~G~G~II (SEQ ID NO: 9) | 16 |
| ERNAGSGIIISDTPV (SEQ ID NO: 10) | 275 | GS~I~IS (SEQ ID NO: 11) | N~~S~I~IS (SEQ ID NO: 12) | 16 |

-continued

| peptide | 15mer index position | TCEMIIa | TCEMIIb | Mutated FC class |
|---|---|---|---|---|
| RNAGSGIIISDTPVH (SEQ ID NO: 13) | 276 | SG~I~SD (SEQ ID NO: 14) | A~~G~I~SD(SEQ ID NO: 15) | 9 |

Examination of the occurrence of these by allele shows that only the two boldfaced in the above table are present for DQA1*01:02/DQB1*06:02, the others are found associated with other alleles. DQA1*01:02/DQB1*06:02 is the only MHC-II allele which has a binding affinity significantly below the mean, hence the only allele of 28 tested that is likely to bind tightly in this region. The exact peptide sequences binding to DQA1*01:02/DQB1*06:02 with high affinity are absent from the hemagglutinin protein of H1N1 influenza virus isolates made earlier in 2009 or in 2010 and is the product of a specific amino acid mutation.

Narcolepsy arises when cells in the hypothalamus with receptors for orexin (hypocretin) are destroyed or cease to function. No direct causal mechanism linking the influenza motif to narcolepsy has been established, although a partial motif match to orexin has been suspected; it is not clear that this provides a causal relationship as it would not explain the loss of hypothalamic cells. The identified motifs can be searched to find their occurrence in self-proteins to determine if any are potentially causally associated with narcolepsy. Example 5 shows how such a search was conducted for one of the motifs. We continue to examine for sources of possible mimics in the hypocretin pathway. Alternative explanations have recently been proposed [7].

Influenza Hemagglutinin "Universal" B-Cell Epitope:

The presence of a highly conserved B-cell epitope in the hemagglutinin of influenza H1, H2 and H5 at position 375-380 is well documented [27,28]. The exact position in this range varies a little depending on the hemagglutinin and isolate. Our own observations have shown that this B-cell epitope, while highly conserved, is in a region devoid of high affinity MHC-II or MHC-I binding and thus unlikely to benefit from T-cell help essential to memory. Only one allele, DQA1*05:01-DQB1*03:01 shows any likelihood of binding to a series of peptides in this stretch of the protein.

Interestingly, the TCEM centered at amino acid position 378 in H1N1 California 2009 (gi 392357062) is found to be a germline motif GS~Y~AD (SEQ ID NO:469) which occurs in germline FC4. In other words it is present in 1 in 16 germline IGHV. Among all microbial proteins we have examined this is an exceptionally high level of germline TCEM frequency. The implication of this is that not only does the TCEM associated with the highly conserved motif have a GEM of low binding affinity but the TCEM would be highly likely to be an immunosuppressive motif. This may well be a contributing factor in the extreme conservation of the B-cell epitope at this point.

Example 8 Evaluation of Potential Immunosuppressive Motifs in Influenza Hemagglutinin The surface proteins of influenza and in particular the hemagglutinin are the target of neutralizing and protective antibodies and as such are the focus of vaccine design. Influenza viruses are highly variable both between different classes of hemagglutinin (H1, H3, H5, H7 etc.) and within any one hemagglutinin class; they undergo constant antigenic drift. Thus there is considerable focus on designing vaccines which can provide high antibody titers responsive to each newly emerging strain of the virus. By applying the classification of TCEM motifs to a multiplicity of the sequences of influenza HA isolated over the years we determined that each HA (from any different isolate) may carry from about 3 up to about 20 TCEM motifs which are found with high frequency in immunoglobulins (FC10 or lower as previously defined in this invention) and are thus likely to elicit an immunosuppressive T cell response (Treg) whenever they occur in peptides which are also bound by MHC molecules. It would be desirable to eliminate these potentially suppressive motifs to favor a better antibody response. The positions at which such high frequency motifs occur varies but shown some consistency within HA class (H7 vs H1 etc.). We describe here the analysis of HA1 sequences from 447 H3N2 isolates made between 1968 and 2003 and demonstrate the distribution of potentially immunosuppressive TCEM motifs. We then propose substitutions of 1-3 amino acids which can change the frequency category of a TCEM motif from likely immunosuppressive (<FC10) to likely immunostimulatory (FC14-16 or >16). While this example addresses a panel of H3 isolates, the same approach is equally applicable to isolates of other HA classes and thus the example is not considered limiting. The following steps were employed:

a. Array sequences of HA by position and FC motif and class, for each of TCEM IIA, IIB and TCEM I
b. Determine positions which have motifs of TCEM<FC10.
c. Evaluate peptides of other isolates in the panel of >400 hemagglutinins at the same or adjacent amino acid position to identify motifs functional in other isolates that have a higher frequency category.
d. Identify the substitution which will achieve a change of FC category to >FC14 and preferably to FC 16 or >16.
e. Evaluate where the motifs are found within the human proteome to determine if any potential adverse targeting may occur through the creation of a substitute motif.

Overall 50 TCEM IIA, 48 TCEM IIB and 51 TCEM I motifs of FC 10 were found the panel of H3N2 isolates. Some such motifs occurred in >400 isolates, some occurred in as few as one isolate. Substitution motifs were identified for each. In the interests of space we provide an illustrative subset of the results for all motif positions of all the viruses.

Any single virus isolate or vaccine candidate can be evaluated by the same means; evaluation of the larger database allows substitution of motifs known to be functional in comparable isolates of influenza. Within any given isolate the modifications of TCEM IIA, IIB and TCEM I have to be reconciled internally to make sure that improvements to one motif do not adversely affect an alternate TCEM register.

TABLE 6

| TCEM IIA | | | | | |
|---|---|---|---|---|---|
| pos | TCR II (2, 3, 5, 7, 8) | FC TCR II (2, 3, 5, 7, 8) | Occurrences in 447 isolates N Rows | FC TCR II (2, 3, 5, 7, 8) | TCR II (2, 3, 5, 7, 8) |
| Wild type | | | Substitution | | |
| 32 | VP~G~LV (SEQ ID NO: 16) | 10 | 435 | VP~G~IV (SEQ ID NO: 17) | 16 |
| 33 | VP~G~LV (SEQ ID NO: 16) | 10 | 2 | VP~G~IV (SEQ ID NO: 17) | 16 |
| 37 | VP~G~LV (SEQ ID NO: 16) | 10 | 1 | VP~G~IV (SEQ ID NO: 17) | 16 |
| 45 | VP~G~LV (SEQ ID NO: 16) | 10 | 1 | VP~G~IV (SEQ ID NO: 17) | 16 |
| 60 | TG~I~GS (SEQ ID NO: 18) | 10 | 1 | TG~I~DS (SEQ ID NO: 19) | >16 |
| 119 | SL~S~VA (SEQ ID NO: 20) | 10 | 439 | SL~S~IA (SEQ ID NO: 21) | 13 |

TABLE 7

| TCEM IIB | | | | | |
|---|---|---|---|---|---|
| pos | TCR II -1, 3, 5, 7, 8) | FC TCR II (-1, 3, 5, 7, 8) | Occurrences in 447 isolates N Rows | Substitution | |
| 37 | G~~V~T~TN (SEQ ID NO: 22) | 0 | 366 | G~~V~T~TD (SEQ ID NO: 23) | 14 |
| 38 | G~~V~T~TN (SEQ ID NO: 22) | 0 | 2 | G~~V~T~TD (SEQ ID NO: 23) | 14 |
| 42 | G~~V~T~TN (SEQ ID NO: 22) | 0 | 1 | G~~V~T~TD (SEQ ID NO: 23) | 14 |
| 50 | G~~V~T~TN (SEQ ID NO: 22) | 0 | 1 | G~~V~T~TD (SEQ ID NO: 23) | 14 |
| 54 | T~~V~S~ST (SEQ ID NO: 24) | 7 | 421 | T~~V~S~TT (SEQ ID NO: 25) | 16 |
| 55 | T~~V~S~ST (SEQ ID NO: 24) | 7 | 2 | T~~V~S~TT (SEQ ID NO: 25) | 16 |

TABLE 8

| TCEM I | | | | | |
|---|---|---|---|---|---|
| pos | TCR I (4, 5, 6, 7, 8) | FC TCR I (4, 5, 6, 7, 8) | Occurrences in 447 isolates N Rows | Substitution | |
| 4 | ~~~LSYIS~ (SEQ ID NO: 26) | 9 | 1 | ~~~LSYIF~ (SEQ ID NO: 27) | 14 |
| 22 | ~~~STATL~ (SEQ ID NO: 28) | 10 | 441 | ~~~RTATL~ (SEQ ID NO: 29) | 13 |
| 23 | ~~~STATL~ (SEQ ID NO: 28) | 10 | 2 | ~~~RTATL~ (SEQ ID NO: 29) | 13 |
| 35 | ~~~STATL~ (SEQ ID NO: 28) | 10 | 1 | ~~~RTATL~ (SEQ ID NO: 29) | 13 |
| 58 | ~~~GSSTG~ (SEQ ID NO: 30) | 8 | 1 | ~~~SSSTG~ (SEQ ID NO: 31) | 12 |

When the proposed substitute motifs were compared to motifs occurring in the proteome the number of matches, again for the subset shown above, are those shown in Table 9.

TABLE 9

| TCR II (2, 3, 5, 7, 8) | Occurrences in proteome N Rows | TCR II (-1, 3, 5, 7, 8) | Occurrences in proteome N Rows | TCR I (4, 5, 6, 7, 8) | Occurrences in proteome N Rows |
|---|---|---|---|---|---|
| SL~S~IA (SEQ ID NO: 32) | 80 | G~~V~T~TD (SEQ ID NO: 23) | 17 | ~~~LSYIF~ (SEQ ID NO: 27) | 14 |
| TG~I~DS (SEQ ID NO: 33) | 23 | T~~V~S~TT (SEQ ID NO: 24) | 61 | ~~~RSTAY~ (SEQ ID NO: 34) | 8 |
| VP~G~IV (SEQ ID NO: 17) | 20 | | | ~~~RTATL~ (SEQ ID NO: 29) | 28 |
| | | | | ~~~SSSTG~ (SEQ ID NO: 31) | 166 |

The identity of each protein with a match was determined and reviewed. The corresponding subset of this dataset for TCEM IIA only is shown in Table 9.

TABLE 10

| TCR II (2,3,5,7,8) | protein_id | pos | peptide |
|---|---|---|---|
| SL~S~IA (SEQ ID NO: 32) | CTGEF_HUMAN | 179 | DESKSLKSQIAEAKI (SEQ ID NO: 35) |
| SL~S~IA (SEQ ID NO: 32) | CTGE9_HUMAN | 179 | DESKSLKSQIAEAKI (SEQ ID NO: 35) |
| SL~S~IA (SEQ ID NO: 32) | A8MXH5_HUMAN | 1245 | APGISLPSLIAGQPG (SEQ ID NO: 36) |
| SL~S~IA (SEQ ID NO: 32) | B4DDH2_HUMAN | 176 | WIIQSLASAIAYLHN (SEQ ID NO: 37) |
| SL~S~IA (SEQ ID (SEQ ID NO: 32) | C9J319_HUMAN | 176 | WIIQSLASAIAYLHN (SEQ ID NO: 37) |
| SL~S~IA (SEQ ID NO: 32) | C9J5X9_HUMAN | 768 | VTLSSLSSAIAKHES (SEQ ID NO: 38) |
| SL~S~IA (SEQ ID NO: 32) | C9J6X7_HUMAN | 176 | WIIQSLASAIAYLHN (SEQ ID NO: 37) |
| SL~S~IA (SEQ ID NO: 32) | D6RBI9_HUMAN | 34 | GPPSSLMSEIADLTF (SEQ ID NO: 39) |
| SL~S~IA (SEQ ID NO: 32) | D6RBR6_HUMAN | 34 | GPPSSLMSEIADLTF (SEQ ID NO: 39) |
| SL~S~IA (SEQ ID NO: 32) | D6REL6_HUMAN | 34 | GPPSSLMSEIADLTF (SEQ ID NO: 39) |
| SL~S~IA (SEQ ID NO: 32) | D6RFG3_HUMAN | 34 | GPPSSLMSEIADLTF (SEQ ID NO: 39) |
| SL~S~IA (SEQ ID NO: 32) | E7EU13_HUMAN | 55 | SLSLSLPSTIAAPHP (SEQ ID NO: 40) |

TABLE 10-continued

| TCR II (2,3,5,7,8) | protein_id | pos | peptide |
|---|---|---|---|
| SL~S~IA (SEQ ID NO: 32) | F5GZX4_HUMAN | 699 | LFPHSLLSVIANFIP (SEQ ID NO: 41) |
| SL~S~IA (SEQ ID NO: 32) | F5H3Q5_HUMAN | 1220 | APGISLPSLIAGQPG (SEQ ID NO: 42) |
| SL~S~IA (SEQ ID NO: 32) | F5H643_HUMAN | 450 | LFPHSLLSVIANFIP (SEQ ID NO: 43) |
| SL~S~IA (SEQ ID NO: 32) | F5H851_HUMAN | 1220 | APGISLPSLIAGQPG (SEQ ID NO: 42) |
| SL~S~IA (SEQ ID NO: 32) | F8W898_HUMAN | 478 | LFPHSLLSVIANFIP (SEQ ID NO: 43) |
| SL~S~IA (SEQ ID NO: 32) | F8WAK5_HUMAN | 30 | WIIQSLASAIAYLHN (SEQ ID NO: 44) |
| SL~S~IA (SEQ ID NO: 32) | H0Y2S9_HUMAN | 939 | ALEASLISQIADSLK (SEQ ID NO: 45) |
| SL~S~IA (SEQ ID NO: 32) | H0Y7E2_HUMAN | 249 | ALEASLISQIADSLK (SEQ ID NO: 45) |
| SL~S~IA (SEQ ID NO: 32) | H0YEZ7_HUMAN | 129 | WIIQSLASAIAYLHN (SEQ ID NO: 44) |
| SL~S~IA (SEQ ID NO: 32) | H0YL06_HUMAN | 79 | VNLFSLGSAIAYSAY (SEQ ID NO: 46) |
| SL~S~IA (SEQ ID NO: 32) | H7C4U7_HUMAN | 501 | NDTVSLASSIATQPE (SEQ ID NO: 47) |
| SL~S~IA (SEQ ID NO: 32) | H7C535_HUMAN | 507 | NDTVSLASSIATQPE (SEQ ID NO: 47) |
| SL~S~IA (SEQ ID NO: 32) | H7C5T8_HUMAN | 412 | NDTVSLASSIATQPE (SEQ ID NO: 47) |

TABLE 10-continued

| TCR II (2,3,5,7,8) | protein_id | pos | peptide |
|---|---|---|---|
| SL~S~IA (SEQ ID NO: 32) | I6L9I8_HUMAN | 34 | GPPSSLMSEIADLTF (SEQ ID NO: 48) |
| SL~S~IA (SEQ ID NO: 32) | J3KTP8_HUMAN | 304 | LGEQSLQSRIAALTV (SEQ ID NO: 49) |
| SL~S~IA (SEQ ID NO: 32) | J3QSH4_HUMAN | 114 | SSRTSLVSTIAGILS (SEQ ID NO: 50) |
| SL~S~IA (SEQ ID NO: 32) | K7EJN9_HUMAN | 57 | PQITSLPSNIALSPT (SEQ ID NO: 51) |
| SL~S~IA (SEQ ID NO: 32) | K7ENM8_HUMAN | 255 | PQITSLPSNIALSPT (SEQ ID NO: 51) |
| SL~S~IA (SEQ ID NO: 32) | K7EQH3_HUMAN | 147 | PQITSLPSNIALSPT (SEQ ID NO: 51) |
| SL~S~IA (SEQ ID NO: 32) | ECM2_HUMAN | 160 | TVSYSLLSGIALNDR (SEQ ID NO: 52) |
| SL~S~IA (SEQ ID NO: 32) | CTGE8_HUMAN | 179 | DESKSLKSQIAEAKI (SEQ ID NO: 53) |
| SL~S~IA (SEQ ID NO: 32) | CLD2_HUMAN | 167 | GIISSLFSLIAGIIL (SEQ ID NO: 54) |
| SL~S~IA (SEQ ID NO: 32) | CO4A6_HUMAN | 1245 | APGISLPSLIAGQPG (SEQ ID NO: 55) |
| SL~S~IA (SEQ ID NO: 32) | CO4A6_HUMAN | 1244 | APGISLPSLIAGQPG (SEQ ID NO: 55) |
| SL~S~IA (SEQ ID NO: 32) | VEZF1_HUMAN | 123 | SSRTSLVSTIAGILS (SEQ ID NO: 56) |
| SL~S~IA (SEQ ID NO: 32) | K2022_HUMAN | 96 | VNAISLTSGIAKGLN (SEQ ID NO: 57) |
| SL~S~IA (SEQ ID NO: 32) | GP179_HUMAN | 1450 | ECSGSLGSGIAEVCL (SEQ ID NO: 58) |
| SL~S~IA (SEQ ID NO: 32) | RFIP1_HUMAN | 593 | SVFSSLSSPIAAPIS (SEQ ID NO: 59) |
| SL~S~IA (SEQ ID (SEQ ID NO: 32) | CTGE6_HUMAN | 179 | DESKSLKSQIAEAKI (SEQ ID NO: 60) |
| SL~S~IA (SEQ ID NO: 32) | MTMRD_HUMAN | 147 | SLNVSLESLIANLCA (SEQ ID NO: 61) |
| SL~S~IA (SEQ ID NO: 32) | MTMRD_HUMAN | 147 | SLNVSLESLIANLCA (SEQ ID NO: 61) |
| SL~S~IA (SEQ ID NO: 32) | TRI42_HUMAN | 332 | ERAASLFSAIAKFKA (SEQ ID NO: 62) |

TABLE 10-continued

| TCR II (2,3,5,7,8) | protein_id | pos | peptide |
|---|---|---|---|
| SL~S~IA (SEQ ID NO: 32) | TRI42_HUMAN | 332 | ERAASLFSAIAKFKA (SEQ ID NO: 62) |
| SL~S~IA (SEQ ID NO: 32) | CTGE4_HUMAN | 179 | DESKSLKSQIAEAKI (SEQ ID NO: 63) |
| SL~S~IA (SEQ ID NO: 32) | FANCB_HUMAN | 768 | VTLSSLSSAIAKHES (SEQ ID NO: 64) |
| SL~S~IA (SEQ ID NO: 32) | ARAP1_HUMAN | 300 | SLSLSLPSTIAAPHP (SEQ ID NO: 65) |
| SL~S~IA (SEQ ID NO: 32) | ARAP1_HUMAN | 60 | SLSLSLPSTIAAPHP (SEQ ID NO: 65) |
| SL~S~IA (SEQ ID NO: 32) | ARAP1_HUMAN | 60 | SLSLSLPSTIAAPHP (SEQ ID NO: 65) |
| SL~S~IA (SEQ ID NO: 32) | ARAP1_HUMAN | 300 | SLSLSLPSTIAAPHP (SEQ ID NO: 65) |
| SL~S~IA (SEQ ID NO: 32) | ARAP1_HUMAN | 55 | SLSLSLPSTIAAPHP (SEQ ID NO: 65) |
| SL~S~IA (SEQ ID NO: 32) | ARAP1_HUMAN | 55 | SLSLSLPSTIAAPHP (SEQ ID NO: 65) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | MAGI1_HUMAN | 626 | NDTVSLASSIATQPE (SEQ ID NO: 66) |
| SL~S~IA (SEQ ID NO: 32) | YIPF2_HUMAN | 294 | PQITSLPSNIALSPT (SEQ ID NO: 67) |
| SL~S~IA (SEQ ID NO: 32) | STK33_HUMAN | 217 | WIIQSLASAIAYLHN (SEQ ID NO: 68) |
| SL~S~IA (SEQ ID NO: 32) | STK33_HUMAN | 217 | WIIQSLASAIAYLHN (SEQ ID NO: 68) |

TABLE 10-continued

| TCR II (2,3,5,7,8) | protein_id | pos | peptide |
|---|---|---|---|
| SL~S~IA (SEQ ID NO: 32) | ZMY15_HUMAN | 468 | WRGLSLDSPIAVLLT (SEQ ID NO: 69) |
| SL~S~IA (SEQ ID NO: 32) | ZMY15_HUMAN | 468 | WRGLSLDSPIAVLLT (SEQ ID NO: 69) |
| SL~S~IA (SEQ ID NO: 32) | EPN3_HUMAN | 34 | GPPSSLMSEIADLTF (SEQ ID NO: 70) |
| SL~S~IA (SEQ ID NO: 32) | EPN3_HUMAN | 34 | GPPSSLMSEIADLTF (SEQ ID NO: 70) |
| SL~S~IA (SEQ ID NO: 32) | O51V1_HUMAN | 98 | IREISLDSCIAQSYF (SEQ ID NO: 71) |
| SL~S~IA (SEQ ID NO: 32) | RPA2_HUMAN | 661 | LFPHSLLSVIANFIP (SEQ ID NO: 72) |
| SL~S~IA (SEQ ID NO: 32) | RPA2_HUMAN | 605 | LFPHSLLSVIANFIP (SEQ ID NO: 72) |
| SL~S~IA (SEQ ID NO: 32) | T184C_HUMAN | 90 | VPIYSLDSWIALKYP (SEQ ID NO: 73) |
| SL~S~IA (SEQ ID NO: 32) | T184C_HUMAN | 90 | VPIYSLDSWIALKYP (SEQ ID NO: 73) |
| SL~S~IA (SEQ ID NO: 32) | MPRG_HUMAN | 123 | VNLFSLGSAIAYSAY (SEQ ID NO: 74) |
| SL~S~IA (SEQ ID NO: 32) | SCN8A_HUMAN | 1271 | IVAVSLVSLIANALG (SEQ ID NO: 75) |
| SL~S~IA (SEQ ID NO: 32) | SCN8A_HUMAN | 1271 | IVAVSLVSLIANALG (SEQ ID NO: 75) |
| SL~S~IA (SEQ ID NO: 32) | SCN8A_HUMAN | 1282 | IVAVSLVSLIANALG (SEQ ID NO: 75) |
| SL~S~IA (SEQ ID NO: 32) | PCDB7_HUMAN | 347 | LLLSSLTSPIAENSP (SEQ ID NO: 76) |
| SL~S~IA (SEQ ID NO: 32) | EPN1_HUMAN | 34 | GPSSSLMSEIADLTY (SEQ ID NO: 77) |
| SL~S~IA (SEQ ID NO: 32) | EPN1_HUMAN | 145 | GPSSSLMSEIADLTY (SEQ ID NO: 77) |
| SL~S~IA (SEQ ID NO: 32) | EPN1_HUMAN | 34 | GPSSSLMSEIADLTY (SEQ ID NO: 77) |
| VP~G~IV (SEQ ID NO: 17) | A8MT40_HUMAN | 451 | NDLDVPVGHIVHTGM (SEQ ID NO: 86) |
| VP~G~IV (SEQ ID NO: 17) | D6RB49_HUMAN | 658 | VVYKVPKGKIVPNLN (SEQ ID NO: 78) |

TABLE 10-continued

| TCR II (2,3,5,7,8) | protein_id | pos | peptide |
|---|---|---|---|
| VP~G~IV (SEQ ID NO: 17) | E9PD98_HUMAN | 1700 | LLHEVPTGEIVVRLD (SEQ ID NO: 79) |
| VP~G~IV (SEQ ID NO: 17) | F8WDR2_HUMAN | 183 | NWGAVPFGKIVGKFP (SEQ ID NO: 80) |
| VP~G~IV (SEQ ID NO: 17) | H0Y6Q5_HUMAN | 27 | CVPSVPVGPIVLTSA (SEQ ID NO: 81) |
| VP~G~IV (SEQ ID NO: 17) | USH2A_HUMAN | 1548 | FRTKVPEGLIVFAAS (SEQ ID NO: 82) |
| VP~G~IV (SEQ ID NO: 17) | USH2A_HUMAN | 1548 | FRTKVPEGLIVFAAS (SEQ ID NO: 82) |
| VP~G~IV (SEQ ID NO: 17) | EF2_HUMAN | 460 | PIEDVPCGNIVGLVG (SEQ ID NO: 83) |
| VP~G~IV (SEQ ID NO: 17) | ITSN1_HUMAN | 1700 | LLHEVPTGEIVVRLD (SEQ ID NO: 84) |
| VP~G~IV (SEQ ID NO: 17) | ITSN1_HUMAN | 1629 | LLHEVPTGEIVVRLD (SEQ ID NO: 84) |
| VP~G~IV (SEQ ID NO: 17) | ITSN1_HUMAN | 1695 | LLHEVPTGEIVVRLD (SEQ ID NO: 84) |
| VP~G~IV (SEQ ID NO: 17) | ITSN1_HUMAN | 1639 | LLHEVPTGEIVVRLD (SEQ ID NO: 84) |
| VP~G~IV (SEQ ID NO: 17) | DTHD1_HUMAN | 618 | VVYKVPKGKIVPNLN (SEQ ID NO: 85) |
| VP~G~IV (SEQ ID NO: 17) | DTHD1_HUMAN | 453 | VVYKVPKGKIVPNLN (SEQ ID NO: 85) |
| VP~G~IV (SEQ ID NO: 17) | PDPR_HUMAN | 551 | NDLDVPVGHIVHTGM (SEQ ID NO: 86) |
| VP~G~IV (SEQ ID NO: 17) | SHCBP_HUMAN | 235 | LEDRVPSGLIVDYHN (SEQ ID NO: 87) |
| VP~G~IV (SEQ ID NO: 17) | HASP_HUMAN | 314 | QEASVPKGRIVPRGI (SEQ ID NO: 88) |
| VP~G~IV (SEQ ID NO: 17) | FAP24_HUMAN | 10 | GPVHVPLGHIVANEK (SEQ ID NO: 89) |
| VP~G~IV (SEQ ID NO: 17) | TR61B_HUMAN | 183 | NWGAVPFGKIVGKFP (SEQ ID NO: 90) |

TABLE 10-continued

| TCR II (2,3,5,7,8) | protein_id | pos | peptide |
|---|---|---|---|
| VP~G~IV (SEQ ID NO: 17) | FNDC4_HUMAN | 65 | VSWDVPEGNIVIGYS (SEQ ID NO: 91) |

Example 9 Example of a Join with Human Proteome

In Example 4 we describe certain TCEM motifs found in the hemagglutinin of a specific strain of influenza and having a high binding affinity to DQA1*01:02/DQB1*06:02 DQ.

As described in Example 1 we have extracted the TCEM motifs found in the human proteome. By matching (joining) motif datasets from influenza and the human proteome we demonstrated that the motifs AG~G~II (SEQ ID NO: 470) and NA~S~II (SEQ ID NO: 471) are found in proteins shown in FIG. 13. This illustrates the process by which we approach the search for a TCEM mimic in self-proteins.

Example 10. Identification of Probable Treg Motifs in Tumor Associated Antigen Proteins We examined a number of tumor associated antigens (TAA) for the presence of TCEM motifs which might contribute to down regulation of the immune response to tumors thereby creating tolerance. Some TAA have distinct and highly probable Treg motifs (e.g. PMEL). In other cases the balance of immunostimulation and immunosuppression appears more subtle (e.g. MART, MAGE). In neoplasias a consideration which differs from healthy tissues is that there is a density of cells locally or metastasized, all expressing the same motifs, which can lead to a shift in the relative emphasis or frequency of a given motif locally or systemically, potentially starting a downward spiral of suppression and tolerance. Hence what appears as a FC14 relative to the normal frequency in a balanced database of IgV may locally become much more common and lead to an accumulation of cognate T cells. This is especially the case when the GEM binding is particularly high affinity, ensuring that the TCEM exposure to T cells is extended.

In this example we examine TCEM motifs in TAA, PMEL MART and MAGE-1. These are examples and should not therefore be considered limiting. Rather the intent is to show an approach that allows examination of the TCEMs in determining overall outcome of the tumor immune response.

The same approach is applicable to characterizing the TCEM in a tumor neo antigen created by a novel mutation and thus enabling characterization of the immune response to a neo antigen and enabling various intervention strategies. Thus the examples applied to well recognize tumor associated antigens should not be considered limiting.

Identification of Probable Treg Peptides in PMEL

Figure 14:
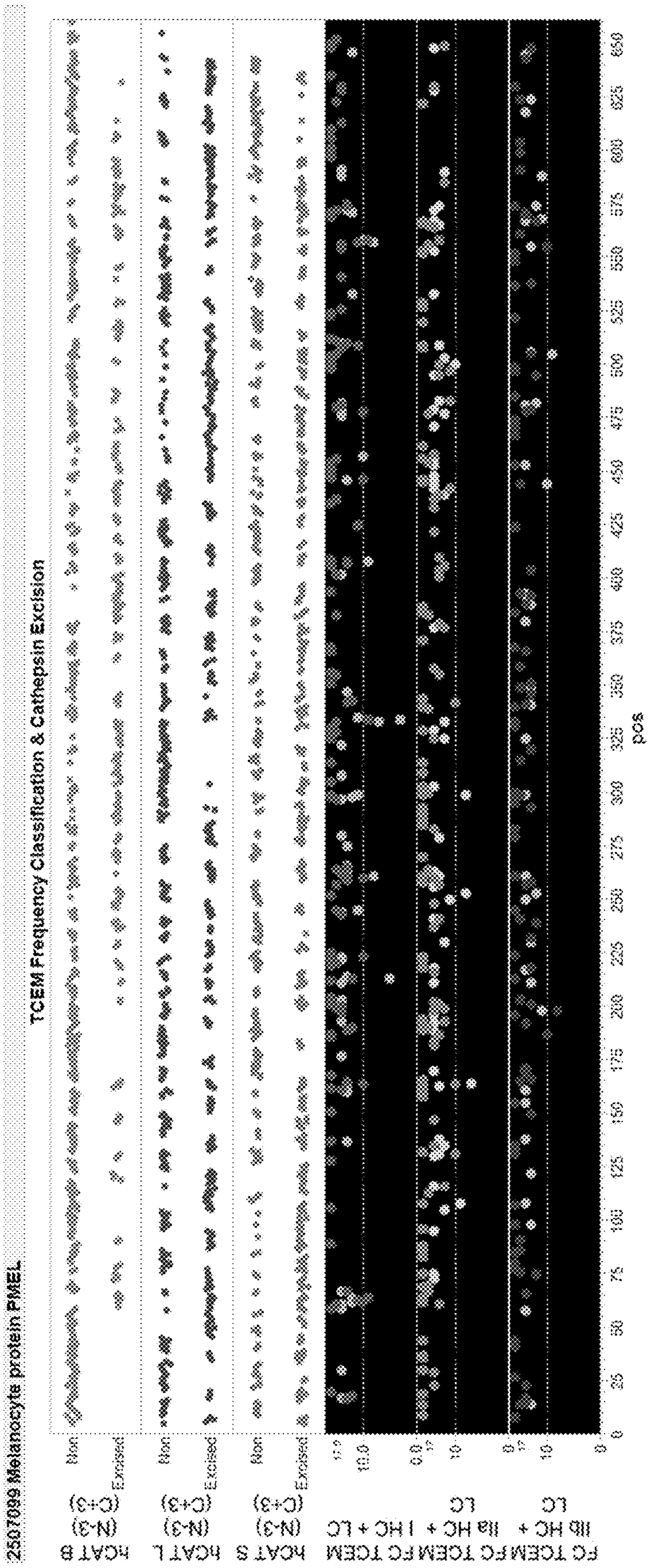
FIG. 14: PMEL showing the distribution of TCEM found in the IgV database. The upper tier indicates motifs in peptides with high probability of being excised by cathepsin. The lower tier indicates the location of IgV TCEM. In each of the three TCEM registers. In each row the dotted white line indicates FC 10 and any point lying below the dotted line is a high frequency motif capable of acting as a Tregulatory motif.

An evaluation of the TCEM in PMEL (gi 2507099 Melanocyte protein PMEL) was conducted based on comparison with the frequency of occurrence of TCEM motifs in the immunoglobulin variable region reference databases comprising both heavy and light chains. Two probable Treg motifs are identified (FIG. 14). These both have binding to MHC I alleles. The peptide with index position of its 9 mer at 213 is a FC5 peptide found in light chain variable regions, ~~SVSVS~ (SEQ ID NO: 472); the 9-mer peptide with index position at 334 is a light chain FC 3 ~~PGQAP~ (SEQ ID NO: 473). When evaluated along with their corresponding GEM binding both have several high binding alleles and generate suppressive indices of 33,519 and 20,179 respectively. This indicates more high binding alleles for the peptide at 213. Either peptide would be expected to cause significant down regulation of a response to PMEL.

When two isoforms of PMEL (gi 318037593 melanocyte protein PMEL isoform 2 precursor and gi318037595 melanocyte protein PMEL isoform 1 precursor) are compared, the isoform 1 is found to contain both motifs whereas the isoform 2 only contains ~~PGQAP~. Potential Tregs in PMEL are recorded in Table 12

MART-1

The distribution of TCEM motifs in MART presents a more subtle picture.

The MART-1 protein (Melanoma antigen recognized by T-cells 1) was recognized in 1994 to be overexpressed in melanoma (Coulie, [29] Kawakami [30,31]). It was subsequently found to be expressed in some other cancers, including but not limited to breast cancer. Specific peptides were identified which upregulated CD8+ responses in melanoma patients (Kawakami [31]), in particular a peptide AAGIGILTV (SEQ ID NO: 474) which comprises amino acid positions 27-35 was identified as an immunodominant CD8+ epitope restricted by HLA A 0201. This peptide has been deployed as therapeutic vaccines for melanoma [32, 33]. Notably this work was with isolated peptides. Other peptides in MART-1 have further been described as having binding affinity for other MHC-I HLA alleles [34] and for certain MHC-II alleles [35]. It has further been shown that the co-administration of a drug which curtails Treg activity enhances the immune response to the peptide aa27-35 used as a therapeutic melanoma vaccine [36,37]. This suggests that Tregs may play a key role in modulating the response to MART.

Figure 15:
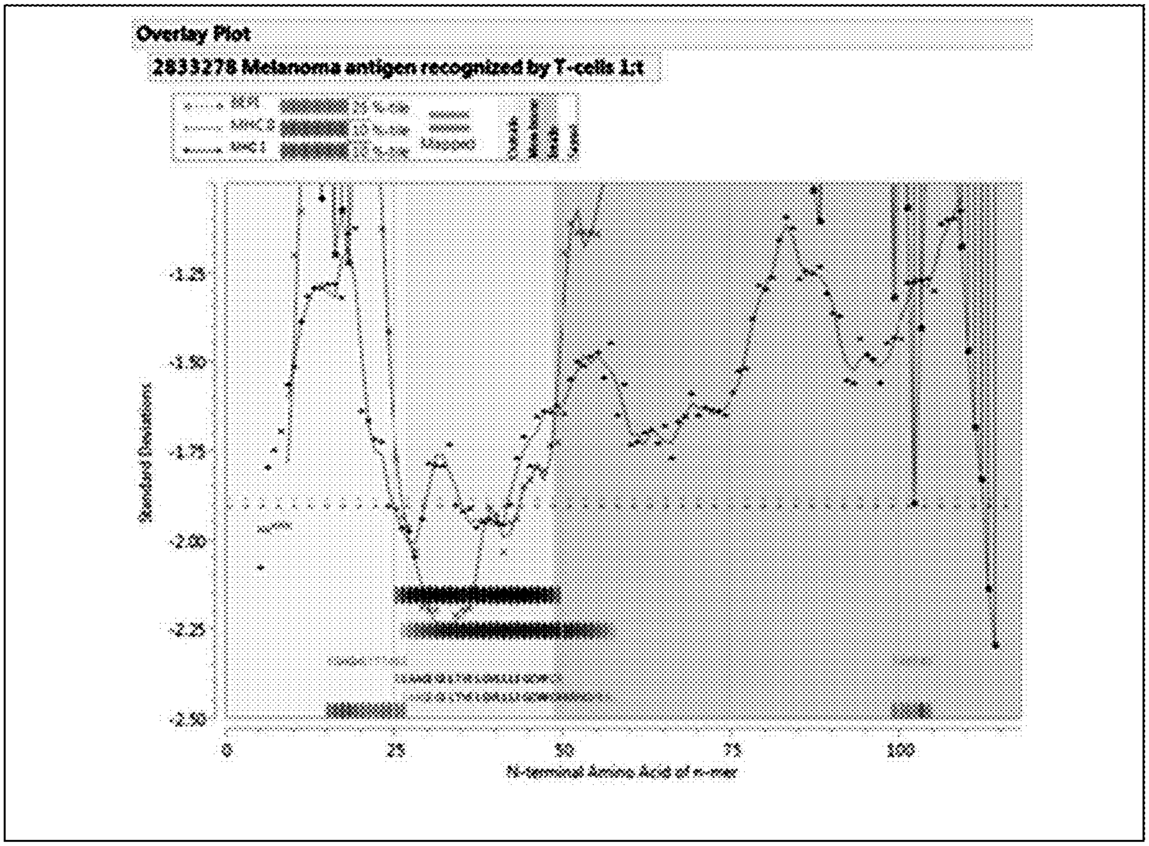
FIG. 15: MART-1 population permuted plot shows a single epitope dense region in this relatively small protein, lying between amino acids 25-50, as indicated by the blue and red lines. The permuted average of predicted MHC binding affinity is calculated for each sequential peptide. For MHC-I 9-mers are used, for MHC-II 15-mers, each with a single amino acid displacement. At each sequential peptide position we examine every possible heterozygous pair of HLA and mouse MHC alleles and determine which allele of the pair has a higher predicted binding affinity. For each of the higher binding alleles of each pair, the mean and standard deviation of predicted binding affinities is calculated. The predicted binding affinity is represented in standard deviation units relative to the mean for all the peptides in the protein as a whole. As the lines on the graphic show the permuted average, any individual allele affinity may differ from the average. X axis: Sequential peptides are arrayed and numbered N-C. Positions are for the index amino acid of each sequential peptide, with a single amino acid displacement. The Red line shows the permuted average predicted MHC-IA and B (37 alleles) binding affinity by index position of sequential 9-mer peptides. The Blue line shows the permuted average predicted MHC-II DRB allele (16 alleles) binding affinity by index position of sequential 15-mer peptides. Both are plotted in standard deviation units, shown on the Y axis. Orange lines show the predicted probability of B-cell binding ("BEPI") for an amino acid centered in each sequential 9-mer peptide. Note that the standardized B-cell metric has been inverted (multiplied by −1) in order to overlay the standardized probability onto the same scale as the MHC data. Low numbers for MHC data represent high binding affinity, whereas low numbers equate to high BEPI contact probability. Ribbons (Red: MHC-I, Blue: MHC-II) indicate the 10% highest predicted affinity binding. Orange ribbons indicate the top 25% predicted probability B-cell binding. Background shading shows membrane (green) extramembrane (yellow), intramembrane (pink) location. Signal peptides have white background.

In order to better understand the balance of up-regulating and down-regulating immune responses invoked by the MART-1 protein we first examined the predicted MHC binding affinity as determined by the methods previously described (PCT US2011/029192, incorporated herein by reference). This identified a cluster of peptides around 25-50 which have high binding affinity for various MHC-I alleles. This is shown in FIG. 15 and Table 11.

Table 11 shows that a number of MHC-I alleles have high binding affinity for peptides with their index positions between 25 and 50. The binding affinity is shown in standard deviation units, with higher binding indicated by more negative numbers.

| index amino acid | 9-mer | nA_0201 |
|---|---|---|
| 25 | EEAAGIGIL (SEQ ID NO: 92) | 0.71 |
| 26 | EAAGIGILT(SEQ ID NO: 93) | 0.10 |
| **27** | **AAGIGILTV**(SEQ ID NO: 94) | **-1.17** |
| 28 | AGIGILTVI(SEQ ID NO: 95) | -1.25 |
| 29 | GIGILTVIL(SEQ ID NO: 96) | -1.42 |
| 30 | IGILTVILG(SEQ ID NO: 97) | -1.50 |
| 31 | GILTVILGV(SEQ ID NO: 98) | -2.23 |
| 32 | ILTVILGVL(SEQ ID NO: 99) | -2.02 |

-continued

| index amino acid | 9-mer | nA_0201 |
|---|---|---|
| 33 | LTVILGVLL(SEQ ID NO: 100) | -1.61 |
| 34 | TVILGVLLL(SEQ ID NO: 101) | -1.59 |
| 35 | VILGVLLLI(SEQ ID NO: 102) | -2.17 |
| 36 | ILGVLLLIG(SEQ ID NO: 103) | -2.05 |
| 37 | LGVLLLIGC(SEQ ID NO: 104) | -1.41 |
| 38 | GVLLLIGCW(SEQ ID NO: 105) | 0.31 |
| 39 | VLLLIGCWY(SEQ ID NO: 106) | -1.12 |
| 40 | LLLIGCWYC(SEQ ID NO: 107) | -1.73 |
| 41 | LLIGCWYCR(SEQ ID NO: 108) | -0.55 |
| 42 | LIGCWYCRR(SEQ ID NO: 109) | 0.47 |
| 43 | IGCWYCRRR(SEQ ID NO: 110) | 0.95 |
| 44 | GCWYCRRRN(SEQ ID NO: 111) | 0.95 |
| 45 | CWYCRRRNG(SEQ ID NO: 112) | -1.09 |
| 46 | WYCRRRNGY(SEQ ID NO: 113) | -0.27 |
| 47 | YCRRRNGYR(SEQ ID NO: 114) | 0.83 |
| 48 | CRRRNGYRA(SEQ ID NO: 115) | -0.08 |
| 49 | RRRNGYRAL(SEQ ID NO: 116) | -0.41 |
| 50 | RRNGYRALM(SEQ ID NO: 117) | -0.12 |

We further showed, by application of the methods described in PCT US2014/041525, incorporated herein by reference, that many of the high binding peptides are excised by cathepsin enabling their binding by MHC. Notably for A*0201 several peptides have higher predicted binding affinity than that which has its index position at aa 27 (AAGIGILTV), as seen in Table 3. However Kawakami [31] showed that only those with index at 27 and 29 stimulated a response. Index position 28 was not tested by Kawakami.

Figure 16:
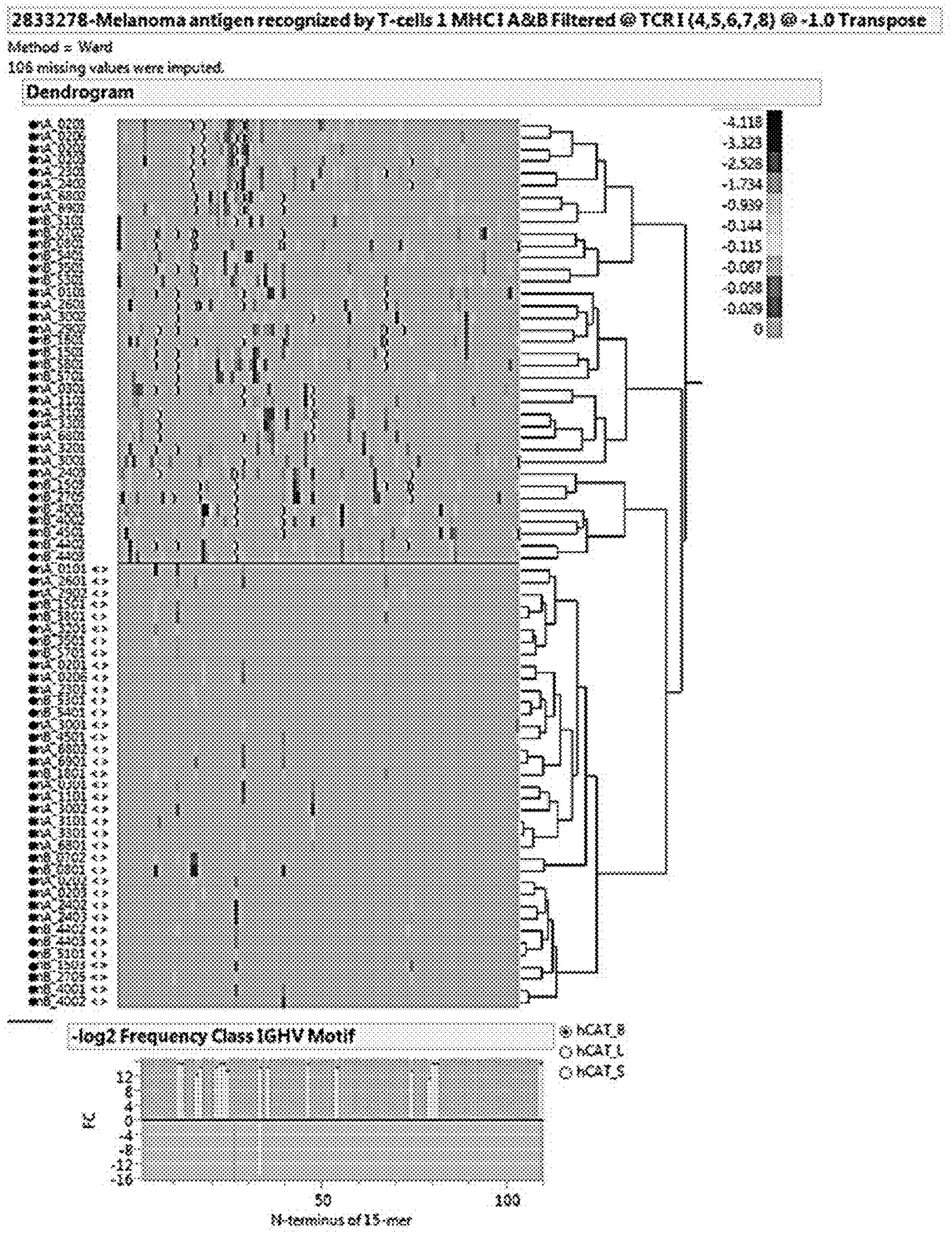
FIG. 16: Identification of MHC-I T-cell exposed motifs of IGHV origin in MART 1 that are found in the database of IGHV Affinities used in the comparisons were based on zero mean unit variance, within-protein transformed data. A database of approximately 40,000 IGHV was used as the reference comparison as described in Example 1. As any particular T-cell exposed motif in the IGHV is found up to thousands of times with different groove exposed motifs (GEMS) each motif has a different characteristic mean affinities (zero mean, unit variance) that was used in the comparison. For this visualization of locations of IGHV motifs in the MART 1 target protein a statistical threshold was selected of −1 standard deviation below the mean affinity for BOTH the target protein AND the IGHV comparative motifs. The locations of the matching TCEMs were then identified using the threshold mask. As a visual aid the locations of the TCEM from the IGHV that match those in the target protein are shown by a missing rectangle and X. Thus a missing rectangle corresponds to the location of a TCEM with a high affinity in the IGHV that is also found in the target protein with a high affinity. The lower panel shows a hierarchical cluster of MHC I alleles showing peptides which contain TCEM motifs which are present in the IGHV database in FC class 16 or more common, and which have a GEM binding affinity denoted by the pixel color of $-1\sigma$ or more. The top panel shows the peptides in the protein of interest MART-1 which have a binding affinity greater than $-1\sigma$, with those peptides which are present in the lower panel denoted on the top panel by X. Darker blue pixels indicate positions with higher binding affinity (as shown in the thermometer). In the bottom panel it is noted that a TCEM I at index position 33 is excised by cathepsin B and has high binding affinity for a majority of alleles.
Figure 17:
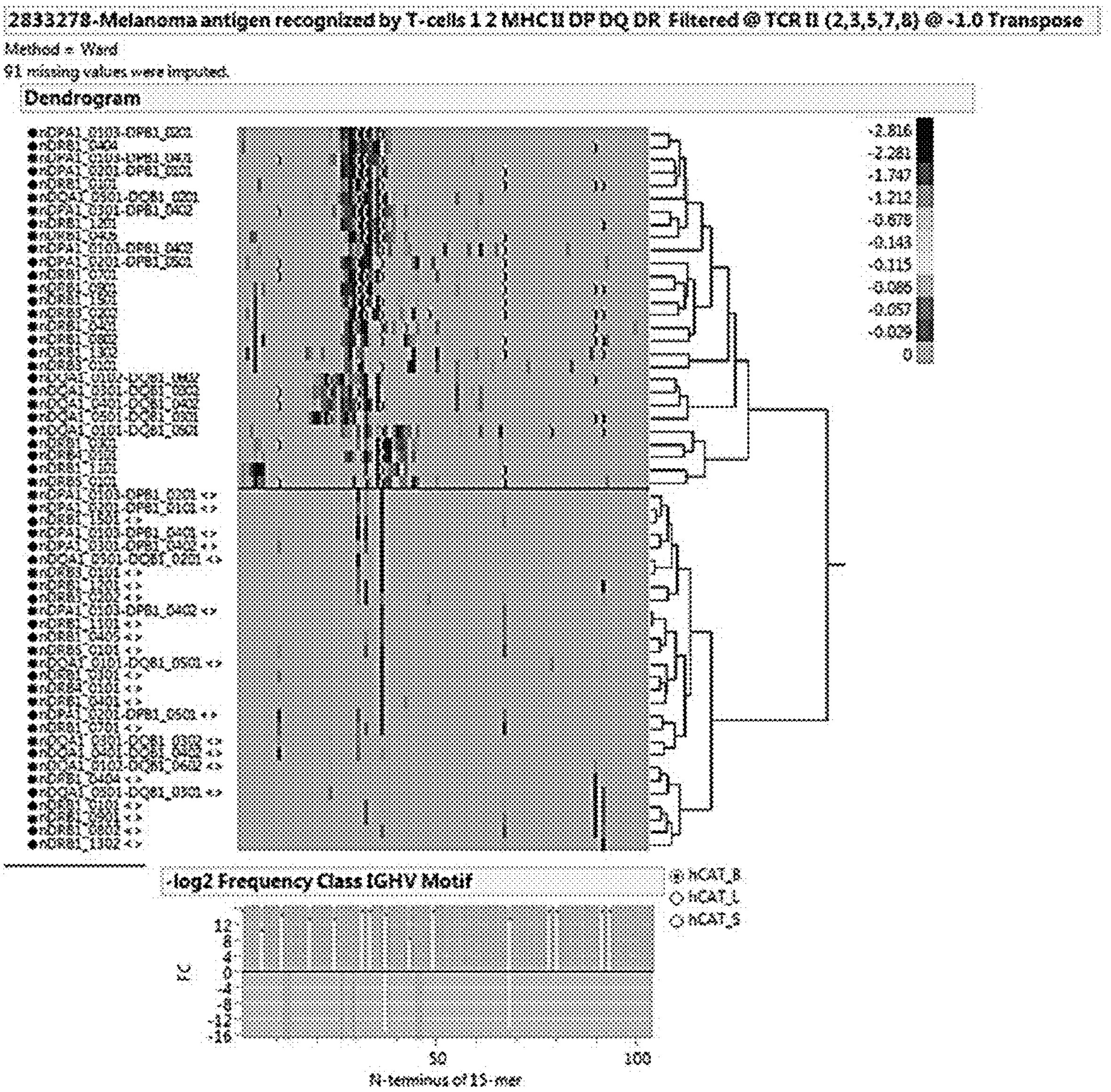
FIGS. 17 and 18: The same process is followed for MHC-II as was done for MHC-I in the prior figure. TCEM IIa and TCEM IIb motifs found in both MART I and the IGHV database are shown in the lower panel with the pixel color indicating affinity of GEM binding. The upper panel shows the high affinity binding peptides in MART I with the TCEM motifs from the lower panel denoted by X. The bottom ribbon indicates the frequency of the TCEM in the IGHV dataset and also whether the peptide is excised by any of the 3 cathepsins B, L or S. In both cases a high affinity TCEM is seen with index position 37, binding to nearly alleles and excised by cathepsin B.
Figure 18:
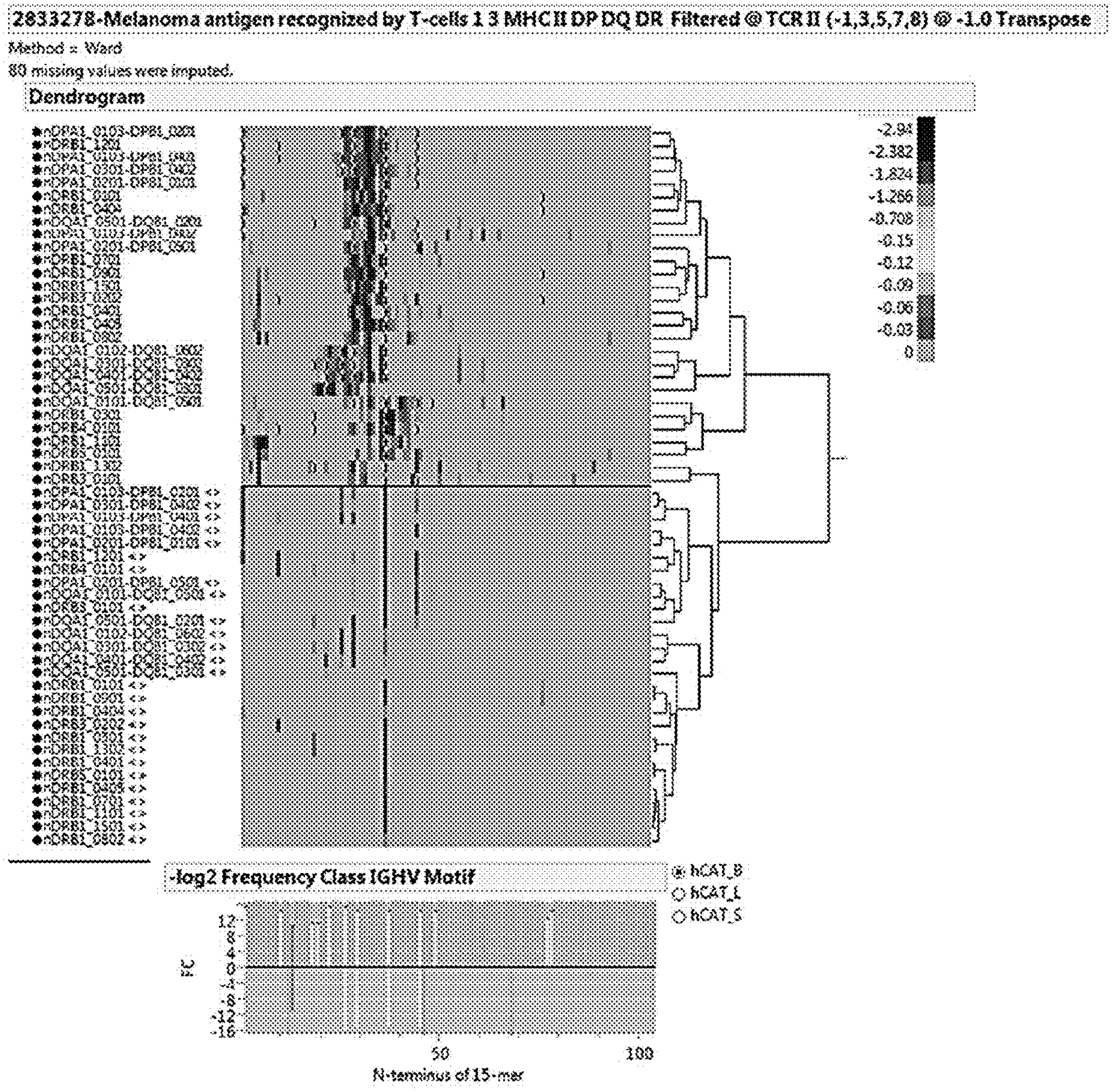

We then conducted an analysis to identify whether TCEM motifs in MART-1 were present in the reference database of IGHV described in Example 2. The results are shown in FIGS. 16, 17 and 18. FIG. 16 shows the comparative output for MHC-I motifs. FIGS. 17 and 18 shows output for TCEM IIa and TCEM IIb.

While several alleles of MHC-II have a strong binding affinity across the 25-50 positions, it is also noted that 15-mer peptides with index position at 37 are found to have high affinity TCEM IIa and TCEM IIb motifs for almost all MHC-II alleles, and these motifs are also in the IGHV reference database where they show consistently high predicted MHC binding affinity. The frequency of occurrence of the TCEM motif with index position 37 in the IgV database is TCEM IIA=FC 14 and TCEM IIB=FC 15. Thus the peptide with index at 37 is would find a preexisting cognate T cell population and would bind strongly to MHC II, for almost all MHC-II alleles. This peptide overlaps all those with MHC-I binding positions except those with index position 27 or lower. Specifically the Treg motifs in this instance are those contained in peptide LGVLLLIGCWYCRRR (SEQ ID NO: 475), where the underscores indicate TCEM IIa motif LLXGXWY (SEQ ID NO: 476) and LGVLLLIGCWYCRRR (SEQ ID NO: 477) where the underscores indicate TCEM IIb motif VXXLXGXWY (SEQ ID NO: 478). This is shown in FIG. 19

The finding of a potential Treg in this position is consistent with the observations of Kawakami that peptide index 27 binding A*0201 is an active immune up-regulator, while those in adjacent higher amino acid positions are not. It is also consistent with the observations of Mahnke and Rasku that depletion of Tregs enhances the immune response. Identification of this Treg offers opportunities to design interventions in which the Treg function is eliminated by specific T-cell targeting and thus enhances the therapeutic vaccine effect. Potential Tregs are recorded in Table 5

MAGE Proteins

Melanoma antigen E (MAGE) family antigens belong to the so-called cancer/testis TAA subclass and are expressed in normal tissues but particularly overexpressed in melanoma and several other tumor types. Epitopes derived from MAGE and recognized by cytotoxic T cells have been identified and are the subject of efforts to build anti-cancer vaccines.

We analyzed 19 proteins which are members of the melanoma associated antigen protein family and determined the presence of potential Tregs in each. As one example in particular the MAGE-1 protein (gi 148276977) was analyzed. Potential Tregs are recorded in Table 5

TABLE 12

Potential Tregs in Tumor associated antigens. In Motif column "X" indicates any amino acid.

| Index amino acid | 9-mer or 15-mer peptide | TCEM register | Motif |
|---|---|---|---|
| PMEL gi 2507099 | | | |
| 213 | SEQ ID NO: 118: PFSVSVSQ | TCEM I | SEQ ID NO: 119: XXSVSVSX |
| 334 | SEQ ID NO: 120: TTPGQAPT | TCEM I | SEQ ID NO: 121: XXPGQAPX |
| MART-1 gi 2833278 | | | |
| 37 | SEQ ID NO: 122: LGVLLLIGCWYCRRR | TCEM I | SEQ ID NO: 123: LLXGXWY |

TABLE 12-continued

Potential Tregs in Tumor associated antigens. In Motif column "X" indicates any amino acid.

| Index amino acid | 9-mer or 15-mer peptide | TCEM register | Motif |
|---|---|---|---|
| | | TCEM I | SEQ ID NO: 124: VXXLXGXWY |
| | MAGE-1 gi 148276977 | | |
| 33 | SEQ ID NO: 125: SSSSPLVLGTLEEVP | TCEM IIb | SEQ ID NO: 126: SXXLXLXTL |
| 34 | SEQ ID NO: 127: SSSPLVLGTLEEVPT | TCEM IIa | SEQ ID NO: 128: LVXGXLE |
| 36 | SEQ ID NO: 129: SPLVLGTLEEVPTAG | TCEM IIa | SEQ ID NO: 130: LGXLXEV |
| 192 | SEQ ID NO: 131: TGFLIIVLVMIAMEG | TCEM IIa | SEQ ID NO: 132: IIXLXMI |
| 193 | SEQ ID NO: 133: GFLIIVLVMIAMEGG | TCEM IIb | SEQ ID NO: 134: DXVXVXIA |

Example 11 Identification of TCEM Motifs in Myelin Basic Protein

Figure 20:
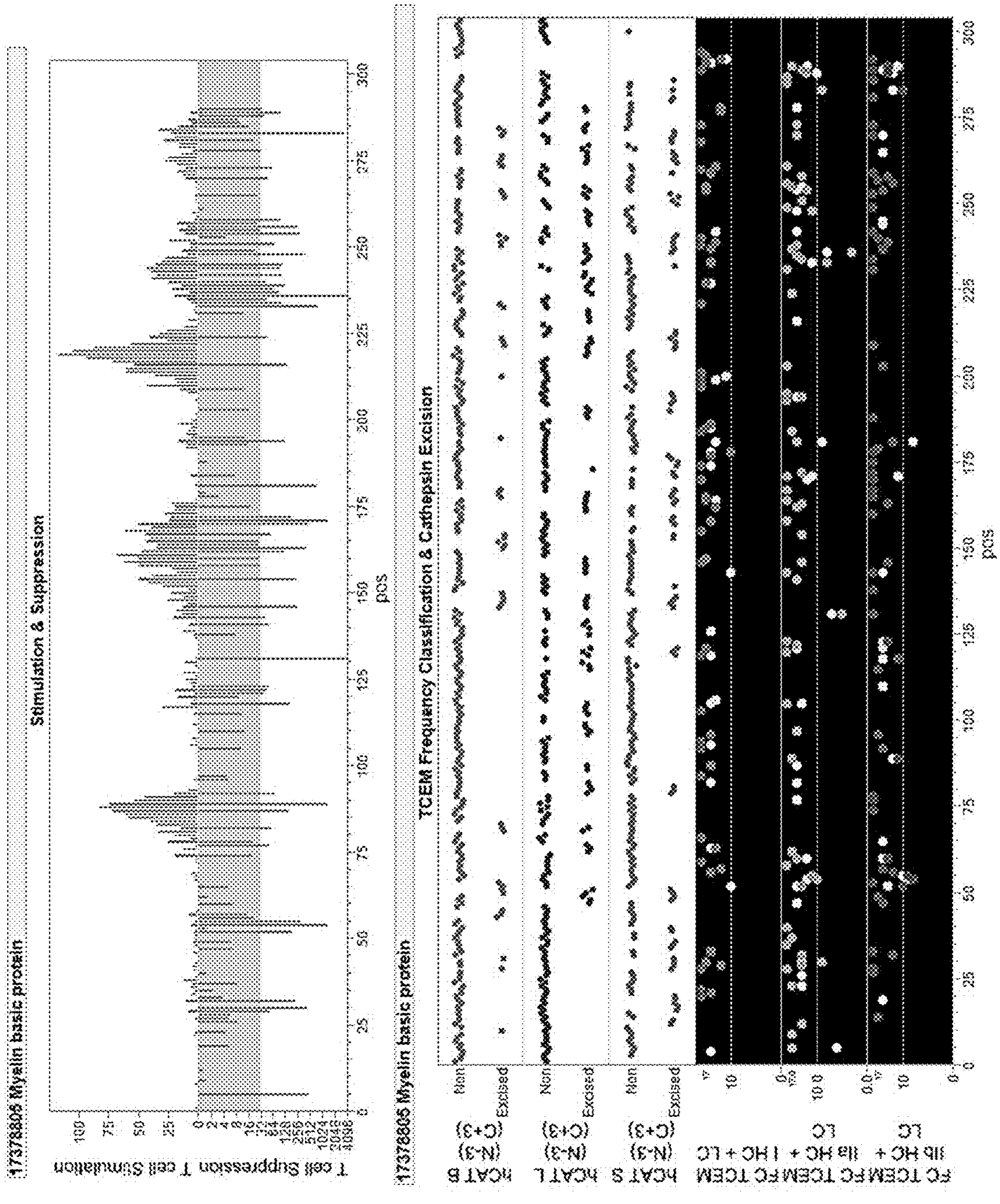
FIG. 20: Myelin basic protein showing the distribution of TCEM found in the IgV database. The upper tier indicates motifs in peptides with high probability of being excised by cathepsin. The lower tier indicates the location of IgV TCEM. In each of the three TCEM registers. In each row the dotted white line indicates FC 10 and any point lying below the dotted line is a high frequency motif capable of acting as a Tregulatory motif.

Myelin basic protein has been implicated as a target of autoimmune disease in which a demyelination occurs. We examined myelin basic protein including isotypes 1-4 and examined the occurrence of peptides with TCEMs that occur at high frequency in IGHV. Several TCEM IIa are present with Frequency Categories in IgV less than FC10 as shown in FIG. 20. Three of these in particular, at index positions 131, (FC5), 236 (FC3) and 283 (FC9) are also associated with high MHC binding affinity giving them a high suppressive index as shown in FIG. 20. These are summarized in Table 13.

TABLE 13

| Index amino acid | 15-mer peptide | TCEM register | Motif |
|---|---|---|---|
| | Myelin basic protein gi 17378805 | | |
| 131 | SEQ ID NO: 135: LDVMASQKRPSQRHG | TCEM IIa | SEQ ID NO: 136: ASXKXPS |
| 236 | SEQ ID NO: 137: SQGKGRGLSLSRFSW | TCEM IIa | SEQ ID NO: 138: GRXLXLS |
| 283 | SEQ ID NO: 139: TLSKIFKLGGRDSRS | TCEM IIa | SEQ ID NO: 140: IFXLXGR |

Example 11: Identification of TCEM Motifs Viral Infections

Hepatitis B Virus Core Protein

The association of chronic hepatitis B virus infection with incidence of liver cancer is well documented. There has not been a proven causal association, rather a strong association [38]. Recent reports have noted the relationship of increased Treg activity with progression of chronic hepatitis B. One report has linked increased Tregs directed to the core protein with chronic hepatitis B infection [39]. Vaccination using various formulations of hepatitis S antigen (HbsAg, surface protein) has been very effective at prevention of hepatitis B infection. However it has not been possible to design vaccines which aid the resolution of chronic infection. Hepatitis B has a particularly high incidence in China, although it is unclear whether this has a relationship with ethnicity or environmental factors enhancing transmission. There are however several reports of relationships between HLA alleles and incidence of hepatitis B [40,41]. Hepatitis B has been categorized into multiple genotypes (reviewed by Kramvis et al [42]).

We examined all the proteins of multiple strains of hepatitis B virus in order to determine if TCEM motifs that are found at high frequency in the 40K IGHV database referenced elsewhere in this application are represented and if so whether they have predicted high binding affinity to IGHV as well as in the hepatitis protein of interest.

Examination of MHC-I TCEMs showed no notable features. In proteins X, polymerase, large S, PreS and S some high binding peptides were noted but all were of Frequency class 16, indicating the motifs occur only once in the 40,000 IGHV database. The observations of the core protein and the precore and core protein were notably different. In the core protein the 15mer peptide with index position 120, VSFGVWIRTPPAYRP (SEQ ID NO: 479), showed both high frequency and high predicted binding in both frameworks of TCEM-II. TCEM-IIa showed binding in Frequency class 12 (1 in every 4096 heavy chain variable regions) and binding of greater than 1σ for all DR and for all DP except DPA1_0103-DPB1_0402. No binding occurred to DQ alleles (except at low affinity to DQA1_0101_DQB1_0501. When TCEM-IIB was examined the same peptide with index position 120 was found to have a Frequency Class of 8, indicating this motif is resent in 1 of every 256 heavy chain variable regions. Furthermore binding occurred as above to all DR, almost all DP and no DQ alleles except DQA1_0101_DQB1_0501. For TCEM-IIA the motif is F~~W~R~PP (SEQ ID NO: 480) whereas for TCEM IIB the motif is VW~R~PP (SEQ ID NO: 481). The peptide with index position 120 is excised by cathepsin B.

Figure 21:
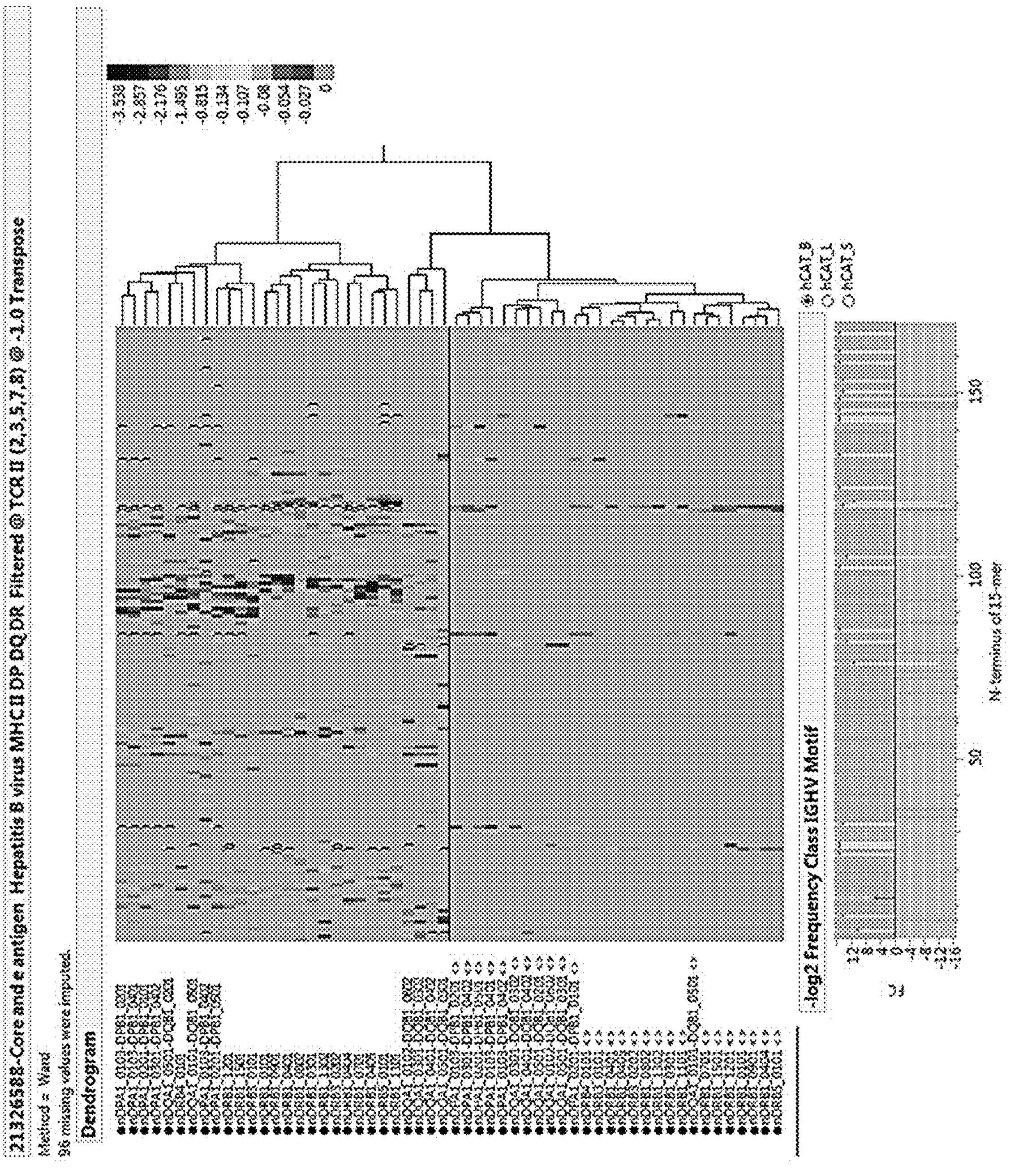
FIG. 21: TCEM IIA Motifs in Hepatitis B virus core protein. TCEM IIA motifs found in both hepatitis B core protein and the IGHV database are shown in the lower panel with the pixel color indicating affinity of GEM binding. The upper panel shows the high affinity binding peptides in hepatitis B core protein with the TCEM motifs from the lower panel denoted by X. Note peptide with index at position 120 this has a FC=12 equivalent to 1 in 4096 variable regions and is excised by cathepsin B.
Figure 22:
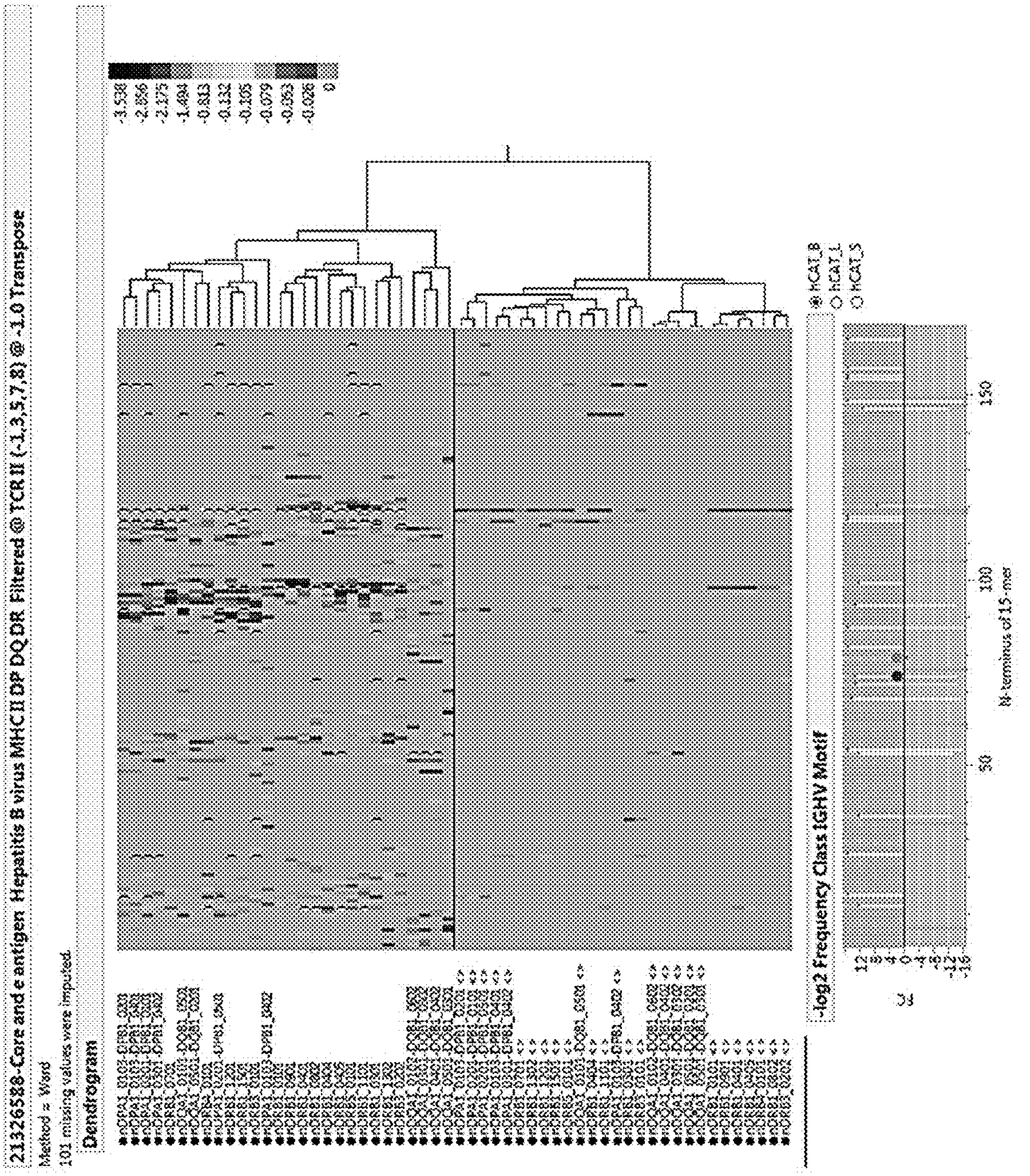
FIG. 22: TCEM IIB Motifs in Hepatitis B virus core protein. In this register the peptide with index position 120 is of FC 8 (1 in 256 variable regions) and is excised by cathepsin B.

FIGS. 21 and 22 show the binding patterns of peptides in the hepatitis core protein and motif matches with the IGHV database.

The peptide VSFGVWIRTPPAYRP (SEQ ID NO: 482) and the motifs it includes F~~W~R~PP (SEQ ID NO: 483) and VW~R~PP (SEQ ID NO: 484) are conserved across all genotypes A-H of hepatitis B. Other changes occur in the core protein between genotypes but this peptide is conserved.

These motifs have all the characteristics of T regulatory motifs and are present in all strains of hepatitis B virus. The presence of a strong conserved T regulatory motif in chronic cases of hepatitis B would inhibit the mounting of an immune response capable of eliminating dysplastic or neoplastic cells arising in the liver. Hence chronic hepatitis B would be permissive to the progression of cancer in the liver. It follows that it would be possible to target T regulatory cells specifically by using a synthetic construct of the identified peptide or the TCEM IIA or TCEM IIB motifs it encompasses and an MHC molecule to deliver a cytotoxin to eliminate the Treg cells.

Human Papillomavirus.

Human papillomavirus is a cause of squamous cell carcinoma of the cervix and oropharynx, and a cause of genital warts. A clear association of certain strains of HPV with progression of infection to cancer is reported, with strain HPV 16 being associated with 70% of reported cervical cancer cases. Strains 31, 33 and several others are known to be particularly aggressive in oncogenesis, whereas others such as type 6 and 11 are not associated with cancer [43-45]. While a preventive vaccine has been developed based on the surface proteins L1 and L2, there is as yet no vaccine approved for treatment of established infections. The oncogenic protein E7 has been the focus of efforts to develop such a vaccine [46,47]. Using the tools developed and described in the present invention we mapped the TCEMs in all proteins of selected strains (16, 18, 6, 11) and in the E7 proteins of 78 strains. For 31 strains we mapped, information was available documenting the degree of risk of progression to carcinoma. We documented the "immunosuppression index:" as a measure of the number and frequency (FC class) of TCEM found in the 40K set multiplied by the alleles binding these TCEM. The highest index of immunosuppression was observed in TCEM type II of strains 16, 31, 33, 18, 45, 58 and 68. These are all strains documented as being of higher risk of progression [48].

The TCEM motifs contributing most to the immunosuppression score were determined and also plotted on graphics. The cathepsin excision of the TCEM of interest was verified. Comparative plots of low risk strains again verified that these motifs were absent. Results are shown in Table 7. The TCEM shown are thus apparent Tregs associated with risk of progression.

Figure 23:
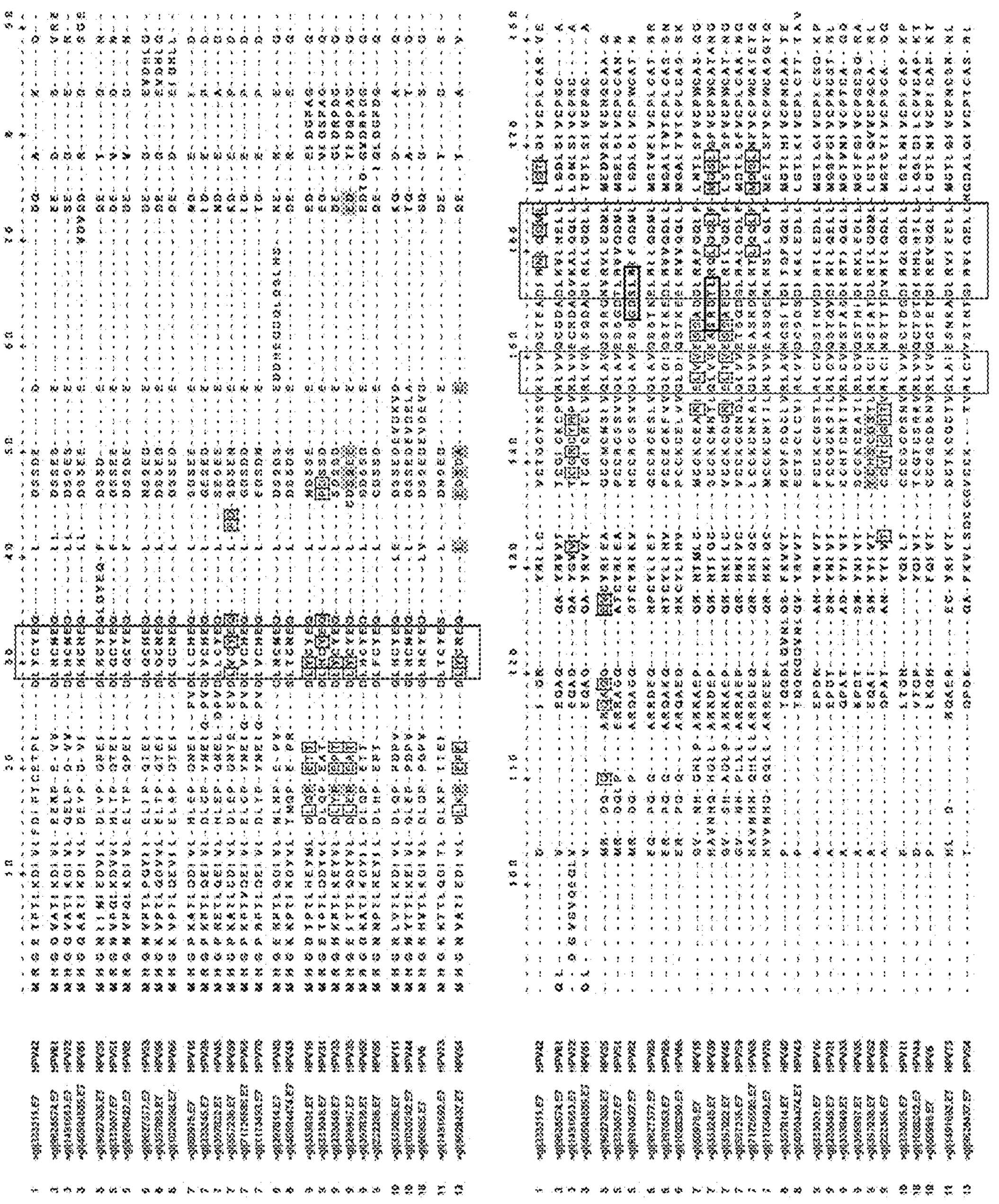
FIG. 23: Location of high frequency TCEM motifs in reference sequences of each E7 protein. Type IIa motifs are shaded grey, type IIb motifs are individually boxed, type I motifs are boldface and framed. The pRB binding site is framed, as are two secondary sites needed for pRB binding.
Figure 24:
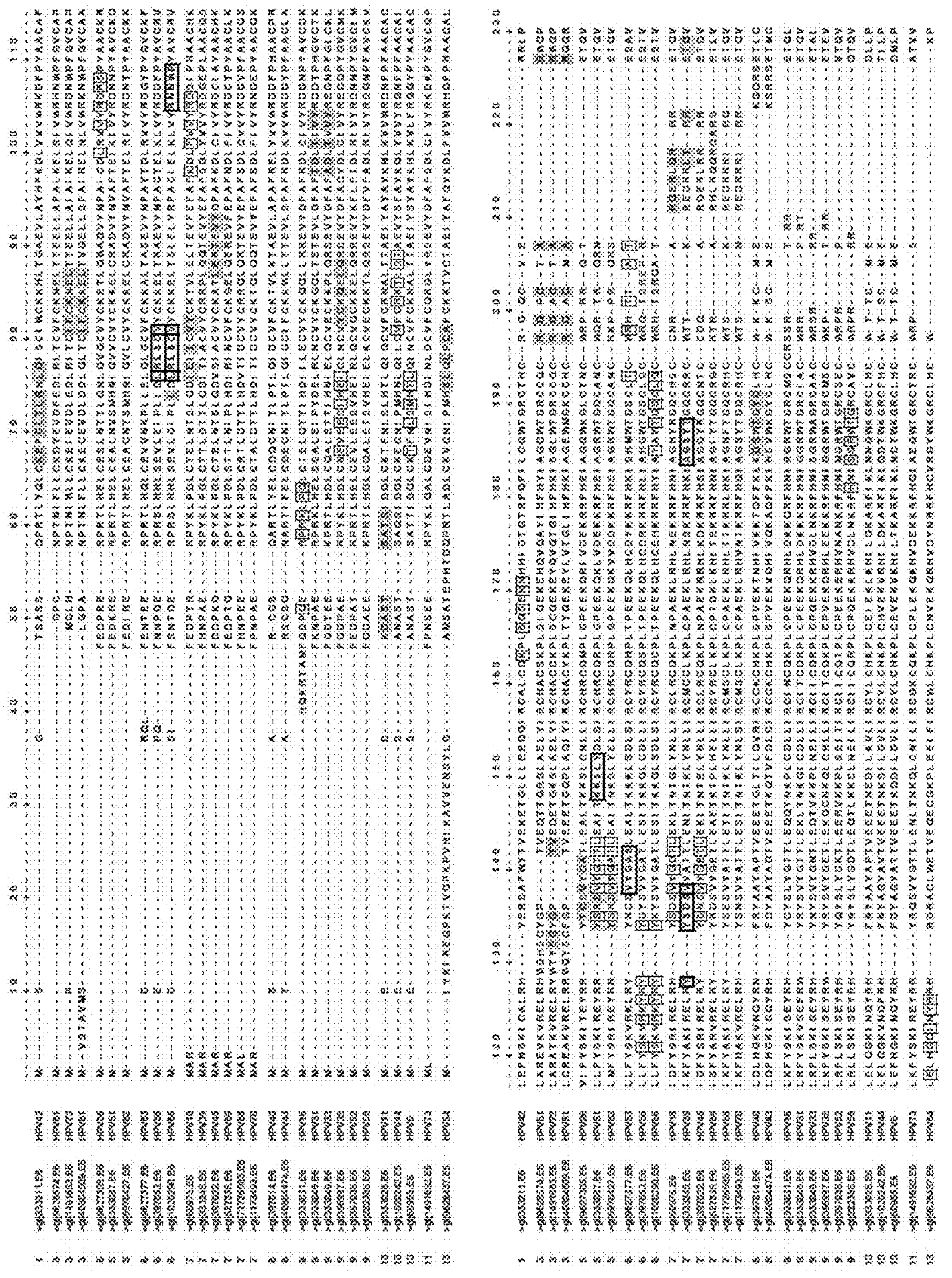
FIG. 24: Location of high frequency TCEM motifs in reference sequences of each E6 protein. Type IIa motifs are shaded grey, type IIb motifs are individually boxed, type I motifs are boldface and framed.
Figure 25A:
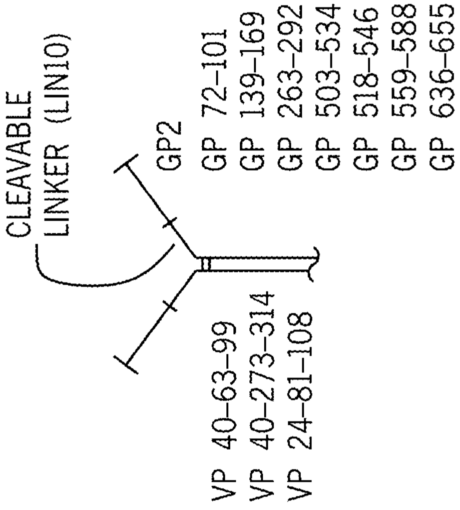
FIG. 25: Shows configuration of constructs for an Ebola vaccine as descried. A. Peptides attached to N terminal of heavy chain of an immunoglobulin with a cleavable linker B. peptides attached to both light and heavy chain N terminal C. Triple peptides with linkers assembled on a immunoglobulin heavy chain D. Triple peptides assembled with extended linkers allowing assembly as in natural spike protein.
Figure 25B:
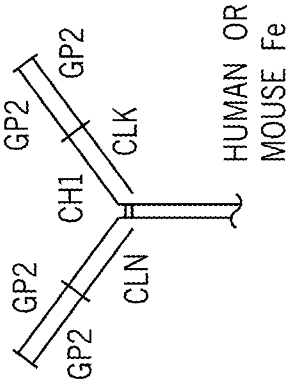
Figure 25C:
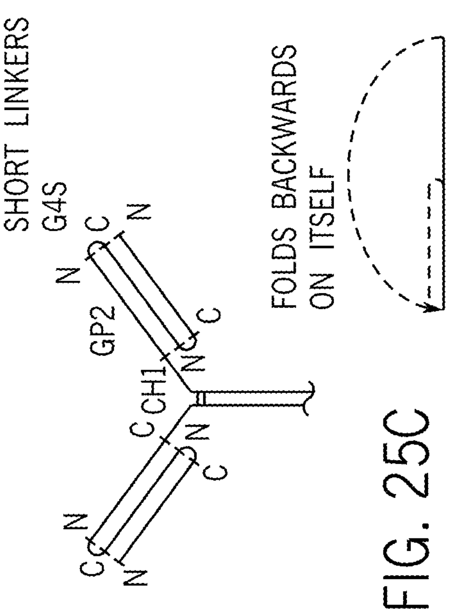
Figure 25D:
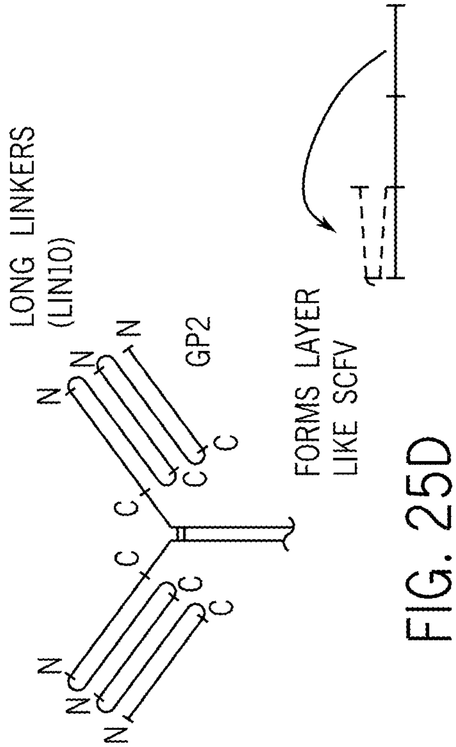

Analysis was conducted of the E7 and E6 proteins of HPV strains from the Alpha papillomaviruses species Alpha 1, 3, 5, 6, 7, 8, 9, 10, 11 and 13 available from the NIH Papillomavirus Episteme Database. This identified additional TCEMs in E7 and added motifs in E6, which are occurring at high frequency and binding with high affinity in the reference database. These are predicted Treg motifs. Initially TCEMs were identified which correspond to high frequency motifs in the IGHV and IGLV databases. Each of these was then evaluated individually to assess the probability of cathepsin cleavage to enable presentation in a MHC molecule and to evaluate how many HLA alleles bind the peptide containing the TCEM. Those TCEMs which are not bound or predicted to be excised were eliminated from the list. Table 7 and Table 8 show the resulting motifs identified for E7 and E6 respectively. FIGS. 23 and 24 show the location of the motifs in the protein sequences.

TABLE 14

E7 Critical motifs
In these tables the ~ character implies the presence of GEM sequences not seen by the T-cell The IARC risk category refers to the classification in Muñoz et al 2003 New Eng J Med 348, 518-527.

| ALPHA | Type | IARC Risk class | Motif based Classification | IIA | FCIIa | IIB | FCIIb | I | FC1 |
|---|---|---|---|---|---|---|---|---|---|
| 1 | 42 | L | H | | | N~~Q~GT (SEQ ID NO: 141) | 6 | | |
| 3 | 61 | L | LL | | | | | | |
| 3 | 72 | L | L | | | V~~C~R~YR(SEQ ID NO: 142) | 10 | | |
| 3 | 81 | L | LL | | | | | | |
| 5 | 26 | *H | H | | | Q~~Q~G~EV(SEQ ID NO: 143) | 4 | | |
| 5 | 51 | H | LL | | | | | | |
| 5 | 82 | H | H | | | | | GDSLR (SEQ ID NO: 199) | 6 |
| 6 | 53 | *H | LL | | | | | | |
| 6 | 56 | H | LL | | | | | | |
| 6 | 66 | *H | LL | | | | | | |
| 7 | 18 | H | H | | | R~~L~V~SS(SEQ ID NO: 144) | 8 | | |

TABLE 14-continued

E7 Critical motifs
In these tables the ~ character implies the presence of GEM sequences not seen by the T-cell The IARC risk category refers to the classification in Muñoz et al 2003 New Eng J Med 348, 518-527.

| ALPHA | Type | IARC Risk class | Motif based Classification | IIA | FCIIa | IIB | FCIIb | I | FC1 |
|---|---|---|---|---|---|---|---|---|---|
| 7 | 39 | H | HH | | | L~~L~M~SL(SEQ ID NO: 145) | 9 | SRDTL(SEQ ID NO: 200) | 10 |
| 7 | 45 | H | H | | | R~~L~V~SS(SEQ ID NO: 144) | 8 | | |
| 7 | 59 | H | H | | | L~~Y~Q~PD(SEQ ID NO: 146) | 10 | | |
| 7 | 68 | H | HH | | | L~~L~M~SL(SEQ ID NO: 147) | 9 | | |
| 7 | 70 | ? | LL | | | | 9 | | |
| 8 | 40 | L | LL | | | | | | |
| 8 | 43 | L | LL | | | | | | |
| 9 | 16 | H | HH | PE~T~LY(SEQ ID NO: 148) | 8 | L~~E~T~LY(SEQ ID NO: 149) | 5 | | |
| 9 | 31 | H | HH | | | L~~Y~Q~PD(SEQ ID NO: 146) | 10 | | |
| 9 | 33 | H | HH | PE~T~LY(SEQ ID NO: 148) | 8 | L~~E~T~LY(SEQ ID NO: 149) | 5 | | |
| 9 | 35 | H | HH | SS~E~ED(SEQ ID NO:)<br>PE~T~LY(SEQ ID NO: 148) | 5<br>8 | S~~K~K~TL(SEQ ID NO: 150)<br>L~~E~T~LY(SEQ ID NO: 149) | 9<br>5 | | |
| 9 | 52 | H | HH | YC~~S~DS(SEQ ID NO: 151) | 4 | | | | |
| 9 | 58 | H | HH | | | T~~Y~CTT(SEQ ID NO: 152) | 10 | | |
| 10 | 6 | L | LL | | | | | | |
| 10 | 11 | L | LL | | | | | | |
| 10 | 44 | L | LL | | | | | | |
| 11 | 73 | ? | LL | | | | | | |
| 13 | 54 | L | HH | PE~F~LY(SEQ ID NO: 153) | 9 | L~~E~F~LY(SEQ ID NO: 154) | 9 | | |

TABLE 15

E6 Critical Motifs

| ALPHA | Type | IARC Risk class | Motif based Classification | IIA | FCIIa | IIB | FCIIb | I | FC1 |
|---|---|---|---|---|---|---|---|---|---|
| 1 | 42 | L | H | KE~G~TL(SEQ ID NO: 155)<br>LT~R~LQ(SEQ ID NO: 157) | 9<br>10 | K~~S~S~KN(SEQ ID NO: 156) | 9 | | |
| 3 | 61 | L | H | RG~C~AR(SEQ ID NO: 158) | 8 | | | | |
| 3 | 72 | L | HH | RG~C~AR(SEQ ID NO: 158)<br>IF~K~EL(SEQ ID NO: 159) | 8<br>8 | | | | |

TABLE 15-continued

E6 Critical Motifs

| ALPHA | Type | IARC Risk class | Motif based Classification | IIA | FCIIa | IIB | FCIIb | I | FC1 |
|---|---|---|---|---|---|---|---|---|---|
| | | | | SG~G~TV(SEQ ID NO: 160) | 10 | | | | |
| 3 | 81 | L | HH | RG~C~AR(SEQ ID NO: 158)<br>IF~K~EL(SEQ ID NO: 159) | 8<br>8 | | | | |
| 5 | 26 | *H | HH | TC~V~GA(SEQ ID NO: 161) | 8 | L~~V~R~RS(SEQ ID NO: 162) | 9 | | |
| 5 | 51 | H | HH | YS~S~YG(SEQ ID NO: 163) | 10 | S~~V~G~TL(SEQ ID NO: 164) | 9 | ~~KKSLY~(SEQ ID NO: 165) | 8 |
| 5 | 82 | H | HH | YS~S~YG(SEQ ID NO: 163) | 10 | S~~V~G~TL(SEQ ID NO: 164) | 9 | | |
| 6 | 53 | *H | HH | | | T~~R~T~AT(SEQ ID NO: 166) | 10 | ~~VYGAS~(SEQ ID NO: 167) | 9 |
| 6 | 56 | H | HHH | | | S~~R~Y~~YY(SEQ ID NO: 168) | 10 | ~~LRLSC~(SEQ ID NO: 169)<br>~~RLSCV~(SEQ ID NO: 170) | 1<br>6 |
| 6 | 66 | *H | HHH | LL~L~LS(SEQ ID NO: 171) | 10 | Y~~T~S~LQ(SEQ ID NO: 172)<br>S~~R~Y~YY(SEQ ID NO: 168) | 8<br>9 | ~~LRLSC~(SEQ ID NO: 173)<br>~~RLSCV~(SEQ ID NO: 174)<br>~~RNNWP~(SEQ ID NO: 175) | 1<br>6<br>10 |
| 7 | 18 | H | HH | IE~T~VY(SEQ ID NO: 176)<br>RQ~R~QR(SEQ ID NO: 177) | 8<br>10 | K~~F~V~RD(SEQ ID NO: 178)<br>S~~V~G~TL(SEQ ID NO: 179) | 6<br>9 | | |
| 7 | 39 | H | HH | LT~R~TQ(SEQ ID NO: 180) | 9 | | | ~~YSDSV~(SEQ ID NO: 181)<br>~~YYSDS~(SEQ ID NO: 182)<br>~~AGSYT~(SEQ ID NO: 183) | 8<br>9<br>9 |
| 7 | 45 | H | HH | LE~T~VY(SEQ ID NO: 184) | 10 | S~~V~G~TL(SEQ ID NO: 185) | 9 | | |
| 7 | 59 | H | L | | | | | | |
| 7 | 68 | H | L | | | | | | |
| 7 | 70 | ? | L | | | | | | |
| 8 | 40 | L | H | DS~T~YC(SEQ ID NO: 186) | 8 | | | | |
| 8 | 43 | L | L | | | | | | |
| 9 | 16 | H | H | | | Q~~P~K~PQ(SEQ ID NO: 187) | 8 | | |
| 9 | 31 | H | H | TD~T~VY(SEQ ID NO: 188) | 9 | | | | |
| 9 | 33 | H | H | AD~T~VY(SEQ ID NO: 189) | 6 | | | | |
| 9 | 35 | H | H | YC~Q~LQ(SEQ ID NO: 190) | 6 | E~~E~I~EI(SEQ ID NO: 191) | 10 | | |
| 9 | 52 | H | L | | | | | | |
| 9 | 58 | H | H | | | H~~S~R~TG(SEQ ID NO: 192) | 8 | | |

TABLE 15-continued

| E6 Critical Motifs | | | | | | | | | |
|---|---|---|---|---|---|---|---|---|---|
| ALPHA | Type | IARC Risk class | Motif based Classification | IIA | FCIIa | IIB | FCIIb | I | FC1 |
| 10 | 6 | L | H | | | T~~L~M~TL(SEQ ID NO: 193) | 8 | | |
| 10 | 11 | L | HH | AS~S~TS(SEQ ID NO: 194)<br>DA~T~AT(SEQ ID NO: 195) | 7<br>9 | | | | |
| 10 | 44 | L | H | | | V~~R~T~ST(SEQ ID NO: 196) | 10 | | |
| 11 | 73 | ? | L | | | | | | |
| 13 | 54 | L | H | SL~L~CA(SEQ ID NO: 197) | 2 | E~~G~I~YR(SEQ ID NO: 198) | 10 | | |

Tables 14 and 15 show critical motifs which were derived initially based on reference strains for HPV (NIH Papillomavirus Episteme Database). We then evaluated up to ten strains of each type. The TCEMs tabulated in Tables 7 and 8 are well conserved. When multiple strains of HPV type 16 were evaluated we observed complete conservation between strains in these peptides, however in some types, for example type 31, there was more diversity of E7 between isolates. In addition, there are differences in individual amino acids which comprise the GEM motif (~) within the corresponding peptide, while retaining the conserved TCEM. Other isolates of HPV may contain additional TCEMs with properties likely to confer Treg stimulation. In the case of the Alpha 6 species, high frequency TCEM motifs are found for MHC I in protein E6, rather than for MHC II motifs in E7 as for the other Alpha species. We further evaluated the predicted binding affinity to 28 HLA Type II and 35 MHC Type I alleles and determined which alleles had the highest binding affinity for each motif.

The probable Treg motifs in HPV were identified (Tables 14 and 15) and the proteome database was searched to identify other human proteins which have these motifs. Relatively few such proteins were found. The proteins in which the motifs occurred are of interest as they could be the target of adverse targeting by immunotherapeutics; such proteins have now been identified. The summary of numbers of matches is shown in Table 16.

TABLE 16

| Proteome matches of critical HPV TCEM motifs | | | | | |
|---|---|---|---|---|---|
| | | | Motif | FC | Proteome matches |
| E7 | | | | | |
| Alpha 9 | 16, 33 | TCEM IIA | PE~T~LY(SEQ ID NO: 201) | 8 | 16 |
| Alpha 9 | 35 | TCEM IIA | SS~E~ED(SEQ ID NO: 202) | 5 | 167 |
| Alpha 9 | 52 | TCEM IIA | YC~S~DS(SEQ ID NO: 203) | 4 | 0 |
| Alpha 7 | 39, 68 | TCEM IIB | L~~L~M~SL(SEQ ID NO: 204) | 9 | 38 |

TABLE 16-continued

| Proteome matches of critical HPV TCEM motifs | | | | | |
|---|---|---|---|---|---|
| | | | Motif | FC | Proteome matches |
| Alpha 7 | 18, 45 | TCEM IIB | R~~L~V~SS(SEQ ID NO: 205) | 8 | 56 |
| Alpha 9&7 | 59, 31 | TCEM IIB | L~~Y~Q~PD(SEQ ID NO: 206) | 10 | 2 |
| Alpha 9 | 16, 33 | TCEM IIB | L~~E~T~LY(SEQ ID NO: 207) | 5 | 36 |
| Alpha 9 | 58 | TCEM IIB | T~~Y~C~TT(SEQ ID NO: 208) | 10 | 0 |
| Alpha 9 | 35 | TCEM IIB | S~~K~K~TL(SEQ ID NO: 209) | 9 | 50 |
| E6 | | | | | |
| Alpha 6 | 66 | TCEM IIA | LL~L~LS(SEQ ID NO: 210) | 10 | 436 |
| Alpha 7 | 18 | TCEM IIA | IE~T~VY(SEQ ID NO: 211) | 8 | 12 |
| Alpha 7 | 45 | TCEM IIA | LE~T~VY(SEQ ID NO: 212) | 10 | 1 |
| Alpha 7 | 39 | TCEM IIA | LT~R~TQ(SEQ ID NO: 213) | 9 | 3 |
| Alpha 7 | 18 | TCEM IIA | RQ~R~QR(SEQ ID NO: 214) | 10 | 27 |
| Alpha 9 | 31 | TCEM IIA | TD~T~VY(SEQ ID NO: 215) | 9 | 15 |
| Alpha 9 | 35 | TCEM IIA | YC~Q~LQ (SEQ ID NO: 216) | 6 | 8 |
| Alpha 9 | 33 | TCEM IIA | AD~T~VY(SEQ ID NO: 217) | 6 | 0 |
| Alpha 10 | 11 | TCEM IIA | AS~S~TS(SEQ ID NO: 218) | 7 | 127 |
| Alpha 10 | 11 | TCEM IIA | DA~T~AT(SEQ ID NO: 219) | 9 | 12 |

TABLE 16-continued

| Proteome matches of critical HPV TCEM motifs | | | | | |
|---|---|---|---|---|---|
| | | | Motif | FC | Proteome matches |
| Alpha 6 | 66 | TCEM IIB | Y~~T~S~LQ(SEQ ID NO: 220) | 8 | 24 |
| Alpha 6 | 56, 66 | TCEM IIB | S~~R~Y~YY(SEQ ID NO: 221) | 9 | 0 |
| Alpha 6 | 53 | TCEM IIB | T~~R~T~AT(SEQ ID NO: 222) | 10 | 17 |
| Alpha 7 | 18 | TCEM IIB | K~~F~V~RD(SEQ ID NO: 223) | 6 | 14 |
| Alpha 7 | 18, 45 | TCEM IIB | S~~V~G~TL(SEQ ID NO: 224) | 9 | 59 |
| Alpha 9 | 35 | TCEM IIB | E~~E~I~EI(SEQ ID NO: 225) | 10 | 48 |
| Alpha 9 | 16 | TCEM IIB | Q~~P~K~PQ(SEQ ID NO: 226) | 8 | 11 |
| Alpha 9 | 58 | TCEM IIB | H~~S~R~TG(SEQ ID NO: 227) | 8 | 16 |
| Alpha 10 | 6 | TCEM IIB | T~~L~M~TL(SEQ ID NO: 228) | 8 | 43 |
| Alpha 10 | 44 | TCEM IIB | V~~R~T~ST(SEQ ID NO: 229) | 10 | 32 |
| Alpha 6 | 53 | TCEM I | ~~~VYGAS~(SEQ ID NO: 230) | 9 | 19 |
| Alpha 6 | 56, 66 | TCEM I | ~~~LRLSC~(SEQ ID NO: 231) | 1 | 0 |
| Alpha 6 | 56, 66 | TCEM I | ~~~RLSCV~(SEQ ID NO: 232) | 6 | 0 |
| Alpha 6 | 66 | TCEM I | ~~~RNNWP~(SEQ ID NO: 233) | 10 | 0 |
| Alpha 7 | 39 | TCEM I | ~~~YSDSV~(SEQ ID NO: 234) | 8 | 0 |
| Alpha 7 | 39 | TCEM I | ~~~YYSDS~(SEQ ID NO: 235) | 9 | 0 |
| Alpha 7 | 39 | TCEM I | ~~~AGSYT~(SEQ ID NO: 236) | 9 | 0 |

TABLE 17

Viral target sequences of interest
Based on the above analyses of viral motifs from hepatitis b virus and human papillomavirus, the following sequences are identified as being of relevance to interventions. Amino acids indicated by X may be any amino acid.

| Source | 9-mer or 15-mer peptide | TCEM register | Motif |
|---|---|---|---|
| Hepatitis B | | | |
| Core protein | SEQ ID NO: 46724: VSFGVWIRTPPAYRP | TCEM IIa | SEQ ID NO: 237: VWXRXPP |
| | | TCEM IIb | SEQ ID 238: FXXWXRXPP |
| Human Papilloma virus | | | |
| E6 protein | | TCEM IIa | SEQ ID NO: 239: TCXVXGA |
| | | | SEQ ID NO: 240: YSXSXYG |
| | | | SEQ ID NO: 241: YSXSXYG |
| | | | SEQ ID NO: 242 LLXLX LS |
| | | | SEQ ID NO: 243 IEXTXVY |
| | | | SEQ ID NO: 244 RQXRXQR |
| | | | SEQ ID NO: 245 LTXRXTQ |
| | | | SEQ ID NO: 246 LEXTXVY |
| | | | SEQ ID NO: 247 TDXTXVY |
| | | | SEQ ID NO: 248 ADXTXVY |
| | | | SEQ ID NO: 249 YCXQXLQ |
| | | TCEM IIb | SEQ ID NO: 250 D(XVXRXRS |

TABLE 17-continued

Viral target sequences of interest
Based on the above analyses of viral motifs from hepatitis b virus and human papillomavirus, the following sequences are identified as being of relevance to interventions. Amino acids indicated by X may be any amino acid.

| Source | 9-mer or 15-mer peptide | TCEM register | Motif |
|---|---|---|---|
| | | | SEQ ID NO: 251 SXXVXGXTL |
| | | | SEQ ID NO: 252 TXXRXTXAT |
| | | | SEQ ID NO: 253 SXXRXYXYY |
| | | | SEQ ID NO: 254: YXXTXSXLQ |
| | | | SEQ ID NO: 255 KXXFXVXRD |
| | | | SEQ ID NO: 256 QXXPXKXPQ |
| | | | SEQ ID NO: 257 EXXEXIXEI |
| | | | SEQ ID NO: 258 HXXSXRXTG |
| | | | SEQ ID NO: TXXLXMXTL |
| | SEQ ID NO: 259 LIDLRLSCV (HPV56) | TCEM I | SEQ ID NO: 263 XXKKSLYX |
| | SEQ ID NO: 260 IDLRLSCVY (HPV56) | | |
| | SEQ ID NO: 261 LLDLRLSCV (HPV 66) | | SEQ ID NO: 264 XXVYGASX |
| | SEQ ID NO: 262 LDLRLSCVY (HPV 66) | | |
| | | | SEQ ID NO: 265 XXLRLSCX |
| | | | SEQ ID NO: 266 XXRLSCVX |
| | | | SEQ ID NO: 267 XXRNNWPX |
| | | | SEQ ID NO: 268 XXYSDSVX |
| | | | SEQ ID NO: 269 XXYYSDSX |
| | | | SEQ ID NO: 270 XXAGSYTX |
| E7 protein | SEQ ID NO: 271 LDLQPETTDLYCYEQ (HPV 16) | TCEM IIa | SEQ ID NO: 274 SSXEXED |
| | SEQ ID NO: 272 LDLQPEATDLYCYEQ (HPV 31) | | SEQ ID NO: 275 PEXTXLY |
| | SEQ ID NO: 273 LDLYPEPTDLYCYEQ (HPV 33) | | SEQ ID NO: 276 YCXSXDS |
| | SEQ ID NO: 277 EARIELVVESSADDL (HPV 18) | TCEM IIb | SEQ ID NO: 279 RXXLXVXSS |
| | SEQ ID NO: 278 IVTCCYTCGTTVRLC (HPV 58) | | SEQ ID NO: 280 LXXLXMXSL |
| | | | SEQ ID NO: 281 LXXYXQXPD |
| | | | SEQ ID NO: 282 LXXEXTXLY |
| | | | SEQ ID NO: 283 SXXKXKXTL |
| | | | SEQ ID NO: 284 TXXYXCTT |
| | | TCEM I | SEQ ID NO: 285 XXSRDTLX |

Example 13 Selection of Immunogenic Epitopes in Ebola Virus (EBOV) Membrane Associated Proteins In light of the 2014 outbreak of EBOV, we elected to examine the epitopes in the principal proteins of EBOV. Included in our evaluation were the following reference strains of the virus.

TABLE 18

| Reference strain name | Date of isolation | Representative proteins identifiers/ accession numbers |
|---|---|---|
| Zaire Mayinga | 1976 | Q05320.1 GI: 465411 |
| Sudan ebolavirus Boniface | 1976 | Q66814.1 GI: 8479515 |

TABLE 18-continued

| Reference strain name | Date of isolation | Representative proteins identifiers/ accession numbers |
|---|---|---|
| Musoke Marburg | 1980 | P35253.1 GI: 465412 |
| Uganda Bundibugyo | 2007 | YP_003815435.1 GI: 302371218 |
| Cote D'Ivoire Tai Forest | 1994 | Q66810.1 GI: 8479513 |

Also included in the analysis were the 99 field isolates in 2014 from Guinea and Sierra Leone published by Gire et al (Science. 2014 Sep. 12; 345(6202):1369-72. doi: 10.1126/science.1259657. Epub 2014 Aug. 28. PMID: 25214632). The sequences available from these isolates are deposited at ncbi.nln.nih.gov/bioproject/PRJNA257197 and comprise 891 individual proteins. Many of the proteins of the 2014 isolates were identical having been isolated within a short time span and geographical area. The identical sequences were identified and a single representative of each identity group analyzed. For both 2014 and reference strains particular attention was paid to analysis of the envelope spike glycoprotein GP and the two other membrane associated proteins VP24, and VP40. Analysis of B-cell epitope sequences and MHC I and II binding, cathepsin cleavage and topology was conducted as previously described on all non-identical proteins (see PCT US2011/029192, PCT US2012/055038, and PCT US2014/014523, each of which is incorporated herein by reference). Analysis of TCEM was then conducted as described elsewhere in the present invention. The TCEM motifs found in the EBOV proteins of interest were categorized by reference to the frequency categories in a database of 56,000 heavy and light chain variable regions.

Peptides were identified which spanned contiguous epitope group regions (CEGs) where high affinity MHC I and MHC II binding peptides overlap and where a B-cell linear epitope occurs within 3-10 amino acids of said MHC binding. These were further analyzed for the presence of potential immunosuppressive peptides which were likely, based on a combination of (a) their high frequency occurrence in the immunoglobulin reference database and (b) their binding at high affinity (≤1σ below the mean binding affinity for the protein) to multiple MHC alleles. High value peptides were identified by applying the above two criteria. A cross evaluation between the multiple strains of virus was made to determine the degree of conservation of the high value peptides.

A number of T-independent epitopes, comprising B cell binding regions but very little MHC binding, were identified especially in the GP1 mucin like region of the envelope spike glycoprotein (Fields' Virology, Fifth Edition, Volume 1, Chapter 40, 2004). These correspond to sequences previously identified as capable of producing antibody mediated enhancement of virus replication (Takada A, et al. J Infect Dis. 2007 Nov. 15; 196 Suppl 2:S347-56). Given the absence of MHC binding these epitopes are considered unlikely to be capable of generating a recall memory. These are sequences which are not selected for vaccine or immunogen inclusion.

The identification of both high value target peptides, and those peptides which should be avoided, leads to the ability to design a vaccine based on single, or in a preferred embodiment multiple subunit immunogen peptides. Said immunogen peptides may be expressed singly or as antibody Fc fusions or as fusions to other peptides or polypeptides. The peptides of interest may be further incorporated into a number of different vaccine configurations known to the art including but not limited to virus like particles, DNA, and virus vectored vaccines.

Two strategies were developed for generating antibodies and vaccines to EBOV envelope glycoprotein:

A. Focus on the N terminal of GP1: this is the region 1-375 located to the N terminal side of the mucin like region of GP0 which is also shared by sGP and ssGP, which are secreted and form part of an "antigenic subversion" by binding antibodies (Mohan et al 2012, Plos Path 8(12) e1003065). In this case the focus is on small highly immunogenic epitope dense sequences which avoid potential Tregs. Such proteins may have utility as vaccine components but are unlikely to be good targets for targeting antibody based therapeutics given the epitope overlap with sGP and ssGP.

B. The second strategy is to focus on the GP2 which forms the membrane inserted core and assembles as trimers. This region can be used in a near complete sequence or the most immunogenic epitope dense regions can be expressed individually. One identified potential immunosuppressive motif is located in the peptide with index position 503 and comprising the TCEM IIB motif V~~Q~K~NP (SEQ ID NO: 485) which is a FC6 motif found in 1 in every 64 antibody variable regions. This may be modified to reduce the immunosuppressive effect. As the transmembrane domain may inhibit secretion truncation of the C terminal end facilitates expression.

The TCEM motifs were compared to the database of frequency categories determined by reference to the database of 56,000 immunoglobulin variable regions. Based on this the following potential immunosuppressive or Treg motifs were identified

TABLE 19

| Amino acid position | TCEM IIA Frequency category | Motif | TCEM IIB Frequency category | Motif | peptide |
|---|---|---|---|---|---|
| Envelope glycoprotein | | | | | |
| 2014 isolates 98 represented by gi 667853357 | | | | | |
| 363 | 10 | TL~T~ST (SEQ ID NO: 186) | | | SHLTTLATISTSPQP (SEQ ID NO: 287) |
| 391 | 9 | KL~I~EA (SEQ ID NO: 288) | | | TPVYKLDISEATQVG (SEQ ID NO: 289) |

TABLE 19-continued

| Amino acid position | TCEM IIA Frequency category | Motif | TCEM IIB Frequency category | Motif | peptide |
|---|---|---|---|---|---|
| Envelope glycoprotein | | | | | |
| 209 | 7 | YY~T~IR (SEQ ID NO: 290) | | | PSSGYYSTTIRYQAT (SEQ ID NO: 291) |
| 247 | 5 | QF~L~LN (SEQ ID NO: 292) | | | RFTPQFLLQLNETIY (SEQ ID NO: 293) |
| 365 | 5 | AT~S~SP (SEQ ID NO: 294) | | | LTTLATISTSPQPPT (SEQ ID NO: 295) |
| 438 | | | 10 | S~~S~D~AT (SEQ ID NO: 296) | SKSADSLDLATTTSP (SEQ ID NO: 297) |
| 217 | | | 9 | R~~A~G~GT (SEQ ID NO: 298) | TIRYQATGFGTNETE (SEQ ID NO: 299) |
| 209 | | | 8 | S~~Y~T~IR (SEQ ID NO: 300) | PSSGYYSTTIRYQAT (SEQ ID NO: 301) |
| 503 | | | 6 | V~~Q~K~NP (SEQ ID NO: 302) | VIVNAQPKCNPNLHY (SEQ ID NO: 303) |
| EBOV Zaire Mayinga gi 465411 | | | | | |
| 363 | 10 | TL~T~ST (SEQ ID NO: 304) | | | SHLTTLATISTSPQS (SEQ ID NO: 305) |
| 391 | 9 | KL~I~EA (SEQ ID NO: 306) | | | TPVYKLDISEATQVE (SEQ ID NO: 307) |
| 209 | 7 | YY~T~IR (SEQ ID NO: 308) | | | PSSGYYSTTIRYQAT (SEQ ID NO: 309) |
| 434 | 6 | SK~T~FL (SEQ ID NO: 310) | | | NTNTSKSTDFLDPAT (SEQ ID NO: 311) |
| 247 | 5 | QF~L~LN (SEQ ID NO: 312) | | | RFTPQFLLQLNETIY (SEQ ID NO: 313) |
| 365 | 5 | AT~S~SP (SEQ ID NO: 314) | | | LTTLATISTSPQSLT (SEQ ID NO: 315) |
| 217 | | | 9 | R~~A~G~GT (SEQ ID NO: 316) | TIRYQATGFGTNETE (SEQ ID NO: 317) |
| 209 | | | 8 | S~~Y~T~IR (SEQ ID NO: 318) | PSSGYYSTTIRYQAT (SEQ ID NO: 319) |
| 503 | | | 6 | V~~Q~K~NP (SEQ ID NO: 320) | AIVNAQPKCNPNLHY (SEQ ID NO: 321) |
| EBOV Sudan Boniface gi 8479515 | | | | | |
| 69 | 10 | SG~S~DI (SEQ ID NO: 322) | | | PSQNSTEGRRVDVNT (SEQ ID NO: 323) |

TABLE 19-continued

| Envelope glycoprotein | | | | | |
|---|---|---|---|---|---|
| Amino acid position | TCEM IIA Frequency category | Motif | TCEM IIB Frequency category | Motif | peptide |
| 363 | 10 | ST~G~RV (SEQ ID NO: 324) | | | NLEGSGVSTDIPSAT (SEQ ID NO: 325) |
| 209 | 9 | YA~S~LE (SEQ ID NO: 326) | | | GLSSSQILSSSPTMA (SEQ ID NO: 327) |
| 404 | 9 | SQ~L~SS (SEQ ID NO: 328) | | | TSSYYATSYLEYEIE (SEQ ID NO: 329) |
| 378 | 4 | TE~T~TI (SEQ ID NO: 330) | | | QETITETTATIIGTN (SEQ ID NO: 331) |
| 375 | | | 10 | T~~T~T~TT (SEQ ID NO: 332) | VNTQETITETTATII (SEQ ID NO: 333) |
| 405 | | | 10 | S~~I~S~SP (SEQ ID NO: 334) | LSSSQILSSSPTMAP (SEQ ID NO: 335) |
| 365 | | | 10 | S~~G~R~DV (SEQ ID NO: 336) | QNSTEGRRVDVNTQE (SEQ ID NO: 337) |
| 264 | | | 10 | L~~T~G~LI (SEQ ID NO: 338) | QQLSNTTGKLIWTLD (SEQ ID NO: 339) |
| 88 | | | 9 | S~~P~Q~VS (SEQ ID NO: 340) | FRSGVPPQVVSYEAG (SEQ ID NO: 341) |
| 577 | | | 9 | L~~Y~I~NR (SEQ ID NO: 342) | TELRTYTILNRKAID (SEQ ID NO: 343) |
| 136 | | | 7 | V~~A~G~GP (SEQ ID NO: 344) | RYVHKAQGTGPCPGD (SEQ ID NO: 345) |

From this analysis and examination of the MHC binding and proximity to linear B cell epitopes the following peptides were selected for expression of immunogens from the envelope glycoprotein of Mayinga. It is noted that Seq 503-534 contains a FC6 TCEM IIA motif but that this is absent from the other selected peptides. It is further noted that position 503 contains an A503V mutation in the 2014 isolates, this conservative change is not likely to cause a significant change in recognition. It was further established by reference to cathepsin cleavage probabilities that each peptide contains appropriate excision sites to permit binding. As an initial application is to immunize mice for antibody production, the predicted MHC binding of Balb/c and C57 mice was determined.

Region A (SEQ ID NO: 346)
72 GNGVATDVPSATKRWGFRSGVPPKVVNYEA 101

(SEQ ID NO: 347)
139 HKVSGTGPCAGDFAFHKEGAFFLYDRLASTVI 169

(SEQ ID NO: 348)
263 SGKRSNTTGKLIWKVNPEIDTTIGEWAFWE 292

-continued

Region B (SEQ ID NO: 349)
503 AIVNAQPKCNPNLHYWTTQDEGAAIGLAWIPY 534

(SEQ ID NO: 350)
518 WTTQDEGAAIGLAWIPYFGPAAEGIYIEGL 546

(SEQ ID NO: 351)
559 RQLANETTQALQLFLRATTELRTFSILNRKA 588

(SEQ ID NO: 352)
636 PDQGDNDNWWTGWRQWIPAG 655

(SEQ ID NO: 353)
505 VNAQPKCNPNLHYWTTQDEGAAIGLAWIPYFGPAAEGIYIEGLMHN
QDGLICGLRQLANETTQALQLFLRATTELRTFSILNRKAIDFLLQRWGGT
CHILGPDCCIEPHDWTKNITDKIDQIIHDFVDKTLPDQGDNDNWWTGWRQ
WIPAG 655

Other EBOV membrane proteins were examined using a similar approach. TCEM analysis was conducted as described above for VP24 and VP 40. The potentially immunosuppressive peptides based on TCEMs found with high frequency in heavy and light chain immunoglobulin variable regions are as shown in Tables 13 and 14.

TABLE 20

| Amino acid position | TCEM IIA Frequency category | Motif | TCEM IIB Frequency category | Motif | Peptide |
|---|---|---|---|---|---|
| VP40 | | | | | |
| 2014 isolates 98 represented by gi 667853356 | | | | | |
| 141 | 10 | HP~R~LR (SEQ ID NO: 354) | | | GIPDHPLRLLRIGNQ (SEQ ID NO: 355) |
| 74 | 8 | MV~V~SG (SEQ ID NO: 356) | | | ILEAMVNVISGPKVL (SEQ ID NO: 357) |
| 222 | 3 | GN~A~LT (SEQ ID NO: 358) | | | SGKKGNSADLTSPEK (SEQ ID NO: 359) |
| 192 | | | 10 | D~~T~S~GA (SEQ ID NO: 360) | TDDTPTGSNGALRPG (SEQ ID NO: 361) |
| 105 | | | 9 | S~~S~T~AI (SEQ ID NO: 362) | TYSFDSTTAAIMLAS (SEQ ID NO: 363) |
| 174 | | | 9 | L~~L~L~TQ (SEQ ID NO: 364) | FDLTALKLITQPLPA (SEQ ID NO: 365) |
| 60 | | | 8 | A~~T~G~VS (SEQ ID NO: 366) | DHASHTPGSVSSAFI (SEQ ID NO: 367) |
| 190 | | | 8 | T~~T~T~SN (SEQ ID NO: 368) | TWTDDTPTGSNGALR (SEQ ID NO: 369) |
| 270 | | | 7 | T~~K~T~KN (SEQ ID NO: 370) | KLTGKKVTSKNGQPI (SEQ ID NO: 371) |
| 222 | | | 4 | K~~N~A~LT (SEQ ID NO: 372) | SGKKGNSADLTSPEK (SEQ ID NO: 373) |
| EBOV Zaire Mayinga gi 10313993 | | | | | |
| 141 | 10 | HP~R~LR (SEQ ID NO: 374) | | | GIPDHPLRLLRIGNQ (SEQ ID NO: 375) |
| 74 | 8 | MV~V~SG (SEQ ID NO: 376) | | | ILEAMVNVISGPKVL (SEQ ID NO: 377) |
| 222 | 3 | GN~A~LT (SEQ ID NO: 378) | | | SGKKGNSADLTSPEK (SEQ ID NO: 379) |
| 192 | | | 10 | D~~T~S~GA (SEQ ID NO: 380) | TDDTPTGSNGALRPG (SEQ ID NO: 381) |
| 105 | | | 9 | S~~S~T~AI (SEQ ID NO: 382) | TYSFDSTTAAIMLAS (SEQ ID NO: 383) |
| 174 | | | 9 | L~~L~L~TQ (SEQ ID NO: 384) | FDLTALKLITQPLPA (SEQ ID NO: 385) |
| 60 | | | 8 | A~~T~G~VS (SEQ ID NO: 386) | DHASHTPGSVSSAFI (SEQ ID NO: 387) |

TABLE 20-continued

| VP40 | | | | | |
|---|---|---|---|---|---|
| Amino acid position | TCEM IIA Frequency category | Motif | TCEM IIB Frequency category | Motif | Peptide |
| 190 | | | 8 | T~~T~T~SN (SEQ ID NO: 388) | TWTDDTPTGSNGALR (SEQ ID NO: 389) |
| 270 | | | 7 | T~~K~T~KN (SEQ ID NO: 390) | KLTGKKVTSKNGQPI (SEQ ID NO: 391) |
| 222 | | | 4 | K~~N~A~LT (SEQ ID NO: 392) | SGKKGNSADLTSPEK (SEQ ID NO: 393) |

TABLE 21

| VP24 | | | | | |
|---|---|---|---|---|---|
| Amino acid position | TCEM IIA Frequency category | Motif | TCEM IIB Frequency category | Motif | Peptide |
| 2014 isolates 98 represented by gi 667853361 | | | | | |
| 8 | 6 | SP~K~LE (SEQ ID NO: 394) | | | YNLISPKKDLEKGVV (SEQ ID NO: 395) |
| 142 | 6 | SL~M~SL (SEQ ID NO: 396) | | | KEQLSLKMLSLIRSN (SEQ ID NO: 397) |
| EBOV Zaire Mayinga gi 10313998 | | | | | |
| 8 | 6 | SP~K~LE (SEQ ID NO: 398) | | | YNLISPKKDLEKGVV (SEQ ID NO: 399) |
| 142 | 6 | SL~M~SL (SEQ ID NO: 400) | | | KEQLSLKMLSLIRSN (SEQ ID NO: 401) |

Following a review of the MHC binding and CEG identification the following peptides were selected from VP40 of gi 667853361 and VP 24 of gi 667853361 as immunogens

VP40

(SEQ ID NO: 402)
63 SHTPGSVSSAFILEAMVNVISGPKVLMKQIPIWLPLG 99

(SEQ ID NO: 403)
273 GKKVTSKNGQPIIPVLLPKYIGLDPVAPGDLTMVITQDCDTC 314

VP24

(SEQ ID NO: 404)
81 PNSTIESPLWALRVILAAGIQDQLID 108

A number of strategies were developed for constructing immunogens. These are illustrated in FIG. 25.

A. Immunoglobulin Fc carrier, one construct design: human or mouse Fc+hinge region, GP2 or 10 different peptides from the GP, VP24 and VP40 proteins. All peptides are attached to the N-terminus of the hinge region via cleavable linker (Lin10).

B. Immunoglobulin constant region carrier: This is a 2-construct design: Construct 1: Make a human or mouse constant heavy chain using the CH(1-3) region with the Ebola protein GP2 (505-655) fused to the N-terminus of the CH(1-3), no linker is used for this design. Construct 2: Light chain kappa (CLkappa) constant region with the Ebola protein GP2 (505-655) fused to the N-terminus of CLkappa. The two constructs are co-transduced into CHO expression cells. They should self-assemble similar to full size antibody heavy and light chain.

C. One construct design anti-parallel folding of GP2: human or mouse constant heavy chain using the CH(1-3) region with N-terminal fusion to 3 repeats of the Ebola protein GP2 (505-655). The GP2 repeats are linked together via short linkers (GGGGS (SEQ ID NO: 486)). This design should allow anti-parallel folding of the 3 GP protein repeat onto each other.

D. One construct design to encourage parallel folding of GP2: human or mouse constant heavy chain using the CH(1-3) region with N-terminal fusion to 3 repeats of the Ebola protein GP2 (505-655). The GP2 repeats are linked together via long linker (Lin10). This design should allow parallel folding of the 3 GP2 protein.

The sequences listed are for the following constructs corresponding to the description above.

TABLE 22

| Sequence | Construct | Description |
|---|---|---|
| SEQ ID NO: 405 | A1 | GP2-Lin10-hFc |
| SEQ ID NO: 406 | A2 | GP2-Lin10-mFc |
| SEQ ID NO: 407 | A3 | GP72-101-Lin10-hFc |
| SEQ ID NO: 408 | A4 | GP72-101-Lin10-mFc |
| SEQ ID NO: 409 | A5 | GP139-169-Lin10-hFc |
| SEQ ID NO: 410 | A6 | GP139-169-Lin10-mFc |
| SEQ ID NO: 411 | A7 | GP263-292-Lin10-hFc |
| SEQ ID NO: 412 | A8 | GP263-292-Lin10-mFc |
| SEQ ID NO: 413 | A9 | GP503-534-Lin10-hFc |
| SEQ ID NO: 414 | A10 | GP503-534-Lin10-mFc |
| SEQ ID NO: 415 | A11 | GP518-546-Lin10-hFc |
| SEQ ID NO: 416 | A12 | GP518-546-Lin10-mFc |
| SEQ ID NO: 417 | A13 | GP559-588-Lin10-hFc |
| SEQ ID NO: 418 | A14 | GP559-588-Lin10-mFc |
| SEQ ID NO: 419 | A15 | GP636-655-Lin10-hFc |
| SEQ ID NO: 420 | A16 | GP636-655-Lin10-mFc |
| SEQ ID NO: 421 | A17 | VP40-63-99-Lin10-hFc |
| SEQ ID NO: 422 | A18 | VP40-63-99-Lin10-mFc |
| SEQ ID NO: 423 | A19 | VP40-273-314-Lin10-hFc |
| SEQ ID NO: 424 | A20 | VP40-273-314-Lin10-mFc |
| SEQ ID NO: 425 | A21 | VP24-81-108-Lin10-hFc |
| SEQ ID NO: 426 | A22 | VP24-81-108--Lin10-mFc |
| SEQ ID NO: 427 | B1 | GP2-hCH1-3 |
| SEQ ID NO: 428 | B2 | GP2-hCL |
| SEQ ID NO: 429 | B3 | GP2-mCH1-3 |
| SEQ ID NO: 430 | B4 | GP2-mCL |
| SEQ ID NO: 431 | C1 | GP2-(G4S)-GP2-(G4S)-GP2-hCH1-3 |
| SEQ ID NO: 432 | C2 | GP2-(G4S)-GP2-(G4S)-GP2-mCH1-3 |
| SEQ ID NO: 433 | D1 | GP2-(Lin10)-GP2-(Lin10)-GP2-hCH1-3 |
| SEQ ID NO: 434 | D2 | GP2-(Lin10)-GP2-(Lin10)-GP2-mCH1-3 |

SEQ ID NO 405: A1. GP2-Lin10-hFc, amino acid sequence,

```
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

DKTLPDQGDNDNWWTGWRQWIPAGGGGGSGGGGSGGPGSGGGGSGGGGSA

STEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTVD

KSRWQQGNVFSCSVMHEALHNHYTQKSLSLSPGK.
```

```
  1-23  Signal peptide
 24-174 GP2
175-199 Linker Variant 10
200-434 hG1(CH2-3)
```

SEQ ID NO 406: Seq. A2. GP2-Lin10-mFc, amino acid sequence,

```
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

DKTLPDQGDNDNWWTGWRQWIPAGGGGGSGGGGSGGPGSGGGGSGGGGSV

DEPRGPTIKPCPPCKCPAPNLLGGPSVFIFPPKIKDVLMISLSPIVTCVV

VDVSEDDPDVQISWFVNNVEVHTAQTQTHREDYNSTLRVVSALPIQHQDW
```

-continued

```
MSGKEFKCKVNNKDLPAPIERTISKPKGSVRAPQVYVLPPPEEEMTKKQV

TLTCMVTDFMPEDIYVEWTNNGKTELNYKNTEPVLDSDGSYFMYSKLRVE

KKNWVERNSYSCSVVHEGLHNHHTTKSFSRTPGK.
```

```
  1-23  Signal peptide
 24-174 GP2
175-199 Linker Variant 10
200-434 mG2a(CH2-3)
```

SEQ ID NO 407: A3. GP(72-101)-Lin10-hFc, amino acid sequence,

```
.........o.........o.........o.........o.........o
METDTLLLWVLLLWVPGSTGDTRGNGVATDVPSATKRWGFRSGVPPKVVN

YEAGGGGSGGGGSGGPGSGGGGSGGGGSASTEPKSCDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHN

HYTQKSLSLSPGK.
```

```
  1-23  Signal peptide
 24-53  GP(72-101)
 54-78  Linker Variant 10
 79-313 hG1(CH2-3)
```

SEQ ID NO 408: A4. GP(72-101)-Lin10-mFc, amino acid sequence,

```
.........o.........o.........o.........o.........o
METDTLLLWVLLLWVPGSTGDTRGNGVATDVPSATKRWGFRSGVPPKVVN

YEAGGGGSGGGGSGGPGSGGGGSGGGGSVDEPRGPTIKPCPPCKCPAPNL

LGGPSVFIFPPKIKDVLMISLSPIVTCVVVDVSEDDPDVQISWFVNNVEV

HTAQTQTHREDYNSTLRVVSALPIQHQDWMSGKEFKCKVNNKDLPAPIER

TISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLHN

HHTTKSFSRTPGK.
```

```
  1-23  Signal peptide
 24-53  GP(72-101)
 54-78  Linker Variant 10
 79-313 mG2a(CH2-3)
```

SEQ ID NO 409: A5. GP(139-169)-Lin10-hFc, amino acid sequence,

```
.........o.........o.........o.........o.........o
METDTLLLWVLLLWVPGSTGDTRHKVSGTGPCAGDFAFHKEGAFFLYDRL

ASTVIGGGGSGGGGSGGPGSGGGGSGGGGSASTEPKSCDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK.
```

-continued 1-23 Signal peptide
24-55 GP(139-169)
56-80 Linker Variant 10
81-315 hG1(CH2-3)

SEQ ID NO 410: A6. GP(139-169)-Lin10-mFc, amino acid sequence,

.........o.........o.........o.........o.........o

METDTLLLWVLLLWVPGSTGDTRHKVSGTGPCAGDFAFHKEGAFFLYDRL

ASTVIGGGGSGGGGSGGPGSGGGGSGGGGSVDEPRGPTIKPCPPCKCPAP

NLLGGPSVFIFPPKIKDVLMISLSPIVTCVVVDVSEDDPDVQISWFVNNV

EVHTAQTQTHREDYNSTLRVVSALPIQHQDWMSGKEFKCKVNNKDLPAPI

ERTISKPKGSVRAPQVYVLPPPEEEMTKKQVTLTCMVTDFMPEDIYVEWT

NNGKTELNYKNTEPVLDSDGSYFMYSKLRVEKKNWVERNSYSCSVVHEGL

HNHHTTKSFSRTPGK.

1-23 Signal peptide
24-55 GP(139-169)
56-80 Linker Variant 10
81-315 mG2a(CH2-3)

SEQ ID NO 411: A7. GP(263-292)Lin10-hFc, amino acid sequence,

.........o.........o.........o.........o.........o

METDTLLLWVLLLWVPGSTGDTRSGKRSNTTGKLIWKVNPEIDTTIGEWA

FWEGGGGSGGGGSGGPGSGGGGSGGGGSASTEPKSCDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHN

HYTQKSLSLSPGK.

1-23 Signal peptide
24-53 GP(263-292)
54-78 Linker Variant 10
79-313 hG1(CH2-3)

SEQ ID NO 412. GP(263-292)-Lin10-mFc, amino acid sequence,

.........o.........o.........o.........o.........o

METDTLLLWVLLLWVPGSTGDTRSGKRSNTTGKLIWKVNPEIDTTIGEWA

FWEGGGGSGGGGSGGPGSGGGGSGGGGSVDEPRGPTIKPCPPCKCPAPNL

LGGPSVFIFPPKIKDVLMISLSPIVTCVVVDVSEDDPDVQISWFVNNVEV

HTAQTQTHREDYNSTLRVVSALPIQHQDWMSGKEFKCKVNNKDLPAPIER

TISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLHN

HHTTKSFSRTPGK.

1-23 Signal peptide
24-53 GP(263-292)
54-78 Linker Variant 10
79-313 mG2a(CH2-3)

SEQ ID NO 413. GP(503-534)-Lin10-hFc, amino acid sequence,

.........o.........o.........o.........o.........o

METDTLLLWVLLLWVPGSTGDTRAIVNAQPKCNPNLHYWTTQDEGAAIGL

AWIPYGGGGSGGGGSGGPGSGGGGSGGGGSASTEPKSCDKTHTCPPCPAP

ELLGGPSVFLFPPKPKDTLMISRTPEVTCVVVDVSHEDPEVKFNWYVDGV

-continued

EVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK.

1-23 Signal peptide
24-55 GP(503-534)
56-80 Linker Variant 10
81-315 hG1(CH2-3)

SEQ ID NO 414: A10. GP(503-534)-Lin10-mFc, amino acid sequence,

.........o.........o.........o.........o.........o

METDTLLLWVLLLWVPGSTGDTRAIVNAQPKCNPNLHYWTTQDEGAAIGL

AWIPYGGGGSGGGGSGGPGSGGGGSGGGGSVDEPRGPTIKPCPPCKCPAP

NLLGGPSVFIFPPKIKDVLMISLSPIVTCVVVDVSEDDPDVQISWFVNNV

EVHTAQTQTHREDYNSTLRVVSALPIQHQDWMSGKEFKCKVNNKDLPAPI

ERTISKPKGSVRAPQVYVLPPPEEEMTKKQVTLTCMVTDFMPEDIYVEWT

NNGKTELNYKNTEPVLDSDGSYFMYSKLRVEKKNWVERNSYSCSVVHEGL

HNHHTTKSFSRTPGK.

1-23 Signal peptide
24-55 GP(503-534)
56-80 Linker Variant 10
81-315 mG2a(CH2-3)

SEQ ID NO 415 A11. GP(518-546)-Lin10-hFc, amino acid sequence,

.........o.........o.........o.........o.........o

METDTLLLWVLLLWVPGSTGDTRWTTQDEGAAIGLAWIPYFGPAAEGIYI

EGLGGGGSGGGGSGGPGSGGGGSGGGGSASTEPKSCDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHN

HYTQKSLSLSPGK.

1-23 Signal peptide
24-53 GP(518-546)
54-78 Linker Variant 10
79-313 hG1(CH2-3)

SEQ ID NO 416 A12. GP(518-546)-Lin10-mFc, amino acid sequence,

.........o.........o.........o.........o.........o

METDTLLLWVLLLWVPGSTGDTRWTTQDEGAAIGLAWIPYFGPAAEGIYI

EGLGGGGSGGGGSGGPGSGGGGSGGGGSVDEPRGPTIKPCPPCKCPAPNL

LGGPSVFIFPPKIKDVLMISLSPIVTCVVVDVSEDDPDVQISWFVNNVEV

HTAQTQTHREDYNSTLRVVSALPIQHQDWMSGKEFKCKVNNKDLPAPIER

TISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLHN

HHTTKSFSRTPGK.

-continued 1-23 Signal peptide
24-53 GP(518-546)
54-78 Linker Variant 10
79-313 mG2a(CH2-3)

SEQ ID NO 417 A13. GP(559-588)-Lin10-hFc, amino acid sequence,

.........o.........o.........o.........o.........o
METDTLLLWVLLLWVPGSTGDTRRQLANETTQALQLFLRATTELRTFSIL

NRKAGGGGSGGGGSGGPGSGGGGSGGGGSASTEPKSCDKTHTCPPCPAPE

LLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALH

NHYTQKSLSLSPGK.

1-23 Signal peptide
24-54 GP(559-588)
55-79 Linker Variant 10
80-314 hG1(CH2-3)

SEQ ID NO 418 A14. GP(559-588)-Lin10-mFc, amino acid sequence,

.........o.........o.........o.........o.........o
METDTLLLWVLLLWVPGSTGDTRRQLANETTQALQLFLRATTELRTFSIL

NRKAGGGGSGGGGSGGPGSGGGGSGGGGSVDEPRGPTIKPCPPCKCPAPN

LLGGPSVFIFPPKIKDVLMISLSPIVTCVVVDVSEDDPDVQISWFVNNVE

VHTAQTQTHREDYNSTLRVVSALPIQHQDWMSGKEFKCKVNNKDLPAPIE

RTISKPKGSVRAPQVYVLPPPEEEMTKKQVTLTCMVTDFMPEDIYVEWTN

NGKTELNYKNTEPVLDSDGSYFMYSKLRVEKKNWVERNSYSCSVVHEGLH

NHHTTKSFSRTPGK.

1-23 Signal peptide
24-54 GP(559-588)
55-79 Linker Variant 10
80-314 mG2a(CH2-3)

SEQ ID NO 419 A15. GP(636-655)-Lin10-hFc, amino acid sequence,

.........o.........o.........o.........o.........o
METDTLLLWVLLLWVPGSTGDTRPDQGDNDNWWTGWRQWIPAGGGGGSGG

GGSGGPGSGGGGSGGGGSASTEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK.

1-23 Signal peptide
24-43 GP(636-655)
44-68 Linker Variant 10
69-303 hG1(CH2-3)

SEQ ID NO 420 A16. GP(636-655)-Lin10-mFc, amino acid sequence,

.........o.........o.........o.........o.........o
METDTLLLWVLLLWVPGSTGDTRPDQGDNDNWWTGWRQWIPAGGGGGSGG

GGSGGPGSGGGGSGGGGSVDEPRGPTIKPCPPCKCPAPNLLGGPSVFIFP

PKIKDVLMISLSPIVTCVVVDVSEDDPDVQISWFVNNVEVHTAQTQTHRE

-continued

DYNSTLRVVSALPIQHQDWMSGKEFKCKVNNKDLPAPIERTISKPKGSVR

APQVYVLPPPEEEMTKKQVTLTCMVTDFMPEDIYVEWTNNGKTELNYKNT

EPVLDSDGSYFMYSKLRVEKKNWVERNSYSCSVVHEGLHNHHTTKSFSRT

PGK.

1-23 Signal peptide
24-43 GP(636-655)
44-68 Linker Variant 10
69-303 mG2a(CH2-3)

SEQ ID NO 421 A17. VP40(63-99)-Lin10-hFc, amino acid sequence,

.........o.........o.........o.........o.........o
METDTLLLWVLLLWVPGSTGDTRSHTPGSVSSAFILEAMVNVISGPKVLM

KQIPIWLPLGGGGGSGGGGSGGPGSGGGGSGGGGSASTEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK.

1-23 Signal peptide
24-60 VP40(63-99)
61-85 Linker Variant 10
86-320 hG1(CH2-3)

SEQ ID NO 422 A18. VP40(63-99)-Lin10-mFc, amino acid sequence,

.........o.........o.........o.........o.........o
METDTLLLWVLLLWVPGSTGDTRSHTPGSVSSAFILEAMVNVISGPKVLM

KQIPIWLPLGGGGGSGGGGSGGPGSGGGGSGGGGSVDEPRGPTIKPCPPC

KCPAPNLLGGPSVFIFPPKIKDVLMISLSPIVTCVVVDVSEDDPDVQISW

FVNNVEVHTAQTQTHREDYNSTLRVVSALPIQHQDWMSGKEFKCKVNNKD

LPAPIERTISKPKGSVRAPQVYVLPPPEEEMTKKQVTLTCMVTDFMPEDI

YVEWTNNGKTELNYKNTEPVLDSDGSYFMYSKLRVEKKNWVERNSYSCSV

VHEGLHNHHTTKSFSRTPGK.

1-23 Signal peptide
24-60 VP40(63-99)
61-85 Linker Variant 10
86-320 mG2a(CH2-3)

SEQ ID NO 423 A19. VP40(273-314)-Lin10-hFc, amino acid sequence,

.........o.........o.........o.........o.........o
METDTLLLWVLLLWVPGSTGDTRGKKVTSKNGQPIIPVLLPKYIGLDPVA

PGDLTMVITQDCDTCGGGGSGGGGSGGPGSGGGGSGGGGSASTEPKSCDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK.

-continued 1-23 Signal peptide
24-65 VP40(273-314)
66-90 Linker Variant 10
91-325 hG1(CH2-3)

SEQ ID NO 424 A20. VP40(273-314)-Lin10-mFc, amino acid sequence,
.........o.........o.........o.........o.........o
METDTLLLWVLLLWVPGSTGDTRGKKVTSKNGQPIIPVLLPKYIGLDPVA

PGDLTMVITQDCDTCGGGGSGGGGSGGPGSGGGGSGGGGSVDEPRGPTIK

PCPPCKCPAPNLLGGPSVFIFPPKIKDVLMISLSPIVTCVVVDVSEDDPD

VQISWFVNNVEVHTAQTQTHREDYNSTLRVVSALPIQHQDWMSGKEFKCK

VNNKDLPAPIERTISKPKGSVRAPQVYVLPPPEEEMTKKQVTLTCMVTDF

MPEDIYVEWTNNGKTELNYKNTEPVLDSDGSYFMYSKLRVEKKNWVERNS

YSCSVVHEGLHNHHTTKSFSRTPGK.

1-23 Signal peptide
24-65 VP40(273-314)
66-90 Linker Variant 10
91-325 mG2a(CH2-3)

SEQ ID NO 425 A21. VP24(81-108)-Lin10-hFc, amino acid sequence,
.........o.........o.........o.........o.........o
METDTLLLWVLLLWVPGSTGDTRPNSTIESPLWALRVILAAGIQDQLIDG

GGGSGGGGSGGPGSGGGGSGGGGSASTEPKSCDKTHTCPPCPAPELLGGP

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK.

1-23 Signal peptide
24-49 VP24(81-108)
50-74 Linker Variant 10
75-309 hG1(CH2-3)

SEQ ID NO 426 A22. VP24(81-108)-Lin10-mFc, amino acid sequence,
.........o.........o.........o.........o.........o
METDTLLLWVLLLWVPGSTGDTRPNSTIESPLWALRVILAAGIQDQLIDG

GGGSGGGGSGGPGSGGGGSGGGGSVDEPRGPTIKPCPPCKCPAPNLLGGP

SVFIFPPKIKDVLMISLSPIVTCVVVDVSEDDPDVQISWFVNNVEVHTAQ

TQTHREDYNSTLRVVSALPIQHQDWMSGKEFKCKVNNKDLPAPIERTISK

PKGSVRAPQVYVLPPPEEEMTKKQVTLTCMVTDFMPEDIYVEWTNNGKTE

LNYKNTEPVLDSDGSYFMYSKLRVEKKNWVERNSYSCSVVHEGLHNHHTT

KSFSRTPGK.

1-23 Signal peptide
24-49 VP24(81-108)
50-74 Linker Variant 10
75-309 mG2a(CH2-3)

SEQ ID NO 427 B1. GP2-h(CH1-3), amino acid sequence,
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

-continued

DKTLPDQGDNDNWWTGWRQWIPAGASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPGK.

1-23 Signal peptide
24-174 GP2
175-504 hG1(CH1-3)

SEQ ID NO 428 B2. GP2-hCL, amino acid sequence,
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

DKTLPDQGDNDNWWTGWRQWIPAGTVAAPSVFIFPPSDEQLKSGTASVVC

LLNNFYPREAKVQWKVDNALQSGNSQESVTEQDSKDSTYSLSSTLTLSKA

DYEKHKVYACEVTHQGLSSPVTKSFNRGEC.

1-23 Signal peptide
24-174 GP2
175-280 human constant light region

SEQ ID NO 429 B3. GP2-m(CH1-3), amino acid sequence,
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

DKTLPDQGDNDNWWTGWRQWIPAGAKTTAPSVYPLAPVCGDTTGSSVTLG

CLVKGYFPEPVTLTWNSGSLSSGVHTFPAVLQSDLYTLSSSVTVTSSTWP

SQSITCNVAHPASSTKVDKKIEPRGPTIKPCPPCKCPAPNLLGGPSVFIF

PPKIKDVLMISLSPIVTCVVVDVSEDDPDVQISWFVNNVEVHTAQTQTHR

EDYNSTLRVVSALPIQHQDWMSGKEFKCKVNNKDLPAPIERTISKPKGSV

RAPQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSFSR

TPGK.

1-23 Signal peptide
24-174 GP2
175-504 mG2a(CH1-3)

SEQ ID NO 430 B4. GP2-mCL, amino acid sequence,
.........o.........o.........o.........o.........o
METDTLLLWVLLLWVPGSTGDTRVNAQPKCNPNLHYWTTQDEGAAIGLAW

IPYFGPAAEGIYIEGLMHNQDGLICGLRQLANETTQALQLFLRATTELRT

FSILNRKAIDFLLQRWGGTCHILGPDCCIEPHDWTKNITDKIDQIIHDFV

DKTLPDQGDNDNWWTGWRQWIPAGKRADAAPTVSIFPPSSEQLTSGGASV

VCFLNNFYPKDINVKWKIDGSERQNGVLNSWTDQDSKDSTYSMSSTLTLT

KDEYERHNSYTCEATHKTSTSPIVKSFNRNEC.

-continued 1-23 Signal peptide
24-174 GP2
175-282 murine constant light region

SEQ ID NO 431 C1. GP2-(G45)-GP2-(G45)-GP2-h(CH1-3), amino acid sequence,

.........o.........o.........o.........o.........o

METDTLLLWVLLLWVPGSTGDTRVNAQPKCNPNLHYWTTQDEGAAIGLAW
IPYFGPAAEGIYIEGLMHNQDGLICGLRQLANETTQALQLFLRATTELRT
FSILNRKAIDFLLQRWGGTCHILGPDCCIEPHDWTKNITDKIDQIIHDFV
DKTLPDQGDNDNWWTGWRQWIPAGGGGGSVNAQPKCNPNLHYWTTQDEGA
AIGLAWIPYFGPAAEGIYIEGLMHNQDGLICGLRQLANETTQALQLFLRA
TTELRTFSILNRKAIDFLLQRWGGTCHILGPDCCIEPHDWTKNITDKIDQ
IIHDFVDKTLPDQGDNDNWWTGWRQWIPAGGGGGSVNAQPKCNPNLHYWT
TQDEGAAIGLAWIPYFGPAAEGIYIEGLMHNQDGLICGLRQLANETTQAL
QLFLRATTELRTFSILNRKAIDFLLQRWGGTCHILGPDCCIEPHDWTKNI
TDKIDQIIHDFVDKTLPDQGDNDNWWTGWRQWIPAGASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK.

1-23 Signal peptide
24-174 GP2
175-179 G4S Linker
180-330 GP2
331-335 G4S Linker
336-486 GP2
487-816 hG1(CH1-3)

SEQ ID NO 432 C2. GP2-(G45)-GP2-(G45)-GP2-m(CH1-3), amino acid sequence,

.........o.........o.........o.........o.........o

METDTLLLWVLLLWVPGSTGDTRVNAQPKCNPNLHYWTTQDEGAAIGLAW
IPYFGPAAEGIYIEGLMHNQDGLICGLRQLANETTQALQLFLRATTELRT
FSILNRKAIDFLLQRWGGTCHILGPDCCIEPHDWTKNITDKIDQIIHDFV
DKTLPDQGDNDNWWTGWRQWIPAGGGGGSVNAQPKCNPNLHYWTTQDEGA
AIGLAWIPYFGPAAEGIYIEGLMHNQDGLICGLRQLANETTQALQLFLRA
TTELRTFSILNRKAIDFLLQRWGGTCHILGPDCCIEPHDWTKNITDKIDQ
IIHDFVDKTLPDQGDNDNWWTGWRQWIPAGGGGGSVNAQPKCNPNLHYWT
TQDEGAAIGLAWIPYFGPAAEGIYIEGLMHNQDGLICGLRQLANETTQAL
QLFLRATTELRTFSILNRKAIDFLLQRWGGTCHILGPDCCIEPHDWTKNI
TDKIDQIIHDFVDKTLPDQGDNDNWWTGWRQWIPAGAKTTAPSVYPLAPV
CGDTTGSSVTLGCLVKGYFPEPVTLTWNSGSLSSGVHTFPAVLQSDLYTL
SSSVTVTSSTWPSQSITCNVAHPASSTKVDKKIEPRGPTIKPCPPCKCPA
PNLLGGPSVFIFPPKIKDVLMISLSPIVTCVVVDVSEDDPDVQISWFVNN
VEVHTAQTQTHREDYNSTLRVVSALPIQHQDWMSGKEFKCKVNNKDLPAP
IERTISKPKGSVRAPQVYVLPPPEEEMTKKQVTLTCMVTDFMPEDIYVEW
TNNGKTELNYKNTEPVLDSDGSYFMYSKLRVEKKNWVERNSYSCSVVHEG
LHNHHTTKSFSRTPGK.

1-23 Signal peptide
24-174 GP2
175-179 G4S Linker
180-330 GP2
331-335 G4S Linker
336-486 GP2
487-816 mG2a(CH1-3)

SEQ ID NO 433 D1. GP2-(Lin10)-GP2-(Lin10)-GP2-h(CH1-3), amino acid sequence,

.........o.........o.........o.........o.........o

METDTLLLWVLLLWVPGSTGDTRVNAQPKCNPNLHYWTTQDEGAAIGLAW
IPYFGPAAEGIYIEGLMHNQDGLICGLRQLANETTQALQLFLRATTELRT
FSILNRKAIDFLLQRWGGTCHILGPDCCIEPHDWTKNITDKIDQIIHDFV
DKTLPDQGDNDNWWTGWRQWIPAGGGGGSGGGGSGGPGSGGGGSGGGGSV
NAQPKCNPNLHYWTTQDEGAAIGLAWIPYFGPAAEGIYIEGLMHNQDGLI
CGLRQLANETTQALQLFLRATTELRTFSILNRKAIDFLLQRWGGTCHILG
PDCCIEPHDWTKNITDKIDQIIHDFVDKTLPDQGDNDNWWTGWRQWIPAG
GGGGSGGGGSGGPGSGGGGSGGGGSVNAQPKCNPNLHYWTTQDEGAAIGL
AWIPYFGPAAEGIYIEGLMHNQDGLICGLRQLANETTQALQLFLRATTEL
RTFSILNRKAIDFLLQRWGGTCHILGPDCCIEPHDWTKNITDKIDQIIHD
FVDKTLPDQGDNDNWWTGWRQWIPAGASTKGPSVFPLAPSSKSTSGGTAA
LGCLVKDYFPEPVTVSWNSGALTSGVHTFPAVLQSSGLYSLSSVVTVPSS
SLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSL
SLSPGK.

1-23 Signal peptide
24-174 GP2
175-199 Linker Variant 10
200-350 GP2
351-375 Linker Variant 10
376-526 GP2
527-856 hG1(CH1-3)

SEQ ID NO: 434 D2. GP2-(Lin10)-GP2-(Lin10)-GP2-m(CH1-3), amino acid sequence,

.........o.........o.........o.........o.........o

METDTLLLWVLLLWVPGSTGDTRVNAQPKCNPNLHYWTTQDEGAAIGLAW
IPYFGPAAEGIYIEGLMHNQDGLICGLRQLANETTQALQLFLRATTELRT
FSILNRKAIDFLLQRWGGTCHILGPDCCIEPHDWTKNITDKIDQIIHDFV
DKTLPDQGDNDNWWTGWRQWIPAGGGGGSGGGGSGGPGSGGGGSGGGGSV
NAQPKCNPNLHYWTTQDEGAAIGLAWIPYFGPAAEGIYIEGLMHNQDGLI
CGLRQLANETTQALQLFLRATTELRTFSILNRKAIDFLLQRWGGTCHILG
PDCCIEPHDWTKNITDKIDQIIHDFVDKTLPDQGDNDNWWTGWRQWIPAG
GGGGSGGGGSGGPGSGGGGSGGGGSVNAQPKCNPNLHYWTTQDEGAAIGL
AWIPYFGPAAEGIYIEGLMHNQDGLICGLRQLANETTQALQLFLRATTEL

-continued

RTFSILNRKAIDFLLQRWGGTCHILGPDCCIEPHDWTKNITDKIDQIIHD

FVDKTLPDQGDNDNWWTGWRQWIPAGAKTTAPSVYPLAPVCGDTTGSSVT

LGCLVKGYFPEPVTLTWNSGSLSSGVHTFPAVLQSDLYTLSSSVTVTSST

WPSQSITCNVAHPASSTKVDKKIEPRGPTIKPCPPCKCPAPNLLGGPSVF

IFPPKIKDVLMISLSPIVTCVVVDVSEDDPDVQISWFVNNVEVHTAQTQT

HREDYNSTLRVVSALPIQHQDWMSGKEFKCKVNNKDLPAPIERTISKPKG

SVRAPQVYVLPPPEEEMTKKQVTLTCMVTDFMPEDIYVEWTNNGKTELNY

KNTEPVLDSDGSYFMYSKLRVEKKNWVERNSYSCSVVHEGLHNHHTTKSF

SRTPGK.

1-23 Signal peptide
24-174 GP2
175-199 Linker Variant 10
200-350 GP2
351-375 Linker Variant 10
376-526 GP2
527-856 mG2a(CH1-3)

SEQ ID NO: 435
Linker Variant 10
GGTGGTGGCGGTTCAGGCGGAGGTGGCTCTGGCGGTCCCGGATCCGGCGG

AGGTGGCTCTGGCGGAGGAGGGTCT

SEQ ID NO: 436
Linker Variant 10
GGGGSGGGGSGGPGSGGGGSGGGGS

The constructs described above are expressed in CHO cells. This is accomplished using a retrovector based gene transfer system described elsewhere (see, e.g., U.S. Pat. No. 6,852,510, incorporated herein by reference).

In one application of the immunogens thus designed they are incorporated into a vaccine and for this purpose comprise immunoglobulin components. In yet another specific application the Fc fusion is constructed using a murine Fc. The fusion protein is then used to immunize mouse for the reparation of hybridomas. This follows protocols well known to the art (Kohler and Milstein, Nature, 1975, 256 (5517):495-7). Immunoglobulin variable regions are extracted from the hybridomas as previously described (see, e.g., U.S. Pat. No. 8,703,134, incorporated herein by reference) and constructed with human Fc and transfected into CHO cells, or other mammalian cell lines, using a retrovector system as previously described. The resultant recombinant immunoglobulin is evaluated for its neutralizing capability may be used as an immunotherapeutic. In a further embodiment the recombinant antibody is expressed as a fusion with a microbiocide which is virucidal for enveloped viruses. The specific antibody binding targets the virucide to conserved epitopes on the surface of the virus. Specific virucides which may be incorporated include, but are not limited to, cathelicidins, defensins, and phospholipase A2 (see, e.g., Bezzine, et al 2002. J Biol. Chem. 277:48523-48534; Bezzine et al. 2000. J Biol. Chem. 275:3179-3191; Buck et al 2006. Proc. Natl. Acad. Sci. U.S.A 103:1516-1521; Daher et al. J. Virol. 60:1068-1074; Klotman, M. E. and T. L. Chang. 2006. Nat. Rev. Immunol. 6:447-456; Koduri et al 2002. J. Biol. Chem. 277:5849-5857; Ganz, T. 2004. J Leukoc. Biol. 75:34-38.).

Example 14 Design of Optimized Peptides

The ability to specifically identify probable Treg motifs in HPV, or indeed in other oncoproteins or tumor associated antigens of interest, opens the way to developing immunotherapies targeted to such pMHC complexes, or developing diagnostic tools to track the appearance of Tregs binding such pMHC. The TCR recognizes the exposed motif (TCEM) in the context of the MHC molecule of the patient's allele. To develop diagnostic or therapeutic reagents, it may be beneficial to select TCEM combined with intercalated GEM motifs which provide high binding affinity and hence a stable MHC-peptide relationship.

Figure 26:
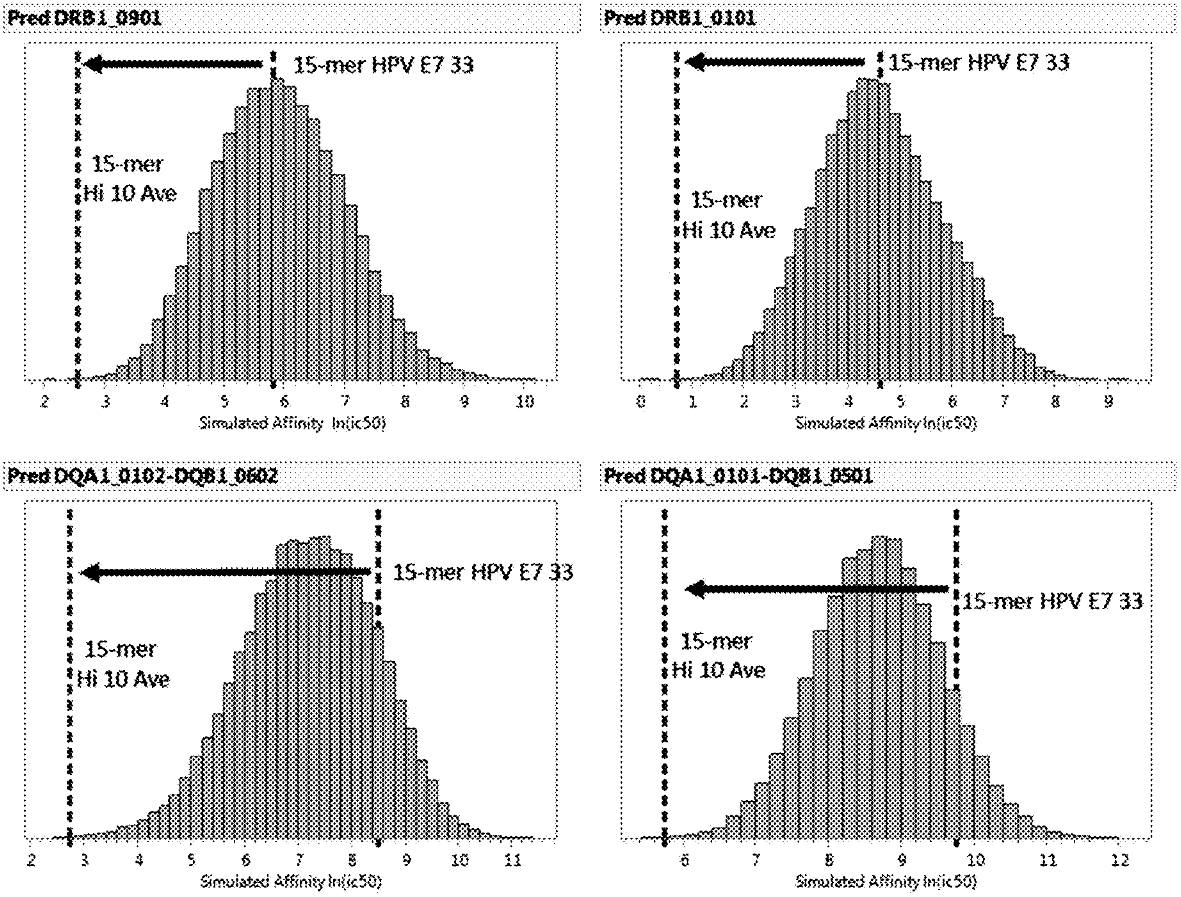
FIG. 26: Affinity distribution of 50,000 peptides generated by Monte Carlo simulation, which maintain the amino acid principal components of two overlapping TCEM frames comprising positions −1, 2, 3, 5, 7, 8 constant for four selected alleles and varied all the remaining amino acid positions. Arrows show the mean and top 10 peptides.

As an example we therefore generated in silico high binding affinity peptides comprising two of the conserved high frequency motifs in Alpha 9 species HPV E7, PE~T~LY (SEQ ID NO: 487) and the overlapping L~~E~T~LY (SEQ ID NO: 488). We selected two of the highest binding alleles for these two motifs, Dr1*09:01 and DR1*01:01 and two lower binders DQA1*0102:DQB1*0602 and DQA1*0101:DQB1*0501 and generated peptides which would have at least ten fold higher affinity. Monte Carlo simulation was used to generate 50,000 unique peptides with modified GEM sequences, while holding the TCEM sequence constant across two frames, a hexamer corresponding to the −1, 2, 3, 5, 7, 8 positions in the naturally occurring 13-mer with index position at amino acid 13 (in HPV33 reference strain gi 218931424). The 50,000 peptides generated in silico were predicted to have a range of affinities, as shown in FIG. 26 with mean ln(ic50) at 7-9. For each allele of interest up to ten top binding peptides were selected, as shown in Table 10. As shown in FIG. 27, the predicted affinity of the top peptides created for each allele was ln(ic50) 0.08 to 5.87, depending on the allele. The selected peptides have a higher affinity and therefore a higher residence time in the binding groove as compared to the original peptide while keeping the same amino acid side chains exposed for T-cell recognition and binding.

These are illustrative examples and other different peptides with similar binding properties could be derived by applying this approach for the same or other predicted Treg TCEM motifs, and are thus embodied in this description. The examples are not considered limiting.

TABLE 23

Example of high affinity peptides for specific alleles which will present HPV E7 TCEM motifs PE~T~LY (SEQ ID NO: 487) and L~~E~T~LY (SEQ ID NO: 488). The TCEM motifs are boldfaced and underlined in the first line of each group. Random generation results in some repeated peptides.

| DRB1*01:01 Hi 10 | DRB1*09:01 Hi 10 |
|---|---|
| RW**L**Y**PE**S**T**V**LY**FTFH (SEQ ID NO: 437) | LF**L**M**PE**M**T**F**LY**GAII (SEQ ID NO: 438) |
| DDLWPELTSLYVVFT (SEQ ID NO: 439) | IQLLPEGTVLYVCPT (SEQ ID NO: 440) |
| MSLMPELTGLYISYV (SEQ ID NO: 441) | LLLFPEATNLYTIEK (SEQ ID NO: 442) |
| MSLMPELTGLYISYV (SEQ ID NO: 441) | FVLFPEATKLYLHGV (SEQ ID NO: 444) |

TABLE 23-continued

Example of high affinity peptides for specific alleles which will present HPV E7 TCEM motifs PE~T~LY (SEQ ID NO: 487) and L~~E~T~LY (SEQ ID NO: 488). The TCEM motifs are boldfaced and underlined in the first line of each group. Random generation results in some repeated peptides.

| | |
|---|---|
| KRLYPESTLLYVSLC (SEQ ID NO: 445) | LELLPEGTLLYVCPI (SEQ ID NO: 446) |
| RWLYPESTVLYFTFH (SEQ ID NO: 447) | LELLPEGTLLYVCPI (SEQ ID NO: 446) |
| RWLYPESTVLYFTFH (SEQ ID NO: 447) | LQLVPEGTALYLYEL (SEQ ID NO: 448) |
| FWLQPEYTALYAMLD (SEQ ID NO: 449) | LQLMPEGTLLYVCPG (SEQ ID NO: 450) |
| QMLLPELTVLYPGCA (SEQ ID NO: 451) | LLLKPECTSLYSMLI (SEQ ID NO: 452) |
| LSLLPEITALYMLIQ (SEQ ID NO: 453) | IVLVPEITQLYLRLC (SEQ ID NO: 454) |
| DQA1*01:02-DQB1*06:02 | DQA1*01:01-DQB1*05:01 |
| MLLNPEGTVLYTCAQ(SEQ ID NO: 455) | CHLCPETTRLYIHST (SEQ ID NO: 456) |
| LLLGPEGTVLYICSQ (SEQ ID NO: 457) | ICLRPECTQLYKRHV (SEQ ID NO: 458) |
| LLLGPEGTVLYICSQ (SEQ ID NO: 457) | CCLCPETTRLYVQST (SEQ ID NO: 459) |
| LLLGPEGTVLYICSQ (SEQ ID NO: 457) | CHLCPETTRLYIHST (SEQ ID NO: 460) |
| LLLGPEGTVLYNCST(SEQ ID NO: 461) | LHLEPEDTFLYEQLC (SEQ ID NO: 462) |
| LLLGPEGTVLYICSQ (SEQ ID NO: 457) | CHLCPETTRLYIHST (SEQ ID NO: 463) |
| LLLGPEGTVLYICSQ (SEQ ID NO: 457) | CCLCPETTRLYVQST (SEQ ID NO: 464) |
| LLLGPEGTVLYICSQ (SEQ ID NO: 457) | CCLCPETTRLYVQST (SEQ ID NO: 464) |
| LQLMPEGTLLYVCPG (SEQ ID NO: 450) | RCLKPEDTGLYRDIV (SEQ ID NO: 465) |
| LLLGPEGTVLYNCST (SEQ ID NO: 461) | CCLCPETTRLYVQST (SEQ ID NO: 464) |

Example 15 Selective T-Cell Targeting for In Vivo and In Vitro Use

Two strategies are envisioned in which a TCEM attached to an MHC is combined with a third peptide which may be a cytotoxin or a cytokine. In the first strategy the combination is configured as TCEM-MHC-Peptide in the second it is configured as MHC-TCEM-peptide The invention described herein identifies Treg binding peptides which are specific to tumor proteins. In one example described above these are TCEM motifs identified in HPV oncoproteins, in another they are PMEL, MART or HBV associated motifs. By identifying TCEMs which bind specifically to Tregs, the possibility is created of attaching or incorporating a cytotoxin to such a peptide which, when mounted in an MHC molecule as a pMHC, binds specifically to a T cell. This allows for the very specific depletion of T cells and, depending on the choice of TCEM, specifically depleting Tregs. The stability of the pMHC complex can be increased by adjusting the GEM amino acids to provide increased binding affinity. The MHC is selected to match that of a particular patient. The selection of cytotoxin depends on the particular disease. One group of cytotoxins are radionuclides. Among the radionuclides are alpha emitters, Auger electron emitters or positron emitters. For labeling peptides containing tyrosine, or to which tyrosine is added iodine 125 has particular ease of use and as an Auger emitter offers a very focused cytotoxic effect on the binding cell.

In the case of HPV cancers, the peptides listed in Tables 9 are examples of motifs which may be incorporated into a peptide to target Tregs.

As a particular example of this in the case of HPV type 16 and type 33, the peptide which in the natural sequence of E7 initiates at index position 13 as shown underlined below and contains the high frequency TCEMs PE~T~LY (SEQ ID NO: 487) and L~~E~T~LY (SEQ ID NO: 488). The same process can be applied to other peptides in Table 9, as well as those occurring on other strains or isolates of HPV, so this example is not limiting.

>gi|333031.E7|genpept|HPV16-E7.1| Human papillomavirus 16 (HPV16), E7 protein (SEQ ID NO: 465)

MHGDTPTLHEYMLDLQPETTDLYCYEQLNDSSEEEDEIDGPAGQAEPDR

AHYNIVTFCCKCDSTLRLCVQSTHVDIRTLEDLLMGTLGIVCPICSQKP

>gi|333049.E7|genpept|HPV33-E7.1| Human papillomavirus 33 (HPV33), E7 protein (SEQ ID NO: 466)

MRGHKPTLKEYVLDLYPEPTDLYCYEQLSDSSDEDEGLDRPDGQAQPAT

ADYYIVTCCHTCNTTVRLCVNSTASDLRTIQQLLMGTVNIVCPTCAQQ

The peptide (for HPV 16) LDLQPETTDLYCYEQ (SEQ ID NO: 271) or (for HPV 33) LDLYPEPTDLYCYEQ (SEQ ID NO: 273) is selected for use as a T-cell target. In some instances a short extension of a few amino acids, 1-4 amino-acids, may be retained on one or both ends of this peptide to facilitate addition of labels or cytotoxins. The intercalated amino acids may be changed to enhance binding affinity for a patient allele of choice as shown above in Table 10. Such optimization has the added advantage of removing by mutation the pRB binding site motif LXCXE, thereby reducing any perceived risk associated with administration.

In one particular case iodination with 1125 allows the delivery of Auger electrons. The methods of iodination are well known to those skilled in the art (See Hunter, R. M. & Greenwood, F. C. Preparation of iodine-131 labelled human growth hormone of high specific activity. Nature 194, 495-496 (1962); Bolton, A. E. & Hunter, W. M. The labeling of proteins to high specific radioactivities by conjugation to a 1251-containing acylating agent. Biochem. J. 133, 529-539 (1973); Garg, P. K., Archer, G. E., Bigner, D. D. & Zalutsky, M. R. Synthesis of radioiodinated N-succinimidyl iodobenzoate: optimization for use in antibody labelling. Appl. Radiat. Isot. 40, 485-490 (1989); Wilbur, D. S. Radiohalogenation of proteins: an overview of radionuclides, labeling methods, and reagents for conjugate labeling. Bioconjugate Chem. 3, 433-470 (1992); Preparation of N-succinimidyl 3-[*I]iodobenzoate: an agent for the indirect radioiodination of proteins. Vaidyanathan G[1], Zalutsky M R. Nat Protoc. 2006; 1(2):707-13.

The most common method for the radioiodination of proteins involves direct electrophilic substitution on tyrosine residues. This method has several problems with some molecules and to counter these problems, conjugation-labeling methods were developed, wherein a labeled prosthetic group was conjugated to mAbs and other proteins under mild conditions through modification of lysine e-amino groups8. N-succinimidyl 3-(4-hydroxy-3-iodophenyl) propionate, popularly known as Bolton-Hunter reagent, is perhaps the best known conjugation-labeling agent. Although the Bolton-Hunter reagent does not create a labeled tyrosine on the protein, the iodine is positioned ortho to a phenolic hydroxyl group, making it susceptible to deiodination. An alternative procedure is the synthesis of N-succinimidyl 3-iodobenzoate labeled with any iodine isotope ([*I]SIB), which is an agent used in the radioiodination of proteins and peptides, from its tin precursor N-succinimidyl 3-(tri-n-butylstannyl)benzoate. Radioiododestannylation of STB using tert-butylhydroperoxide as the oxidant gives [*I]SIB in 80% radiochemical yields. Use of [*I]SIB yields radioiodinated proteins that are more stable in vivo than those radioiodinated by the direct electrophilic method Example 16 Generation of a Generic Immunosuppressive Peptide Combination In order to examine the immunosuppressive content of a randomly generated peptide mixture we proceeded as follows. In order to select four amino acids, we examined the IGHV variable region amino acid positions 37 and 38. These positions are located in the CDR1 and are a region characterized by high binding. In the 40K reference database of IGHV sequences we determined that the commonest occurring amino acids were alanine (A) Glutamine (Q), Valine (V) and Tryptophan (W). Further we determined that the ration of frequency of these at positions 37 and 38 is A(12):Q(22):V(17):W(10).

Using this ratio of amino acids we created 10,000 random 15-mer peptides. We then compared the TCEM motifs in the randomly generated set to those occurring in the naturally derived 40K database of IGHV. Approximately 6% of our random peptides were also found in the 40K database. In addition 42 also matched motifs found in heavy chain constant regions. Table 6 shows the total occurrence of each type of motif and the frequency class to which they belong.

| TCEM IIA Frequencies | | | TCEM IIB Frequencies | | | TCEM I Frequencies | | |
|---|---|---|---|---|---|---|---|---|
| Level | Count | Prob | Level | Count | Prob | Level | Count | Prob |
| 10 | 28 | 0.04643 | 12 | 24 | 0.03954 | 9 | 5 | 0.00828 |
| 12 | 11 | 0.01824 | 13 | 82 | 0.13509 | 10 | 25 | 0.04139 |
| 13 | 22 | 0.03648 | 14 | 15 | 0.02471 | 11 | 14 | 0.02318 |
| 14 | 60 | 0.09950 | 15 | 108 | 0.17792 | 12 | 25 | 0.04139 |
| 15 | 87 | 0.14428 | 16 | 378 | 0.62273 | 13 | 47 | 0.07781 |
| 16 | 395 | 0.65506 | Total | 607 | 1.00000 | 14 | 128 | 0.21192 |
| Total | 603 | 1.00000 | | | | 15 | 84 | 0.13907 |
| | | | | | | 16 | 276 | 0.45695 |
| | | | | | | Total | 604 | 1.00000 |

A MHC molecule is expressed by retrovector transfection into CHO cells as both alpha and beta subunits. In the case of DR1-0101 the alpha and beta subunits are each constructed into a retrovector and alpha and beta subunits transfected sequentially into dividing CHO cells when transfected with both sub chains the CHO cells express the assembled DRB1. The retrovector transfection methods have been described elsewhere (see, e.g., U.S. Pat. Nos. 8,703,134; 8,394,379; 7,566,447; and 20130230516; each of which is incorporated herein by reference in its entirety). Following a recovery period the cells are subject to single cell dilution and allowed to grow back as clonal populations. Yield of the secreted MHC molecules is determined using an immunoassay and antibody to the alphachain and MHC molecules are harvested and purified. The cytotoxin-labeled affinity-optimized peptide is combined with the MHC molecule to generate a pMHC.

Patients are HLA allele matched to the MHC delivering the labeled peptide. Administration of the pMHC to the patient delivers the cytotoxin directly to the binding reaction with the T-cell.

In a variant of this method, instead of a cytotoxin the peptide is labelled with streptavidin and the allele matched patent cells added to the pMHC in vitro. T cells recognizing the TCEM in the pMHC will bind and other cells may be separated, allowing the bound cells to be enumerated.

Table 24 Shows the frequency class (level) and count of IGHV TCEM motifs found in 10,000 randomly generated 15mer peptides comprised of 4 amino acids.

Therefore a total of 39 TCEM IIA (28×FC 10+11×FC12), 24 TCEM IIB and 69 TCEM I (comprising FC 9-12) plus 42 HC motifs were identified which would be expected to elicit immunosuppression. The sequences of these were recorded. The peptides comprising these motifs, singly or collectively could be administered as a general immunosuppressive.

It should be noted that although 4 specific amino acids were selected to generate the peptides in this example, the same approach could be applied to any small set of amino acids selected by other means and to any selected ratio of amino acids. Hence the method described in the example is not limited to the four amino acids or the particular ratio demonstrated here.

Example 17 Modified HLA Secretion

In a further variation on the expression of the HLA molecules the alpha chain or beta chain is made as a fusion with an immunoglobulin Fc region. The Fc region may be derived from IgG or IgA or IgM. In some instances the cysteine cross bridges are removed to prevent assembly of the Fc regions as dimers. The presence of the Fc region enables detection using standard immunoassays (e.g. using an anti Fc detection antibody). It further provides a site for addition of tags, cytotoxins and labels. To express Fc fusion HLA, in this example the DR1 the alpha chain is constructed as a fusion to IgG Fc and transfected into CHO cells as described above. An exemplary sequence of such a fusion is shown in SEQ ID NOs: 467 and 468.

```
SEQ ID NO: 467 Theoretical p500X01 (eSP-DR1alpha'-
G1-mVhC HC) nucleotide:
atggccataagtggagtccctgtgctaggatttttcatcatagctgtgct

gatgagcgctcaggaatcatgggctatcaaagaagaacatgtgatcatcc

aggccgagttctatctgaatcctgaccaatcaggcgagtttatgtttgac

tttgatggtgatgagattttccatgtggatatggcaaagaaggagacggt

ctggcggcttgaagaatttggacgatttgccagctttgaggctcaaggtg

cattggccaacatagctgtggacaaagccaacctggaaatcatgacaaag

cgctccaactatactccgatcaccaatgtacctccagaggtaactgtgct

cacGaacagccctgtggaactgagagagcccaacgtcctcatctgtttca

tCgacaagttcaccccaccagtggtcaatgtcacgtggcttcgaaatgga

aaacctgtcaccacaggagtgtcagagacagtcttcctgcccagggaaga

ccacctttccgcaagttccactatctcccttcctgccctcaactgagg

acgtttacgactgcagggtggagcactggggcttggatgagcctcttctc

aagcactgggagtttgatgtgTCgaccaagggcccatcggtcttccccct

ggcaccctctagcaagagcacctctgggggcacagcggccctgggctgcc

tggtcaaggactacttccccgaaccggtgacggtgtcgtggaactcaggc

gccctgaccagcggcgtgcacaccttcccggctgtcctacagtcctcagg

actctactccctcagcagcgtggtgaccgtgccctccagcagcttgggca

cccagacctacatctgcaacgtgaatcacaagcccagcaacaccaaggtg

gacaagagagttgagcccaaatcttgtgacaaaactcacacatgcccaCC

GTGCCCAgcacctgaactcctggggggaccgtcagtcttcctcttccccc

caaaacccaaggacaccctcatgatctcccggacccctgaggtcacatgc

gtggtggtggacgtgagccacgaagaccctgaggtcaagttcaactggta

cgtggacggcgtggaggtgcataatgccaagacaaagccgcgggaggagc

agtacaacagcacgtaccgtgtggtcagcgtcctcaccgtcctgcaccag

gactggctgaatggcaaggagtacaagtgcaaggtctccaacaaagccct

cccagcccccatcgagaaaaccatctccaaagccaaagggcagccccgag

aaccacaggtgtacaccctgcccccatcccgggaggagatgaccaagaac

caggtcagcctgacctgcctggtcaaaggcttctatcccagcgacatcgc

cgtggagtgggagagcaatgggcagccggagaacaactacaagaccacgc

ctcccgtgctggactccga cggctccttcttcctctatagcaagctcac

cgtggacaagagcaggtggcagcaggggaacgtcttctcatgctccgtga

tgcatgaggctctgcacaaccactacacgcagaagagcctctccctgtct

ccgggtaaatga

SEQ ID NO: 468 Theoretical p500X01 (eSP-DR1alpha'-
G1-mVhC HC) protein:
MAISGVPVLGFFIIAVLMSAQESWAIKEEHVIIQAEFYLNPDQSGEFMFD

FDGDEIFHVDMAKKETVWRLEEFGRFASFEAQGALANIAVDKANLEIMTK

RSNYTPITNVPPEVTVLTNSPVELREPNVLICFIDKFTPPVVNVTWLRNG
```

-continued

```
KPVTTGVSETVFLPREDHLFRKFHYLPFLPSTEDVYDCRVEHWGLDEPLL

KHWEFDVSTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLT

VDKSRWQQGNVFSCSVMHEALHNHYTQKSLSLSPGK.
```

REFERENCE LIST

1. De Groot A S, Moise L, McMurry J A, Wambre E, Van Overtvelt L, et al. (2008) Activation of natural regulatory T cells by IgG Fc-derived peptide “Tregitopes”. Blood 112: 3303-3311.
2. Rudolph M G, Stanfield R L, Wilson I A (2006) How TCRs bind MHCs, peptides, and coreceptors. Annu Rev Immunol 24: 419-466.
3. Lefranc M P, Giudicelli V, Ginestoux C, Jabado-Michaloud J, Folch G, et al. (2009) IMGT, the international ImMunoGeneTics information system. Nucleic Acids Res 37: D1006-1012.
4. Weiss S, Bogen B (1989) B-lymphoma cells process and present their endogenous immunoglobulin to major histocompatibility complex-restricted T cells. Proc Natl Acad Sci USA 86: 282-286.
5. Chakrabarti D, Ghosh S K (1992) Induction of syngeneic cytotoxic T lymphocytes against a B cell tumor. III. MHC class I-restricted CTL recognizes the processed form(s) of idiotype. Cell Immunol 144: 455-464.
6. De Groot A S, Moise L, McMurry J A, Wambre E, Van O L, et al. (2008) Activation of natural regulatory T cells by IgG Fc-derived peptide “Tregitopes”. Blood 112: 3303-3311.
7. Ahmed S S, Volkmuth W, Duca J, Corti L, Pallaoro M, et al. (2015) Antibodies to influenza nucleoprotein cross-react with human hypocretin receptor 2. Sci Transl Med 7: 294ra105.
8. Lalive P H, Neuhaus O, Benkhoucha M, Burger D, Hohlfeld R, et al. (2011) Glatiramer acetate in the treatment of multiple sclerosis: emerging concepts regarding its mechanism of action. CNS Drugs 25: 401-414.
9. Kerzel S, Rogosch T, Struecker B, Maier R F, Zemlin M (2010) IgE transcripts in the circulation of allergic children reflect a classical antigen-driven B cell response and not a superantigen-like activation. J Immunol 185: 2253-2260.
10. Davies J M, O’Hehir R E (2004) VH gene usage in immunoglobulin E responses of seasonal rhinitis patients allergic to grass pollen is oligoclonal and antigen driven. Clin Exp Allergy 34: 429-436.
11. Snow R E, Djukanovic R, Stevenson F K (1999) Analysis of immunoglobulin E VH transcripts in a bronchial biopsy of an asthmatic patient confirms bias towards VH5, and indicates local clonal expansion, somatic mutation and isotype switch events. Immunology 98: 646-651.
12. Bowers E, Scamurra R W, Asrani A, Beniguel L, MaWhinney S, et al. (2014) Decreased mutation frequencies among immunoglobulin G variable region genes during viremic HIV-1 infection. PLoS One 9: e81913.

13. Bremel R D, Homan E J (2013) Recognition of higher order patterns in proteins: immunologic kernels. PLoS One 8: e70115.
14. Greenbaum J, Sidney J, Chung J, Brander C, Peters B, et al. (2011) Functional classification of class II human leukocyte antigen (HLA) molecules reveals seven different supertypes and a surprising degree of repertoire sharing across supertypes. Immunogenetics 63: 325-335.
15. Wang P, Sidney J, Dow C, Mothe B, Sette A, et al. (2008) A systematic assessment of MHC class II peptide binding predictions and evaluation of a consensus approach. PLoSComputBiol 4: e1000048.
16. Tholen S, Biniossek M L, Gessler A L, Muller S, Weisser J, et al. (2011) Contribution of cathepsin L to secretome composition and cleavage pattern of mouse embryonic fibroblasts. BiolChem 392: 961-971.
17. Biniossek M L, Nagler D K, Becker-Pauly C, Schilling O (2011) Proteomic identification of protease cleavage sites characterizes prime and non-prime specificity of cysteine cathepsins B, L, and S. JProteomeRes 10: 5363-5373.
18. Impens F, Colaert N, Helsens K, Ghesquiere B, Timmerman E, et al. (2010) A quantitative proteomics design for systematic identification of protease cleavage events. MolCell Proteomics 9: 2327-2333.
19. Chicz R M, Urban R G, Gorga J C, Vignali D A, Lane W S, et al. (1993) Specificity and promiscuity among naturally processed peptides bound to HLA-DR alleles. J Exp Med 178: 27-47.
20. Costantino C M, Spooner E, Ploegh H L, Hafler D A (2012) Class II MHC self-antigen presentation in human B and T lymphocytes. PLoS One 7: e29805.
21. Wattam A R, Abraham D, Dalay O, Disz T L, Driscoll T, et al. (2014) PATRIC, the bacterial bioinformatics database and analysis resource. Nucleic Acids Res 42: D581-591.
22. Bremel R D, Homan E J (2014) Frequency Patterns of T-Cell Exposed Amino Acid Motifs in Immunoglobulin Heavy Chain Peptides Presented by MHCs. Front Immunol 5: 541.
23. Han F, Lin L, Li J, Dong S X, An P, et al. (2012) HLA-DQ association and allele competition in Chinese narcolepsy. Tissue Antigens 80: 328-335.
24. Mignot E, Lin L, Rogers W, Honda Y, Qiu X, et al. (2001) Complex HLA-DR and -DQ interactions confer risk of narcolepsy-cataplexy in three ethnic groups. Am J Hum Genet 68: 686-699.
25. Han F, Faraco J, Dong X S, Ollila H M, Lin L, et al. (2013) Genome wide analysis of narcolepsy in China implicates novel immune loci and reveals changes in association prior to versus after the 2009 H1N1 influenza pandemic. PLoS Genet 9: e1003880.
26. Drysdale S B (2013) Narcolepsy risk after A/H1N1 2009 influenza vaccination. Thorax.
27. Corti D, Voss J, Gamblin S J, Codoni G, Macagno A, et al. (2011) A neutralizing antibody selected from plasma cells that binds to group 1 and group 2 influenza A hemagglutinins. Science 333: 850-856.
28. Ekiert D C, Friesen R H, Bhabha G, Kwaks T, Jongeneelen M, et al. (2011) A highly conserved neutralizing epitope on group 2 influenza A viruses. Science 333: 843-850.
29. Coulie P G, Brichard V, Van Pel A, Wolfel T, Schneider J, et al. (1994) A new gene coding for a differentiation antigen recognized by autologous cytolytic T lymphocytes on HLA-A2 melanomas. J Exp Med 180: 35-42.
30. Kawakami Y, Eliyahu S, Delgado C H, Robbins P F, Sakaguchi K, et al. (1994) Identification of a human melanoma antigen recognized by tumor-infiltrating lymphocytes associated with in vivo tumor rejection. Proc Natl Acad Sci USA 91: 6458-6462.
31. Kawakami Y, Eliyahu S, Sakaguchi K, Robbins P F, Rivoltini L, et al. (1994) Identification of the immunodominant peptides of the MART-1 human melanoma antigen recognized by the majority of HLA-A2-restricted tumor infiltrating lymphocytes. J Exp Med 180: 347-352.
32. Cormier J N, Salgaller M L, Prevette T, Barracchini K C, Rivoltini L, et al. (1997) Enhancement of cellular immunity in melanoma patients immunized with a peptide from MART-1/Melan A. Cancer J Sci Am 3: 37-44.
33. Reynolds S R, Oratz R, Shapiro R L, Hao P, Yun Z, et al. (1997) Stimulation of CD8+ T cell responses to MAGE-3 and Melan A/MART-1 by immunization to a polyvalent melanoma vaccine. Int J Cancer 72: 972-976.
34. Schneider J, Brichard V, Boon T, Meyer zum Buschenfelde K H, Wolfel T (1998) Overlapping peptides of melanocyte differentiation antigen Melan-A/MART-1 recognized by autologous cytolytic T lymphocytes in association with HLA-B45.1 and HLA-A2.1. Int J Cancer 75: 451-458.
35. Bioley G, Jandus C, Tuyaerts S, Rimoldi D, Kwok W W, et al. (2006) Melan-A/MART-1-specific CD4 T cells in melanoma patients: identification of new epitopes and ex vivo visualization of specific T cells by MHC class II tetramers. J Immunol 177: 6769-6779.
36. Mahnke K, Schonfeld K, Fondel S, Ring S, Karakhanova S, et al. (2007) Depletion of CD4+CD25+ human regulatory T cells in vivo: kinetics of Treg depletion and alterations in immune functions in vivo and in vitro. Int J Cancer 120: 2723-2733.
37. Rasku M A, Clem A L, Telang S, Taft B, Gettings K, et al. (2008) Transient T cell depletion causes regression of melanoma metastases. J Transl Med 6: 12.
38. Rehermann B, Nascimbeni M (2005) Immunology of hepatitis B virus and hepatitis C virus infection. Nat Rev Immunol 5: 215-229.
39. Li J, Shi J, Ren W, Wu W, Chen Z (2014) Regulatory Role of CD4CD25 Foxp3 Regulatory T Cells on IL-17-Secreting T Cells in Chronic Hepatitis B Patients. Dig Dis Sci.
40. Han Y, Jiang Z Y, Jiao L X, Yao C, Lin Q F, et al. (2012) Association of human leukocyte antigen-DRB1 alleles with chronic hepatitis B virus infection in the Han Chinese of Northeast China. Mol Med Rep 5: 1347-1351.
41. Huang Y W, Hu C Y, Chen C L, Liao Y T, Liu O, et al. (2009) Human leukocyte antigen-DRB1*1101 correlates with less severe hepatitis in Taiwanese male carriers of hepatitis B virus. J Med Virol 81: 588-593.
42. Kramvis A, Kew M, Francois G (2005) Hepatitis B virus genotypes. Vaccine 23: 2409-2423.
43. Burk R D, Chen Z, Van D K (2009) Human papillomaviruses: genetic basis of carcinogenicity. Public Health Genomics 12: 281-290.
44. Clifford G, Franceschi S, Diaz M, Munoz N, Villa L L (2006) Chapter 3: HPV type-distribution in women with and without cervical neoplastic diseases. Vaccine 24 Suppl 3: S3/26-34.
45. Munoz N, Castellsague X, de Gonzalez A B, Gissmann L (2006) Chapter 1: HPV in the etiology of human cancer. Vaccine 24 Suppl 3: S3/1-10.
46. Whitehead M, Ohlschlager P, Almajhdi F N, Alloza L, Marzabal P, et al. (2014) Human papillomavirus (HPV)

type 16 E7 protein bodies cause tumour regression in mice. BMC Cancer 14: 367.
47. Bahrami A A, Ghaemi A, Tabarraei A, Sajadian A, Gorji A, et al. (2014) DNA vaccine encoding HPV-16 E7 with mutation in L-Y-C-Y-E pRb-binding motif induces potent anti-tumor responses in mice. J Virol Methods 206C: 12-18.
48. Munoz N, Castellsague X, de Gonzalez A B, Gissmann L (2006) Chapter 1: HPV in the etiology of human cancer. Vaccine 24 Suppl 3: S3/1-S310.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

What is claimed is:

1. A method to identify peptides in a target protein having one or more T-cell-exposed motifs with a known frequency of occurrence in a reference database of T-cell-exposed motifs and synthesize a biomolecule encoding the identified peptides comprising:

establishing a reference database of T-cell-exposed motifs by:

assembling a database of reference proteins comprising at least 40,000 proteins, extracting all sequential 9-mer and 15-mer peptide sequences with a single amino acid displacement from said reference proteins, wherein said T-cell-exposed motifs are those subsets of amino acids within a peptide which, if bound in a MHC molecule, are directed outwards and exposed to T-cell binding, comprising for a possible MHC I binding 9-mer peptide, amino acid positions 4, 5, 6, 7, 8 of a 9-mer and comprising, for a possible MHC II binding 15-mer peptide, amino acid positions 2, 3, 5, 7, 8 or -1, 3, 5, 7, 8 based on a 15-mer peptide with a central core of 9 amino acids numbered 1-9 and positions outside that core numbered as negative (N terminal) or positive (C terminal), identifying said T-cell-exposed motifs in said peptide sequences, and categorizing said T-cell: exposed motifs based on the frequency of occurrence of said T-cell-exposed motifs in said reference database; and determining the relative frequency of each of said T-cell-exposed motifs, thereby providing said reference database of T-cell-exposed motifs;

extracting peptide sequences from said target protein and identifying T-cell exposed motifs in said target protein;

comparing said T-cell-exposed motifs from said target protein to the frequency of occurrence of the same T-cell-exposed motifs in said reference database of T-cell-exposed motifs to identify one or more peptides in said target peptide containing one or more T-cell-exposed motifs having a known frequency of occurrence in said reference database; and cloning said one or more peptides from said target peptide into an expression vector and recombinantly synthesizing a biomolecule selected from the group consisting of a protein and nucleic acid encoding the one or more peptides.

2. The method of claim 1 wherein said reference proteins are selected from the group consisting of immunoglobulin proteins, proteins of the human proteome other than immunoglobulins, protein allergens and microorganism proteins.

3. The method of claim 1, wherein said categorizing further comprises determining whether said T-cell-exposed motifs in said target protein occur with a frequency of greater than 1 in 64 in said reference database of T-cell-exposed motifs.

4. The method of claim 1, wherein said categorizing further comprises determining whether said T-cell-exposed motifs in said target protein occur with a frequency of greater or less than 1 in 1024 in said reference database of T-cell-exposed motifs.

5. The method of claim 1, further comprising the step of characterizing the overall immunogenicity of said target protein by ranking of the frequency of occurrence of a plurality of said T-cell-exposed motifs in said target protein.

6. The method of claim 1, further comprising determining the predicted WIC binding affinity of said peptide sequences comprising said T-cell-exposed motifs derived from said target protein by determining the WIC allele-specific binding of the groove exposed motifs corresponding to each T-cell-exposed motif and modifying the one or more peptide sequences to have an increased or decreased WIC binding affinity.

7. The method of claim 1, further comprising designing modifications in the one or more peptides selected from said target protein wherein said modifications are selected to provide a lower or higher frequency of representation of T-cell-exposed motifs as compared to said reference database of T-cell-exposed motifs.

* * * * *

SEQUENCE LISTING

```
<160> NUMBER OF SEQ ID NOS: 501

<210> SEQ ID NO 1
<211> LENGTH: 15
<212> TYPE: PRT
<213> ORGANISM: artificial sequence
<220> FEATURE:
<223> OTHER INFORMATION: synthetic

<400> SEQUENCE: 1

Phe Ala Met Glu Arg Asn Ala Gly Ser Gly Ile Ile Ile Ser Asp
1               5                   10                  15


<210> SEQ ID NO 2
<211> LENGTH: 5
<212> TYPE: PRT
<213> ORGANISM: artificial sequence
<220> FEATURE:
<223> OTHER INFORMATION: synthetic

<400> SEQUENCE: 2

Arg Asn Gly Gly Ile
1               5


<210> SEQ ID NO 3
<211> LENGTH: 5
<212> TYPE: PRT
<213> ORGANISM: artificial sequence
<220> FEATURE:
<223> OTHER INFORMATION: synthetic

<400> SEQUENCE: 3

Met Asn Gly Gly Ile
1               5


<210> SEQ ID NO 4
<211> LENGTH: 15
<212> TYPE: PRT
<213> ORGANISM: artificial sequence
<220> FEATURE:
<223> OTHER INFORMATION: synthetic

<400> SEQUENCE: 4

Ala Met Glu Arg Asn Ala Gly Ser Gly Ile Ile Ile Ser Asp Thr
1               5                   10                  15


<210> SEQ ID NO 5
<211> LENGTH: 5
<212> TYPE: PRT
<213> ORGANISM: artificial sequence
<220> FEATURE:
<223> OTHER INFORMATION: synthetic

<400> SEQUENCE: 5
```

Asn Ala Ser Ile Ile
1 5

<210> SEQ ID NO 6
<211> LENGTH: 5
<212> TYPE: PRT
<213> ORGANISM: artificial sequence
<220> FEATURE:
<223> OTHER INFORMATION: synthetic

<400> SEQUENCE: 6

Glu Ala Ser Ile Ile
1 5

<210> SEQ ID NO 7
<211> LENGTH: 15
<212> TYPE: PRT
<213> ORGANISM: artificial sequence
<220> FEATURE:
<223> OTHER INFORMATION: synthetic

<400> SEQUENCE: 7

Met Glu Arg Asn Ala Gly Ser Gly Ile Ile Ile Ser Asp Thr Pro
1 5 10 15

<210> SEQ ID NO 8
<211> LENGTH: 5
<212> TYPE: PRT
<213> ORGANISM: artificial sequence
<220> FEATURE:
<223> OTHER INFORMATION: synthetic

<400> SEQUENCE: 8

Ala Gly Gly Ile Ile
1 5

<210> SEQ ID NO 9
<211> LENGTH: 5
<212> TYPE: PRT
<213> ORGANISM: artificial sequence
<220> FEATURE:
<223> OTHER INFORMATION: synthetic

<400> SEQUENCE: 9

Arg Gly Gly Ile Ile
1 5

<210> SEQ ID NO 10
<211> LENGTH: 15
<212> TYPE: PRT
<213> ORGANISM: artificial sequence
<220> FEATURE:
<223> OTHER INFORMATION: synthetic

<400> SEQUENCE: 10

Glu Arg Asn Ala Gly Ser Gly Ile Ile Ile Ser Asp Thr Pro Val
1 5 10 15

<210> SEQ ID NO 11
<211> LENGTH: 5
<212> TYPE: PRT
<213> ORGANISM: artificial sequence
<220> FEATURE:
<223> OTHER INFORMATION: synthetic

<400> SEQUENCE: 11

-continued

```
Gly Ser Ile Ile Ser
1               5


<210> SEQ ID NO 12
<211> LENGTH: 5
<212> TYPE: PRT
<213> ORGANISM: artificial sequence
<220> FEATURE:
<223> OTHER INFORMATION: synthetic

<400> SEQUENCE: 12

Asn Ser Ile Ile Ser
1               5


<210> SEQ ID NO 13
<211> LENGTH: 15
<212> TYPE: PRT
<213> ORGANISM: artificial sequence
<220> FEATURE:
<223> OTHER INFORMATION: synthetic

<400> SEQUENCE: 13

Arg Asn Ala Gly Ser Gly Ile Ile Ile Ser Asp Thr Pro Val His
1               5                   10                  15


<210> SEQ ID NO 14
<211> LENGTH: 5
<212> TYPE: PRT
<213> ORGANISM: artificial sequence
<220> FEATURE:
<223> OTHER INFORMATION: synthetic

<400> SEQUENCE: 14

Ser Gly Ile Ser Asp
1               5


<210> SEQ ID NO 15
<211> LENGTH: 5
<212> TYPE: PRT
<213> ORGANISM: artificial sequence
<220> FEATURE:
<223> OTHER INFORMATION: synthetic

<400> SEQUENCE: 15

Ala Gly Ile Ser Asp
1               5


<210> SEQ ID NO 16
<211> LENGTH: 5
<212> TYPE: PRT
<213> ORGANISM: artificial sequence
<220> FEATURE:
<223> OTHER INFORMATION: synthetic

<400> SEQUENCE: 16

Val Pro Gly Leu Val
1               5


<210> SEQ ID NO 17
<211> LENGTH: 5
<212> TYPE: PRT
<213> ORGANISM: artificial sequence
<220> FEATURE:
<223> OTHER INFORMATION: synthetic

<400> SEQUENCE: 17

Val Pro Gly Ile Val
```

1 5

<210> SEQ ID NO 18
<211> LENGTH: 5
<212> TYPE: PRT
<213> ORGANISM: artificial sequence
<220> FEATURE:
<223> OTHER INFORMATION: synthetic

<400> SEQUENCE: 18

Thr Gly Ile Gly Ser
1 5

<210> SEQ ID NO 19
<211> LENGTH: 5
<212> TYPE: PRT
<213> ORGANISM: artificial sequence
<220> FEATURE:
<223> OTHER INFORMATION: synthetic

<400> SEQUENCE: 19

Thr Gly Ile Asp Ser
1 5

<210> SEQ ID NO 20
<211> LENGTH: 5
<212> TYPE: PRT
<213> ORGANISM: artificial sequence
<220> FEATURE:
<223> OTHER INFORMATION: synthetic

<400> SEQUENCE: 20

Ser Leu Ser Val Ala
1 5

<210> SEQ ID NO 21
<211> LENGTH: 5
<212> TYPE: PRT
<213> ORGANISM: artificial sequence
<220> FEATURE:
<223> OTHER INFORMATION: synthetic

<400> SEQUENCE: 21

Ser Leu Ser Ile Ala
1 5

<210> SEQ ID NO 22
<211> LENGTH: 5
<212> TYPE: PRT
<213> ORGANISM: artificial sequence
<220> FEATURE:
<223> OTHER INFORMATION: synthetic

<400> SEQUENCE: 22

Gly Val Thr Thr Asn
1 5

<210> SEQ ID NO 23
<211> LENGTH: 5
<212> TYPE: PRT
<213> ORGANISM: artificial sequence
<220> FEATURE:
<223> OTHER INFORMATION: synthetic

<400> SEQUENCE: 23

Gly Val Thr Thr Asp
1 5

<210> SEQ ID NO 24
<211> LENGTH: 5
<212> TYPE: PRT
<213> ORGANISM: artificial sequence
<220> FEATURE:
<223> OTHER INFORMATION: synthetic

<400> SEQUENCE: 24

Thr Val Ser Ser Thr
1               5

<210> SEQ ID NO 25
<211> LENGTH: 5
<212> TYPE: PRT
<213> ORGANISM: artificial sequence
<220> FEATURE:
<223> OTHER INFORMATION: synthetic

<400> SEQUENCE: 25

Thr Val Ser Thr Thr
1               5

<210> SEQ ID NO 26
<211> LENGTH: 5
<212> TYPE: PRT
<213> ORGANISM: artificial sequence
<220> FEATURE:
<223> OTHER INFORMATION: synthetic

<400> SEQUENCE: 26

Leu Ser Tyr Ile Ser
1               5

<210> SEQ ID NO 27
<211> LENGTH: 5
<212> TYPE: PRT
<213> ORGANISM: artificial sequence
<220> FEATURE:
<223> OTHER INFORMATION: synthetic

<400> SEQUENCE: 27

Leu Ser Tyr Ile Phe
1               5

<210> SEQ ID NO 28
<211> LENGTH: 5
<212> TYPE: PRT
<213> ORGANISM: artificial sequence
<220> FEATURE:
<223> OTHER INFORMATION: synthetic

<400> SEQUENCE: 28

Ser Thr Ala Thr Leu
1               5

<210> SEQ ID NO 29
<211> LENGTH: 5
<212> TYPE: PRT
<213> ORGANISM: artificial sequence
<220> FEATURE:
<223> OTHER INFORMATION: synthetic

<400> SEQUENCE: 29

Arg Thr Ala Thr Leu
1               5

<210> SEQ ID NO 30
<211> LENGTH: 5
<212> TYPE: PRT
<213> ORGANISM: artificial sequence
<220> FEATURE:
<223> OTHER INFORMATION: synthetic

<400> SEQUENCE: 30

Gly Ser Ser Thr Gly
1 5

<210> SEQ ID NO 31
<211> LENGTH: 5
<212> TYPE: PRT
<213> ORGANISM: artificial sequence
<220> FEATURE:
<223> OTHER INFORMATION: synthetic

<400> SEQUENCE: 31

Ser Ser Ser Thr Gly
1 5

<210> SEQ ID NO 32
<211> LENGTH: 5
<212> TYPE: PRT
<213> ORGANISM: artificial sequence
<220> FEATURE:
<223> OTHER INFORMATION: synthetic

<400> SEQUENCE: 32

Ser Leu Ser Ile Ala
1 5

<210> SEQ ID NO 33
<211> LENGTH: 5
<212> TYPE: PRT
<213> ORGANISM: artificial sequence
<220> FEATURE:
<223> OTHER INFORMATION: synthetic

<400> SEQUENCE: 33

Thr Gly Ile Asp Ser
1 5

<210> SEQ ID NO 34
<211> LENGTH: 5
<212> TYPE: PRT
<213> ORGANISM: artificial sequence
<220> FEATURE:
<223> OTHER INFORMATION: synthetic

<400> SEQUENCE: 34

Arg Ser Thr Ala Tyr
1 5

<210> SEQ ID NO 35
<211> LENGTH: 15
<212> TYPE: PRT
<213> ORGANISM: artificial sequence
<220> FEATURE:
<223> OTHER INFORMATION: synthetic

<400> SEQUENCE: 35

Asp Glu Ser Lys Ser Leu Lys Ser Gln Ile Ala Glu Ala Lys Ile
1 5 10 15

<210> SEQ ID NO 36
<211> LENGTH: 15
<212> TYPE: PRT
<213> ORGANISM: artificial sequence
<220> FEATURE:
<223> OTHER INFORMATION: synthetic

<400> SEQUENCE: 36

Ala Pro Gly Ile Ser Leu Pro Ser Leu Ile Ala Gly Gln Pro Gly
1 5 10 15

<210> SEQ ID NO 37
<211> LENGTH: 15
<212> TYPE: PRT
<213> ORGANISM: artificial sequence
<220> FEATURE:
<223> OTHER INFORMATION: synthetic

<400> SEQUENCE: 37

Trp Ile Ile Gln Ser Leu Ala Ser Ala Ile Ala Tyr Leu His Asn
1 5 10 15

<210> SEQ ID NO 38
<211> LENGTH: 15
<212> TYPE: PRT
<213> ORGANISM: artificial sequence
<220> FEATURE:
<223> OTHER INFORMATION: synthetic

<400> SEQUENCE: 38

Val Thr Leu Ser Ser Leu Ser Ser Ala Ile Ala Lys His Glu Ser
1 5 10 15

<210> SEQ ID NO 39
<211> LENGTH: 15
<212> TYPE: PRT
<213> ORGANISM: artificial sequence
<220> FEATURE:
<223> OTHER INFORMATION: synthetic

<400> SEQUENCE: 39

Gly Pro Pro Ser Ser Leu Met Ser Glu Ile Ala Asp Leu Thr Phe
1 5 10 15

<210> SEQ ID NO 40
<211> LENGTH: 15
<212> TYPE: PRT
<213> ORGANISM: artificial sequence
<220> FEATURE:
<223> OTHER INFORMATION: synthetic

<400> SEQUENCE: 40

Ser Leu Ser Leu Ser Leu Pro Ser Thr Ile Ala Ala Pro His Pro
1 5 10 15

<210> SEQ ID NO 41
<211> LENGTH: 15
<212> TYPE: PRT
<213> ORGANISM: artificial sequence
<220> FEATURE:
<223> OTHER INFORMATION: synthetic

<400> SEQUENCE: 41

Leu Phe Pro His Ser Leu Leu Ser Val Ile Ala Asn Phe Ile Pro
1 5 10 15

<210> SEQ ID NO 42

<211> LENGTH: 15
<212> TYPE: PRT
<213> ORGANISM: artificial sequence
<220> FEATURE:
<223> OTHER INFORMATION: synthetic

<400> SEQUENCE: 42

Ala Pro Gly Ile Ser Leu Pro Ser Leu Ile Ala Gly Gln Pro Gly
1 5 10 15

<210> SEQ ID NO 43
<211> LENGTH: 15
<212> TYPE: PRT
<213> ORGANISM: artificial sequence
<220> FEATURE:
<223> OTHER INFORMATION: synthetic

<400> SEQUENCE: 43

Leu Phe Pro His Ser Leu Leu Ser Val Ile Ala Asn Phe Ile Pro
1 5 10 15

<210> SEQ ID NO 44
<211> LENGTH: 15
<212> TYPE: PRT
<213> ORGANISM: artificial sequence
<220> FEATURE:
<223> OTHER INFORMATION: synthetic

<400> SEQUENCE: 44

Trp Ile Ile Gln Ser Leu Ala Ser Ala Ile Ala Tyr Leu His Asn
1 5 10 15

<210> SEQ ID NO 45
<211> LENGTH: 15
<212> TYPE: PRT
<213> ORGANISM: artificial sequence
<220> FEATURE:
<223> OTHER INFORMATION: synthetic

<400> SEQUENCE: 45

Ala Leu Glu Ala Ser Leu Ile Ser Gln Ile Ala Asp Ser Leu Lys
1 5 10 15

<210> SEQ ID NO 46
<211> LENGTH: 15
<212> TYPE: PRT
<213> ORGANISM: artificial sequence
<220> FEATURE:
<223> OTHER INFORMATION: synthetic

<400> SEQUENCE: 46

Val Asn Leu Phe Ser Leu Gly Ser Ala Ile Ala Tyr Ser Ala Tyr
1 5 10 15

<210> SEQ ID NO 47
<211> LENGTH: 15
<212> TYPE: PRT
<213> ORGANISM: artificial sequence
<220> FEATURE:
<223> OTHER INFORMATION: synthetic

<400> SEQUENCE: 47

Asn Asp Thr Val Ser Leu Ala Ser Ser Ile Ala Thr Gln Pro Glu
1 5 10 15

<210> SEQ ID NO 48
<211> LENGTH: 15

<212> TYPE: PRT
<213> ORGANISM: artificial sequence
<220> FEATURE:
<223> OTHER INFORMATION: synthetic

<400> SEQUENCE: 48

Gly Pro Pro Ser Ser Leu Met Ser Glu Ile Ala Asp Leu Thr Phe
1 5 10 15

<210> SEQ ID NO 49
<211> LENGTH: 15
<212> TYPE: PRT
<213> ORGANISM: artificial sequence
<220> FEATURE:
<223> OTHER INFORMATION: synthetic

<400> SEQUENCE: 49

Leu Gly Glu Gln Ser Leu Gln Ser Arg Ile Ala Ala Leu Thr Val
1 5 10 15

<210> SEQ ID NO 50
<211> LENGTH: 15
<212> TYPE: PRT
<213> ORGANISM: artificial sequence
<220> FEATURE:
<223> OTHER INFORMATION: synthetic

<400> SEQUENCE: 50

Ser Ser Arg Thr Ser Leu Val Ser Thr Ile Ala Gly Ile Leu Ser
1 5 10 15

<210> SEQ ID NO 51
<211> LENGTH: 15
<212> TYPE: PRT
<213> ORGANISM: artificial sequence
<220> FEATURE:
<223> OTHER INFORMATION: synthetic

<400> SEQUENCE: 51

Pro Gln Ile Thr Ser Leu Pro Ser Asn Ile Ala Leu Ser Pro Thr
1 5 10 15

<210> SEQ ID NO 52
<211> LENGTH: 15
<212> TYPE: PRT
<213> ORGANISM: artificial sequence
<220> FEATURE:
<223> OTHER INFORMATION: synthetic

<400> SEQUENCE: 52

Thr Val Ser Tyr Ser Leu Leu Ser Gly Ile Ala Leu Asn Asp Arg
1 5 10 15

<210> SEQ ID NO 53
<211> LENGTH: 15
<212> TYPE: PRT
<213> ORGANISM: artificial sequence
<220> FEATURE:
<223> OTHER INFORMATION: synthetic

<400> SEQUENCE: 53

Asp Glu Ser Lys Ser Leu Lys Ser Gln Ile Ala Glu Ala Lys Ile
1 5 10 15

<210> SEQ ID NO 54
<211> LENGTH: 15
<212> TYPE: PRT

<213> ORGANISM: artificial sequence
<220> FEATURE:
<223> OTHER INFORMATION: synthetic

<400> SEQUENCE: 54

Gly Ile Ile Ser Ser Leu Phe Ser Leu Ile Ala Gly Ile Ile Leu
1 5 10 15

<210> SEQ ID NO 55
<211> LENGTH: 15
<212> TYPE: PRT
<213> ORGANISM: artificial sequence
<220> FEATURE:
<223> OTHER INFORMATION: synthetic

<400> SEQUENCE: 55

Ala Pro Gly Ile Ser Leu Pro Ser Leu Ile Ala Gly Gln Pro Gly
1 5 10 15

<210> SEQ ID NO 56
<211> LENGTH: 15
<212> TYPE: PRT
<213> ORGANISM: artificial sequence
<220> FEATURE:
<223> OTHER INFORMATION: synthetic

<400> SEQUENCE: 56

Ser Ser Arg Thr Ser Leu Val Ser Thr Ile Ala Gly Ile Leu Ser
1 5 10 15

<210> SEQ ID NO 57
<211> LENGTH: 15
<212> TYPE: PRT
<213> ORGANISM: artificial sequence
<220> FEATURE:
<223> OTHER INFORMATION: synthetic

<400> SEQUENCE: 57

Val Asn Ala Ile Ser Leu Thr Ser Gly Ile Ala Lys Gly Leu Asn
1 5 10 15

<210> SEQ ID NO 58
<211> LENGTH: 15
<212> TYPE: PRT
<213> ORGANISM: artificial sequence
<220> FEATURE:
<223> OTHER INFORMATION: synthetic

<400> SEQUENCE: 58

Glu Cys Ser Gly Ser Leu Gly Ser Gly Ile Ala Glu Val Cys Leu
1 5 10 15

<210> SEQ ID NO 59
<211> LENGTH: 15
<212> TYPE: PRT
<213> ORGANISM: artificial sequence
<220> FEATURE:
<223> OTHER INFORMATION: synthetic

<400> SEQUENCE: 59

Ser Val Phe Ser Ser Leu Ser Ser Pro Ile Ala Ala Pro Ile Ser
1 5 10 15

<210> SEQ ID NO 60
<211> LENGTH: 15
<212> TYPE: PRT
<213> ORGANISM: artificial sequence
<220> FEATURE:
<223> OTHER INFORMATION: synthetic

<400> SEQUENCE: 60

Asp Glu Ser Lys Ser Leu Lys Ser Gln Ile Ala Glu Ala Lys Ile
1               5                   10                  15

<210> SEQ ID NO 61
<211> LENGTH: 15
<212> TYPE: PRT
<213> ORGANISM: artificial sequence
<220> FEATURE:
<223> OTHER INFORMATION: synthetic

<400> SEQUENCE: 61

Ser Leu Asn Val Ser Leu Glu Ser Leu Ile Ala Asn Leu Cys Ala
1               5                   10                  15

<210> SEQ ID NO 62
<211> LENGTH: 15
<212> TYPE: PRT
<213> ORGANISM: artificial sequence
<220> FEATURE:
<223> OTHER INFORMATION: synthetic

<400> SEQUENCE: 62

Glu Arg Ala Ala Ser Leu Phe Ser Ala Ile Ala Lys Phe Lys Ala
1               5                   10                  15

<210> SEQ ID NO 63
<211> LENGTH: 15
<212> TYPE: PRT
<213> ORGANISM: artificial sequence
<220> FEATURE:
<223> OTHER INFORMATION: synthetic

<400> SEQUENCE: 63

Asp Glu Ser Lys Ser Leu Lys Ser Gln Ile Ala Glu Ala Lys Ile
1               5                   10                  15

<210> SEQ ID NO 64
<211> LENGTH: 15
<212> TYPE: PRT
<213> ORGANISM: artificial sequence
<220> FEATURE:
<223> OTHER INFORMATION: synthetic

<400> SEQUENCE: 64

Val Thr Leu Ser Ser Leu Ser Ser Ala Ile Ala Lys His Glu Ser
1               5                   10                  15

<210> SEQ ID NO 65
<211> LENGTH: 15
<212> TYPE: PRT
<213> ORGANISM: artificial sequence
<220> FEATURE:
<223> OTHER INFORMATION: synthetic

<400> SEQUENCE: 65

Ser Leu Ser Leu Ser Leu Pro Ser Thr Ile Ala Ala Pro His Pro
1               5                   10                  15

<210> SEQ ID NO 66
<211> LENGTH: 15
<212> TYPE: PRT
<213> ORGANISM: artificial sequence
<220> FEATURE:

<223> OTHER INFORMATION: synthetic

<400> SEQUENCE: 66

Asn Asp Thr Val Ser Leu Ala Ser Ser Ile Ala Thr Gln Pro Glu
1 5 10 15

<210> SEQ ID NO 67
<211> LENGTH: 15
<212> TYPE: PRT
<213> ORGANISM: artificial sequence
<220> FEATURE:
<223> OTHER INFORMATION: synthetic

<400> SEQUENCE: 67

Pro Gln Ile Thr Ser Leu Pro Ser Asn Ile Ala Leu Ser Pro Thr
1 5 10 15

<210> SEQ ID NO 68
<211> LENGTH: 15
<212> TYPE: PRT
<213> ORGANISM: artificial sequence
<220> FEATURE:
<223> OTHER INFORMATION: synthetic

<400> SEQUENCE: 68

Trp Ile Ile Gln Ser Leu Ala Ser Ala Ile Ala Tyr Leu His Asn
1 5 10 15

<210> SEQ ID NO 69
<211> LENGTH: 15
<212> TYPE: PRT
<213> ORGANISM: artificial sequence
<220> FEATURE:
<223> OTHER INFORMATION: synthetic

<400> SEQUENCE: 69

Trp Arg Gly Leu Ser Leu Asp Ser Pro Ile Ala Val Leu Leu Thr
1 5 10 15

<210> SEQ ID NO 70
<211> LENGTH: 15
<212> TYPE: PRT
<213> ORGANISM: artificial sequence
<220> FEATURE:
<223> OTHER INFORMATION: synthetic

<400> SEQUENCE: 70

Gly Pro Pro Ser Ser Leu Met Ser Glu Ile Ala Asp Leu Thr Phe
1 5 10 15

<210> SEQ ID NO 71
<211> LENGTH: 15
<212> TYPE: PRT
<213> ORGANISM: artificial sequence
<220> FEATURE:
<223> OTHER INFORMATION: synthetic

<400> SEQUENCE: 71

Ile Arg Glu Ile Ser Leu Asp Ser Cys Ile Ala Gln Ser Tyr Phe
1 5 10 15

<210> SEQ ID NO 72
<211> LENGTH: 15
<212> TYPE: PRT
<213> ORGANISM: artificial sequence
<220> FEATURE:
<223> OTHER INFORMATION: synthetic

<400> SEQUENCE: 72

Leu Phe Pro His Ser Leu Leu Ser Val Ile Ala Asn Phe Ile Pro
1 5 10 15

<210> SEQ ID NO 73
<211> LENGTH: 15
<212> TYPE: PRT
<213> ORGANISM: artificial sequence
<220> FEATURE:
<223> OTHER INFORMATION: synthetic

<400> SEQUENCE: 73

Val Pro Ile Tyr Ser Leu Asp Ser Trp Ile Ala Leu Lys Tyr Pro
1 5 10 15

<210> SEQ ID NO 74
<211> LENGTH: 15
<212> TYPE: PRT
<213> ORGANISM: artificial sequence
<220> FEATURE:
<223> OTHER INFORMATION: synthetic

<400> SEQUENCE: 74

Val Asn Leu Phe Ser Leu Gly Ser Ala Ile Ala Tyr Ser Ala Tyr
1 5 10 15

<210> SEQ ID NO 75
<211> LENGTH: 15
<212> TYPE: PRT
<213> ORGANISM: artificial sequence
<220> FEATURE:
<223> OTHER INFORMATION: synthetic

<400> SEQUENCE: 75

Ile Val Ala Val Ser Leu Val Ser Leu Ile Ala Asn Ala Leu Gly
1 5 10 15

<210> SEQ ID NO 76
<211> LENGTH: 15
<212> TYPE: PRT
<213> ORGANISM: artificial sequence
<220> FEATURE:
<223> OTHER INFORMATION: synthetic

<400> SEQUENCE: 76

Leu Leu Leu Ser Ser Leu Thr Ser Pro Ile Ala Glu Asn Ser Pro
1 5 10 15

<210> SEQ ID NO 77
<211> LENGTH: 15
<212> TYPE: PRT
<213> ORGANISM: artificial sequence
<220> FEATURE:
<223> OTHER INFORMATION: synthetic

<400> SEQUENCE: 77

Gly Pro Ser Ser Ser Leu Met Ser Glu Ile Ala Asp Leu Thr Tyr
1 5 10 15

<210> SEQ ID NO 78
<211> LENGTH: 15
<212> TYPE: PRT
<213> ORGANISM: artificial sequence
<220> FEATURE:
<223> OTHER INFORMATION: synthetic

<400> SEQUENCE: 78

Val Val Tyr Lys Val Pro Lys Gly Lys Ile Val Pro Asn Leu Asn
1 5 10 15

<210> SEQ ID NO 79
<211> LENGTH: 15
<212> TYPE: PRT
<213> ORGANISM: artificial sequence
<220> FEATURE:
<223> OTHER INFORMATION: synthetic

<400> SEQUENCE: 79

Leu Leu His Glu Val Pro Thr Gly Glu Ile Val Val Arg Leu Asp
1 5 10 15

<210> SEQ ID NO 80
<211> LENGTH: 15
<212> TYPE: PRT
<213> ORGANISM: artificial sequence
<220> FEATURE:
<223> OTHER INFORMATION: synthetic

<400> SEQUENCE: 80

Asn Trp Gly Ala Val Pro Phe Gly Lys Ile Val Gly Lys Phe Pro
1 5 10 15

<210> SEQ ID NO 81
<211> LENGTH: 15
<212> TYPE: PRT
<213> ORGANISM: artificial sequence
<220> FEATURE:
<223> OTHER INFORMATION: synthetic

<400> SEQUENCE: 81

Cys Val Pro Ser Val Pro Val Gly Pro Ile Val Leu Thr Ser Ala
1 5 10 15

<210> SEQ ID NO 82
<211> LENGTH: 15
<212> TYPE: PRT
<213> ORGANISM: artificial sequence
<220> FEATURE:
<223> OTHER INFORMATION: synthetic

<400> SEQUENCE: 82

Phe Arg Thr Lys Val Pro Glu Gly Leu Ile Val Phe Ala Ala Ser
1 5 10 15

<210> SEQ ID NO 83
<211> LENGTH: 15
<212> TYPE: PRT
<213> ORGANISM: artificial sequence
<220> FEATURE:
<223> OTHER INFORMATION: synthetic

<400> SEQUENCE: 83

Pro Ile Glu Asp Val Pro Cys Gly Asn Ile Val Gly Leu Val Gly
1 5 10 15

<210> SEQ ID NO 84
<211> LENGTH: 15
<212> TYPE: PRT
<213> ORGANISM: artificial sequence
<220> FEATURE:
<223> OTHER INFORMATION: synthetic

<400> SEQUENCE: 84

```
Leu Leu His Glu Val Pro Thr Gly Glu Ile Val Val Arg Leu Asp
1               5                   10                  15


<210> SEQ ID NO 85
<211> LENGTH: 15
<212> TYPE: PRT
<213> ORGANISM: artificial sequence
<220> FEATURE:
<223> OTHER INFORMATION: synthetic

<400> SEQUENCE: 85

Val Val Tyr Lys Val Pro Lys Gly Lys Ile Val Pro Asn Leu Asn
1               5                   10                  15


<210> SEQ ID NO 86
<211> LENGTH: 15
<212> TYPE: PRT
<213> ORGANISM: artificial sequence
<220> FEATURE:
<223> OTHER INFORMATION: synthetic

<400> SEQUENCE: 86

Asn Asp Leu Asp Val Pro Val Gly His Ile Val His Thr Gly Met
1               5                   10                  15


<210> SEQ ID NO 87
<211> LENGTH: 15
<212> TYPE: PRT
<213> ORGANISM: artificial sequence
<220> FEATURE:
<223> OTHER INFORMATION: synthetic

<400> SEQUENCE: 87

Leu Glu Asp Arg Val Pro Ser Gly Leu Ile Val Asp Tyr His Asn
1               5                   10                  15


<210> SEQ ID NO 88
<211> LENGTH: 15
<212> TYPE: PRT
<213> ORGANISM: artificial sequence
<220> FEATURE:
<223> OTHER INFORMATION: synthetic

<400> SEQUENCE: 88

Gln Glu Ala Ser Val Pro Lys Gly Arg Ile Val Pro Arg Gly Ile
1               5                   10                  15


<210> SEQ ID NO 89
<211> LENGTH: 15
<212> TYPE: PRT
<213> ORGANISM: artificial sequence
<220> FEATURE:
<223> OTHER INFORMATION: synthetic

<400> SEQUENCE: 89

Gly Pro Val His Val Pro Leu Gly His Ile Val Ala Asn Glu Lys
1               5                   10                  15


<210> SEQ ID NO 90
<211> LENGTH: 15
<212> TYPE: PRT
<213> ORGANISM: artificial sequence
<220> FEATURE:
<223> OTHER INFORMATION: synthetic

<400> SEQUENCE: 90
```

-continued

Asn Trp Gly Ala Val Pro Phe Gly Lys Ile Val Gly Lys Phe Pro
1 5 10 15

<210> SEQ ID NO 91
<211> LENGTH: 15
<212> TYPE: PRT
<213> ORGANISM: artificial sequence
<220> FEATURE:
<223> OTHER INFORMATION: synthetic

<400> SEQUENCE: 91

Val Ser Trp Asp Val Pro Glu Gly Asn Ile Val Ile Gly Tyr Ser
1 5 10 15

<210> SEQ ID NO 92
<211> LENGTH: 9
<212> TYPE: PRT
<213> ORGANISM: artificial sequence
<220> FEATURE:
<223> OTHER INFORMATION: synthetic

<400> SEQUENCE: 92

Glu Glu Ala Ala Gly Ile Gly Ile Leu
1 5

<210> SEQ ID NO 93
<211> LENGTH: 9
<212> TYPE: PRT
<213> ORGANISM: artificial sequence
<220> FEATURE:
<223> OTHER INFORMATION: synthetic

<400> SEQUENCE: 93

Glu Ala Ala Gly Ile Gly Ile Leu Thr
1 5

<210> SEQ ID NO 94
<211> LENGTH: 9
<212> TYPE: PRT
<213> ORGANISM: artificial sequence
<220> FEATURE:
<223> OTHER INFORMATION: synthetic

<400> SEQUENCE: 94

Ala Ala Gly Ile Gly Ile Leu Thr Val
1 5

<210> SEQ ID NO 95
<211> LENGTH: 9
<212> TYPE: PRT
<213> ORGANISM: artificial sequence
<220> FEATURE:
<223> OTHER INFORMATION: synthetic

<400> SEQUENCE: 95

Ala Gly Ile Gly Ile Leu Thr Val Ile
1 5

<210> SEQ ID NO 96
<211> LENGTH: 9
<212> TYPE: PRT
<213> ORGANISM: artificial sequence
<220> FEATURE:
<223> OTHER INFORMATION: synthetic

<400> SEQUENCE: 96

Gly Ile Gly Ile Leu Thr Val Ile Leu 1 5

<210> SEQ ID NO 97
<211> LENGTH: 9
<212> TYPE: PRT
<213> ORGANISM: artificial sequence
<220> FEATURE:
<223> OTHER INFORMATION: synthetic

<400> SEQUENCE: 97

Ile Gly Ile Leu Thr Val Ile Leu Gly
1 5

<210> SEQ ID NO 98
<211> LENGTH: 9
<212> TYPE: PRT
<213> ORGANISM: artificial sequence
<220> FEATURE:
<223> OTHER INFORMATION: synthetic

<400> SEQUENCE: 98

Gly Ile Leu Thr Val Ile Leu Gly Val
1 5

<210> SEQ ID NO 99
<211> LENGTH: 9
<212> TYPE: PRT
<213> ORGANISM: artificial sequence
<220> FEATURE:
<223> OTHER INFORMATION: synthetic

<400> SEQUENCE: 99

Ile Leu Thr Val Ile Leu Gly Val Leu
1 5

<210> SEQ ID NO 100
<211> LENGTH: 9
<212> TYPE: PRT
<213> ORGANISM: artificial sequence
<220> FEATURE:
<223> OTHER INFORMATION: synthetic

<400> SEQUENCE: 100

Leu Thr Val Ile Leu Gly Val Leu Leu
1 5

<210> SEQ ID NO 101
<211> LENGTH: 9
<212> TYPE: PRT
<213> ORGANISM: artificial sequence
<220> FEATURE:
<223> OTHER INFORMATION: synthetic

<400> SEQUENCE: 101

Thr Val Ile Leu Gly Val Leu Leu Leu
1 5

<210> SEQ ID NO 102
<211> LENGTH: 9
<212> TYPE: PRT
<213> ORGANISM: artificial sequence
<220> FEATURE:
<223> OTHER INFORMATION: synthetic

<400> SEQUENCE: 102

Val Ile Leu Gly Val Leu Leu Leu Ile
1 5

<210> SEQ ID NO 103
<211> LENGTH: 9
<212> TYPE: PRT
<213> ORGANISM: artificial sequence
<220> FEATURE:
<223> OTHER INFORMATION: synthetic

<400> SEQUENCE: 103

Ile Leu Gly Val Leu Leu Leu Ile Gly
1               5

<210> SEQ ID NO 104
<211> LENGTH: 9
<212> TYPE: PRT
<213> ORGANISM: artificial sequence
<220> FEATURE:
<223> OTHER INFORMATION: synthetic

<400> SEQUENCE: 104

Leu Gly Val Leu Leu Leu Ile Gly Cys
1               5

<210> SEQ ID NO 105
<211> LENGTH: 9
<212> TYPE: PRT
<213> ORGANISM: artificial sequence
<220> FEATURE:
<223> OTHER INFORMATION: synthetic

<400> SEQUENCE: 105

Gly Val Leu Leu Leu Ile Gly Cys Trp
1               5

<210> SEQ ID NO 106
<211> LENGTH: 9
<212> TYPE: PRT
<213> ORGANISM: artificial sequence
<220> FEATURE:
<223> OTHER INFORMATION: synthetic

<400> SEQUENCE: 106

Val Leu Leu Leu Ile Gly Cys Trp Tyr
1               5

<210> SEQ ID NO 107
<211> LENGTH: 9
<212> TYPE: PRT
<213> ORGANISM: artificial sequence
<220> FEATURE:
<223> OTHER INFORMATION: synthetic

<400> SEQUENCE: 107

Leu Leu Leu Ile Gly Cys Trp Tyr Cys
1               5

<210> SEQ ID NO 108
<211> LENGTH: 9
<212> TYPE: PRT
<213> ORGANISM: artificial sequence
<220> FEATURE:
<223> OTHER INFORMATION: synthetic

<400> SEQUENCE: 108

Leu Leu Ile Gly Cys Trp Tyr Cys Arg
1               5

<210> SEQ ID NO 109
<211> LENGTH: 9
<212> TYPE: PRT
<213> ORGANISM: artificial sequence
<220> FEATURE:
<223> OTHER INFORMATION: synthetic

<400> SEQUENCE: 109

Leu Ile Gly Cys Trp Tyr Cys Arg Arg
1 5

<210> SEQ ID NO 110
<211> LENGTH: 9
<212> TYPE: PRT
<213> ORGANISM: artificial sequence
<220> FEATURE:
<223> OTHER INFORMATION: synthetic

<400> SEQUENCE: 110

Ile Gly Cys Trp Tyr Cys Arg Arg Arg
1 5

<210> SEQ ID NO 111
<211> LENGTH: 9
<212> TYPE: PRT
<213> ORGANISM: artificial sequence
<220> FEATURE:
<223> OTHER INFORMATION: synthetic

<400> SEQUENCE: 111

Gly Cys Trp Tyr Cys Arg Arg Arg Asn
1 5

<210> SEQ ID NO 112
<211> LENGTH: 9
<212> TYPE: PRT
<213> ORGANISM: artificial sequence
<220> FEATURE:
<223> OTHER INFORMATION: synthetic

<400> SEQUENCE: 112

Cys Trp Tyr Cys Arg Arg Arg Asn Gly
1 5

<210> SEQ ID NO 113
<211> LENGTH: 9
<212> TYPE: PRT
<213> ORGANISM: artificial sequence
<220> FEATURE:
<223> OTHER INFORMATION: synthetic

<400> SEQUENCE: 113

Trp Tyr Cys Arg Arg Arg Asn Gly Tyr
1 5

<210> SEQ ID NO 114
<211> LENGTH: 9
<212> TYPE: PRT
<213> ORGANISM: artificial sequence
<220> FEATURE:
<223> OTHER INFORMATION: synthetic

<400> SEQUENCE: 114

Tyr Cys Arg Arg Arg Asn Gly Tyr Arg
1 5

<210> SEQ ID NO 115
<211> LENGTH: 9
<212> TYPE: PRT
<213> ORGANISM: artificial sequence
<220> FEATURE:
<223> OTHER INFORMATION: synthetic

<400> SEQUENCE: 115

Cys Arg Arg Arg Asn Gly Tyr Arg Ala
1               5

<210> SEQ ID NO 116
<211> LENGTH: 9
<212> TYPE: PRT
<213> ORGANISM: artificial sequence
<220> FEATURE:
<223> OTHER INFORMATION: synthetic

<400> SEQUENCE: 116

Arg Arg Arg Asn Gly Tyr Arg Ala Leu
1               5

<210> SEQ ID NO 117
<211> LENGTH: 9
<212> TYPE: PRT
<213> ORGANISM: artificial sequence
<220> FEATURE:
<223> OTHER INFORMATION: synthetic

<400> SEQUENCE: 117

Arg Arg Asn Gly Tyr Arg Ala Leu Met
1               5

<210> SEQ ID NO 118
<211> LENGTH: 8
<212> TYPE: PRT
<213> ORGANISM: artificial sequence
<220> FEATURE:
<223> OTHER INFORMATION: synthetic

<400> SEQUENCE: 118

Pro Phe Ser Val Ser Val Ser Gln
1               5

<210> SEQ ID NO 119
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 119

Xaa Xaa Ser Val Ser Val Ser Xaa
1               5

<210> SEQ ID NO 120
<211> LENGTH: 8
<212> TYPE: PRT
<213> ORGANISM: artificial sequence
<220> FEATURE:
<223> OTHER INFORMATION: synthetic

<400> SEQUENCE: 120

Thr Thr Pro Gly Gln Ala Pro Thr
1 5

<210> SEQ ID NO 121
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 121

Xaa Xaa Pro Gly Gln Ala Pro Xaa
1 5

<210> SEQ ID NO 122
<211> LENGTH: 15
<212> TYPE: PRT
<213> ORGANISM: artificial sequence
<220> FEATURE:
<223> OTHER INFORMATION: synthetic

<400> SEQUENCE: 122

Leu Gly Val Leu Leu Leu Ile Gly Cys Trp Tyr Cys Arg Arg Arg
1 5 10 15

<210> SEQ ID NO 123
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 123

Leu Leu Xaa Gly Xaa Trp Tyr
1 5

<210> SEQ ID NO 124
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)

-continued

<223> OTHER INFORMATION: Xaa can be any naturally occurring amino acid

<400> SEQUENCE: 124

Val Xaa Xaa Leu Xaa Gly Xaa Trp Tyr
1               5

<210> SEQ ID NO 125
<211> LENGTH: 15
<212> TYPE: PRT
<213> ORGANISM: artificial sequence
<220> FEATURE:
<223> OTHER INFORMATION: synthetic

<400> SEQUENCE: 125

Ser Ser Ser Ser Pro Leu Val Leu Gly Thr Leu Glu Glu Val Pro
1               5                   10                  15

<210> SEQ ID NO 126
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 126

Ser Xaa Xaa Leu Xaa Leu Xaa Thr Leu
1               5

<210> SEQ ID NO 127
<211> LENGTH: 15
<212> TYPE: PRT
<213> ORGANISM: artificial sequence
<220> FEATURE:
<223> OTHER INFORMATION: synthetic

<400> SEQUENCE: 127

Ser Ser Ser Pro Leu Val Leu Gly Thr Leu Glu Glu Val Pro Thr
1               5                   10                  15

<210> SEQ ID NO 128
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 128

Leu Val Xaa Gly Xaa Leu Glu
1               5

<210> SEQ ID NO 129
<211> LENGTH: 15
<212> TYPE: PRT
<213> ORGANISM: artificial sequence
<220> FEATURE:
<223> OTHER INFORMATION: synthetic

<400> SEQUENCE: 129

Ser Pro Leu Val Leu Gly Thr Leu Glu Glu Val Pro Thr Ala Gly
1 5 10 15

<210> SEQ ID NO 130
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 130

Leu Gly Xaa Leu Xaa Glu Val
1 5

<210> SEQ ID NO 131
<211> LENGTH: 15
<212> TYPE: PRT
<213> ORGANISM: artificial sequence
<220> FEATURE:
<223> OTHER INFORMATION: synthetic

<400> SEQUENCE: 131

Thr Gly Phe Leu Ile Ile Val Leu Val Met Ile Ala Met Glu Gly
1 5 10 15

<210> SEQ ID NO 132
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 132

Ile Ile Xaa Leu Xaa Met Ile
1 5

<210> SEQ ID NO 133
<211> LENGTH: 15
<212> TYPE: PRT
<213> ORGANISM: artificial sequence
<220> FEATURE:
<223> OTHER INFORMATION: synthetic

<400> SEQUENCE: 133

Gly Phe Leu Ile Ile Val Leu Val Met Ile Ala Met Glu Gly Gly 1 5 10 15

<210> SEQ ID NO 134
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 134

Leu Xaa Val Xaa Val Xaa Ile Ala
1 5

<210> SEQ ID NO 135
<211> LENGTH: 15
<212> TYPE: PRT
<213> ORGANISM: artificial sequence
<220> FEATURE:
<223> OTHER INFORMATION: synthetic

<400> SEQUENCE: 135

Leu Asp Val Met Ala Ser Gln Lys Arg Pro Ser Gln Arg His Gly
1 5 10 15

<210> SEQ ID NO 136
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 136

Ala Ser Xaa Lys Xaa Pro Ser
1 5

<210> SEQ ID NO 137
<211> LENGTH: 15
<212> TYPE: PRT
<213> ORGANISM: artificial sequence
<220> FEATURE:
<223> OTHER INFORMATION: synthetic

<400> SEQUENCE: 137

Ser Gln Gly Lys Gly Arg Gly Leu Ser Leu Ser Arg Phe Ser Trp
1 5 10 15

<210> SEQ ID NO 138
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 138

Gly Arg Xaa Leu Xaa Leu Ser
1 5

<210> SEQ ID NO 139
<211> LENGTH: 15
<212> TYPE: PRT
<213> ORGANISM: artificial sequence
<220> FEATURE:
<223> OTHER INFORMATION: synthetic

<400> SEQUENCE: 139

Thr Leu Ser Lys Ile Phe Lys Leu Gly Gly Arg Asp Ser Arg Ser
1 5 10 15

<210> SEQ ID NO 140
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 140

Ile Phe Xaa Leu Xaa Gly Arg
1 5

<210> SEQ ID NO 141
<211> LENGTH: 5
<212> TYPE: PRT
<213> ORGANISM: artificial sequence
<220> FEATURE:
<223> OTHER INFORMATION: synthetic

<400> SEQUENCE: 141

Asn Gln Leu Gly Thr
1 5

<210> SEQ ID NO 142
<211> LENGTH: 5
<212> TYPE: PRT
<213> ORGANISM: artificial sequence
<220> FEATURE:
<223> OTHER INFORMATION: synthetic

<400> SEQUENCE: 142

Val Cys Arg Tyr Arg
1 5

<210> SEQ ID NO 143
<211> LENGTH: 5

<212> TYPE: PRT
<213> ORGANISM: artificial sequence
<220> FEATURE:
<223> OTHER INFORMATION: synthetic

<400> SEQUENCE: 143

Gln Gln Gly Glu Val
1               5

<210> SEQ ID NO 144
<211> LENGTH: 5
<212> TYPE: PRT
<213> ORGANISM: artificial sequence
<220> FEATURE:
<223> OTHER INFORMATION: synthetic

<400> SEQUENCE: 144

Arg Leu Val Ser Ser
1               5

<210> SEQ ID NO 145
<211> LENGTH: 5
<212> TYPE: PRT
<213> ORGANISM: artificial sequence
<220> FEATURE:
<223> OTHER INFORMATION: synthetic

<400> SEQUENCE: 145

Leu Leu Met Ser Leu
1               5

<210> SEQ ID NO 146
<211> LENGTH: 5
<212> TYPE: PRT
<213> ORGANISM: artificial sequence
<220> FEATURE:
<223> OTHER INFORMATION: synthetic

<400> SEQUENCE: 146

Leu Tyr Gln Pro Asp
1               5

<210> SEQ ID NO 147
<211> LENGTH: 5
<212> TYPE: PRT
<213> ORGANISM: artificial sequence
<220> FEATURE:
<223> OTHER INFORMATION: synthetic

<400> SEQUENCE: 147

Leu Leu Met Ser Leu
1               5

<210> SEQ ID NO 148
<211> LENGTH: 5
<212> TYPE: PRT
<213> ORGANISM: artificial sequence
<220> FEATURE:
<223> OTHER INFORMATION: synthetic

<400> SEQUENCE: 148

Pro Glu Thr Leu Tyr
1               5

<210> SEQ ID NO 149
<211> LENGTH: 5
<212> TYPE: PRT

<213> ORGANISM: artificial sequence
<220> FEATURE:
<223> OTHER INFORMATION: synthetic

<400> SEQUENCE: 149

Leu Glu Thr Leu Tyr
1 5

<210> SEQ ID NO 150
<211> LENGTH: 5
<212> TYPE: PRT
<213> ORGANISM: artificial sequence
<220> FEATURE:
<223> OTHER INFORMATION: synthetic

<400> SEQUENCE: 150

Ser Lys Lys Thr Leu
1 5

<210> SEQ ID NO 151
<211> LENGTH: 5
<212> TYPE: PRT
<213> ORGANISM: artificial sequence
<220> FEATURE:
<223> OTHER INFORMATION: synthetic

<400> SEQUENCE: 151

Tyr Cys Ser Asp Ser
1 5

<210> SEQ ID NO 152
<211> LENGTH: 5
<212> TYPE: PRT
<213> ORGANISM: artificial sequence
<220> FEATURE:
<223> OTHER INFORMATION: synthetic

<400> SEQUENCE: 152

Thr Tyr Cys Thr Thr
1 5

<210> SEQ ID NO 153
<211> LENGTH: 5
<212> TYPE: PRT
<213> ORGANISM: artificial sequence
<220> FEATURE:
<223> OTHER INFORMATION: synthetic

<400> SEQUENCE: 153

Pro Glu Phe Leu Tyr
1 5

<210> SEQ ID NO 154
<211> LENGTH: 5
<212> TYPE: PRT
<213> ORGANISM: artificial sequence
<220> FEATURE:
<223> OTHER INFORMATION: synthetic

<400> SEQUENCE: 154

Leu Glu Phe Leu Tyr
1 5

<210> SEQ ID NO 155
<211> LENGTH: 5
<212> TYPE: PRT
<213> ORGANISM: artificial sequence
<220> FEATURE:
<223> OTHER INFORMATION: synthetic

<400> SEQUENCE: 155

Lys Glu Gly Thr Leu
1 5

<210> SEQ ID NO 156
<211> LENGTH: 5
<212> TYPE: PRT
<213> ORGANISM: artificial sequence
<220> FEATURE:
<223> OTHER INFORMATION: synthetic

<400> SEQUENCE: 156

Lys Ser Ser Lys Asn
1 5

<210> SEQ ID NO 157
<211> LENGTH: 5
<212> TYPE: PRT
<213> ORGANISM: artificial sequence
<220> FEATURE:
<223> OTHER INFORMATION: synthetic

<400> SEQUENCE: 157

Leu Thr Arg Leu Gln
1 5

<210> SEQ ID NO 158
<211> LENGTH: 5
<212> TYPE: PRT
<213> ORGANISM: artificial sequence
<220> FEATURE:
<223> OTHER INFORMATION: synthetic

<400> SEQUENCE: 158

Arg Gly Cys Ala Arg
1 5

<210> SEQ ID NO 159
<211> LENGTH: 5
<212> TYPE: PRT
<213> ORGANISM: artificial sequence
<220> FEATURE:
<223> OTHER INFORMATION: synthetic

<400> SEQUENCE: 159

Ile Phe Lys Glu Leu
1 5

<210> SEQ ID NO 160
<211> LENGTH: 5
<212> TYPE: PRT
<213> ORGANISM: artificial sequence
<220> FEATURE:
<223> OTHER INFORMATION: synthetic

<400> SEQUENCE: 160

Ser Gly Gly Thr Val
1 5

<210> SEQ ID NO 161
<211> LENGTH: 5
<212> TYPE: PRT
<213> ORGANISM: artificial sequence
<220> FEATURE:

<223> OTHER INFORMATION: synthetic

<400> SEQUENCE: 161

Thr Cys Val Gly Ala
1               5

<210> SEQ ID NO 162
<211> LENGTH: 5
<212> TYPE: PRT
<213> ORGANISM: artificial sequence
<220> FEATURE:
<223> OTHER INFORMATION: synthetic

<400> SEQUENCE: 162

Leu Val Arg Arg Ser
1               5

<210> SEQ ID NO 163
<211> LENGTH: 5
<212> TYPE: PRT
<213> ORGANISM: artificial sequence
<220> FEATURE:
<223> OTHER INFORMATION: synthetic

<400> SEQUENCE: 163

Tyr Ser Ser Tyr Gly
1               5

<210> SEQ ID NO 164
<211> LENGTH: 5
<212> TYPE: PRT
<213> ORGANISM: artificial sequence
<220> FEATURE:
<223> OTHER INFORMATION: synthetic

<400> SEQUENCE: 164

Ser Val Gly Thr Leu
1               5

<210> SEQ ID NO 165
<211> LENGTH: 5
<212> TYPE: PRT
<213> ORGANISM: artificial sequence
<220> FEATURE:
<223> OTHER INFORMATION: synthetic

<400> SEQUENCE: 165

Lys Lys Ser Leu Tyr
1               5

<210> SEQ ID NO 166
<211> LENGTH: 5
<212> TYPE: PRT
<213> ORGANISM: artificial sequence
<220> FEATURE:
<223> OTHER INFORMATION: synthetic

<400> SEQUENCE: 166

Thr Arg Thr Ala Thr
1               5

<210> SEQ ID NO 167
<211> LENGTH: 5
<212> TYPE: PRT
<213> ORGANISM: artificial sequence
<220> FEATURE:
<223> OTHER INFORMATION: synthetic

<400> SEQUENCE: 167

Val Tyr Gly Ala Ser
1 5

<210> SEQ ID NO 168
<211> LENGTH: 5
<212> TYPE: PRT
<213> ORGANISM: artificial sequence
<220> FEATURE:
<223> OTHER INFORMATION: synthetic

<400> SEQUENCE: 168

Ser Arg Tyr Tyr Tyr
1 5

<210> SEQ ID NO 169
<211> LENGTH: 5
<212> TYPE: PRT
<213> ORGANISM: artificial sequence
<220> FEATURE:
<223> OTHER INFORMATION: synthetic

<400> SEQUENCE: 169

Leu Arg Leu Ser Cys
1 5

<210> SEQ ID NO 170
<211> LENGTH: 5
<212> TYPE: PRT
<213> ORGANISM: artificial sequence
<220> FEATURE:
<223> OTHER INFORMATION: synthetic

<400> SEQUENCE: 170

Arg Leu Ser Cys Val
1 5

<210> SEQ ID NO 171
<211> LENGTH: 5
<212> TYPE: PRT
<213> ORGANISM: artificial sequence
<220> FEATURE:
<223> OTHER INFORMATION: synthetic

<400> SEQUENCE: 171

Leu Leu Leu Leu Ser
1 5

<210> SEQ ID NO 172
<211> LENGTH: 5
<212> TYPE: PRT
<213> ORGANISM: artificial sequence
<220> FEATURE:
<223> OTHER INFORMATION: synthetic

<400> SEQUENCE: 172

Tyr Thr Ser Leu Gln
1 5

<210> SEQ ID NO 173
<211> LENGTH: 5
<212> TYPE: PRT
<213> ORGANISM: artificial sequence
<220> FEATURE:
<223> OTHER INFORMATION: synthetic

<400> SEQUENCE: 173

Leu Arg Leu Ser Cys
1 5

<210> SEQ ID NO 174
<211> LENGTH: 5
<212> TYPE: PRT
<213> ORGANISM: artificial sequence
<220> FEATURE:
<223> OTHER INFORMATION: synthetic

<400> SEQUENCE: 174

Arg Leu Ser Cys Val
1 5

<210> SEQ ID NO 175
<211> LENGTH: 5
<212> TYPE: PRT
<213> ORGANISM: artificial sequence
<220> FEATURE:
<223> OTHER INFORMATION: synthetic

<400> SEQUENCE: 175

Arg Asn Asn Trp Pro
1 5

<210> SEQ ID NO 176
<211> LENGTH: 5
<212> TYPE: PRT
<213> ORGANISM: artificial sequence
<220> FEATURE:
<223> OTHER INFORMATION: synthetic

<400> SEQUENCE: 176

Ile Glu Thr Val Tyr
1 5

<210> SEQ ID NO 177
<211> LENGTH: 5
<212> TYPE: PRT
<213> ORGANISM: artificial sequence
<220> FEATURE:
<223> OTHER INFORMATION: synthetic

<400> SEQUENCE: 177

Arg Gln Arg Gln Arg
1 5

<210> SEQ ID NO 178
<211> LENGTH: 5
<212> TYPE: PRT
<213> ORGANISM: artificial sequence
<220> FEATURE:
<223> OTHER INFORMATION: synthetic

<400> SEQUENCE: 178

Lys Phe Val Arg Asp
1 5

<210> SEQ ID NO 179
<211> LENGTH: 5
<212> TYPE: PRT
<213> ORGANISM: artificial sequence
<220> FEATURE:
<223> OTHER INFORMATION: synthetic

<400> SEQUENCE: 179

Ser Val Gly Thr Leu
1 5

<210> SEQ ID NO 180
<211> LENGTH: 5
<212> TYPE: PRT
<213> ORGANISM: artificial sequence
<220> FEATURE:
<223> OTHER INFORMATION: synthetic

<400> SEQUENCE: 180

Leu Thr Arg Thr Gln
1 5

<210> SEQ ID NO 181
<211> LENGTH: 5
<212> TYPE: PRT
<213> ORGANISM: artificial sequence
<220> FEATURE:
<223> OTHER INFORMATION: synthetic

<400> SEQUENCE: 181

Tyr Ser Asp Ser Val
1 5

<210> SEQ ID NO 182
<211> LENGTH: 5
<212> TYPE: PRT
<213> ORGANISM: artificial sequence
<220> FEATURE:
<223> OTHER INFORMATION: synthetic

<400> SEQUENCE: 182

Tyr Tyr Ser Asp Ser
1 5

<210> SEQ ID NO 183
<211> LENGTH: 5
<212> TYPE: PRT
<213> ORGANISM: artificial sequence
<220> FEATURE:
<223> OTHER INFORMATION: synthetic

<400> SEQUENCE: 183

Ala Gly Ser Tyr Thr
1 5

<210> SEQ ID NO 184
<211> LENGTH: 5
<212> TYPE: PRT
<213> ORGANISM: artificial sequence
<220> FEATURE:
<223> OTHER INFORMATION: synthetic

<400> SEQUENCE: 184

Leu Glu Thr Val Tyr
1 5

<210> SEQ ID NO 185
<211> LENGTH: 5
<212> TYPE: PRT
<213> ORGANISM: artificial sequence
<220> FEATURE:
<223> OTHER INFORMATION: synthetic

<400> SEQUENCE: 185

Ser Val Gly Thr Leu
1 5

<210> SEQ ID NO 186
<211> LENGTH: 5
<212> TYPE: PRT
<213> ORGANISM: artificial sequence
<220> FEATURE:
<223> OTHER INFORMATION: synthetic

<400> SEQUENCE: 186

Asp Ser Thr Tyr Cys
1 5

<210> SEQ ID NO 187
<211> LENGTH: 5
<212> TYPE: PRT
<213> ORGANISM: artificial sequence
<220> FEATURE:
<223> OTHER INFORMATION: synthetic

<400> SEQUENCE: 187

Gln Pro Lys Pro Gln
1 5

<210> SEQ ID NO 188
<211> LENGTH: 5
<212> TYPE: PRT
<213> ORGANISM: artificial sequence
<220> FEATURE:
<223> OTHER INFORMATION: synthetic

<400> SEQUENCE: 188

Thr Asp Thr Val Tyr
1 5

<210> SEQ ID NO 189
<211> LENGTH: 5
<212> TYPE: PRT
<213> ORGANISM: artificial sequence
<220> FEATURE:
<223> OTHER INFORMATION: synthetic

<400> SEQUENCE: 189

Ala Asp Thr Val Tyr
1 5

<210> SEQ ID NO 190
<211> LENGTH: 5
<212> TYPE: PRT
<213> ORGANISM: artificial sequence
<220> FEATURE:
<223> OTHER INFORMATION: synthetic

<400> SEQUENCE: 190

Tyr Cys Gln Leu Gln
1 5

<210> SEQ ID NO 191
<211> LENGTH: 5
<212> TYPE: PRT
<213> ORGANISM: artificial sequence
<220> FEATURE:
<223> OTHER INFORMATION: synthetic

<400> SEQUENCE: 191

Glu Glu Ile Glu Ile 1 5

<210> SEQ ID NO 192
<211> LENGTH: 5
<212> TYPE: PRT
<213> ORGANISM: artificial sequence
<220> FEATURE:
<223> OTHER INFORMATION: synthetic

<400> SEQUENCE: 192

His Ser Arg Thr Gly
1 5

<210> SEQ ID NO 193
<211> LENGTH: 5
<212> TYPE: PRT
<213> ORGANISM: artificial sequence
<220> FEATURE:
<223> OTHER INFORMATION: synthetic

<400> SEQUENCE: 193

Thr Leu Met Thr Leu
1 5

<210> SEQ ID NO 194
<211> LENGTH: 5
<212> TYPE: PRT
<213> ORGANISM: artificial sequence
<220> FEATURE:
<223> OTHER INFORMATION: synthetic

<400> SEQUENCE: 194

Ala Ser Ser Thr Ser
1 5

<210> SEQ ID NO 195
<211> LENGTH: 5
<212> TYPE: PRT
<213> ORGANISM: artificial sequence
<220> FEATURE:
<223> OTHER INFORMATION: synthetic

<400> SEQUENCE: 195

Asp Ala Thr Ala Thr
1 5

<210> SEQ ID NO 196
<211> LENGTH: 5
<212> TYPE: PRT
<213> ORGANISM: artificial sequence
<220> FEATURE:
<223> OTHER INFORMATION: synthetic

<400> SEQUENCE: 196

Val Arg Thr Ser Thr
1 5

<210> SEQ ID NO 197
<211> LENGTH: 5
<212> TYPE: PRT
<213> ORGANISM: artificial sequence
<220> FEATURE:
<223> OTHER INFORMATION: synthetic

<400> SEQUENCE: 197

Ser Leu Leu Cys Ala
1 5

<210> SEQ ID NO 198
<211> LENGTH: 5
<212> TYPE: PRT
<213> ORGANISM: artificial sequence
<220> FEATURE:
<223> OTHER INFORMATION: synthetic

<400> SEQUENCE: 198

Glu Gly Ile Tyr Arg
1               5

<210> SEQ ID NO 199
<211> LENGTH: 5
<212> TYPE: PRT
<213> ORGANISM: artificial sequence
<220> FEATURE:
<223> OTHER INFORMATION: synthetic

<400> SEQUENCE: 199

Gly Asp Ser Leu Arg
1               5

<210> SEQ ID NO 200
<211> LENGTH: 5
<212> TYPE: PRT
<213> ORGANISM: artificial sequence
<220> FEATURE:
<223> OTHER INFORMATION: synthetic

<400> SEQUENCE: 200

Ser Arg Asp Thr Leu
1               5

<210> SEQ ID NO 201
<211> LENGTH: 5
<212> TYPE: PRT
<213> ORGANISM: artificial sequence
<220> FEATURE:
<223> OTHER INFORMATION: synthetic

<400> SEQUENCE: 201

Pro Glu Thr Leu Tyr
1               5

<210> SEQ ID NO 202
<211> LENGTH: 5
<212> TYPE: PRT
<213> ORGANISM: artificial sequence
<220> FEATURE:
<223> OTHER INFORMATION: synthetic

<400> SEQUENCE: 202

Ser Ser Glu Glu Asp
1               5

<210> SEQ ID NO 203
<211> LENGTH: 5
<212> TYPE: PRT
<213> ORGANISM: artificial sequence
<220> FEATURE:
<223> OTHER INFORMATION: synthetic

<400> SEQUENCE: 203

Tyr Cys Ser Asp Ser
1               5

<210> SEQ ID NO 204
<211> LENGTH: 5
<212> TYPE: PRT
<213> ORGANISM: artificial sequence
<220> FEATURE:
<223> OTHER INFORMATION: synthetic

<400> SEQUENCE: 204

Leu Leu Met Ser Leu
1 5

<210> SEQ ID NO 205
<211> LENGTH: 5
<212> TYPE: PRT
<213> ORGANISM: artificial sequence
<220> FEATURE:
<223> OTHER INFORMATION: synthetic

<400> SEQUENCE: 205

Arg Leu Val Ser Ser
1 5

<210> SEQ ID NO 206
<211> LENGTH: 5
<212> TYPE: PRT
<213> ORGANISM: artificial sequence
<220> FEATURE:
<223> OTHER INFORMATION: synthetic

<400> SEQUENCE: 206

Leu Tyr Gln Pro Asp
1 5

<210> SEQ ID NO 207
<211> LENGTH: 5
<212> TYPE: PRT
<213> ORGANISM: artificial sequence
<220> FEATURE:
<223> OTHER INFORMATION: synthetic

<400> SEQUENCE: 207

Leu Glu Thr Leu Tyr
1 5

<210> SEQ ID NO 208
<211> LENGTH: 5
<212> TYPE: PRT
<213> ORGANISM: artificial sequence
<220> FEATURE:
<223> OTHER INFORMATION: synthetic

<400> SEQUENCE: 208

Thr Tyr Cys Thr Thr
1 5

<210> SEQ ID NO 209
<211> LENGTH: 5
<212> TYPE: PRT
<213> ORGANISM: artificial sequence
<220> FEATURE:
<223> OTHER INFORMATION: synthetic

<400> SEQUENCE: 209

Ser Lys Lys Thr Leu
1 5

<210> SEQ ID NO 210
<211> LENGTH: 5
<212> TYPE: PRT
<213> ORGANISM: artificial sequence
<220> FEATURE:
<223> OTHER INFORMATION: synthetic

<400> SEQUENCE: 210

Leu Leu Leu Leu Ser
1               5

<210> SEQ ID NO 211
<211> LENGTH: 5
<212> TYPE: PRT
<213> ORGANISM: artificial sequence
<220> FEATURE:
<223> OTHER INFORMATION: synthetic

<400> SEQUENCE: 211

Ile Glu Thr Val Tyr
1               5

<210> SEQ ID NO 212
<211> LENGTH: 5
<212> TYPE: PRT
<213> ORGANISM: artificial sequence
<220> FEATURE:
<223> OTHER INFORMATION: synthetic

<400> SEQUENCE: 212

Leu Glu Thr Val Tyr
1               5

<210> SEQ ID NO 213
<211> LENGTH: 5
<212> TYPE: PRT
<213> ORGANISM: artificial sequence
<220> FEATURE:
<223> OTHER INFORMATION: synthetic

<400> SEQUENCE: 213

Leu Thr Arg Thr Gln
1               5

<210> SEQ ID NO 214
<211> LENGTH: 5
<212> TYPE: PRT
<213> ORGANISM: artificial sequence
<220> FEATURE:
<223> OTHER INFORMATION: synthetic

<400> SEQUENCE: 214

Arg Gln Arg Gln Arg
1               5

<210> SEQ ID NO 215
<211> LENGTH: 5
<212> TYPE: PRT
<213> ORGANISM: artificial sequence
<220> FEATURE:
<223> OTHER INFORMATION: synthetic

<400> SEQUENCE: 215

Thr Asp Thr Val Tyr
1               5

<210> SEQ ID NO 216

<211> LENGTH: 5
<212> TYPE: PRT
<213> ORGANISM: artificial sequence
<220> FEATURE:
<223> OTHER INFORMATION: synthetic

<400> SEQUENCE: 216

Tyr Cys Gln Leu Gln
1 5

<210> SEQ ID NO 217
<211> LENGTH: 5
<212> TYPE: PRT
<213> ORGANISM: artificial sequence
<220> FEATURE:
<223> OTHER INFORMATION: synthetic

<400> SEQUENCE: 217

Ala Asp Thr Val Tyr
1 5

<210> SEQ ID NO 218
<211> LENGTH: 5
<212> TYPE: PRT
<213> ORGANISM: artificial sequence
<220> FEATURE:
<223> OTHER INFORMATION: synthetic

<400> SEQUENCE: 218

Ala Ser Ser Thr Ser
1 5

<210> SEQ ID NO 219
<211> LENGTH: 5
<212> TYPE: PRT
<213> ORGANISM: artificial sequence
<220> FEATURE:
<223> OTHER INFORMATION: synthetic

<400> SEQUENCE: 219

Asp Ala Thr Ala Thr
1 5

<210> SEQ ID NO 220
<211> LENGTH: 5
<212> TYPE: PRT
<213> ORGANISM: artificial sequence
<220> FEATURE:
<223> OTHER INFORMATION: synthetic

<400> SEQUENCE: 220

Tyr Thr Ser Leu Gln
1 5

<210> SEQ ID NO 221
<211> LENGTH: 5
<212> TYPE: PRT
<213> ORGANISM: artificial sequence
<220> FEATURE:
<223> OTHER INFORMATION: synthetic

<400> SEQUENCE: 221

Ser Arg Tyr Tyr Tyr
1 5

<210> SEQ ID NO 222
<211> LENGTH: 5

<212> TYPE: PRT
<213> ORGANISM: artificial sequence
<220> FEATURE:
<223> OTHER INFORMATION: synthetic

<400> SEQUENCE: 222

Thr Arg Thr Ala Thr
1 5

<210> SEQ ID NO 223
<211> LENGTH: 5
<212> TYPE: PRT
<213> ORGANISM: artificial sequence
<220> FEATURE:
<223> OTHER INFORMATION: synthetic

<400> SEQUENCE: 223

Lys Phe Val Arg Asp
1 5

<210> SEQ ID NO 224
<211> LENGTH: 5
<212> TYPE: PRT
<213> ORGANISM: artificial sequence
<220> FEATURE:
<223> OTHER INFORMATION: synthetic

<400> SEQUENCE: 224

Ser Val Gly Thr Leu
1 5

<210> SEQ ID NO 225
<211> LENGTH: 5
<212> TYPE: PRT
<213> ORGANISM: artificial sequence
<220> FEATURE:
<223> OTHER INFORMATION: synthetic

<400> SEQUENCE: 225

Glu Glu Ile Glu Ile
1 5

<210> SEQ ID NO 226
<211> LENGTH: 5
<212> TYPE: PRT
<213> ORGANISM: artificial sequence
<220> FEATURE:
<223> OTHER INFORMATION: synthetic

<400> SEQUENCE: 226

Gln Pro Lys Pro Gln
1 5

<210> SEQ ID NO 227
<211> LENGTH: 5
<212> TYPE: PRT
<213> ORGANISM: artificial sequence
<220> FEATURE:
<223> OTHER INFORMATION: synthetic

<400> SEQUENCE: 227

His Ser Arg Thr Gly
1 5

<210> SEQ ID NO 228
<211> LENGTH: 5
<212> TYPE: PRT

<213> ORGANISM: artificial sequence
<220> FEATURE:
<223> OTHER INFORMATION: synthetic

<400> SEQUENCE: 228

Thr Leu Met Thr Leu
1 5

<210> SEQ ID NO 229
<211> LENGTH: 5
<212> TYPE: PRT
<213> ORGANISM: artificial sequence
<220> FEATURE:
<223> OTHER INFORMATION: synthetic

<400> SEQUENCE: 229

Val Arg Thr Ser Thr
1 5

<210> SEQ ID NO 230
<211> LENGTH: 5
<212> TYPE: PRT
<213> ORGANISM: artificial sequence
<220> FEATURE:
<223> OTHER INFORMATION: synthetic

<400> SEQUENCE: 230

Val Tyr Gly Ala Ser
1 5

<210> SEQ ID NO 231
<211> LENGTH: 5
<212> TYPE: PRT
<213> ORGANISM: artificial sequence
<220> FEATURE:
<223> OTHER INFORMATION: synthetic

<400> SEQUENCE: 231

Leu Arg Leu Ser Cys
1 5

<210> SEQ ID NO 232
<211> LENGTH: 5
<212> TYPE: PRT
<213> ORGANISM: artificial sequence
<220> FEATURE:
<223> OTHER INFORMATION: synthetic

<400> SEQUENCE: 232

Arg Leu Ser Cys Val
1 5

<210> SEQ ID NO 233
<211> LENGTH: 5
<212> TYPE: PRT
<213> ORGANISM: artificial sequence
<220> FEATURE:
<223> OTHER INFORMATION: synthetic

<400> SEQUENCE: 233

Arg Asn Asn Trp Pro
1 5

<210> SEQ ID NO 234
<211> LENGTH: 5
<212> TYPE: PRT
<213> ORGANISM: artificial sequence
<220> FEATURE:
<223> OTHER INFORMATION: synthetic

<400> SEQUENCE: 234

Tyr Ser Asp Ser Val
1               5

<210> SEQ ID NO 235
<211> LENGTH: 5
<212> TYPE: PRT
<213> ORGANISM: artificial sequence
<220> FEATURE:
<223> OTHER INFORMATION: synthetic

<400> SEQUENCE: 235

Tyr Tyr Ser Asp Ser
1               5

<210> SEQ ID NO 236
<211> LENGTH: 5
<212> TYPE: PRT
<213> ORGANISM: artificial sequence
<220> FEATURE:
<223> OTHER INFORMATION: synthetic

<400> SEQUENCE: 236

Ala Gly Ser Tyr Thr
1               5

<210> SEQ ID NO 237
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 237

Val Trp Xaa Arg Xaa Pro Pro
1               5

<210> SEQ ID NO 238
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 238

Phe Xaa Xaa Trp Xaa Arg Xaa Pro Pro
1               5

<210> SEQ ID NO 239
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 239

Thr Cys Xaa Val Xaa Gly Ala
1               5

<210> SEQ ID NO 240
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 240

Tyr Ser Xaa Ser Xaa Tyr Gly
1               5

<210> SEQ ID NO 241
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 241

Tyr Ser Xaa Ser Xaa Tyr Gly
1               5

<210> SEQ ID NO 242
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 242

Leu Leu Xaa Leu Xaa Leu Ser
1 5

<210> SEQ ID NO 243
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 243

Ile Glu Xaa Thr Xaa Val Tyr
1 5

<210> SEQ ID NO 244
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 244

Arg Gln Xaa Arg Xaa Gln Arg
1 5

<210> SEQ ID NO 245
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 245

Leu Thr Xaa Arg Xaa Thr Gln
1 5

<210> SEQ ID NO 246
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)

-continued

<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 246

Leu Glu Xaa Thr Xaa Val Tyr
1 5

<210> SEQ ID NO 247
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 247

Thr Asp Xaa Thr Xaa Val Tyr
1 5

<210> SEQ ID NO 248
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 248

Ala Asp Xaa Thr Xaa Val Tyr
1 5

<210> SEQ ID NO 249
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 249

Tyr Cys Xaa Gln Xaa Leu Gln
1 5

<210> SEQ ID NO 250
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 250

Leu Xaa Xaa Val Xaa Arg Xaa Arg Ser
1               5

<210> SEQ ID NO 251
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 251

Ser Xaa Xaa Val Xaa Gly Xaa Thr Leu
1               5

<210> SEQ ID NO 252
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 252

Thr Xaa Xaa Arg Xaa Thr Xaa Ala Thr
1               5

<210> SEQ ID NO 253
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 253

Ser Xaa Xaa Arg Xaa Tyr Xaa Tyr Tyr
1 5

<210> SEQ ID NO 254
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 254

Tyr Xaa Xaa Thr Xaa Ser Xaa Leu Gln
1 5

<210> SEQ ID NO 255
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 255

Lys Xaa Xaa Phe Xaa Val Xaa Arg Asp
1 5

<210> SEQ ID NO 256
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 256

Gln Xaa Xaa Pro Xaa Lys Xaa Pro Gln
1               5

<210> SEQ ID NO 257
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 257

Glu Xaa Xaa Glu Xaa Ile Xaa Glu Ile
1               5

<210> SEQ ID NO 258
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 258

His Xaa Xaa Ser Xaa Arg Xaa Thr Gly
1               5

<210> SEQ ID NO 259
<211> LENGTH: 9
<212> TYPE: PRT
<213> ORGANISM: artificial sequence
<220> FEATURE:
<223> OTHER INFORMATION: synthetic

<400> SEQUENCE: 259

Leu Ile Asp Leu Arg Leu Ser Cys Val
1               5

<210> SEQ ID NO 260
<211> LENGTH: 9
<212> TYPE: PRT

<213> ORGANISM: artificial sequence
<220> FEATURE:
<223> OTHER INFORMATION: synthetic

<400> SEQUENCE: 260

Ile Asp Leu Arg Leu Ser Cys Val Tyr
1 5

<210> SEQ ID NO 261
<211> LENGTH: 9
<212> TYPE: PRT
<213> ORGANISM: artificial sequence
<220> FEATURE:
<223> OTHER INFORMATION: synthetic

<400> SEQUENCE: 261

Leu Leu Asp Leu Arg Leu Ser Cys Val
1 5

<210> SEQ ID NO 262
<211> LENGTH: 9
<212> TYPE: PRT
<213> ORGANISM: artificial sequence
<220> FEATURE:
<223> OTHER INFORMATION: synthetic

<400> SEQUENCE: 262

Leu Asp Leu Arg Leu Ser Cys Val Tyr
1 5

<210> SEQ ID NO 263
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 263

Xaa Xaa Lys Lys Ser Leu Tyr Xaa
1 5

<210> SEQ ID NO 264
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 264

Xaa Xaa Val Tyr Gly Ala Ser Xaa
1 5

<210> SEQ ID NO 265

<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 265

Xaa Xaa Leu Arg Leu Ser Cys Xaa
1 5

<210> SEQ ID NO 266
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 266

Xaa Xaa Arg Leu Ser Cys Val Xaa
1 5

<210> SEQ ID NO 267
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 267

Xaa Xaa Arg Asn Asn Trp Pro Xaa
1 5

<210> SEQ ID NO 268
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 268

Xaa Xaa Tyr Ser Asp Ser Val Xaa
1 5

<210> SEQ ID NO 269
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 269

Xaa Xaa Tyr Tyr Ser Asp Ser Xaa
1 5

<210> SEQ ID NO 270
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 270

Xaa Xaa Ala Gly Ser Tyr Thr Xaa
1 5

<210> SEQ ID NO 271
<211> LENGTH: 15
<212> TYPE: PRT
<213> ORGANISM: artificial sequence
<220> FEATURE:
<223> OTHER INFORMATION: synthetic

<400> SEQUENCE: 271

Leu Asp Leu Gln Pro Glu Thr Thr Asp Leu Tyr Cys Tyr Glu Gln
1 5 10 15

<210> SEQ ID NO 272
<211> LENGTH: 15
<212> TYPE: PRT
<213> ORGANISM: artificial sequence
<220> FEATURE:
<223> OTHER INFORMATION: synthetic

<400> SEQUENCE: 272

Leu Asp Leu Gln Pro Glu Ala Thr Asp Leu Tyr Cys Tyr Glu Gln
1 5 10 15

<210> SEQ ID NO 273
<211> LENGTH: 15
<212> TYPE: PRT
<213> ORGANISM: artificial sequence
<220> FEATURE:
<223> OTHER INFORMATION: synthetic

<400> SEQUENCE: 273

Leu Asp Leu Tyr Pro Glu Pro Thr Asp Leu Tyr Cys Tyr Glu Gln
1 5 10 15

<210> SEQ ID NO 274
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 274

Ser Ser Xaa Glu Xaa Glu Asp
1 5

<210> SEQ ID NO 275
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 275

Pro Glu Xaa Thr Xaa Leu Tyr
1 5

<210> SEQ ID NO 276
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 276

Tyr Cys Xaa Ser Xaa Asp Ser
1 5

<210> SEQ ID NO 277
<211> LENGTH: 15
<212> TYPE: PRT
<213> ORGANISM: artificial sequence
<220> FEATURE:
<223> OTHER INFORMATION: synthetic

<400> SEQUENCE: 277

Glu Ala Arg Ile Glu Leu Val Val Glu Ser Ser Ala Asp Asp Leu 1 5 10 15

<210> SEQ ID NO 278
<211> LENGTH: 15
<212> TYPE: PRT
<213> ORGANISM: artificial sequence
<220> FEATURE:
<223> OTHER INFORMATION: synthetic

<400> SEQUENCE: 278

Ile Val Thr Cys Cys Tyr Thr Cys Gly Thr Thr Val Arg Leu Cys
1 5 10 15

<210> SEQ ID NO 279
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 279

Arg Xaa Xaa Leu Xaa Val Xaa Ser Ser
1 5

<210> SEQ ID NO 280
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 280

Leu Xaa Xaa Leu Xaa Met Xaa Ser Leu
1 5

<210> SEQ ID NO 281
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)

<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 281

Leu Xaa Xaa Tyr Xaa Gln Xaa Pro Asp
1               5

<210> SEQ ID NO 282
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 282

Leu Xaa Xaa Glu Xaa Thr Xaa Leu Tyr
1               5

<210> SEQ ID NO 283
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 283

Ser Xaa Xaa Lys Xaa Lys Xaa Thr Leu
1               5

<210> SEQ ID NO 284
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 284

Thr Xaa Xaa Tyr Xaa Cys Thr Thr
1 5

<210> SEQ ID NO 285
<211> LENGTH: 8
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 285

Xaa Xaa Ser Arg Asp Thr Leu Xaa
1 5

<210> SEQ ID NO 286
<211> LENGTH: 5
<212> TYPE: PRT
<213> ORGANISM: artificial sequence
<220> FEATURE:
<223> OTHER INFORMATION: synthetic

<400> SEQUENCE: 286

Thr Leu Thr Ser Thr
1 5

<210> SEQ ID NO 287
<211> LENGTH: 15
<212> TYPE: PRT
<213> ORGANISM: artificial sequence
<220> FEATURE:
<223> OTHER INFORMATION: synthetic

<400> SEQUENCE: 287

Ser His Leu Thr Thr Leu Ala Thr Ile Ser Thr Ser Pro Gln Pro
1 5 10 15

<210> SEQ ID NO 288
<211> LENGTH: 5
<212> TYPE: PRT
<213> ORGANISM: artificial sequence
<220> FEATURE:
<223> OTHER INFORMATION: synthetic

<400> SEQUENCE: 288

Lys Leu Ile Glu Ala
1 5

<210> SEQ ID NO 289
<211> LENGTH: 15
<212> TYPE: PRT
<213> ORGANISM: artificial sequence
<220> FEATURE:
<223> OTHER INFORMATION: synthetic

<400> SEQUENCE: 289

Thr Pro Val Tyr Lys Leu Asp Ile Ser Glu Ala Thr Gln Val Gly
1 5 10 15

<210> SEQ ID NO 290
<211> LENGTH: 5

<212> TYPE: PRT
<213> ORGANISM: artificial sequence
<220> FEATURE:
<223> OTHER INFORMATION: synthetic

<400> SEQUENCE: 290

Tyr Tyr Thr Ile Arg
1 5

<210> SEQ ID NO 291
<211> LENGTH: 15
<212> TYPE: PRT
<213> ORGANISM: artificial sequence
<220> FEATURE:
<223> OTHER INFORMATION: synthetic

<400> SEQUENCE: 291

Pro Ser Ser Gly Tyr Tyr Ser Thr Thr Ile Arg Tyr Gln Ala Thr
1 5 10 15

<210> SEQ ID NO 292
<211> LENGTH: 5
<212> TYPE: PRT
<213> ORGANISM: artificial sequence
<220> FEATURE:
<223> OTHER INFORMATION: synthetic

<400> SEQUENCE: 292

Gln Phe Leu Leu Asn
1 5

<210> SEQ ID NO 293
<211> LENGTH: 15
<212> TYPE: PRT
<213> ORGANISM: artificial sequence
<220> FEATURE:
<223> OTHER INFORMATION: synthetic

<400> SEQUENCE: 293

Arg Phe Thr Pro Gln Phe Leu Leu Gln Leu Asn Glu Thr Ile Tyr
1 5 10 15

<210> SEQ ID NO 294
<211> LENGTH: 5
<212> TYPE: PRT
<213> ORGANISM: artificial sequence
<220> FEATURE:
<223> OTHER INFORMATION: synthetic

<400> SEQUENCE: 294

Ala Thr Ser Ser Pro
1 5

<210> SEQ ID NO 295
<211> LENGTH: 15
<212> TYPE: PRT
<213> ORGANISM: artificial sequence
<220> FEATURE:
<223> OTHER INFORMATION: synthetic

<400> SEQUENCE: 295

Leu Thr Thr Leu Ala Thr Ile Ser Thr Ser Pro Gln Pro Pro Thr
1 5 10 15

<210> SEQ ID NO 296
<211> LENGTH: 5
<212> TYPE: PRT

<213> ORGANISM: artificial sequence
<220> FEATURE:
<223> OTHER INFORMATION: synthetic

<400> SEQUENCE: 296

Ser Ser Asp Ala Thr
1 5

<210> SEQ ID NO 297
<211> LENGTH: 15
<212> TYPE: PRT
<213> ORGANISM: artificial sequence
<220> FEATURE:
<223> OTHER INFORMATION: synthetic

<400> SEQUENCE: 297

Ser Lys Ser Ala Asp Ser Leu Asp Leu Ala Thr Thr Thr Ser Pro
1 5 10 15

<210> SEQ ID NO 298
<211> LENGTH: 5
<212> TYPE: PRT
<213> ORGANISM: artificial sequence
<220> FEATURE:
<223> OTHER INFORMATION: synthetic

<400> SEQUENCE: 298

Arg Ala Gly Gly Thr
1 5

<210> SEQ ID NO 299
<211> LENGTH: 15
<212> TYPE: PRT
<213> ORGANISM: artificial sequence
<220> FEATURE:
<223> OTHER INFORMATION: synthetic

<400> SEQUENCE: 299

Thr Ile Arg Tyr Gln Ala Thr Gly Phe Gly Thr Asn Glu Thr Glu
1 5 10 15

<210> SEQ ID NO 300
<211> LENGTH: 5
<212> TYPE: PRT
<213> ORGANISM: artificial sequence
<220> FEATURE:
<223> OTHER INFORMATION: synthetic

<400> SEQUENCE: 300

Ser Tyr Thr Ile Arg
1 5

<210> SEQ ID NO 301
<211> LENGTH: 15
<212> TYPE: PRT
<213> ORGANISM: artificial sequence
<220> FEATURE:
<223> OTHER INFORMATION: synthetic

<400> SEQUENCE: 301

Pro Ser Ser Gly Tyr Tyr Ser Thr Thr Ile Arg Tyr Gln Ala Thr
1 5 10 15

<210> SEQ ID NO 302
<211> LENGTH: 5
<212> TYPE: PRT
<213> ORGANISM: artificial sequence
<220> FEATURE:
<223> OTHER INFORMATION: synthetic

<400> SEQUENCE: 302

Val Gln Lys Asn Pro
1               5

<210> SEQ ID NO 303
<211> LENGTH: 15
<212> TYPE: PRT
<213> ORGANISM: artificial sequence
<220> FEATURE:
<223> OTHER INFORMATION: synthetic

<400> SEQUENCE: 303

Val Ile Val Asn Ala Gln Pro Lys Cys Asn Pro Asn Leu His Tyr
1               5                   10                  15

<210> SEQ ID NO 304
<211> LENGTH: 5
<212> TYPE: PRT
<213> ORGANISM: artificial sequence
<220> FEATURE:
<223> OTHER INFORMATION: synthetic

<400> SEQUENCE: 304

Thr Leu Thr Ser Thr
1               5

<210> SEQ ID NO 305
<211> LENGTH: 15
<212> TYPE: PRT
<213> ORGANISM: artificial sequence
<220> FEATURE:
<223> OTHER INFORMATION: synthetic

<400> SEQUENCE: 305

Ser His Leu Thr Thr Leu Ala Thr Ile Ser Thr Ser Pro Gln Ser
1               5                   10                  15

<210> SEQ ID NO 306
<211> LENGTH: 5
<212> TYPE: PRT
<213> ORGANISM: artificial sequence
<220> FEATURE:
<223> OTHER INFORMATION: synthetic

<400> SEQUENCE: 306

Lys Leu Ile Glu Ala
1               5

<210> SEQ ID NO 307
<211> LENGTH: 15
<212> TYPE: PRT
<213> ORGANISM: artificial sequence
<220> FEATURE:
<223> OTHER INFORMATION: synthetic

<400> SEQUENCE: 307

Thr Pro Val Tyr Lys Leu Asp Ile Ser Glu Ala Thr Gln Val Glu
1               5                   10                  15

<210> SEQ ID NO 308
<211> LENGTH: 5
<212> TYPE: PRT
<213> ORGANISM: artificial sequence
<220> FEATURE:

<223> OTHER INFORMATION: synthetic

<400> SEQUENCE: 308

Tyr Tyr Thr Ile Arg
1               5

<210> SEQ ID NO 309
<211> LENGTH: 15
<212> TYPE: PRT
<213> ORGANISM: artificial sequence
<220> FEATURE:
<223> OTHER INFORMATION: synthetic

<400> SEQUENCE: 309

Pro Ser Ser Gly Tyr Tyr Ser Thr Thr Ile Arg Tyr Gln Ala Thr
1               5                   10                  15

<210> SEQ ID NO 310
<211> LENGTH: 5
<212> TYPE: PRT
<213> ORGANISM: artificial sequence
<220> FEATURE:
<223> OTHER INFORMATION: synthetic

<400> SEQUENCE: 310

Ser Lys Thr Phe Leu
1               5

<210> SEQ ID NO 311
<211> LENGTH: 15
<212> TYPE: PRT
<213> ORGANISM: artificial sequence
<220> FEATURE:
<223> OTHER INFORMATION: synthetic

<400> SEQUENCE: 311

Asn Thr Asn Thr Ser Lys Ser Thr Asp Phe Leu Asp Pro Ala Thr
1               5                   10                  15

<210> SEQ ID NO 312
<211> LENGTH: 5
<212> TYPE: PRT
<213> ORGANISM: artificial sequence
<220> FEATURE:
<223> OTHER INFORMATION: synthetic

<400> SEQUENCE: 312

Gln Phe Leu Leu Asn
1               5

<210> SEQ ID NO 313
<211> LENGTH: 15
<212> TYPE: PRT
<213> ORGANISM: artificial sequence
<220> FEATURE:
<223> OTHER INFORMATION: synthetic

<400> SEQUENCE: 313

Arg Phe Thr Pro Gln Phe Leu Leu Gln Leu Asn Glu Thr Ile Tyr
1               5                   10                  15

<210> SEQ ID NO 314
<211> LENGTH: 5
<212> TYPE: PRT
<213> ORGANISM: artificial sequence
<220> FEATURE:
<223> OTHER INFORMATION: synthetic

<400> SEQUENCE: 314

Ala Thr Ser Ser Pro
1 5

<210> SEQ ID NO 315
<211> LENGTH: 15
<212> TYPE: PRT
<213> ORGANISM: artificial sequence
<220> FEATURE:
<223> OTHER INFORMATION: synthetic

<400> SEQUENCE: 315

Leu Thr Thr Leu Ala Thr Ile Ser Thr Ser Pro Gln Ser Leu Thr
1 5 10 15

<210> SEQ ID NO 316
<211> LENGTH: 5
<212> TYPE: PRT
<213> ORGANISM: artificial sequence
<220> FEATURE:
<223> OTHER INFORMATION: synthetic

<400> SEQUENCE: 316

Arg Ala Gly Gly Thr
1 5

<210> SEQ ID NO 317
<211> LENGTH: 15
<212> TYPE: PRT
<213> ORGANISM: artificial sequence
<220> FEATURE:
<223> OTHER INFORMATION: synthetic

<400> SEQUENCE: 317

Thr Ile Arg Tyr Gln Ala Thr Gly Phe Gly Thr Asn Glu Thr Glu
1 5 10 15

<210> SEQ ID NO 318
<211> LENGTH: 5
<212> TYPE: PRT
<213> ORGANISM: artificial sequence
<220> FEATURE:
<223> OTHER INFORMATION: synthetic

<400> SEQUENCE: 318

Ser Tyr Thr Ile Arg
1 5

<210> SEQ ID NO 319
<211> LENGTH: 15
<212> TYPE: PRT
<213> ORGANISM: artificial sequence
<220> FEATURE:
<223> OTHER INFORMATION: synthetic

<400> SEQUENCE: 319

Pro Ser Ser Gly Tyr Tyr Ser Thr Thr Ile Arg Tyr Gln Ala Thr
1 5 10 15

<210> SEQ ID NO 320
<211> LENGTH: 5
<212> TYPE: PRT
<213> ORGANISM: artificial sequence
<220> FEATURE:
<223> OTHER INFORMATION: synthetic

<400> SEQUENCE: 320

Val Gln Lys Asn Pro
1 5

<210> SEQ ID NO 321
<211> LENGTH: 15
<212> TYPE: PRT
<213> ORGANISM: artificial sequence
<220> FEATURE:
<223> OTHER INFORMATION: synthetic

<400> SEQUENCE: 321

Ala Ile Val Asn Ala Gln Pro Lys Cys Asn Pro Asn Leu His Tyr
1 5 10 15

<210> SEQ ID NO 322
<211> LENGTH: 5
<212> TYPE: PRT
<213> ORGANISM: artificial sequence
<220> FEATURE:
<223> OTHER INFORMATION: synthetic

<400> SEQUENCE: 322

Ser Gly Ser Asp Ile
1 5

<210> SEQ ID NO 323
<211> LENGTH: 15
<212> TYPE: PRT
<213> ORGANISM: artificial sequence
<220> FEATURE:
<223> OTHER INFORMATION: synthetic

<400> SEQUENCE: 323

Pro Ser Gln Asn Ser Thr Glu Gly Arg Arg Val Asp Val Asn Thr
1 5 10 15

<210> SEQ ID NO 324
<211> LENGTH: 5
<212> TYPE: PRT
<213> ORGANISM: artificial sequence
<220> FEATURE:
<223> OTHER INFORMATION: synthetic

<400> SEQUENCE: 324

Ser Thr Gly Arg Val
1 5

<210> SEQ ID NO 325
<211> LENGTH: 15
<212> TYPE: PRT
<213> ORGANISM: artificial sequence
<220> FEATURE:
<223> OTHER INFORMATION: synthetic

<400> SEQUENCE: 325

Asn Leu Glu Gly Ser Gly Val Ser Thr Asp Ile Pro Ser Ala Thr
1 5 10 15

<210> SEQ ID NO 326
<211> LENGTH: 5
<212> TYPE: PRT
<213> ORGANISM: artificial sequence
<220> FEATURE:
<223> OTHER INFORMATION: synthetic

<400> SEQUENCE: 326

Tyr Ala Ser Leu Glu
1 5

<210> SEQ ID NO 327
<211> LENGTH: 15
<212> TYPE: PRT
<213> ORGANISM: artificial sequence
<220> FEATURE:
<223> OTHER INFORMATION: synthetic

<400> SEQUENCE: 327

Gly Leu Ser Ser Ser Gln Ile Leu Ser Ser Ser Pro Thr Met Ala
1 5 10 15

<210> SEQ ID NO 328
<211> LENGTH: 5
<212> TYPE: PRT
<213> ORGANISM: artificial sequence
<220> FEATURE:
<223> OTHER INFORMATION: synthetic

<400> SEQUENCE: 328

Ser Gln Leu Ser Ser
1 5

<210> SEQ ID NO 329
<211> LENGTH: 15
<212> TYPE: PRT
<213> ORGANISM: artificial sequence
<220> FEATURE:
<223> OTHER INFORMATION: synthetic

<400> SEQUENCE: 329

Thr Ser Ser Tyr Tyr Ala Thr Ser Tyr Leu Glu Tyr Glu Ile Glu
1 5 10 15

<210> SEQ ID NO 330
<211> LENGTH: 5
<212> TYPE: PRT
<213> ORGANISM: artificial sequence
<220> FEATURE:
<223> OTHER INFORMATION: synthetic

<400> SEQUENCE: 330

Thr Glu Thr Thr Ile
1 5

<210> SEQ ID NO 331
<211> LENGTH: 15
<212> TYPE: PRT
<213> ORGANISM: artificial sequence
<220> FEATURE:
<223> OTHER INFORMATION: synthetic

<400> SEQUENCE: 331

Gln Glu Thr Ile Thr Glu Thr Thr Ala Thr Ile Ile Gly Thr Asn
1 5 10 15

<210> SEQ ID NO 332
<211> LENGTH: 5
<212> TYPE: PRT
<213> ORGANISM: artificial sequence
<220> FEATURE:
<223> OTHER INFORMATION: synthetic

<400> SEQUENCE: 332

Thr Thr Thr Thr Thr
1 5

<210> SEQ ID NO 333
<211> LENGTH: 15
<212> TYPE: PRT
<213> ORGANISM: artificial sequence
<220> FEATURE:
<223> OTHER INFORMATION: synthetic

<400> SEQUENCE: 333

Val Asn Thr Gln Glu Thr Ile Thr Glu Thr Thr Ala Thr Ile Ile
1 5 10 15

<210> SEQ ID NO 334
<211> LENGTH: 5
<212> TYPE: PRT
<213> ORGANISM: artificial sequence
<220> FEATURE:
<223> OTHER INFORMATION: synthetic

<400> SEQUENCE: 334

Ser Ile Ser Ser Pro
1 5

<210> SEQ ID NO 335
<211> LENGTH: 15
<212> TYPE: PRT
<213> ORGANISM: artificial sequence
<220> FEATURE:
<223> OTHER INFORMATION: synthetic

<400> SEQUENCE: 335

Leu Ser Ser Ser Gln Ile Leu Ser Ser Ser Pro Thr Met Ala Pro
1 5 10 15

<210> SEQ ID NO 336
<211> LENGTH: 5
<212> TYPE: PRT
<213> ORGANISM: artificial sequence
<220> FEATURE:
<223> OTHER INFORMATION: synthetic

<400> SEQUENCE: 336

Ser Gly Arg Asp Val
1 5

<210> SEQ ID NO 337
<211> LENGTH: 15
<212> TYPE: PRT
<213> ORGANISM: artificial sequence
<220> FEATURE:
<223> OTHER INFORMATION: synthetic

<400> SEQUENCE: 337

Gln Asn Ser Thr Glu Gly Arg Arg Val Asp Val Asn Thr Gln Glu
1 5 10 15

<210> SEQ ID NO 338
<211> LENGTH: 5
<212> TYPE: PRT
<213> ORGANISM: artificial sequence
<220> FEATURE:
<223> OTHER INFORMATION: synthetic

<400> SEQUENCE: 338

Leu Thr Gly Leu Ile 1 5

<210> SEQ ID NO 339
<211> LENGTH: 15
<212> TYPE: PRT
<213> ORGANISM: artificial sequence
<220> FEATURE:
<223> OTHER INFORMATION: synthetic

<400> SEQUENCE: 339

Gln Gln Leu Ser Asn Thr Thr Gly Lys Leu Ile Trp Thr Leu Asp
1 5 10 15

<210> SEQ ID NO 340
<211> LENGTH: 5
<212> TYPE: PRT
<213> ORGANISM: artificial sequence
<220> FEATURE:
<223> OTHER INFORMATION: synthetic

<400> SEQUENCE: 340

Ser Pro Gln Val Ser
1 5

<210> SEQ ID NO 341
<211> LENGTH: 15
<212> TYPE: PRT
<213> ORGANISM: artificial sequence
<220> FEATURE:
<223> OTHER INFORMATION: synthetic

<400> SEQUENCE: 341

Phe Arg Ser Gly Val Pro Pro Gln Val Val Ser Tyr Glu Ala Gly
1 5 10 15

<210> SEQ ID NO 342
<211> LENGTH: 5
<212> TYPE: PRT
<213> ORGANISM: artificial sequence
<220> FEATURE:
<223> OTHER INFORMATION: synthetic

<400> SEQUENCE: 342

Leu Tyr Ile Asn Arg
1 5

<210> SEQ ID NO 343
<211> LENGTH: 15
<212> TYPE: PRT
<213> ORGANISM: artificial sequence
<220> FEATURE:
<223> OTHER INFORMATION: synthetic

<400> SEQUENCE: 343

Thr Glu Leu Arg Thr Tyr Thr Ile Leu Asn Arg Lys Ala Ile Asp
1 5 10 15

<210> SEQ ID NO 344
<211> LENGTH: 5
<212> TYPE: PRT
<213> ORGANISM: artificial sequence
<220> FEATURE:
<223> OTHER INFORMATION: synthetic

<400> SEQUENCE: 344

Val Ala Gly Gly Pro
1 5

<210> SEQ ID NO 345
<211> LENGTH: 15
<212> TYPE: PRT
<213> ORGANISM: artificial sequence
<220> FEATURE:
<223> OTHER INFORMATION: synthetic

<400> SEQUENCE: 345

Arg Tyr Val His Lys Ala Gln Gly Thr Gly Pro Cys Pro Gly Asp
1 5 10 15

<210> SEQ ID NO 346
<211> LENGTH: 30
<212> TYPE: PRT
<213> ORGANISM: artificial sequence
<220> FEATURE:
<223> OTHER INFORMATION: synthetic

<400> SEQUENCE: 346

Gly Asn Gly Val Ala Thr Asp Val Pro Ser Ala Thr Lys Arg Trp Gly
1 5 10 15

Phe Arg Ser Gly Val Pro Pro Lys Val Val Asn Tyr Glu Ala
20 25 30

<210> SEQ ID NO 347
<211> LENGTH: 32
<212> TYPE: PRT
<213> ORGANISM: artificial sequence
<220> FEATURE:
<223> OTHER INFORMATION: synthetic

<400> SEQUENCE: 347

His Lys Val Ser Gly Thr Gly Pro Cys Ala Gly Asp Phe Ala Phe His
1 5 10 15

Lys Glu Gly Ala Phe Phe Leu Tyr Asp Arg Leu Ala Ser Thr Val Ile
20 25 30

<210> SEQ ID NO 348
<211> LENGTH: 30
<212> TYPE: PRT
<213> ORGANISM: artificial sequence
<220> FEATURE:
<223> OTHER INFORMATION: synthetic

<400> SEQUENCE: 348

Ser Gly Lys Arg Ser Asn Thr Thr Gly Lys Leu Ile Trp Lys Val Asn
1 5 10 15

Pro Glu Ile Asp Thr Thr Ile Gly Glu Trp Ala Phe Trp Glu
20 25 30

<210> SEQ ID NO 349
<211> LENGTH: 32
<212> TYPE: PRT
<213> ORGANISM: artificial sequence
<220> FEATURE:
<223> OTHER INFORMATION: synthetic

<400> SEQUENCE: 349

Ala Ile Val Asn Ala Gln Pro Lys Cys Asn Pro Asn Leu His Tyr Trp
1 5 10 15

Thr Thr Gln Asp Glu Gly Ala Ala Ile Gly Leu Ala Trp Ile Pro Tyr
20 25 30

<210> SEQ ID NO 350
<211> LENGTH: 30
<212> TYPE: PRT
<213> ORGANISM: artificial sequence
<220> FEATURE:
<223> OTHER INFORMATION: synthetic

<400> SEQUENCE: 350

```
Trp Thr Thr Gln Asp Glu Gly Ala Ala Ile Gly Leu Ala Trp Ile Pro
1               5                   10                  15

Tyr Phe Gly Pro Ala Ala Glu Gly Ile Tyr Ile Glu Gly Leu
            20                  25                  30
```

<210> SEQ ID NO 351
<211> LENGTH: 31
<212> TYPE: PRT
<213> ORGANISM: artificial sequence
<220> FEATURE:
<223> OTHER INFORMATION: synthetic

<400> SEQUENCE: 351

```
Arg Gln Leu Ala Asn Glu Thr Thr Gln Ala Leu Gln Leu Phe Leu Arg
1               5                   10                  15

Ala Thr Thr Glu Leu Arg Thr Phe Ser Ile Leu Asn Arg Lys Ala
            20                  25                  30
```

<210> SEQ ID NO 352
<211> LENGTH: 20
<212> TYPE: PRT
<213> ORGANISM: artificial sequence
<220> FEATURE:
<223> OTHER INFORMATION: synthetic

<400> SEQUENCE: 352

```
Pro Asp Gln Gly Asp Asn Asp Asn Trp Trp Thr Gly Trp Arg Gln Trp
1               5                   10                  15

Ile Pro Ala Gly
            20
```

<210> SEQ ID NO 353
<211> LENGTH: 151
<212> TYPE: PRT
<213> ORGANISM: artificial sequence
<220> FEATURE:
<223> OTHER INFORMATION: synthetic

<400> SEQUENCE: 353

```
Val Asn Ala Gln Pro Lys Cys Asn Pro Asn Leu His Tyr Trp Thr Thr
1               5                   10                  15

Gln Asp Glu Gly Ala Ala Ile Gly Leu Ala Trp Ile Pro Tyr Phe Gly
            20                  25                  30

Pro Ala Ala Glu Gly Ile Tyr Ile Glu Gly Leu Met His Asn Gln Asp
        35                  40                  45

Gly Leu Ile Cys Gly Leu Arg Gln Leu Ala Asn Glu Thr Thr Gln Ala
    50                  55                  60

Leu Gln Leu Phe Leu Arg Ala Thr Thr Glu Leu Arg Thr Phe Ser Ile
65                  70                  75                  80

Leu Asn Arg Lys Ala Ile Asp Phe Leu Leu Gln Arg Trp Gly Gly Thr
                85                  90                  95

Cys His Ile Leu Gly Pro Asp Cys Cys Ile Glu Pro His Asp Trp Thr
            100                 105                 110

Lys Asn Ile Thr Asp Lys Ile Asp Gln Ile Ile His Asp Phe Val Asp
```

115 120 125

Lys Thr Leu Pro Asp Gln Gly Asp Asn Asp Asn Trp Trp Thr Gly Trp
130 135 140

Arg Gln Trp Ile Pro Ala Gly
145 150

<210> SEQ ID NO 354
<211> LENGTH: 5
<212> TYPE: PRT
<213> ORGANISM: artificial sequence
<220> FEATURE:
<223> OTHER INFORMATION: synthetic

<400> SEQUENCE: 354

His Pro Arg Leu Arg
1 5

<210> SEQ ID NO 355
<211> LENGTH: 15
<212> TYPE: PRT
<213> ORGANISM: artificial sequence
<220> FEATURE:
<223> OTHER INFORMATION: synthetic

<400> SEQUENCE: 355

Gly Ile Pro Asp His Pro Leu Arg Leu Leu Arg Ile Gly Asn Gln
1 5 10 15

<210> SEQ ID NO 356
<211> LENGTH: 5
<212> TYPE: PRT
<213> ORGANISM: artificial sequence
<220> FEATURE:
<223> OTHER INFORMATION: synthetic

<400> SEQUENCE: 356

Met Val Val Ser Gly
1 5

<210> SEQ ID NO 357
<211> LENGTH: 15
<212> TYPE: PRT
<213> ORGANISM: artificial sequence
<220> FEATURE:
<223> OTHER INFORMATION: synthetic

<400> SEQUENCE: 357

Ile Leu Glu Ala Met Val Asn Val Ile Ser Gly Pro Lys Val Leu
1 5 10 15

<210> SEQ ID NO 358
<211> LENGTH: 5
<212> TYPE: PRT
<213> ORGANISM: artificial sequence
<220> FEATURE:
<223> OTHER INFORMATION: synthetic

<400> SEQUENCE: 358

Gly Asn Ala Leu Thr
1 5

<210> SEQ ID NO 359
<211> LENGTH: 15
<212> TYPE: PRT
<213> ORGANISM: artificial sequence
<220> FEATURE:

<223> OTHER INFORMATION: synthetic

<400> SEQUENCE: 359

Ser Gly Lys Lys Gly Asn Ser Ala Asp Leu Thr Ser Pro Glu Lys
1 5 10 15

<210> SEQ ID NO 360
<211> LENGTH: 5
<212> TYPE: PRT
<213> ORGANISM: artificial sequence
<220> FEATURE:
<223> OTHER INFORMATION: synthetic

<400> SEQUENCE: 360

Asp Thr Ser Gly Ala
1 5

<210> SEQ ID NO 361
<211> LENGTH: 15
<212> TYPE: PRT
<213> ORGANISM: artificial sequence
<220> FEATURE:
<223> OTHER INFORMATION: synthetic

<400> SEQUENCE: 361

Thr Asp Asp Thr Pro Thr Gly Ser Asn Gly Ala Leu Arg Pro Gly
1 5 10 15

<210> SEQ ID NO 362
<211> LENGTH: 5
<212> TYPE: PRT
<213> ORGANISM: artificial sequence
<220> FEATURE:
<223> OTHER INFORMATION: synthetic

<400> SEQUENCE: 362

Ser Ser Thr Ala Ile
1 5

<210> SEQ ID NO 363
<211> LENGTH: 15
<212> TYPE: PRT
<213> ORGANISM: artificial sequence
<220> FEATURE:
<223> OTHER INFORMATION: synthetic

<400> SEQUENCE: 363

Thr Tyr Ser Phe Asp Ser Thr Thr Ala Ala Ile Met Leu Ala Ser
1 5 10 15

<210> SEQ ID NO 364
<211> LENGTH: 5
<212> TYPE: PRT
<213> ORGANISM: artificial sequence
<220> FEATURE:
<223> OTHER INFORMATION: synthetic

<400> SEQUENCE: 364

Leu Leu Leu Thr Gln
1 5

<210> SEQ ID NO 365
<211> LENGTH: 15
<212> TYPE: PRT
<213> ORGANISM: artificial sequence
<220> FEATURE:
<223> OTHER INFORMATION: synthetic

<400> SEQUENCE: 365

Phe Asp Leu Thr Ala Leu Lys Leu Ile Thr Gln Pro Leu Pro Ala
1 5 10 15

<210> SEQ ID NO 366
<211> LENGTH: 5
<212> TYPE: PRT
<213> ORGANISM: artificial sequence
<220> FEATURE:
<223> OTHER INFORMATION: synthetic

<400> SEQUENCE: 366

Ala Thr Gly Val Ser
1 5

<210> SEQ ID NO 367
<211> LENGTH: 15
<212> TYPE: PRT
<213> ORGANISM: artificial sequence
<220> FEATURE:
<223> OTHER INFORMATION: synthetic

<400> SEQUENCE: 367

Asp His Ala Ser His Thr Pro Gly Ser Val Ser Ser Ala Phe Ile
1 5 10 15

<210> SEQ ID NO 368
<211> LENGTH: 5
<212> TYPE: PRT
<213> ORGANISM: artificial sequence
<220> FEATURE:
<223> OTHER INFORMATION: synthetic

<400> SEQUENCE: 368

Thr Thr Thr Ser Asn
1 5

<210> SEQ ID NO 369
<211> LENGTH: 15
<212> TYPE: PRT
<213> ORGANISM: artificial sequence
<220> FEATURE:
<223> OTHER INFORMATION: synthetic

<400> SEQUENCE: 369

Thr Trp Thr Asp Asp Thr Pro Thr Gly Ser Asn Gly Ala Leu Arg
1 5 10 15

<210> SEQ ID NO 370
<211> LENGTH: 5
<212> TYPE: PRT
<213> ORGANISM: artificial sequence
<220> FEATURE:
<223> OTHER INFORMATION: synthetic

<400> SEQUENCE: 370

Thr Lys Thr Lys Asn
1 5

<210> SEQ ID NO 371
<211> LENGTH: 15
<212> TYPE: PRT
<213> ORGANISM: artificial sequence
<220> FEATURE:
<223> OTHER INFORMATION: synthetic

<400> SEQUENCE: 371

Lys Leu Thr Gly Lys Lys Val Thr Ser Lys Asn Gly Gln Pro Ile
1               5                   10                  15

<210> SEQ ID NO 372
<211> LENGTH: 5
<212> TYPE: PRT
<213> ORGANISM: artificial sequence
<220> FEATURE:
<223> OTHER INFORMATION: synthetic

<400> SEQUENCE: 372

Lys Asn Ala Leu Thr
1               5

<210> SEQ ID NO 373
<211> LENGTH: 15
<212> TYPE: PRT
<213> ORGANISM: artificial sequence
<220> FEATURE:
<223> OTHER INFORMATION: synthetic

<400> SEQUENCE: 373

Ser Gly Lys Lys Gly Asn Ser Ala Asp Leu Thr Ser Pro Glu Lys
1               5                   10                  15

<210> SEQ ID NO 374
<211> LENGTH: 5
<212> TYPE: PRT
<213> ORGANISM: artificial sequence
<220> FEATURE:
<223> OTHER INFORMATION: synthetic

<400> SEQUENCE: 374

His Pro Arg Leu Arg
1               5

<210> SEQ ID NO 375
<211> LENGTH: 15
<212> TYPE: PRT
<213> ORGANISM: artificial sequence
<220> FEATURE:
<223> OTHER INFORMATION: synthetic

<400> SEQUENCE: 375

Gly Ile Pro Asp His Pro Leu Arg Leu Leu Arg Ile Gly Asn Gln
1               5                   10                  15

<210> SEQ ID NO 376
<211> LENGTH: 5
<212> TYPE: PRT
<213> ORGANISM: artificial sequence
<220> FEATURE:
<223> OTHER INFORMATION: synthetic

<400> SEQUENCE: 376

Met Val Val Ser Gly
1               5

<210> SEQ ID NO 377
<211> LENGTH: 15
<212> TYPE: PRT
<213> ORGANISM: artificial sequence
<220> FEATURE:
<223> OTHER INFORMATION: synthetic

<400> SEQUENCE: 377

Ile Leu Glu Ala Met Val Asn Val Ile Ser Gly Pro Lys Val Leu
1 5 10 15

<210> SEQ ID NO 378
<211> LENGTH: 5
<212> TYPE: PRT
<213> ORGANISM: artificial sequence
<220> FEATURE:
<223> OTHER INFORMATION: synthetic

<400> SEQUENCE: 378

Gly Asn Ala Leu Thr
1 5

<210> SEQ ID NO 379
<211> LENGTH: 15
<212> TYPE: PRT
<213> ORGANISM: artificial sequence
<220> FEATURE:
<223> OTHER INFORMATION: synthetic

<400> SEQUENCE: 379

Ser Gly Lys Lys Gly Asn Ser Ala Asp Leu Thr Ser Pro Glu Lys
1 5 10 15

<210> SEQ ID NO 380
<211> LENGTH: 5
<212> TYPE: PRT
<213> ORGANISM: artificial sequence
<220> FEATURE:
<223> OTHER INFORMATION: synthetic

<400> SEQUENCE: 380

Asp Thr Ser Gly Ala
1 5

<210> SEQ ID NO 381
<211> LENGTH: 15
<212> TYPE: PRT
<213> ORGANISM: artificial sequence
<220> FEATURE:
<223> OTHER INFORMATION: synthetic

<400> SEQUENCE: 381

Thr Asp Asp Thr Pro Thr Gly Ser Asn Gly Ala Leu Arg Pro Gly
1 5 10 15

<210> SEQ ID NO 382
<211> LENGTH: 5
<212> TYPE: PRT
<213> ORGANISM: artificial sequence
<220> FEATURE:
<223> OTHER INFORMATION: synthetic

<400> SEQUENCE: 382

Ser Ser Thr Ala Ile
1 5

<210> SEQ ID NO 383
<211> LENGTH: 15
<212> TYPE: PRT
<213> ORGANISM: artificial sequence
<220> FEATURE:
<223> OTHER INFORMATION: synthetic

<400> SEQUENCE: 383

Thr Tyr Ser Phe Asp Ser Thr Thr Ala Ala Ile Met Leu Ala Ser
1 5 10 15

<210> SEQ ID NO 384
<211> LENGTH: 5
<212> TYPE: PRT
<213> ORGANISM: artificial sequence
<220> FEATURE:
<223> OTHER INFORMATION: synthetic

<400> SEQUENCE: 384

Leu Leu Leu Thr Gln
1 5

<210> SEQ ID NO 385
<211> LENGTH: 15
<212> TYPE: PRT
<213> ORGANISM: artificial sequence
<220> FEATURE:
<223> OTHER INFORMATION: synthetic

<400> SEQUENCE: 385

Phe Asp Leu Thr Ala Leu Lys Leu Ile Thr Gln Pro Leu Pro Ala
1 5 10 15

<210> SEQ ID NO 386
<211> LENGTH: 5
<212> TYPE: PRT
<213> ORGANISM: artificial sequence
<220> FEATURE:
<223> OTHER INFORMATION: synthetic

<400> SEQUENCE: 386

Ala Thr Gly Val Ser
1 5

<210> SEQ ID NO 387
<211> LENGTH: 15
<212> TYPE: PRT
<213> ORGANISM: artificial sequence
<220> FEATURE:
<223> OTHER INFORMATION: synthetic

<400> SEQUENCE: 387

Asp His Ala Ser His Thr Pro Gly Ser Val Ser Ser Ala Phe Ile
1 5 10 15

<210> SEQ ID NO 388
<211> LENGTH: 5
<212> TYPE: PRT
<213> ORGANISM: artificial sequence
<220> FEATURE:
<223> OTHER INFORMATION: synthetic

<400> SEQUENCE: 388

Thr Thr Thr Ser Asn
1 5

<210> SEQ ID NO 389
<211> LENGTH: 15
<212> TYPE: PRT
<213> ORGANISM: artificial sequence
<220> FEATURE:
<223> OTHER INFORMATION: synthetic

<400> SEQUENCE: 389

Thr Trp Thr Asp Asp Thr Pro Thr Gly Ser Asn Gly Ala Leu Arg 1 5 10 15

<210> SEQ ID NO 390
<211> LENGTH: 5
<212> TYPE: PRT
<213> ORGANISM: artificial sequence
<220> FEATURE:
<223> OTHER INFORMATION: synthetic

<400> SEQUENCE: 390

Thr Lys Thr Lys Asn
1 5

<210> SEQ ID NO 391
<211> LENGTH: 15
<212> TYPE: PRT
<213> ORGANISM: artificial sequence
<220> FEATURE:
<223> OTHER INFORMATION: synthetic

<400> SEQUENCE: 391

Lys Leu Thr Gly Lys Lys Val Thr Ser Lys Asn Gly Gln Pro Ile
1 5 10 15

<210> SEQ ID NO 392
<211> LENGTH: 5
<212> TYPE: PRT
<213> ORGANISM: artificial sequence
<220> FEATURE:
<223> OTHER INFORMATION: synthetic

<400> SEQUENCE: 392

Lys Asn Ala Leu Thr
1 5

<210> SEQ ID NO 393
<211> LENGTH: 15
<212> TYPE: PRT
<213> ORGANISM: artificial sequence
<220> FEATURE:
<223> OTHER INFORMATION: synthetic

<400> SEQUENCE: 393

Ser Gly Lys Lys Gly Asn Ser Ala Asp Leu Thr Ser Pro Glu Lys
1 5 10 15

<210> SEQ ID NO 394
<211> LENGTH: 5
<212> TYPE: PRT
<213> ORGANISM: artificial sequence
<220> FEATURE:
<223> OTHER INFORMATION: synthetic

<400> SEQUENCE: 394

Ser Pro Lys Leu Glu
1 5

<210> SEQ ID NO 395
<211> LENGTH: 15
<212> TYPE: PRT
<213> ORGANISM: artificial sequence
<220> FEATURE:
<223> OTHER INFORMATION: synthetic

<400> SEQUENCE: 395

Tyr Asn Leu Ile Ser Pro Lys Lys Asp Leu Glu Lys Gly Val Val
1 5 10 15

<210> SEQ ID NO 396
<211> LENGTH: 5
<212> TYPE: PRT
<213> ORGANISM: artificial sequence
<220> FEATURE:
<223> OTHER INFORMATION: synthetic

<400> SEQUENCE: 396

Ser Leu Met Ser Leu
1               5

<210> SEQ ID NO 397
<211> LENGTH: 15
<212> TYPE: PRT
<213> ORGANISM: artificial sequence
<220> FEATURE:
<223> OTHER INFORMATION: synthetic

<400> SEQUENCE: 397

Lys Glu Gln Leu Ser Leu Lys Met Leu Ser Leu Ile Arg Ser Asn
1               5                   10                  15

<210> SEQ ID NO 398
<211> LENGTH: 5
<212> TYPE: PRT
<213> ORGANISM: artificial sequence
<220> FEATURE:
<223> OTHER INFORMATION: synthetic

<400> SEQUENCE: 398

Ser Pro Lys Leu Glu
1               5

<210> SEQ ID NO 399
<211> LENGTH: 15
<212> TYPE: PRT
<213> ORGANISM: artificial sequence
<220> FEATURE:
<223> OTHER INFORMATION: synthetic

<400> SEQUENCE: 399

Tyr Asn Leu Ile Ser Pro Lys Lys Asp Leu Glu Lys Gly Val Val
1               5                   10                  15

<210> SEQ ID NO 400
<211> LENGTH: 5
<212> TYPE: PRT
<213> ORGANISM: artificial sequence
<220> FEATURE:
<223> OTHER INFORMATION: synthetic

<400> SEQUENCE: 400

Ser Leu Met Ser Leu
1               5

<210> SEQ ID NO 401
<211> LENGTH: 15
<212> TYPE: PRT
<213> ORGANISM: artificial sequence
<220> FEATURE:
<223> OTHER INFORMATION: synthetic

<400> SEQUENCE: 401

Lys Glu Gln Leu Ser Leu Lys Met Leu Ser Leu Ile Arg Ser Asn
1               5                   10                  15

<210> SEQ ID NO 402
<211> LENGTH: 37
<212> TYPE: PRT
<213> ORGANISM: artificial sequence
<220> FEATURE:
<223> OTHER INFORMATION: synthetic

<400> SEQUENCE: 402

Ser His Thr Pro Gly Ser Val Ser Ser Ala Phe Ile Leu Glu Ala Met
1               5                   10                  15

Val Asn Val Ile Ser Gly Pro Lys Val Leu Met Lys Gln Ile Pro Ile
            20                  25                  30

Trp Leu Pro Leu Gly
        35

<210> SEQ ID NO 403
<211> LENGTH: 42
<212> TYPE: PRT
<213> ORGANISM: artificial sequence
<220> FEATURE:
<223> OTHER INFORMATION: synthetic

<400> SEQUENCE: 403

Gly Lys Lys Val Thr Ser Lys Asn Gly Gln Pro Ile Ile Pro Val Leu
1               5                   10                  15

Leu Pro Lys Tyr Ile Gly Leu Asp Pro Val Ala Pro Gly Asp Leu Thr
            20                  25                  30

Met Val Ile Thr Gln Asp Cys Asp Thr Cys
        35                  40

<210> SEQ ID NO 404
<211> LENGTH: 26
<212> TYPE: PRT
<213> ORGANISM: artificial sequence
<220> FEATURE:
<223> OTHER INFORMATION: synthetic

<400> SEQUENCE: 404

Pro Asn Ser Thr Ile Glu Ser Pro Leu Trp Ala Leu Arg Val Ile Leu
1               5                   10                  15

Ala Ala Gly Ile Gln Asp Gln Leu Ile Asp
            20                  25

<210> SEQ ID NO 405
<211> LENGTH: 434
<212> TYPE: PRT
<213> ORGANISM: artificial sequence
<220> FEATURE:
<223> OTHER INFORMATION: synthetic

<400> SEQUENCE: 405

Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
85 90 95

Glu Leu Arg Thr Phe Ser Ile Leu Asn Arg Lys Ala Ile Asp Phe Leu
100 105 110

Leu Gln Arg Trp Gly Gly Thr Cys His Ile Leu Gly Pro Asp Cys Cys
115 120 125

Ile Glu Pro His Asp Trp Thr Lys Asn Ile Thr Asp Lys Ile Asp Gln
130 135 140

Ile Ile His Asp Phe Val Asp Lys Thr Leu Pro Asp Gln Gly Asp Asn
145 150 155 160

Asp Asn Trp Trp Thr Gly Trp Arg Gln Trp Ile Pro Ala Gly Gly Gly
165 170 175

Gly Gly Ser Gly Gly Gly Gly Ser Gly Gly Pro Gly Ser Gly Gly Gly
180 185 190

Gly Ser Gly Gly Gly Gly Ser Ala Ser Thr Glu Pro Lys Ser Cys Asp
195 200 205

Lys Thr His Thr Cys Pro Pro Cys Pro Ala Pro Glu Leu Leu Gly Gly
210 215 220

Pro Ser Val Phe Leu Phe Pro Pro Lys Pro Lys Asp Thr Leu Met Ile
225 230 235 240

Ser Arg Thr Pro Glu Val Thr Cys Val Val Val Asp Val Ser His Glu
245 250 255

Asp Pro Glu Val Lys Phe Asn Trp Tyr Val Asp Gly Val Glu Val His
260 265 270

Asn Ala Lys Thr Lys Pro Arg Glu Glu Gln Tyr Asn Ser Thr Tyr Arg
275 280 285

Val Val Ser Val Leu Thr Val Leu His Gln Asp Trp Leu Asn Gly Lys
290 295 300

Glu Tyr Lys Cys Lys Val Ser Asn Lys Ala Leu Pro Ala Pro Ile Glu
305 310 315 320

Lys Thr Ile Ser Lys Ala Lys Gly Gln Pro Arg Glu Pro Gln Val Tyr
325 330 335

Thr Leu Pro Pro Ser Arg Glu Glu Met Thr Lys Asn Gln Val Ser Leu
340 345 350

Thr Cys Leu Val Lys Gly Phe Tyr Pro Ser Asp Ile Ala Val Glu Trp
355 360 365

Glu Ser Asn Gly Gln Pro Glu Asn Asn Tyr Lys Thr Thr Pro Pro Val
370 375 380

Leu Asp Ser Asp Gly Ser Phe Phe Leu Tyr Ser Lys Leu Thr Val Asp
385 390 395 400

Lys Ser Arg Trp Gln Gln Gly Asn Val Phe Ser Cys Ser Val Met His
405 410 415

Glu Ala Leu His Asn His Tyr Thr Gln Lys Ser Leu Ser Leu Ser Pro
420 425 430

Gly Lys

<210> SEQ ID NO 406
<211> LENGTH: 434
<212> TYPE: PRT
<213> ORGANISM: artificial sequence
<220> FEATURE:
<223> OTHER INFORMATION: synthetic

<400> SEQUENCE: 406

Met Glu Thr Asp Thr Leu Leu Leu Trp Val Leu Leu Leu Trp Val Pro

-continued

```
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Gly Gly
                165                 170                 175

Gly Gly Ser Gly Gly Gly Gly Ser Gly Gly Pro Gly Ser Gly Gly Gly
            180                 185                 190

Gly Ser Gly Gly Gly Gly Ser Val Asp Glu Pro Arg Gly Pro Thr Ile
        195                 200                 205

Lys Pro Cys Pro Pro Cys Lys Cys Pro Ala Pro Asn Leu Leu Gly Gly
    210                 215                 220

Pro Ser Val Phe Ile Phe Pro Pro Lys Ile Lys Asp Val Leu Met Ile
225                 230                 235                 240

Ser Leu Ser Pro Ile Val Thr Cys Val Val Val Asp Val Ser Glu Asp
                245                 250                 255

Asp Pro Asp Val Gln Ile Ser Trp Phe Val Asn Asn Val Glu Val His
            260                 265                 270

Thr Ala Gln Thr Gln Thr His Arg Glu Asp Tyr Asn Ser Thr Leu Arg
        275                 280                 285

Val Val Ser Ala Leu Pro Ile Gln His Gln Asp Trp Met Ser Gly Lys
    290                 295                 300

Glu Phe Lys Cys Lys Val Asn Asn Lys Asp Leu Pro Ala Pro Ile Glu
305                 310                 315                 320

Arg Thr Ile Ser Lys Pro Lys Gly Ser Val Arg Ala Pro Gln Val Tyr
                325                 330                 335

Val Leu Pro Pro Pro Glu Glu Glu Met Thr Lys Lys Gln Val Thr Leu
            340                 345                 350

Thr Cys Met Val Thr Asp Phe Met Pro Glu Asp Ile Tyr Val Glu Trp
        355                 360                 365

Thr Asn Asn Gly Lys Thr Glu Leu Asn Tyr Lys Asn Thr Glu Pro Val
    370                 375                 380

Leu Asp Ser Asp Gly Ser Tyr Phe Met Tyr Ser Lys Leu Arg Val Glu
385                 390                 395                 400

Lys Lys Asn Trp Val Glu Arg Asn Ser Tyr Ser Cys Ser Val Val His
                405                 410                 415

Glu Gly Leu His Asn His His Thr Thr Lys Ser Phe Ser Arg Thr Pro
            420                 425                 430
```

Gly Lys

<210> SEQ ID NO 407
<211> LENGTH: 313
<212> TYPE: PRT
<213> ORGANISM: artificial sequence
<220> FEATURE:
<223> OTHER INFORMATION: synthetic

<400> SEQUENCE: 407

Met Glu Thr Asp Thr Leu Leu Leu Trp Val Leu Leu Leu Trp Val Pro
1 5 10 15

Gly Ser Thr Gly Asp Thr Arg Gly Asn Gly Val Ala Thr Asp Val Pro
20 25 30

Ser Ala Thr Lys Arg Trp Gly Phe Arg Ser Gly Val Pro Pro Lys Val
35 40 45

Val Asn Tyr Glu Ala Gly Gly Gly Gly Ser Gly Gly Gly Gly Ser Gly
50 55 60

Gly Pro Gly Ser Gly Gly Gly Gly Ser Gly Gly Gly Gly Ser Ala Ser
65 70 75 80

Thr Glu Pro Lys Ser Cys Asp Lys Thr His Thr Cys Pro Pro Cys Pro
85 90 95

Ala Pro Glu Leu Leu Gly Gly Pro Ser Val Phe Leu Phe Pro Pro Lys
100 105 110

Pro Lys Asp Thr Leu Met Ile Ser Arg Thr Pro Glu Val Thr Cys Val
115 120 125

Val Val Asp Val Ser His Glu Asp Pro Glu Val Lys Phe Asn Trp Tyr
130 135 140

Val Asp Gly Val Glu Val His Asn Ala Lys Thr Lys Pro Arg Glu Glu
145 150 155 160

Gln Tyr Asn Ser Thr Tyr Arg Val Val Ser Val Leu Thr Val Leu His
165 170 175

Gln Asp Trp Leu Asn Gly Lys Glu Tyr Lys Cys Lys Val Ser Asn Lys
180 185 190

Ala Leu Pro Ala Pro Ile Glu Lys Thr Ile Ser Lys Ala Lys Gly Gln
195 200 205

Pro Arg Glu Pro Gln Val Tyr Thr Leu Pro Pro Ser Arg Glu Glu Met
210 215 220

Thr Lys Asn Gln Val Ser Leu Thr Cys Leu Val Lys Gly Phe Tyr Pro
225 230 235 240

Ser Asp Ile Ala Val Glu Trp Glu Ser Asn Gly Gln Pro Glu Asn Asn
245 250 255

Tyr Lys Thr Thr Pro Pro Val Leu Asp Ser Asp Gly Ser Phe Phe Leu
260 265 270

Tyr Ser Lys Leu Thr Val Asp Lys Ser Arg Trp Gln Gln Gly Asn Val
275 280 285

Phe Ser Cys Ser Val Met His Glu Ala Leu His Asn His Tyr Thr Gln
290 295 300

Lys Ser Leu Ser Leu Ser Pro Gly Lys
305 310

<210> SEQ ID NO 408
<211> LENGTH: 313
<212> TYPE: PRT
<213> ORGANISM: artificial sequence
<220> FEATURE:

<223> OTHER INFORMATION: synthetic

<400> SEQUENCE: 408

Met Glu Thr Asp Thr Leu Leu Leu Trp Val Leu Leu Leu Trp Val Pro
1 5 10 15

Gly Ser Thr Gly Asp Thr Arg Gly Asn Gly Val Ala Thr Asp Val Pro
20 25 30

Ser Ala Thr Lys Arg Trp Gly Phe Arg Ser Gly Val Pro Pro Lys Val
35 40 45

Val Asn Tyr Glu Ala Gly Gly Gly Gly Ser Gly Gly Gly Gly Ser Gly
50 55 60

Gly Pro Gly Ser Gly Gly Gly Gly Ser Gly Gly Gly Gly Ser Val Asp
65 70 75 80

Glu Pro Arg Gly Pro Thr Ile Lys Pro Cys Pro Pro Cys Lys Cys Pro
85 90 95

Ala Pro Asn Leu Leu Gly Gly Pro Ser Val Phe Ile Phe Pro Pro Lys
100 105 110

Ile Lys Asp Val Leu Met Ile Ser Leu Ser Pro Ile Val Thr Cys Val
115 120 125

Val Val Asp Val Ser Glu Asp Asp Pro Asp Val Gln Ile Ser Trp Phe
130 135 140

Val Asn Asn Val Glu Val His Thr Ala Gln Thr Gln Thr His Arg Glu
145 150 155 160

Asp Tyr Asn Ser Thr Leu Arg Val Val Ser Ala Leu Pro Ile Gln His
165 170 175

Gln Asp Trp Met Ser Gly Lys Glu Phe Lys Cys Lys Val Asn Asn Lys
180 185 190

Asp Leu Pro Ala Pro Ile Glu Arg Thr Ile Ser Lys Pro Lys Gly Ser
195 200 205

Val Arg Ala Pro Gln Val Tyr Val Leu Pro Pro Pro Glu Glu Glu Met
210 215 220

Thr Lys Lys Gln Val Thr Leu Thr Cys Met Val Thr Asp Phe Met Pro
225 230 235 240

Glu Asp Ile Tyr Val Glu Trp Thr Asn Asn Gly Lys Thr Glu Leu Asn
245 250 255

Tyr Lys Asn Thr Glu Pro Val Leu Asp Ser Asp Gly Ser Tyr Phe Met
260 265 270

Tyr Ser Lys Leu Arg Val Glu Lys Lys Asn Trp Val Glu Arg Asn Ser
275 280 285

Tyr Ser Cys Ser Val Val His Glu Gly Leu His Asn His His Thr Thr
290 295 300

Lys Ser Phe Ser Arg Thr Pro Gly Lys
305 310

<210> SEQ ID NO 409
<211> LENGTH: 315
<212> TYPE: PRT
<213> ORGANISM: artificial sequence
<220> FEATURE:
<223> OTHER INFORMATION: synthetic

<400> SEQUENCE: 409

Met Glu Thr Asp Thr Leu Leu Leu Trp Val Leu Leu Leu Trp Val Pro
1 5 10 15

Gly Ser Thr Gly Asp Thr Arg His Lys Val Ser Gly Thr Gly Pro Cys
20 25 30

```
Ala Gly Asp Phe Ala Phe His Lys Glu Gly Ala Phe Phe Leu Tyr Asp
        35                  40                  45

Arg Leu Ala Ser Thr Val Ile Gly Gly Gly Gly Ser Gly Gly Gly Gly
    50                  55                  60

Ser Gly Gly Pro Gly Ser Gly Gly Gly Gly Ser Gly Gly Gly Gly Ser
65                  70                  75                  80

Ala Ser Thr Glu Pro Lys Ser Cys Asp Lys Thr His Thr Cys Pro Pro
                85                  90                  95

Cys Pro Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser His Glu Asp Pro Glu Val Lys Phe Asn
    130                 135                 140

Trp Tyr Val Asp Gly Val Glu Val His Asn Ala Lys Thr Lys Pro Arg
145                 150                 155                 160

Glu Glu Gln Tyr Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Ala Leu Pro Ala Pro Ile Glu Lys Thr Ile Ser Lys Ala Lys
        195                 200                 205

Gly Gln Pro Arg Glu Pro Gln Val Tyr Thr Leu Pro Pro Ser Arg Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
            260                 265                 270

Phe Leu Tyr Ser Lys Leu Thr Val Asp Lys Ser Arg Trp Gln Gln Gly
        275                 280                 285

Asn Val Phe Ser Cys Ser Val Met His Glu Ala Leu His Asn His Tyr
    290                 295                 300

Thr Gln Lys Ser Leu Ser Leu Ser Pro Gly Lys
305                 310                 315


<210> SEQ ID NO 410
<211> LENGTH: 314
<212> TYPE: PRT
<213> ORGANISM: artificial sequence
<220> FEATURE:
<223> OTHER INFORMATION: synthetic

<400> SEQUENCE: 410

Met Glu Thr Asp Thr Leu Leu Leu Trp Val Leu Leu Leu Trp Val Pro
1               5                   10                  15

Gly Ser Thr Gly Asp Thr Arg His Lys Val Ser Gly Thr Gly Pro Cys
            20                  25                  30

Ala Gly Asp Phe Ala Phe His Lys Glu Gly Ala Phe Phe Leu Tyr Asp
        35                  40                  45

Arg Leu Ala Ser Thr Val Ile Gly Gly Gly Gly Ser Gly Gly Gly Gly
    50                  55                  60

Ser Gly Gly Pro Gly Ser Gly Gly Gly Gly Ser Gly Gly Gly Gly Ser
65                  70                  75                  80
```

Val Asp Glu Pro Arg Gly Pro Thr Ile Lys Pro Cys Pro Pro Cys Lys
85 90 95

Cys Pro Ala Pro Asn Leu Leu Gly Gly Pro Ser Val Phe Ile Phe Pro
100 105 110

Pro Lys Ile Lys Asp Val Leu Met Ile Ser Leu Ser Pro Ile Val Thr
115 120 125

Cys Val Val Val Asp Val Ser Glu Asp Asp Pro Asp Val Gln Ile Ser
130 135 140

Trp Phe Val Asn Asn Val Glu Val His Thr Ala Gln Thr Gln Thr His
145 150 155 160

Arg Glu Asp Tyr Asn Ser Thr Leu Arg Val Val Ser Ala Leu Pro Ile
165 170 175

Gln His Gln Asp Trp Met Ser Gly Lys Glu Phe Lys Cys Lys Val Asn
180 185 190

Asn Lys Asp Leu Pro Ala Pro Ile Glu Arg Thr Ile Ser Lys Pro Lys
195 200 205

Gly Ser Val Arg Ala Pro Gln Val Tyr Val Leu Pro Pro Pro Glu Glu
210 215 220

Glu Met Thr Lys Lys Gln Val Thr Leu Thr Cys Met Val Thr Asp Phe
225 230 235 240

Met Pro Glu Asp Ile Tyr Val Glu Trp Thr Asn Asn Gly Lys Thr Glu
245 250 255

Leu Asn Tyr Lys Asn Thr Glu Pro Val Leu Asp Ser Asp Gly Ser Tyr
260 265 270

Phe Met Tyr Ser Lys Leu Arg Val Glu Lys Lys Asn Trp Val Glu Arg
275 280 285

Asn Ser Tyr Ser Cys Ser Val Val His Glu Gly Leu His Asn His His
290 295 300

Thr Thr Lys Ser Phe Ser Arg Thr Pro Gly
305 310

<210> SEQ ID NO 411
<211> LENGTH: 313
<212> TYPE: PRT
<213> ORGANISM: artificial sequence
<220> FEATURE:
<223> OTHER INFORMATION: synthetic

<400> SEQUENCE: 411

Met Glu Thr Asp Thr Leu Leu Leu Trp Val Leu Leu Leu Trp Val Pro
1 5 10 15

Gly Ser Thr Gly Asp Thr Arg Ser Gly Lys Arg Ser Asn Thr Thr Gly
20 25 30

Lys Leu Ile Trp Lys Val Asn Pro Glu Ile Asp Thr Thr Ile Gly Glu
35 40 45

Trp Ala Phe Trp Glu Gly Gly Gly Gly Ser Gly Gly Gly Gly Ser Gly
50 55 60

Gly Pro Gly Ser Gly Gly Gly Gly Ser Gly Gly Gly Gly Ser Ala Ser
65 70 75 80

Thr Glu Pro Lys Ser Cys Asp Lys Thr His Thr Cys Pro Pro Cys Pro
85 90 95

Ala Pro Glu Leu Leu Gly Gly Pro Ser Val Phe Leu Phe Pro Pro Lys
100 105 110

Pro Lys Asp Thr Leu Met Ile Ser Arg Thr Pro Glu Val Thr Cys Val
115 120 125

```
Val Val Asp Val Ser His Glu Asp Pro Glu Val Lys Phe Asn Trp Tyr
    130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ala Pro Ile Glu Lys Thr Ile Ser Lys Ala Lys Gly Gln
        195                 200                 205

Pro Arg Glu Pro Gln Val Tyr Thr Leu Pro Pro Ser Arg Glu Glu Met
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
    290                 295                 300

Lys Ser Leu Ser Leu Ser Pro Gly Lys
305                 310


<210> SEQ ID NO 412
<211> LENGTH: 313
<212> TYPE: PRT
<213> ORGANISM: artificial sequence
<220> FEATURE:
<223> OTHER INFORMATION: synthetic

<400> SEQUENCE: 412

Met Glu Thr Asp Thr Leu Leu Leu Trp Val Leu Leu Leu Trp Val Pro
1               5                   10                  15

Gly Ser Thr Gly Asp Thr Arg Ser Gly Lys Arg Ser Asn Thr Thr Gly
            20                  25                  30

Lys Leu Ile Trp Lys Val Asn Pro Glu Ile Asp Thr Thr Ile Gly Glu
        35                  40                  45

Trp Ala Phe Trp Glu Gly Gly Gly Gly Ser Gly Gly Gly Gly Ser Gly
    50                  55                  60

Gly Pro Gly Ser Gly Gly Gly Gly Ser Gly Gly Gly Gly Ser Val Asp
65                  70                  75                  80

Glu Pro Arg Gly Pro Thr Ile Lys Pro Cys Pro Pro Cys Lys Cys Pro
                85                  90                  95

Ala Pro Asn Leu Leu Gly Gly Pro Ser Val Phe Ile Phe Pro Pro Lys
            100                 105                 110

Ile Lys Asp Val Leu Met Ile Ser Leu Ser Pro Ile Val Thr Cys Val
        115                 120                 125

Val Val Asp Val Ser Glu Asp Asp Pro Asp Val Gln Ile Ser Trp Phe
    130                 135                 140

Val Asn Asn Val Glu Val His Thr Ala Gln Thr Gln Thr His Arg Glu
145                 150                 155                 160

Asp Tyr Asn Ser Thr Leu Arg Val Val Ser Ala Leu Pro Ile Gln His
                165                 170                 175
```

Gln Asp Trp Met Ser Gly Lys Glu Phe Lys Cys Lys Val Asn Asn Lys
180 185 190

Asp Leu Pro Ala Pro Ile Glu Arg Thr Ile Ser Lys Pro Lys Gly Ser
195 200 205

Val Arg Ala Pro Gln Val Tyr Val Leu Pro Pro Pro Glu Glu Glu Met
210 215 220

Thr Lys Lys Gln Val Thr Leu Thr Cys Met Val Thr Asp Phe Met Pro
225 230 235 240

Glu Asp Ile Tyr Val Glu Trp Thr Asn Asn Gly Lys Thr Glu Leu Asn
245 250 255

Tyr Lys Asn Thr Glu Pro Val Leu Asp Ser Asp Gly Ser Tyr Phe Met
260 265 270

Tyr Ser Lys Leu Arg Val Glu Lys Lys Asn Trp Val Glu Arg Asn Ser
275 280 285

Tyr Ser Cys Ser Val Val His Glu Gly Leu His Asn His His Thr Thr
290 295 300

Lys Ser Phe Ser Arg Thr Pro Gly Lys
305 310

<210> SEQ ID NO 413
<211> LENGTH: 315
<212> TYPE: PRT
<213> ORGANISM: artificial sequence
<220> FEATURE:
<223> OTHER INFORMATION: synthetic

<400> SEQUENCE: 413

Met Glu Thr Asp Thr Leu Leu Leu Trp Val Leu Leu Leu Trp Val Pro
1 5 10 15

Gly Ser Thr Gly Asp Thr Arg Ala Ile Val Asn Ala Gln Pro Lys Cys
20 25 30

Asn Pro Asn Leu His Tyr Trp Thr Thr Gln Asp Glu Gly Ala Ala Ile
35 40 45

Gly Leu Ala Trp Ile Pro Tyr Gly Gly Gly Gly Ser Gly Gly Gly Gly
50 55 60

Ser Gly Gly Pro Gly Ser Gly Gly Gly Gly Ser Gly Gly Gly Gly Ser
65 70 75 80

Ala Ser Thr Glu Pro Lys Ser Cys Asp Lys Thr His Thr Cys Pro Pro
85 90 95

Cys Pro Ala Pro Glu Leu Leu Gly Gly Pro Ser Val Phe Leu Phe Pro
100 105 110

Pro Lys Pro Lys Asp Thr Leu Met Ile Ser Arg Thr Pro Glu Val Thr
115 120 125

Cys Val Val Val Asp Val Ser His Glu Asp Pro Glu Val Lys Phe Asn
130 135 140

Trp Tyr Val Asp Gly Val Glu Val His Asn Ala Lys Thr Lys Pro Arg
145 150 155 160

Glu Glu Gln Tyr Asn Ser Thr Tyr Arg Val Val Ser Val Leu Thr Val
165 170 175

Leu His Gln Asp Trp Leu Asn Gly Lys Glu Tyr Lys Cys Lys Val Ser
180 185 190

Asn Lys Ala Leu Pro Ala Pro Ile Glu Lys Thr Ile Ser Lys Ala Lys
195 200 205

Gly Gln Pro Arg Glu Pro Gln Val Tyr Thr Leu Pro Pro Ser Arg Glu
210 215 220

Glu Met Thr Lys Asn Gln Val Ser Leu Thr Cys Leu Val Lys Gly Phe
225 230 235 240

Tyr Pro Ser Asp Ile Ala Val Glu Trp Glu Ser Asn Gly Gln Pro Glu
245 250 255

Asn Asn Tyr Lys Thr Thr Pro Pro Val Leu Asp Ser Asp Gly Ser Phe
260 265 270

Phe Leu Tyr Ser Lys Leu Thr Val Asp Lys Ser Arg Trp Gln Gln Gly
275 280 285

Asn Val Phe Ser Cys Ser Val Met His Glu Ala Leu His Asn His Tyr
290 295 300

Thr Gln Lys Ser Leu Ser Leu Ser Pro Gly Lys
305 310 315

<210> SEQ ID NO 414
<211> LENGTH: 315
<212> TYPE: PRT
<213> ORGANISM: artificial sequence
<220> FEATURE:
<223> OTHER INFORMATION: synthetic

<400> SEQUENCE: 414

Met Glu Thr Asp Thr Leu Leu Leu Trp Val Leu Leu Leu Trp Val Pro
1 5 10 15

Gly Ser Thr Gly Asp Thr Arg Ala Ile Val Asn Ala Gln Pro Lys Cys
20 25 30

Asn Pro Asn Leu His Tyr Trp Thr Thr Gln Asp Glu Gly Ala Ala Ile
35 40 45

Gly Leu Ala Trp Ile Pro Tyr Gly Gly Gly Gly Ser Gly Gly Gly Gly
50 55 60

Ser Gly Gly Pro Gly Ser Gly Gly Gly Gly Ser Gly Gly Gly Gly Ser
65 70 75 80

Val Asp Glu Pro Arg Gly Pro Thr Ile Lys Pro Cys Pro Pro Cys Lys
85 90 95

Cys Pro Ala Pro Asn Leu Leu Gly Gly Pro Ser Val Phe Ile Phe Pro
100 105 110

Pro Lys Ile Lys Asp Val Leu Met Ile Ser Leu Ser Pro Ile Val Thr
115 120 125

Cys Val Val Val Asp Val Ser Glu Asp Asp Pro Asp Val Gln Ile Ser
130 135 140

Trp Phe Val Asn Asn Val Glu Val His Thr Ala Gln Thr Gln Thr His
145 150 155 160

Arg Glu Asp Tyr Asn Ser Thr Leu Arg Val Val Ser Ala Leu Pro Ile
165 170 175

Gln His Gln Asp Trp Met Ser Gly Lys Glu Phe Lys Cys Lys Val Asn
180 185 190

Asn Lys Asp Leu Pro Ala Pro Ile Glu Arg Thr Ile Ser Lys Pro Lys
195 200 205

Gly Ser Val Arg Ala Pro Gln Val Tyr Val Leu Pro Pro Pro Glu Glu
210 215 220

Glu Met Thr Lys Lys Gln Val Thr Leu Thr Cys Met Val Thr Asp Phe
225 230 235 240

Met Pro Glu Asp Ile Tyr Val Glu Trp Thr Asn Asn Gly Lys Thr Glu
245 250 255

Leu Asn Tyr Lys Asn Thr Glu Pro Val Leu Asp Ser Asp Gly Ser Tyr
260 265 270

Phe Met Tyr Ser Lys Leu Arg Val Glu Lys Lys Asn Trp Val Glu Arg
275 280 285

Asn Ser Tyr Ser Cys Ser Val Val His Glu Gly Leu His Asn His His
290 295 300

Thr Thr Lys Ser Phe Ser Arg Thr Pro Gly Lys
305 310 315

<210> SEQ ID NO 415
<211> LENGTH: 313
<212> TYPE: PRT
<213> ORGANISM: artificial sequence
<220> FEATURE:
<223> OTHER INFORMATION: synthetic

<400> SEQUENCE: 415

Met Glu Thr Asp Thr Leu Leu Leu Trp Val Leu Leu Leu Trp Val Pro
1 5 10 15

Gly Ser Thr Gly Asp Thr Arg Trp Thr Thr Gln Asp Glu Gly Ala Ala
20 25 30

Ile Gly Leu Ala Trp Ile Pro Tyr Phe Gly Pro Ala Ala Glu Gly Ile
35 40 45

Tyr Ile Glu Gly Leu Gly Gly Gly Gly Ser Gly Gly Gly Gly Ser Gly
50 55 60

Gly Pro Gly Ser Gly Gly Gly Gly Ser Gly Gly Gly Gly Ser Ala Ser
65 70 75 80

Thr Glu Pro Lys Ser Cys Asp Lys Thr His Thr Cys Pro Pro Cys Pro
85 90 95

Ala Pro Glu Leu Leu Gly Gly Pro Ser Val Phe Leu Phe Pro Pro Lys
100 105 110

Pro Lys Asp Thr Leu Met Ile Ser Arg Thr Pro Glu Val Thr Cys Val
115 120 125

Val Val Asp Val Ser His Glu Asp Pro Glu Val Lys Phe Asn Trp Tyr
130 135 140

Val Asp Gly Val Glu Val His Asn Ala Lys Thr Lys Pro Arg Glu Glu
145 150 155 160

Gln Tyr Asn Ser Thr Tyr Arg Val Val Ser Val Leu Thr Val Leu His
165 170 175

Gln Asp Trp Leu Asn Gly Lys Glu Tyr Lys Cys Lys Val Ser Asn Lys
180 185 190

Ala Leu Pro Ala Pro Ile Glu Lys Thr Ile Ser Lys Ala Lys Gly Gln
195 200 205

Pro Arg Glu Pro Gln Val Tyr Thr Leu Pro Pro Ser Arg Glu Glu Met
210 215 220

Thr Lys Asn Gln Val Ser Leu Thr Cys Leu Val Lys Gly Phe Tyr Pro
225 230 235 240

Ser Asp Ile Ala Val Glu Trp Glu Ser Asn Gly Gln Pro Glu Asn Asn
245 250 255

Tyr Lys Thr Thr Pro Pro Val Leu Asp Ser Asp Gly Ser Phe Phe Leu
260 265 270

Tyr Ser Lys Leu Thr Val Asp Lys Ser Arg Trp Gln Gln Gly Asn Val
275 280 285

Phe Ser Cys Ser Val Met His Glu Ala Leu His Asn His Tyr Thr Gln
290 295 300

Lys Ser Leu Ser Leu Ser Pro Gly Lys
305 310

<210> SEQ ID NO 416
<211> LENGTH: 313
<212> TYPE: PRT
<213> ORGANISM: artificial sequence
<220> FEATURE:
<223> OTHER INFORMATION: synthetic

<400> SEQUENCE: 416

```
Met Glu Thr Asp Thr Leu Leu Leu Trp Val Leu Leu Leu Trp Val Pro
1               5                   10                  15

Gly Ser Thr Gly Asp Thr Arg Trp Thr Thr Gln Asp Glu Gly Ala Ala
            20                  25                  30

Ile Gly Leu Ala Trp Ile Pro Tyr Phe Gly Pro Ala Ala Glu Gly Ile
        35                  40                  45

Tyr Ile Glu Gly Leu Gly Gly Gly Gly Ser Gly Gly Gly Gly Ser Gly
    50                  55                  60

Gly Pro Gly Ser Gly Gly Gly Gly Ser Gly Gly Gly Gly Ser Val Asp
65                  70                  75                  80

Glu Pro Arg Gly Pro Thr Ile Lys Pro Cys Pro Pro Cys Lys Cys Pro
                85                  90                  95

Ala Pro Asn Leu Leu Gly Gly Pro Ser Val Phe Ile Phe Pro Pro Lys
            100                 105                 110

Ile Lys Asp Val Leu Met Ile Ser Leu Ser Pro Ile Val Thr Cys Val
        115                 120                 125

Val Val Asp Val Ser Glu Asp Asp Pro Asp Val Gln Ile Ser Trp Phe
    130                 135                 140

Val Asn Asn Val Glu Val His Thr Ala Gln Thr Gln Thr His Arg Glu
145                 150                 155                 160

Asp Tyr Asn Ser Thr Leu Arg Val Val Ser Ala Leu Pro Ile Gln His
                165                 170                 175

Gln Asp Trp Met Ser Gly Lys Glu Phe Lys Cys Lys Val Asn Asn Lys
            180                 185                 190

Asp Leu Pro Ala Pro Ile Glu Arg Thr Ile Ser Lys Pro Lys Gly Ser
        195                 200                 205

Val Arg Ala Pro Gln Val Tyr Val Leu Pro Pro Pro Glu Glu Glu Met
    210                 215                 220

Thr Lys Lys Gln Val Thr Leu Thr Cys Met Val Thr Asp Phe Met Pro
225                 230                 235                 240

Glu Asp Ile Tyr Val Glu Trp Thr Asn Asn Gly Lys Thr Glu Leu Asn
                245                 250                 255

Tyr Lys Asn Thr Glu Pro Val Leu Asp Ser Asp Gly Ser Tyr Phe Met
            260                 265                 270

Tyr Ser Lys Leu Arg Val Glu Lys Lys Asn Trp Val Glu Arg Asn Ser
        275                 280                 285

Tyr Ser Cys Ser Val Val His Glu Gly Leu His Asn His His Thr Thr
    290                 295                 300

Lys Ser Phe Ser Arg Thr Pro Gly Lys
305                 310
```

<210> SEQ ID NO 417
<211> LENGTH: 314
<212> TYPE: PRT
<213> ORGANISM: artificial sequence
<220> FEATURE:
<223> OTHER INFORMATION: synthetic

<400> SEQUENCE: 417

Met Glu Thr Asp Thr Leu Leu Leu Trp Val Leu Leu Leu Trp Val Pro
1 5 10 15

Gly Ser Thr Gly Asp Thr Arg Arg Gln Leu Ala Asn Glu Thr Thr Gln
20 25 30

Ala Leu Gln Leu Phe Leu Arg Ala Thr Thr Glu Leu Arg Thr Phe Ser
35 40 45

Ile Leu Asn Arg Lys Ala Gly Gly Gly Gly Ser Gly Gly Gly Ser
50 55 60

Gly Gly Pro Gly Ser Gly Gly Gly Gly Ser Gly Gly Gly Gly Ser Ala
65 70 75 80

Ser Thr Glu Pro Lys Ser Cys Asp Lys Thr His Thr Cys Pro Pro Cys
85 90 95

Pro Ala Pro Glu Leu Leu Gly Gly Pro Ser Val Phe Leu Phe Pro Pro
100 105 110

Lys Pro Lys Asp Thr Leu Met Ile Ser Arg Thr Pro Glu Val Thr Cys
115 120 125

Val Val Val Asp Val Ser His Glu Asp Pro Glu Val Lys Phe Asn Trp
130 135 140

Tyr Val Asp Gly Val Glu Val His Asn Ala Lys Thr Lys Pro Arg Glu
145 150 155 160

Glu Gln Tyr Asn Ser Thr Tyr Arg Val Val Ser Val Leu Thr Val Leu
165 170 175

His Gln Asp Trp Leu Asn Gly Lys Glu Tyr Lys Cys Lys Val Ser Asn
180 185 190

Lys Ala Leu Pro Ala Pro Ile Glu Lys Thr Ile Ser Lys Ala Lys Gly
195 200 205

Gln Pro Arg Glu Pro Gln Val Tyr Thr Leu Pro Pro Ser Arg Glu Glu
210 215 220

Met Thr Lys Asn Gln Val Ser Leu Thr Cys Leu Val Lys Gly Phe Tyr
225 230 235 240

Pro Ser Asp Ile Ala Val Glu Trp Glu Ser Asn Gly Gln Pro Glu Asn
245 250 255

Asn Tyr Lys Thr Thr Pro Pro Val Leu Asp Ser Asp Gly Ser Phe Phe
260 265 270

Leu Tyr Ser Lys Leu Thr Val Asp Lys Ser Arg Trp Gln Gln Gly Asn
275 280 285

Val Phe Ser Cys Ser Val Met His Glu Ala Leu His Asn His Tyr Thr
290 295 300

Gln Lys Ser Leu Ser Leu Ser Pro Gly Lys
305 310

<210> SEQ ID NO 418
<211> LENGTH: 314
<212> TYPE: PRT
<213> ORGANISM: artificial sequence
<220> FEATURE:
<223> OTHER INFORMATION: synthetic

<400> SEQUENCE: 418

Met Glu Thr Asp Thr Leu Leu Leu Trp Val Leu Leu Leu Trp Val Pro
1 5 10 15

Gly Ser Thr Gly Asp Thr Arg Arg Gln Leu Ala Asn Glu Thr Thr Gln
20 25 30

Ala Leu Gln Leu Phe Leu Arg Ala Thr Thr Glu Leu Arg Thr Phe Ser 35 40 45

Ile Leu Asn Arg Lys Ala Gly Gly Gly Gly Ser Gly Gly Gly Gly Ser
50 55 60

Gly Gly Pro Gly Ser Gly Gly Gly Gly Ser Gly Gly Gly Gly Ser Val
65 70 75 80

Asp Glu Pro Arg Gly Pro Thr Ile Lys Pro Cys Pro Pro Cys Lys Cys
85 90 95

Pro Ala Pro Asn Leu Leu Gly Gly Pro Ser Val Phe Ile Phe Pro Pro
100 105 110

Lys Ile Lys Asp Val Leu Met Ile Ser Leu Ser Pro Ile Val Thr Cys
115 120 125

Val Val Val Asp Val Ser Glu Asp Asp Pro Asp Val Gln Ile Ser Trp
130 135 140

Phe Val Asn Asn Val Glu Val His Thr Ala Gln Thr Gln Thr His Arg
145 150 155 160

Glu Asp Tyr Asn Ser Thr Leu Arg Val Val Ser Ala Leu Pro Ile Gln
165 170 175

His Gln Asp Trp Met Ser Gly Lys Glu Phe Lys Cys Lys Val Asn Asn
180 185 190

Lys Asp Leu Pro Ala Pro Ile Glu Arg Thr Ile Ser Lys Pro Lys Gly
195 200 205

Ser Val Arg Ala Pro Gln Val Tyr Val Leu Pro Pro Pro Glu Glu Glu
210 215 220

Met Thr Lys Lys Gln Val Thr Leu Thr Cys Met Val Thr Asp Phe Met
225 230 235 240

Pro Glu Asp Ile Tyr Val Glu Trp Thr Asn Asn Gly Lys Thr Glu Leu
245 250 255

Asn Tyr Lys Asn Thr Glu Pro Val Leu Asp Ser Asp Gly Ser Tyr Phe
260 265 270

Met Tyr Ser Lys Leu Arg Val Glu Lys Lys Asn Trp Val Glu Arg Asn
275 280 285

Ser Tyr Ser Cys Ser Val Val His Glu Gly Leu His Asn His His Thr
290 295 300

Thr Lys Ser Phe Ser Arg Thr Pro Gly Lys
305 310

<210> SEQ ID NO 419
<211> LENGTH: 303
<212> TYPE: PRT
<213> ORGANISM: artificial sequence
<220> FEATURE:
<223> OTHER INFORMATION: synthetic

<400> SEQUENCE: 419

Met Glu Thr Asp Thr Leu Leu Leu Trp Val Leu Leu Leu Trp Val Pro
1 5 10 15

Gly Ser Thr Gly Asp Thr Arg Pro Asp Gln Gly Asp Asn Asp Asn Trp
20 25 30

Trp Thr Gly Trp Arg Gln Trp Ile Pro Ala Gly Gly Gly Gly Gly Ser
35 40 45

Gly Gly Gly Gly Ser Gly Gly Pro Gly Ser Gly Gly Gly Gly Ser Gly
50 55 60

Gly Gly Gly Ser Ala Ser Thr Glu Pro Lys Ser Cys Asp Lys Thr His
65 70 75 80

Thr Cys Pro Pro Cys Pro Ala Pro Glu Leu Leu Gly Gly Pro Ser Val

```
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300


<210> SEQ ID NO 420
<211> LENGTH: 303
<212> TYPE: PRT
<213> ORGANISM: artificial sequence
<220> FEATURE:
<223> OTHER INFORMATION: synthetic

<400> SEQUENCE: 420

Met Glu Thr Asp Thr Leu Leu Leu Trp Val Leu Leu Leu Trp Val Pro
1               5                   10                  15

Gly Ser Thr Gly Asp Thr Arg Pro Asp Gln Gly Asp Asn Asp Asn Trp
            20                  25                  30

Trp Thr Gly Trp Arg Gln Trp Ile Pro Ala Gly Gly Gly Gly Gly Ser
        35                  40                  45

Gly Gly Gly Gly Ser Gly Gly Pro Gly Ser Gly Gly Gly Gly Ser Gly
    50                  55                  60

Gly Gly Gly Ser Val Asp Glu Pro Arg Gly Pro Thr Ile Lys Pro Cys
65                  70                  75                  80

Pro Pro Cys Lys Cys Pro Ala Pro Asn Leu Leu Gly Gly Pro Ser Val
                85                  90                  95

Phe Ile Phe Pro Pro Lys Ile Lys Asp Val Leu Met Ile Ser Leu Ser
            100                 105                 110

Pro Ile Val Thr Cys Val Val Val Asp Val Ser Glu Asp Asp Pro Asp
        115                 120                 125

Val Gln Ile Ser Trp Phe Val Asn Asn Val Glu Val His Thr Ala Gln
    130                 135                 140

Thr Gln Thr His Arg Glu Asp Tyr Asn Ser Thr Leu Arg Val Val Ser
```

```
145                 150                 155                 160

Ala Leu Pro Ile Gln His Gln Asp Trp Met Ser Gly Lys Glu Phe Lys
                165                 170                 175

Cys Lys Val Asn Asn Lys Asp Leu Pro Ala Pro Ile Glu Arg Thr Ile
            180                 185                 190

Ser Lys Pro Lys Gly Ser Val Arg Ala Pro Gln Val Tyr Val Leu Pro
        195                 200                 205

Pro Pro Glu Glu Glu Met Thr Lys Lys Gln Val Thr Leu Thr Cys Met
    210                 215                 220

Val Thr Asp Phe Met Pro Glu Asp Ile Tyr Val Glu Trp Thr Asn Asn
225                 230                 235                 240

Gly Lys Thr Glu Leu Asn Tyr Lys Asn Thr Glu Pro Val Leu Asp Ser
                245                 250                 255

Asp Gly Ser Tyr Phe Met Tyr Ser Lys Leu Arg Val Glu Lys Lys Asn
            260                 265                 270

Trp Val Glu Arg Asn Ser Tyr Ser Cys Ser Val Val His Glu Gly Leu
        275                 280                 285

His Asn His His Thr Thr Lys Ser Phe Ser Arg Thr Pro Gly Lys
    290                 295                 300


<210> SEQ ID NO 421
<211> LENGTH: 320
<212> TYPE: PRT
<213> ORGANISM: artificial sequence
<220> FEATURE:
<223> OTHER INFORMATION: synthetic

<400> SEQUENCE: 421

Met Glu Thr Asp Thr Leu Leu Leu Trp Val Leu Leu Leu Trp Val Pro
1               5                   10                  15

Gly Ser Thr Gly Asp Thr Arg Ser His Thr Pro Gly Ser Val Ser Ser
            20                  25                  30

Ala Phe Ile Leu Glu Ala Met Val Asn Val Ile Ser Gly Pro Lys Val
        35                  40                  45

Leu Met Lys Gln Ile Pro Ile Trp Leu Pro Leu Gly Gly Gly Gly Gly
    50                  55                  60

Ser Gly Gly Gly Gly Ser Gly Gly Pro Gly Ser Gly Gly Gly Gly Ser
65                  70                  75                  80

Gly Gly Gly Gly Ser Ala Ser Thr Glu Pro Lys Ser Cys Asp Lys Thr
                85                  90                  95

His Thr Cys Pro Pro Cys Pro Ala Pro Glu Leu Leu Gly Gly Pro Ser
            100                 105                 110

Val Phe Leu Phe Pro Pro Lys Pro Lys Asp Thr Leu Met Ile Ser Arg
        115                 120                 125

Thr Pro Glu Val Thr Cys Val Val Val Asp Val Ser His Glu Asp Pro
    130                 135                 140

Glu Val Lys Phe Asn Trp Tyr Val Asp Gly Val Glu Val His Asn Ala
145                 150                 155                 160

Lys Thr Lys Pro Arg Glu Glu Gln Tyr Asn Ser Thr Tyr Arg Val Val
                165                 170                 175

Ser Val Leu Thr Val Leu His Gln Asp Trp Leu Asn Gly Lys Glu Tyr
            180                 185                 190

Lys Cys Lys Val Ser Asn Lys Ala Leu Pro Ala Pro Ile Glu Lys Thr
        195                 200                 205

Ile Ser Lys Ala Lys Gly Gln Pro Arg Glu Pro Gln Val Tyr Thr Leu
```

```
    210                 215                 220

Pro Pro Ser Arg Glu Glu Met Thr Lys Asn Gln Val Ser Leu Thr Cys
225                 230                 235                 240

Leu Val Lys Gly Phe Tyr Pro Ser Asp Ile Ala Val Glu Trp Glu Ser
                245                 250                 255

Asn Gly Gln Pro Glu Asn Asn Tyr Lys Thr Thr Pro Pro Val Leu Asp
            260                 265                 270

Ser Asp Gly Ser Phe Phe Leu Tyr Ser Lys Leu Thr Val Asp Lys Ser
        275                 280                 285

Arg Trp Gln Gln Gly Asn Val Phe Ser Cys Ser Val Met His Glu Ala
    290                 295                 300

Leu His Asn His Tyr Thr Gln Lys Ser Leu Ser Leu Ser Pro Gly Lys
305                 310                 315                 320


<210> SEQ ID NO 422
<211> LENGTH: 320
<212> TYPE: PRT
<213> ORGANISM: artificial sequence
<220> FEATURE:
<223> OTHER INFORMATION: synthetic

<400> SEQUENCE: 422

Met Glu Thr Asp Thr Leu Leu Leu Trp Val Leu Leu Leu Trp Val Pro
1               5                   10                  15

Gly Ser Thr Gly Asp Thr Arg Ser His Thr Pro Gly Ser Val Ser Ser
            20                  25                  30

Ala Phe Ile Leu Glu Ala Met Val Asn Val Ile Ser Gly Pro Lys Val
        35                  40                  45

Leu Met Lys Gln Ile Pro Ile Trp Leu Pro Leu Gly Gly Gly Gly Gly
    50                  55                  60

Ser Gly Gly Gly Gly Ser Gly Gly Pro Gly Ser Gly Gly Gly Gly Ser
65                  70                  75                  80

Gly Gly Gly Gly Ser Val Asp Glu Pro Arg Gly Pro Thr Ile Lys Pro
                85                  90                  95

Cys Pro Pro Cys Lys Cys Pro Ala Pro Asn Leu Leu Gly Gly Pro Ser
            100                 105                 110

Val Phe Ile Phe Pro Pro Lys Ile Lys Asp Val Leu Met Ile Ser Leu
        115                 120                 125

Ser Pro Ile Val Thr Cys Val Val Val Asp Val Ser Glu Asp Asp Pro
    130                 135                 140

Asp Val Gln Ile Ser Trp Phe Val Asn Asn Val Glu Val His Thr Ala
145                 150                 155                 160

Gln Thr Gln Thr His Arg Glu Asp Tyr Asn Ser Thr Leu Arg Val Val
                165                 170                 175

Ser Ala Leu Pro Ile Gln His Gln Asp Trp Met Ser Gly Lys Glu Phe
            180                 185                 190

Lys Cys Lys Val Asn Asn Lys Asp Leu Pro Ala Pro Ile Glu Arg Thr
        195                 200                 205

Ile Ser Lys Pro Lys Gly Ser Val Arg Ala Pro Gln Val Tyr Val Leu
    210                 215                 220

Pro Pro Pro Glu Glu Glu Met Thr Lys Lys Gln Val Thr Leu Thr Cys
225                 230                 235                 240

Met Val Thr Asp Phe Met Pro Glu Asp Ile Tyr Val Glu Trp Thr Asn
                245                 250                 255

Asn Gly Lys Thr Glu Leu Asn Tyr Lys Asn Thr Glu Pro Val Leu Asp
```

-continued

```
            260                 265                 270

Ser Asp Gly Ser Tyr Phe Met Tyr Ser Lys Leu Arg Val Glu Lys Lys
        275                 280                 285

Asn Trp Val Glu Arg Asn Ser Tyr Ser Cys Ser Val Val His Glu Gly
    290                 295                 300

Leu His Asn His His Thr Thr Lys Ser Phe Ser Arg Thr Pro Gly Lys
305                 310                 315                 320


<210> SEQ ID NO 423
<211> LENGTH: 325
<212> TYPE: PRT
<213> ORGANISM: artificial sequence
<220> FEATURE:
<223> OTHER INFORMATION: synthetic

<400> SEQUENCE: 423

Met Glu Thr Asp Thr Leu Leu Leu Trp Val Leu Leu Leu Trp Val Pro
1               5                   10                  15

Gly Ser Thr Gly Asp Thr Arg Gly Lys Lys Val Thr Ser Lys Asn Gly
            20                  25                  30

Gln Pro Ile Ile Pro Val Leu Leu Pro Lys Tyr Ile Gly Leu Asp Pro
        35                  40                  45

Val Ala Pro Gly Asp Leu Thr Met Val Ile Thr Gln Asp Cys Asp Thr
    50                  55                  60

Cys Gly Gly Gly Gly Ser Gly Gly Gly Gly Ser Gly Gly Pro Gly Ser
65                  70                  75                  80

Gly Gly Gly Gly Ser Gly Gly Gly Gly Ser Ala Ser Thr Glu Pro Lys
                85                  90                  95

Ser Cys Asp Lys Thr His Thr Cys Pro Pro Cys Pro Ala Pro Glu Leu
            100                 105                 110

Leu Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Lys Phe Asn Trp Tyr Val Asp Gly Val
145                 150                 155                 160

Glu Val His Asn Ala Lys Thr Lys Pro Arg Glu Glu Gln Tyr Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Ala Leu Pro Ala
        195                 200                 205

Pro Ile Glu Lys Thr Ile Ser Lys Ala Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
```

305 310 315 320

Leu Ser Pro Gly Lys
325

<210> SEQ ID NO 424
<211> LENGTH: 325
<212> TYPE: PRT
<213> ORGANISM: artificial sequence
<220> FEATURE:
<223> OTHER INFORMATION: synthetic

<400> SEQUENCE: 424

Met Glu Thr Asp Thr Leu Leu Leu Trp Val Leu Leu Leu Trp Val Pro
1 5 10 15

Gly Ser Thr Gly Asp Thr Arg Gly Lys Lys Val Thr Ser Lys Asn Gly
20 25 30

Gln Pro Ile Ile Pro Val Leu Leu Pro Lys Tyr Ile Gly Leu Asp Pro
35 40 45

Val Ala Pro Gly Asp Leu Thr Met Val Ile Thr Gln Asp Cys Asp Thr
50 55 60

Cys Gly Gly Gly Gly Ser Gly Gly Gly Gly Ser Gly Gly Pro Gly Ser
65 70 75 80

Gly Gly Gly Gly Ser Gly Gly Gly Gly Ser Val Asp Glu Pro Arg Gly
85 90 95

Pro Thr Ile Lys Pro Cys Pro Pro Cys Lys Cys Pro Ala Pro Asn Leu
100 105 110

Leu Gly Gly Pro Ser Val Phe Ile Phe Pro Pro Lys Ile Lys Asp Val
115 120 125

Leu Met Ile Ser Leu Ser Pro Ile Val Thr Cys Val Val Val Asp Val
130 135 140

Ser Glu Asp Asp Pro Asp Val Gln Ile Ser Trp Phe Val Asn Asn Val
145 150 155 160

Glu Val His Thr Ala Gln Thr Gln Thr His Arg Glu Asp Tyr Asn Ser
165 170 175

Thr Leu Arg Val Val Ser Ala Leu Pro Ile Gln His Gln Asp Trp Met
180 185 190

Ser Gly Lys Glu Phe Lys Cys Lys Val Asn Asn Lys Asp Leu Pro Ala
195 200 205

Pro Ile Glu Arg Thr Ile Ser Lys Pro Lys Gly Ser Val Arg Ala Pro
210 215 220

Gln Val Tyr Val Leu Pro Pro Pro Glu Glu Glu Met Thr Lys Lys Gln
225 230 235 240

Val Thr Leu Thr Cys Met Val Thr Asp Phe Met Pro Glu Asp Ile Tyr
245 250 255

Val Glu Trp Thr Asn Asn Gly Lys Thr Glu Leu Asn Tyr Lys Asn Thr
260 265 270

Glu Pro Val Leu Asp Ser Asp Gly Ser Tyr Phe Met Tyr Ser Lys Leu
275 280 285

Arg Val Glu Lys Lys Asn Trp Val Glu Arg Asn Ser Tyr Ser Cys Ser
290 295 300

Val Val His Glu Gly Leu His Asn His His Thr Thr Lys Ser Phe Ser
305 310 315 320

Arg Thr Pro Gly Lys
325

<210> SEQ ID NO 425
<211> LENGTH: 309
<212> TYPE: PRT
<213> ORGANISM: artificial sequence
<220> FEATURE:
<223> OTHER INFORMATION: synthetic

<400> SEQUENCE: 425

Met Glu Thr Asp Thr Leu Leu Leu Trp Val Leu Leu Leu Trp Val Pro
1               5                   10                  15

Gly Ser Thr Gly Asp Thr Arg Pro Asn Ser Thr Ile Glu Ser Pro Leu
            20                  25                  30

Trp Ala Leu Arg Val Ile Leu Ala Ala Gly Ile Gln Asp Gln Leu Ile
        35                  40                  45

Asp Gly Gly Gly Gly Ser Gly Gly Gly Gly Ser Gly Gly Pro Gly Ser
    50                  55                  60

Gly Gly Gly Gly Ser Gly Gly Gly Gly Ser Ala Ser Thr Glu Pro Lys
65                  70                  75                  80

Ser Cys Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305

<210> SEQ ID NO 426
<211> LENGTH: 309
<212> TYPE: PRT
<213> ORGANISM: artificial sequence
<220> FEATURE:
<223> OTHER INFORMATION: synthetic

<400> SEQUENCE: 426

```
Met Glu Thr Asp Thr Leu Leu Leu Trp Val Leu Leu Leu Trp Val Pro
1               5                   10                  15

Gly Ser Thr Gly Asp Thr Arg Pro Asn Ser Thr Ile Glu Ser Pro Leu
            20                  25                  30

Trp Ala Leu Arg Val Ile Leu Ala Ala Gly Ile Gln Asp Gln Leu Ile
        35                  40                  45

Asp Gly Gly Gly Gly Ser Gly Gly Gly Gly Ser Gly Gly Pro Gly Ser
    50                  55                  60

Gly Gly Gly Gly Ser Gly Gly Gly Gly Ser Val Asp Glu Pro Arg Gly
65                  70                  75                  80

Pro Thr Ile Lys Pro Cys Pro Pro Cys Lys Cys Pro Ala Pro Asn Leu
                85                  90                  95

Leu Gly Gly Pro Ser Val Phe Ile Phe Pro Pro Lys Ile Lys Asp Val
            100                 105                 110

Leu Met Ile Ser Leu Ser Pro Ile Val Thr Cys Val Val Val Asp Val
        115                 120                 125

Ser Glu Asp Asp Pro Asp Val Gln Ile Ser Trp Phe Val Asn Asn Val
    130                 135                 140

Glu Val His Thr Ala Gln Thr Gln Thr His Arg Glu Asp Tyr Asn Ser
145                 150                 155                 160

Thr Leu Arg Val Val Ser Ala Leu Pro Ile Gln His Gln Asp Trp Met
                165                 170                 175

Ser Gly Lys Glu Phe Lys Cys Lys Val Asn Asn Lys Asp Leu Pro Ala
            180                 185                 190

Pro Ile Glu Arg Thr Ile Ser Lys Pro Lys Gly Ser Val Arg Ala Pro
        195                 200                 205

Gln Val Tyr Val Leu Pro Pro Pro Glu Glu Glu Met Thr Lys Lys Gln
    210                 215                 220

Val Thr Leu Thr Cys Met Val Thr Asp Phe Met Pro Glu Asp Ile Tyr
225                 230                 235                 240

Val Glu Trp Thr Asn Asn Gly Lys Thr Glu Leu Asn Tyr Lys Asn Thr
                245                 250                 255

Glu Pro Val Leu Asp Ser Asp Gly Ser Tyr Phe Met Tyr Ser Lys Leu
            260                 265                 270

Arg Val Glu Lys Lys Asn Trp Val Glu Arg Asn Ser Tyr Ser Cys Ser
        275                 280                 285

Val Val His Glu Gly Leu His Asn His His Thr Thr Lys Ser Phe Ser
    290                 295                 300

Arg Thr Pro Gly Lys
305
```

<210> SEQ ID NO 427
<211> LENGTH: 504
<212> TYPE: PRT
<213> ORGANISM: artificial sequence
<220> FEATURE:
<223> OTHER INFORMATION: synthetic

<400> SEQUENCE: 427

```
Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45
```

-continued

```
Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Arg Val
            260                 265                 270

Glu Pro Lys Ser Cys Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
```

465 470 475 480

Ser Cys Ser Val Met His Glu Ala Leu His Asn His Tyr Thr Gln Lys
485 490 495

Ser Leu Ser Leu Ser Pro Gly Lys
500

<210> SEQ ID NO 428
<211> LENGTH: 280
<212> TYPE: PRT
<213> ORGANISM: artificial sequence
<220> FEATURE:
<223> OTHER INFORMATION: synthetic

<400> SEQUENCE: 428

Met Glu Thr Asp Thr Leu Leu Leu Trp Val Leu Leu Leu Trp Val Pro
1 5 10 15

Gly Ser Thr Gly Asp Thr Arg Val Asn Ala Gln Pro Lys Cys Asn Pro
20 25 30

Asn Leu His Tyr Trp Thr Thr Gln Asp Glu Gly Ala Ala Ile Gly Leu
35 40 45

Ala Trp Ile Pro Tyr Phe Gly Pro Ala Ala Glu Gly Ile Tyr Ile Glu
50 55 60

Gly Leu Met His Asn Gln Asp Gly Leu Ile Cys Gly Leu Arg Gln Leu
65 70 75 80

Ala Asn Glu Thr Thr Gln Ala Leu Gln Leu Phe Leu Arg Ala Thr Thr
85 90 95

Glu Leu Arg Thr Phe Ser Ile Leu Asn Arg Lys Ala Ile Asp Phe Leu
100 105 110

Leu Gln Arg Trp Gly Gly Thr Cys His Ile Leu Gly Pro Asp Cys Cys
115 120 125

Ile Glu Pro His Asp Trp Thr Lys Asn Ile Thr Asp Lys Ile Asp Gln
130 135 140

Ile Ile His Asp Phe Val Asp Lys Thr Leu Pro Asp Gln Gly Asp Asn
145 150 155 160

Asp Asn Trp Trp Thr Gly Trp Arg Gln Trp Ile Pro Ala Gly Thr Val
165 170 175

Ala Ala Pro Ser Val Phe Ile Phe Pro Pro Ser Asp Glu Gln Leu Lys
180 185 190

Ser Gly Thr Ala Ser Val Val Cys Leu Leu Asn Asn Phe Tyr Pro Arg
195 200 205

Glu Ala Lys Val Gln Trp Lys Val Asp Asn Ala Leu Gln Ser Gly Asn
210 215 220

Ser Gln Glu Ser Val Thr Glu Gln Asp Ser Lys Asp Ser Thr Tyr Ser
225 230 235 240

Leu Ser Ser Thr Leu Thr Leu Ser Lys Ala Asp Tyr Glu Lys His Lys
245 250 255

Val Tyr Ala Cys Glu Val Thr His Gln Gly Leu Ser Ser Pro Val Thr
260 265 270

Lys Ser Phe Asn Arg Gly Glu Cys
275 280

<210> SEQ ID NO 429
<211> LENGTH: 504
<212> TYPE: PRT
<213> ORGANISM: artificial sequence
<220> FEATURE:
<223> OTHER INFORMATION: synthetic

<400> SEQUENCE: 429

Met Glu Thr Asp Thr Leu Leu Leu Trp Val Leu Leu Leu Trp Val Pro
1 5 10 15

Gly Ser Thr Gly Asp Thr Arg Val Asn Ala Gln Pro Lys Cys Asn Pro
20 25 30

Asn Leu His Tyr Trp Thr Thr Gln Asp Glu Gly Ala Ala Ile Gly Leu
35 40 45

Ala Trp Ile Pro Tyr Phe Gly Pro Ala Ala Glu Gly Ile Tyr Ile Glu
50 55 60

Gly Leu Met His Asn Gln Asp Gly Leu Ile Cys Gly Leu Arg Gln Leu
65 70 75 80

Ala Asn Glu Thr Thr Gln Ala Leu Gln Leu Phe Leu Arg Ala Thr Thr
85 90 95

Glu Leu Arg Thr Phe Ser Ile Leu Asn Arg Lys Ala Ile Asp Phe Leu
100 105 110

Leu Gln Arg Trp Gly Gly Thr Cys His Ile Leu Gly Pro Asp Cys Cys
115 120 125

Ile Glu Pro His Asp Trp Thr Lys Asn Ile Thr Asp Lys Ile Asp Gln
130 135 140

Ile Ile His Asp Phe Val Asp Lys Thr Leu Pro Asp Gln Gly Asp Asn
145 150 155 160

Asp Asn Trp Trp Thr Gly Trp Arg Gln Trp Ile Pro Ala Gly Ala Lys
165 170 175

Thr Thr Ala Pro Ser Val Tyr Pro Leu Ala Pro Val Cys Gly Asp Thr
180 185 190

Thr Gly Ser Ser Val Thr Leu Gly Cys Leu Val Lys Gly Tyr Phe Pro
195 200 205

Glu Pro Val Thr Leu Thr Trp Asn Ser Gly Ser Leu Ser Ser Gly Val
210 215 220

His Thr Phe Pro Ala Val Leu Gln Ser Asp Leu Tyr Thr Leu Ser Ser
225 230 235 240

Ser Val Thr Val Thr Ser Ser Thr Trp Pro Ser Gln Ser Ile Thr Cys
245 250 255

Asn Val Ala His Pro Ala Ser Ser Thr Lys Val Asp Lys Lys Ile Glu
260 265 270

Pro Arg Gly Pro Thr Ile Lys Pro Cys Pro Pro Cys Lys Cys Pro Ala
275 280 285

Pro Asn Leu Leu Gly Gly Pro Ser Val Phe Ile Phe Pro Pro Lys Ile
290 295 300

Lys Asp Val Leu Met Ile Ser Leu Ser Pro Ile Val Thr Cys Val Val
305 310 315 320

Val Asp Val Ser Glu Asp Asp Pro Asp Val Gln Ile Ser Trp Phe Val
325 330 335

Asn Asn Val Glu Val His Thr Ala Gln Thr Gln Thr His Arg Glu Asp
340 345 350

Tyr Asn Ser Thr Leu Arg Val Val Ser Ala Leu Pro Ile Gln His Gln
355 360 365

Asp Trp Met Ser Gly Lys Glu Phe Lys Cys Lys Val Asn Asn Lys Asp
370 375 380

Leu Pro Ala Pro Ile Glu Arg Thr Ile Ser Lys Pro Lys Gly Ser Val
385 390 395 400

Arg Ala Pro Gln Val Tyr Val Leu Pro Pro Pro Glu Glu Glu Met Thr 405 410 415

Lys Lys Gln Val Thr Leu Thr Cys Met Val Thr Asp Phe Met Pro Glu
420 425 430

Asp Ile Tyr Val Glu Trp Thr Asn Asn Gly Lys Thr Glu Leu Asn Tyr
435 440 445

Lys Asn Thr Glu Pro Val Leu Asp Ser Asp Gly Ser Tyr Phe Met Tyr
450 455 460

Ser Lys Leu Arg Val Glu Lys Lys Asn Trp Val Glu Arg Asn Ser Tyr
465 470 475 480

Ser Cys Ser Val Val His Glu Gly Leu His Asn His His Thr Thr Lys
485 490 495

Ser Phe Ser Arg Thr Pro Gly Lys
500

<210> SEQ ID NO 430
<211> LENGTH: 282
<212> TYPE: PRT
<213> ORGANISM: artificial sequence
<220> FEATURE:
<223> OTHER INFORMATION: synthetic

<400> SEQUENCE: 430

Met Glu Thr Asp Thr Leu Leu Leu Trp Val Leu Leu Leu Trp Val Pro
1 5 10 15

Gly Ser Thr Gly Asp Thr Arg Val Asn Ala Gln Pro Lys Cys Asn Pro
20 25 30

Asn Leu His Tyr Trp Thr Thr Gln Asp Glu Gly Ala Ala Ile Gly Leu
35 40 45

Ala Trp Ile Pro Tyr Phe Gly Pro Ala Ala Glu Gly Ile Tyr Ile Glu
50 55 60

Gly Leu Met His Asn Gln Asp Gly Leu Ile Cys Gly Leu Arg Gln Leu
65 70 75 80

Ala Asn Glu Thr Thr Gln Ala Leu Gln Leu Phe Leu Arg Ala Thr Thr
85 90 95

Glu Leu Arg Thr Phe Ser Ile Leu Asn Arg Lys Ala Ile Asp Phe Leu
100 105 110

Leu Gln Arg Trp Gly Gly Thr Cys His Ile Leu Gly Pro Asp Cys Cys
115 120 125

Ile Glu Pro His Asp Trp Thr Lys Asn Ile Thr Asp Lys Ile Asp Gln
130 135 140

Ile Ile His Asp Phe Val Asp Lys Thr Leu Pro Asp Gln Gly Asp Asn
145 150 155 160

Asp Asn Trp Trp Thr Gly Trp Arg Gln Trp Ile Pro Ala Gly Lys Arg
165 170 175

Ala Asp Ala Ala Pro Thr Val Ser Ile Phe Pro Pro Ser Ser Glu Gln
180 185 190

Leu Thr Ser Gly Gly Ala Ser Val Val Cys Phe Leu Asn Asn Phe Tyr
195 200 205

Pro Lys Asp Ile Asn Val Lys Trp Lys Ile Asp Gly Ser Glu Arg Gln
210 215 220

Asn Gly Val Leu Asn Ser Trp Thr Asp Gln Asp Ser Lys Asp Ser Thr
225 230 235 240

Tyr Ser Met Ser Ser Thr Leu Thr Leu Thr Lys Asp Glu Tyr Glu Arg
245 250 255

His Asn Ser Tyr Thr Cys Glu Ala Thr His Lys Thr Ser Thr Ser Pro

```
            260                 265                 270

Ile Val Lys Ser Phe Asn Arg Asn Glu Cys
        275                 280


<210> SEQ ID NO 431
<211> LENGTH: 816
<212> TYPE: PRT
<213> ORGANISM: artificial sequence
<220> FEATURE:
<223> OTHER INFORMATION: synthetic

<400> SEQUENCE: 431

Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Gly Gly
                165                 170                 175

Gly Gly Ser Val Asn Ala Gln Pro Lys Cys Asn Pro Asn Leu His Tyr
            180                 185                 190

Trp Thr Thr Gln Asp Glu Gly Ala Ala Ile Gly Leu Ala Trp Ile Pro
        195                 200                 205

Tyr Phe Gly Pro Ala Ala Glu Gly Ile Tyr Ile Glu Gly Leu Met His
    210                 215                 220

Asn Gln Asp Gly Leu Ile Cys Gly Leu Arg Gln Leu Ala Asn Glu Thr
225                 230                 235                 240

Thr Gln Ala Leu Gln Leu Phe Leu Arg Ala Thr Thr Glu Leu Arg Thr
                245                 250                 255

Phe Ser Ile Leu Asn Arg Lys Ala Ile Asp Phe Leu Leu Gln Arg Trp
            260                 265                 270

Gly Gly Thr Cys His Ile Leu Gly Pro Asp Cys Cys Ile Glu Pro His
        275                 280                 285

Asp Trp Thr Lys Asn Ile Thr Asp Lys Ile Asp Gln Ile Ile His Asp
    290                 295                 300

Phe Val Asp Lys Thr Leu Pro Asp Gln Gly Asp Asn Asp Asn Trp Trp
305                 310                 315                 320

Thr Gly Trp Arg Gln Trp Ile Pro Ala Gly Gly Gly Gly Gly Ser Val
                325                 330                 335

Asn Ala Gln Pro Lys Cys Asn Pro Asn Leu His Tyr Trp Thr Thr Gln
```

```
            340                 345                 350

Asp Glu Gly Ala Ala Ile Gly Leu Ala Trp Ile Pro Tyr Phe Gly Pro
        355                 360                 365

Ala Ala Glu Gly Ile Tyr Ile Glu Gly Leu Met His Asn Gln Asp Gly
    370                 375                 380

Leu Ile Cys Gly Leu Arg Gln Leu Ala Asn Glu Thr Thr Gln Ala Leu
385                 390                 395                 400

Gln Leu Phe Leu Arg Ala Thr Thr Glu Leu Arg Thr Phe Ser Ile Leu
                405                 410                 415

Asn Arg Lys Ala Ile Asp Phe Leu Leu Gln Arg Trp Gly Gly Thr Cys
            420                 425                 430

His Ile Leu Gly Pro Asp Cys Cys Ile Glu Pro His Asp Trp Thr Lys
        435                 440                 445

Asn Ile Thr Asp Lys Ile Asp Gln Ile Ile His Asp Phe Val Asp Lys
    450                 455                 460

Thr Leu Pro Asp Gln Gly Asp Asn Asp Asn Trp Trp Thr Gly Trp Arg
465                 470                 475                 480

Gln Trp Ile Pro Ala Gly Ala Ser Thr Lys Gly Pro Ser Val Phe Pro
                485                 490                 495

Leu Ala Pro Ser Ser Lys Ser Thr Ser Gly Gly Thr Ala Ala Leu Gly
            500                 505                 510

Cys Leu Val Lys Asp Tyr Phe Pro Glu Pro Val Thr Val Ser Trp Asn
        515                 520                 525

Ser Gly Ala Leu Thr Ser Gly Val His Thr Phe Pro Ala Val Leu Gln
    530                 535                 540

Ser Ser Gly Leu Tyr Ser Leu Ser Ser Val Val Thr Val Pro Ser Ser
545                 550                 555                 560

Ser Leu Gly Thr Gln Thr Tyr Ile Cys Asn Val Asn His Lys Pro Ser
                565                 570                 575

Asn Thr Lys Val Asp Lys Arg Val Glu Pro Lys Ser Cys Asp Lys Thr
            580                 585                 590

His Thr Cys Pro Pro Cys Pro Ala Pro Glu Leu Leu Gly Gly Pro Ser
        595                 600                 605

Val Phe Leu Phe Pro Pro Lys Pro Lys Asp Thr Leu Met Ile Ser Arg
    610                 615                 620

Thr Pro Glu Val Thr Cys Val Val Val Asp Val Ser His Glu Asp Pro
625                 630                 635                 640

Glu Val Lys Phe Asn Trp Tyr Val Asp Gly Val Glu Val His Asn Ala
                645                 650                 655

Lys Thr Lys Pro Arg Glu Glu Gln Tyr Asn Ser Thr Tyr Arg Val Val
            660                 665                 670

Ser Val Leu Thr Val Leu His Gln Asp Trp Leu Asn Gly Lys Glu Tyr
        675                 680                 685

Lys Cys Lys Val Ser Asn Lys Ala Leu Pro Ala Pro Ile Glu Lys Thr
    690                 695                 700

Ile Ser Lys Ala Lys Gly Gln Pro Arg Glu Pro Gln Val Tyr Thr Leu
705                 710                 715                 720

Pro Pro Ser Arg Glu Glu Met Thr Lys Asn Gln Val Ser Leu Thr Cys
                725                 730                 735

Leu Val Lys Gly Phe Tyr Pro Ser Asp Ile Ala Val Glu Trp Glu Ser
            740                 745                 750

Asn Gly Gln Pro Glu Asn Asn Tyr Lys Thr Thr Pro Pro Val Leu Asp
        755                 760                 765
```

```
Ser Asp Gly Ser Phe Phe Leu Tyr Ser Lys Leu Thr Val Asp Lys Ser
    770                 775                 780

Arg Trp Gln Gln Gly Asn Val Phe Ser Cys Ser Val Met His Glu Ala
785                 790                 795                 800

Leu His Asn His Tyr Thr Gln Lys Ser Leu Ser Leu Ser Pro Gly Lys
                805                 810                 815


<210> SEQ ID NO 432
<211> LENGTH: 816
<212> TYPE: PRT
<213> ORGANISM: artificial sequence
<220> FEATURE:
<223> OTHER INFORMATION: synthetic

<400> SEQUENCE: 432

Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Gly Gly
                165                 170                 175

Gly Gly Ser Val Asn Ala Gln Pro Lys Cys Asn Pro Asn Leu His Tyr
            180                 185                 190

Trp Thr Thr Gln Asp Glu Gly Ala Ala Ile Gly Leu Ala Trp Ile Pro
        195                 200                 205

Tyr Phe Gly Pro Ala Ala Glu Gly Ile Tyr Ile Glu Gly Leu Met His
    210                 215                 220

Asn Gln Asp Gly Leu Ile Cys Gly Leu Arg Gln Leu Ala Asn Glu Thr
225                 230                 235                 240

Thr Gln Ala Leu Gln Leu Phe Leu Arg Ala Thr Thr Glu Leu Arg Thr
                245                 250                 255

Phe Ser Ile Leu Asn Arg Lys Ala Ile Asp Phe Leu Leu Gln Arg Trp
            260                 265                 270

Gly Gly Thr Cys His Ile Leu Gly Pro Asp Cys Cys Ile Glu Pro His
        275                 280                 285

Asp Trp Thr Lys Asn Ile Thr Asp Lys Ile Asp Gln Ile Ile His Asp
    290                 295                 300

Phe Val Asp Lys Thr Leu Pro Asp Gln Gly Asp Asn Asp Asn Trp Trp
305                 310                 315                 320
```

-continued

```
Thr Gly Trp Arg Gln Trp Ile Pro Ala Gly Gly Gly Gly Gly Ser Val
                325                 330                 335

Asn Ala Gln Pro Lys Cys Asn Pro Asn Leu His Tyr Trp Thr Thr Gln
            340                 345                 350

Asp Glu Gly Ala Ala Ile Gly Leu Ala Trp Ile Pro Tyr Phe Gly Pro
        355                 360                 365

Ala Ala Glu Gly Ile Tyr Ile Glu Gly Leu Met His Asn Gln Asp Gly
    370                 375                 380

Leu Ile Cys Gly Leu Arg Gln Leu Ala Asn Glu Thr Thr Gln Ala Leu
385                 390                 395                 400

Gln Leu Phe Leu Arg Ala Thr Thr Glu Leu Arg Thr Phe Ser Ile Leu
                405                 410                 415

Asn Arg Lys Ala Ile Asp Phe Leu Leu Gln Arg Trp Gly Gly Thr Cys
            420                 425                 430

His Ile Leu Gly Pro Asp Cys Cys Ile Glu Pro His Asp Trp Thr Lys
        435                 440                 445

Asn Ile Thr Asp Lys Ile Asp Gln Ile Ile His Asp Phe Val Asp Lys
    450                 455                 460

Thr Leu Pro Asp Gln Gly Asp Asn Asp Asn Trp Trp Thr Gly Trp Arg
465                 470                 475                 480

Gln Trp Ile Pro Ala Gly Ala Lys Thr Thr Ala Pro Ser Val Tyr Pro
                485                 490                 495

Leu Ala Pro Val Cys Gly Asp Thr Thr Gly Ser Ser Val Thr Leu Gly
            500                 505                 510

Cys Leu Val Lys Gly Tyr Phe Pro Glu Pro Val Thr Leu Thr Trp Asn
        515                 520                 525

Ser Gly Ser Leu Ser Ser Gly Val His Thr Phe Pro Ala Val Leu Gln
    530                 535                 540

Ser Asp Leu Tyr Thr Leu Ser Ser Ser Val Thr Val Thr Ser Ser Thr
545                 550                 555                 560

Trp Pro Ser Gln Ser Ile Thr Cys Asn Val Ala His Pro Ala Ser Ser
                565                 570                 575

Thr Lys Val Asp Lys Lys Ile Glu Pro Arg Gly Pro Thr Ile Lys Pro
            580                 585                 590

Cys Pro Pro Cys Lys Cys Pro Ala Pro Asn Leu Leu Gly Gly Pro Ser
        595                 600                 605

Val Phe Ile Phe Pro Pro Lys Ile Lys Asp Val Leu Met Ile Ser Leu
    610                 615                 620

Ser Pro Ile Val Thr Cys Val Val Val Asp Val Ser Glu Asp Asp Pro
625                 630                 635                 640

Asp Val Gln Ile Ser Trp Phe Val Asn Asn Val Glu Val His Thr Ala
                645                 650                 655

Gln Thr Gln Thr His Arg Glu Asp Tyr Asn Ser Thr Leu Arg Val Val
            660                 665                 670

Ser Ala Leu Pro Ile Gln His Gln Asp Trp Met Ser Gly Lys Glu Phe
        675                 680                 685

Lys Cys Lys Val Asn Asn Lys Asp Leu Pro Ala Pro Ile Glu Arg Thr
    690                 695                 700

Ile Ser Lys Pro Lys Gly Ser Val Arg Ala Pro Gln Val Tyr Val Leu
705                 710                 715                 720

Pro Pro Pro Glu Glu Glu Met Thr Lys Lys Gln Val Thr Leu Thr Cys
                725                 730                 735
```

```
Met Val Thr Asp Phe Met Pro Glu Asp Ile Tyr Val Glu Trp Thr Asn
            740                 745                 750

Asn Gly Lys Thr Glu Leu Asn Tyr Lys Asn Thr Glu Pro Val Leu Asp
        755                 760                 765

Ser Asp Gly Ser Tyr Phe Met Tyr Ser Lys Leu Arg Val Glu Lys Lys
    770                 775                 780

Asn Trp Val Glu Arg Asn Ser Tyr Ser Cys Ser Val Val His Glu Gly
785                 790                 795                 800

Leu His Asn His His Thr Thr Lys Ser Phe Ser Arg Thr Pro Gly Lys
                805                 810                 815


<210> SEQ ID NO 433
<211> LENGTH: 856
<212> TYPE: PRT
<213> ORGANISM: artificial sequence
<220> FEATURE:
<223> OTHER INFORMATION: synthetic

<400> SEQUENCE: 433

Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Gly Gly
                165                 170                 175

Gly Gly Ser Gly Gly Gly Gly Ser Gly Gly Pro Gly Ser Gly Gly Gly
            180                 185                 190

Gly Ser Gly Gly Gly Gly Ser Val Asn Ala Gln Pro Lys Cys Asn Pro
        195                 200                 205

Asn Leu His Tyr Trp Thr Thr Gln Asp Glu Gly Ala Ala Ile Gly Leu
    210                 215                 220

Ala Trp Ile Pro Tyr Phe Gly Pro Ala Ala Glu Gly Ile Tyr Ile Glu
225                 230                 235                 240

Gly Leu Met His Asn Gln Asp Gly Leu Ile Cys Gly Leu Arg Gln Leu
                245                 250                 255

Ala Asn Glu Thr Thr Gln Ala Leu Gln Leu Phe Leu Arg Ala Thr Thr
            260                 265                 270

Glu Leu Arg Thr Phe Ser Ile Leu Asn Arg Lys Ala Ile Asp Phe Leu
        275                 280                 285
```

-continued

```
Leu Gln Arg Trp Gly Gly Thr Cys His Ile Leu Gly Pro Asp Cys Cys
    290                 295                 300

Ile Glu Pro His Asp Trp Thr Lys Asn Ile Thr Asp Lys Ile Asp Gln
305                 310                 315                 320

Ile Ile His Asp Phe Val Asp Lys Thr Leu Pro Asp Gln Gly Asp Asn
                325                 330                 335

Asp Asn Trp Trp Thr Gly Trp Arg Gln Trp Ile Pro Ala Gly Gly Gly
            340                 345                 350

Gly Gly Ser Gly Gly Gly Gly Ser Gly Gly Pro Gly Ser Gly Gly Gly
        355                 360                 365

Gly Ser Gly Gly Gly Gly Ser Val Asn Ala Gln Pro Lys Cys Asn Pro
    370                 375                 380

Asn Leu His Tyr Trp Thr Thr Gln Asp Glu Gly Ala Ala Ile Gly Leu
385                 390                 395                 400

Ala Trp Ile Pro Tyr Phe Gly Pro Ala Ala Glu Gly Ile Tyr Ile Glu
                405                 410                 415

Gly Leu Met His Asn Gln Asp Gly Leu Ile Cys Gly Leu Arg Gln Leu
            420                 425                 430

Ala Asn Glu Thr Thr Gln Ala Leu Gln Leu Phe Leu Arg Ala Thr Thr
        435                 440                 445

Glu Leu Arg Thr Phe Ser Ile Leu Asn Arg Lys Ala Ile Asp Phe Leu
    450                 455                 460

Leu Gln Arg Trp Gly Gly Thr Cys His Ile Leu Gly Pro Asp Cys Cys
465                 470                 475                 480

Ile Glu Pro His Asp Trp Thr Lys Asn Ile Thr Asp Lys Ile Asp Gln
                485                 490                 495

Ile Ile His Asp Phe Val Asp Lys Thr Leu Pro Asp Gln Gly Asp Asn
            500                 505                 510

Asp Asn Trp Trp Thr Gly Trp Arg Gln Trp Ile Pro Ala Gly Ala Ser
        515                 520                 525

Thr Lys Gly Pro Ser Val Phe Pro Leu Ala Pro Ser Ser Lys Ser Thr
    530                 535                 540

Ser Gly Gly Thr Ala Ala Leu Gly Cys Leu Val Lys Asp Tyr Phe Pro
545                 550                 555                 560

Glu Pro Val Thr Val Ser Trp Asn Ser Gly Ala Leu Thr Ser Gly Val
                565                 570                 575

His Thr Phe Pro Ala Val Leu Gln Ser Ser Gly Leu Tyr Ser Leu Ser
            580                 585                 590

Ser Val Val Thr Val Pro Ser Ser Ser Leu Gly Thr Gln Thr Tyr Ile
        595                 600                 605

Cys Asn Val Asn His Lys Pro Ser Asn Thr Lys Val Asp Lys Arg Val
    610                 615                 620

Glu Pro Lys Ser Cys Asp Lys Thr His Thr Cys Pro Pro Cys Pro Ala
625                 630                 635                 640

Pro Glu Leu Leu Gly Gly Pro Ser Val Phe Leu Phe Pro Pro Lys Pro
                645                 650                 655

Lys Asp Thr Leu Met Ile Ser Arg Thr Pro Glu Val Thr Cys Val Val
            660                 665                 670

Val Asp Val Ser His Glu Asp Pro Glu Val Lys Phe Asn Trp Tyr Val
        675                 680                 685

Asp Gly Val Glu Val His Asn Ala Lys Thr Lys Pro Arg Glu Glu Gln
    690                 695                 700

Tyr Asn Ser Thr Tyr Arg Val Val Ser Val Leu Thr Val Leu His Gln
```

-continued

```
705                 710                 715                 720

Asp Trp Leu Asn Gly Lys Glu Tyr Lys Cys Lys Val Ser Asn Lys Ala
                725                 730                 735

Leu Pro Ala Pro Ile Glu Lys Thr Ile Ser Lys Ala Lys Gly Gln Pro
            740                 745                 750

Arg Glu Pro Gln Val Tyr Thr Leu Pro Pro Ser Arg Glu Glu Met Thr
        755                 760                 765

Lys Asn Gln Val Ser Leu Thr Cys Leu Val Lys Gly Phe Tyr Pro Ser
    770                 775                 780

Asp Ile Ala Val Glu Trp Glu Ser Asn Gly Gln Pro Glu Asn Asn Tyr
785                 790                 795                 800

Lys Thr Thr Pro Pro Val Leu Asp Ser Asp Gly Ser Phe Phe Leu Tyr
                805                 810                 815

Ser Lys Leu Thr Val Asp Lys Ser Arg Trp Gln Gln Gly Asn Val Phe
            820                 825                 830

Ser Cys Ser Val Met His Glu Ala Leu His Asn His Tyr Thr Gln Lys
        835                 840                 845

Ser Leu Ser Leu Ser Pro Gly Lys
    850                 855
```

<210> SEQ ID NO 434
<211> LENGTH: 856
<212> TYPE: PRT
<213> ORGANISM: artificial sequence
<220> FEATURE:
<223> OTHER INFORMATION: synthetic

<400> SEQUENCE: 434

```
Met Glu Thr Asp Thr Leu Leu Leu Trp Val Leu Leu Leu Trp Val Pro
1               5                   10                  15

Gly Ser Thr Gly Asp Thr Arg Val Asn Ala Gln Pro Lys Cys Asn Pro
            20                  25                  30

Asn Leu His Tyr Trp Thr Thr Gln Asp Glu Gly Ala Ala Ile Gly Leu
        35                  40                  45

Ala Trp Ile Pro Tyr Phe Gly Pro Ala Ala Glu Gly Ile Tyr Ile Glu
    50                  55                  60

Gly Leu Met His Asn Gln Asp Gly Leu Ile Cys Gly Leu Arg Gln Leu
65                  70                  75                  80

Ala Asn Glu Thr Thr Gln Ala Leu Gln Leu Phe Leu Arg Ala Thr Thr
                85                  90                  95

Glu Leu Arg Thr Phe Ser Ile Leu Asn Arg Lys Ala Ile Asp Phe Leu
            100                 105                 110

Leu Gln Arg Trp Gly Gly Thr Cys His Ile Leu Gly Pro Asp Cys Cys
        115                 120                 125

Ile Glu Pro His Asp Trp Thr Lys Asn Ile Thr Asp Lys Ile Asp Gln
    130                 135                 140

Ile Ile His Asp Phe Val Asp Lys Thr Leu Pro Asp Gln Gly Asp Asn
145                 150                 155                 160

Asp Asn Trp Trp Thr Gly Trp Arg Gln Trp Ile Pro Ala Gly Gly Gly
                165                 170                 175

Gly Gly Ser Gly Gly Gly Gly Ser Gly Gly Pro Gly Ser Gly Gly Gly
            180                 185                 190

Gly Ser Gly Gly Gly Gly Ser Val Asn Ala Gln Pro Lys Cys Asn Pro
        195                 200                 205

Asn Leu His Tyr Trp Thr Thr Gln Asp Glu Gly Ala Ala Ile Gly Leu
```

-continued

```
    210                 215                 220

Ala Trp Ile Pro Tyr Phe Gly Pro Ala Ala Glu Gly Ile Tyr Ile Glu
225                 230                 235                 240

Gly Leu Met His Asn Gln Asp Gly Leu Ile Cys Gly Leu Arg Gln Leu
                245                 250                 255

Ala Asn Glu Thr Thr Gln Ala Leu Gln Leu Phe Leu Arg Ala Thr Thr
            260                 265                 270

Glu Leu Arg Thr Phe Ser Ile Leu Asn Arg Lys Ala Ile Asp Phe Leu
        275                 280                 285

Leu Gln Arg Trp Gly Gly Thr Cys His Ile Leu Gly Pro Asp Cys Cys
    290                 295                 300

Ile Glu Pro His Asp Trp Thr Lys Asn Ile Thr Asp Lys Ile Asp Gln
305                 310                 315                 320

Ile Ile His Asp Phe Val Asp Lys Thr Leu Pro Asp Gln Gly Asp Asn
                325                 330                 335

Asp Asn Trp Trp Thr Gly Trp Arg Gln Trp Ile Pro Ala Gly Gly Gly
            340                 345                 350

Gly Gly Ser Gly Gly Gly Gly Ser Gly Gly Pro Gly Ser Gly Gly Gly
        355                 360                 365

Gly Ser Gly Gly Gly Gly Ser Val Asn Ala Gln Pro Lys Cys Asn Pro
    370                 375                 380

Asn Leu His Tyr Trp Thr Thr Gln Asp Glu Gly Ala Ala Ile Gly Leu
385                 390                 395                 400

Ala Trp Ile Pro Tyr Phe Gly Pro Ala Ala Glu Gly Ile Tyr Ile Glu
                405                 410                 415

Gly Leu Met His Asn Gln Asp Gly Leu Ile Cys Gly Leu Arg Gln Leu
            420                 425                 430

Ala Asn Glu Thr Thr Gln Ala Leu Gln Leu Phe Leu Arg Ala Thr Thr
        435                 440                 445

Glu Leu Arg Thr Phe Ser Ile Leu Asn Arg Lys Ala Ile Asp Phe Leu
    450                 455                 460

Leu Gln Arg Trp Gly Gly Thr Cys His Ile Leu Gly Pro Asp Cys Cys
465                 470                 475                 480

Ile Glu Pro His Asp Trp Thr Lys Asn Ile Thr Asp Lys Ile Asp Gln
                485                 490                 495

Ile Ile His Asp Phe Val Asp Lys Thr Leu Pro Asp Gln Gly Asp Asn
            500                 505                 510

Asp Asn Trp Trp Thr Gly Trp Arg Gln Trp Ile Pro Ala Gly Ala Lys
        515                 520                 525

Thr Thr Ala Pro Ser Val Tyr Pro Leu Ala Pro Val Cys Gly Asp Thr
    530                 535                 540

Thr Gly Ser Ser Val Thr Leu Gly Cys Leu Val Lys Gly Tyr Phe Pro
545                 550                 555                 560

Glu Pro Val Thr Leu Thr Trp Asn Ser Gly Ser Leu Ser Ser Gly Val
                565                 570                 575

His Thr Phe Pro Ala Val Leu Gln Ser Asp Leu Tyr Thr Leu Ser Ser
            580                 585                 590

Ser Val Thr Val Thr Ser Ser Thr Trp Pro Ser Gln Ser Ile Thr Cys
        595                 600                 605

Asn Val Ala His Pro Ala Ser Ser Thr Lys Val Asp Lys Lys Ile Glu
    610                 615                 620

Pro Arg Gly Pro Thr Ile Lys Pro Cys Pro Pro Cys Lys Cys Pro Ala
625                 630                 635                 640
```

Pro Asn Leu Leu Gly Gly Pro Ser Val Phe Ile Phe Pro Pro Lys Ile
645 650 655

Lys Asp Val Leu Met Ile Ser Leu Ser Pro Ile Val Thr Cys Val Val
660 665 670

Val Asp Val Ser Glu Asp Asp Pro Asp Val Gln Ile Ser Trp Phe Val
675 680 685

Asn Asn Val Glu Val His Thr Ala Gln Thr Gln Thr His Arg Glu Asp
690 695 700

Tyr Asn Ser Thr Leu Arg Val Val Ser Ala Leu Pro Ile Gln His Gln
705 710 715 720

Asp Trp Met Ser Gly Lys Glu Phe Lys Cys Lys Val Asn Asn Lys Asp
725 730 735

Leu Pro Ala Pro Ile Glu Arg Thr Ile Ser Lys Pro Lys Gly Ser Val
740 745 750

Arg Ala Pro Gln Val Tyr Val Leu Pro Pro Pro Glu Glu Glu Met Thr
755 760 765

Lys Lys Gln Val Thr Leu Thr Cys Met Val Thr Asp Phe Met Pro Glu
770 775 780

Asp Ile Tyr Val Glu Trp Thr Asn Asn Gly Lys Thr Glu Leu Asn Tyr
785 790 795 800

Lys Asn Thr Glu Pro Val Leu Asp Ser Asp Gly Ser Tyr Phe Met Tyr
805 810 815

Ser Lys Leu Arg Val Glu Lys Lys Asn Trp Val Glu Arg Asn Ser Tyr
820 825 830

Ser Cys Ser Val Val His Glu Gly Leu His Asn His His Thr Thr Lys
835 840 845

Ser Phe Ser Arg Thr Pro Gly Lys
850 855

<210> SEQ ID NO 435
<211> LENGTH: 75
<212> TYPE: DNA
<213> ORGANISM: artificial sequence
<220> FEATURE:
<223> OTHER INFORMATION: synthetic

<400> SEQUENCE: 435
ggtggtggcg gttcaggcgg aggtggctct ggcggtcccg gatccggcgg aggtggctct 60
ggcggaggag ggtct 75

<210> SEQ ID NO 436
<211> LENGTH: 25
<212> TYPE: PRT
<213> ORGANISM: artificial sequence
<220> FEATURE:
<223> OTHER INFORMATION: synthetic

<400> SEQUENCE: 436

Gly Gly Gly Gly Ser Gly Gly Gly Gly Ser Gly Gly Pro Gly Ser Gly
1 5 10 15

Gly Gly Gly Ser Gly Gly Gly Gly Ser
20 25

<210> SEQ ID NO 437
<211> LENGTH: 15
<212> TYPE: PRT
<213> ORGANISM: artificial sequence
<220> FEATURE:

<223> OTHER INFORMATION: synthetic

<400> SEQUENCE: 437

Arg Trp Leu Tyr Pro Glu Ser Thr Val Leu Tyr Phe Thr Phe His
1 5 10 15

<210> SEQ ID NO 438
<211> LENGTH: 15
<212> TYPE: PRT
<213> ORGANISM: artificial sequence
<220> FEATURE:
<223> OTHER INFORMATION: synthetic

<400> SEQUENCE: 438

Leu Phe Leu Met Pro Glu Met Thr Phe Leu Tyr Gly Ala Ile Ile
1 5 10 15

<210> SEQ ID NO 439
<211> LENGTH: 15
<212> TYPE: PRT
<213> ORGANISM: artificial sequence
<220> FEATURE:
<223> OTHER INFORMATION: synthetic

<400> SEQUENCE: 439

Asp Asp Leu Trp Pro Glu Leu Thr Ser Leu Tyr Val Val Phe Thr
1 5 10 15

<210> SEQ ID NO 440
<211> LENGTH: 15
<212> TYPE: PRT
<213> ORGANISM: artificial sequence
<220> FEATURE:
<223> OTHER INFORMATION: synthetic

<400> SEQUENCE: 440

Ile Gln Leu Leu Pro Glu Gly Thr Val Leu Tyr Val Cys Pro Thr
1 5 10 15

<210> SEQ ID NO 441
<211> LENGTH: 15
<212> TYPE: PRT
<213> ORGANISM: artificial sequence
<220> FEATURE:
<223> OTHER INFORMATION: synthetic

<400> SEQUENCE: 441

Met Ser Leu Met Pro Glu Leu Thr Gly Leu Tyr Ile Ser Tyr Val
1 5 10 15

<210> SEQ ID NO 442
<211> LENGTH: 15
<212> TYPE: PRT
<213> ORGANISM: artificial sequence
<220> FEATURE:
<223> OTHER INFORMATION: synthetic

<400> SEQUENCE: 442

Leu Leu Leu Phe Pro Glu Ala Thr Asn Leu Tyr Thr Ile Glu Lys
1 5 10 15

<210> SEQ ID NO 443
<211> LENGTH: 15
<212> TYPE: PRT
<213> ORGANISM: artificial sequence
<220> FEATURE:
<223> OTHER INFORMATION: synthetic

<400> SEQUENCE: 443

Asn Ala Gly Ser Gly Ile Ile Ile Ser Asp Thr Pro Val His Asp
1 5 10 15

<210> SEQ ID NO 444
<211> LENGTH: 15
<212> TYPE: PRT
<213> ORGANISM: artificial sequence
<220> FEATURE:
<223> OTHER INFORMATION: synthetic

<400> SEQUENCE: 444

Phe Val Leu Phe Pro Glu Ala Thr Lys Leu Tyr Leu His Gly Val
1 5 10 15

<210> SEQ ID NO 445
<211> LENGTH: 15
<212> TYPE: PRT
<213> ORGANISM: artificial sequence
<220> FEATURE:
<223> OTHER INFORMATION: synthetic

<400> SEQUENCE: 445

Lys Arg Leu Tyr Pro Glu Ser Thr Leu Leu Tyr Val Ser Leu Cys
1 5 10 15

<210> SEQ ID NO 446
<211> LENGTH: 15
<212> TYPE: PRT
<213> ORGANISM: artificial sequence
<220> FEATURE:
<223> OTHER INFORMATION: synthetic

<400> SEQUENCE: 446

Leu Glu Leu Leu Pro Glu Gly Thr Leu Leu Tyr Val Cys Pro Ile
1 5 10 15

<210> SEQ ID NO 447
<211> LENGTH: 15
<212> TYPE: PRT
<213> ORGANISM: artificial sequence
<220> FEATURE:
<223> OTHER INFORMATION: synthetic

<400> SEQUENCE: 447

Arg Trp Leu Tyr Pro Glu Ser Thr Val Leu Tyr Phe Thr Phe His
1 5 10 15

<210> SEQ ID NO 448
<211> LENGTH: 15
<212> TYPE: PRT
<213> ORGANISM: artificial sequence
<220> FEATURE:
<223> OTHER INFORMATION: synthetic

<400> SEQUENCE: 448

Leu Gln Leu Val Pro Glu Gly Thr Ala Leu Tyr Leu Tyr Glu Leu
1 5 10 15

<210> SEQ ID NO 449
<211> LENGTH: 15
<212> TYPE: PRT
<213> ORGANISM: artificial sequence
<220> FEATURE:
<223> OTHER INFORMATION: synthetic

<400> SEQUENCE: 449

Phe Trp Leu Gln Pro Glu Tyr Thr Ala Leu Tyr Ala Met Leu Asp
1 5 10 15

<210> SEQ ID NO 450
<211> LENGTH: 15
<212> TYPE: PRT
<213> ORGANISM: artificial sequence
<220> FEATURE:
<223> OTHER INFORMATION: synthetic

<400> SEQUENCE: 450

Leu Gln Leu Met Pro Glu Gly Thr Leu Leu Tyr Val Cys Pro Gly
1 5 10 15

<210> SEQ ID NO 451
<211> LENGTH: 15
<212> TYPE: PRT
<213> ORGANISM: artificial sequence
<220> FEATURE:
<223> OTHER INFORMATION: synthetic

<400> SEQUENCE: 451

Gln Met Leu Leu Pro Glu Leu Thr Val Leu Tyr Pro Gly Cys Ala
1 5 10 15

<210> SEQ ID NO 452
<211> LENGTH: 15
<212> TYPE: PRT
<213> ORGANISM: artificial sequence
<220> FEATURE:
<223> OTHER INFORMATION: synthetic

<400> SEQUENCE: 452

Leu Leu Leu Lys Pro Glu Cys Thr Ser Leu Tyr Ser Met Leu Ile
1 5 10 15

<210> SEQ ID NO 453
<211> LENGTH: 15
<212> TYPE: PRT
<213> ORGANISM: artificial sequence
<220> FEATURE:
<223> OTHER INFORMATION: synthetic

<400> SEQUENCE: 453

Leu Ser Leu Leu Pro Glu Ile Thr Ala Leu Tyr Met Leu Ile Gln
1 5 10 15

<210> SEQ ID NO 454
<211> LENGTH: 15
<212> TYPE: PRT
<213> ORGANISM: artificial sequence
<220> FEATURE:
<223> OTHER INFORMATION: synthetic

<400> SEQUENCE: 454

Ile Val Leu Val Pro Glu Ile Thr Gln Leu Tyr Leu Arg Leu Cys
1 5 10 15

<210> SEQ ID NO 455
<211> LENGTH: 15
<212> TYPE: PRT
<213> ORGANISM: artificial sequence
<220> FEATURE:
<223> OTHER INFORMATION: synthetic

<400> SEQUENCE: 455

Met Leu Leu Asn Pro Glu Gly Thr Val Leu Tyr Thr Cys Ala Gln
1 5 10 15

<210> SEQ ID NO 456
<211> LENGTH: 15
<212> TYPE: PRT
<213> ORGANISM: artificial sequence
<220> FEATURE:
<223> OTHER INFORMATION: synthetic

<400> SEQUENCE: 456

Cys His Leu Cys Pro Glu Thr Thr Arg Leu Tyr Ile His Ser Thr
1 5 10 15

<210> SEQ ID NO 457
<211> LENGTH: 15
<212> TYPE: PRT
<213> ORGANISM: artificial sequence
<220> FEATURE:
<223> OTHER INFORMATION: synthetic

<400> SEQUENCE: 457

Leu Leu Leu Gly Pro Glu Gly Thr Val Leu Tyr Ile Cys Ser Gln
1 5 10 15

<210> SEQ ID NO 458
<211> LENGTH: 15
<212> TYPE: PRT
<213> ORGANISM: artificial sequence
<220> FEATURE:
<223> OTHER INFORMATION: synthetic

<400> SEQUENCE: 458

Ile Cys Leu Arg Pro Glu Cys Thr Gln Leu Tyr Lys Arg His Val
1 5 10 15

<210> SEQ ID NO 459
<211> LENGTH: 15
<212> TYPE: PRT
<213> ORGANISM: artificial sequence
<220> FEATURE:
<223> OTHER INFORMATION: synthetic

<400> SEQUENCE: 459

Cys Cys Leu Cys Pro Glu Thr Thr Arg Leu Tyr Val Gln Ser Thr
1 5 10 15

<210> SEQ ID NO 460
<211> LENGTH: 15
<212> TYPE: PRT
<213> ORGANISM: artificial sequence
<220> FEATURE:
<223> OTHER INFORMATION: synthetic

<400> SEQUENCE: 460

Cys His Leu Cys Pro Glu Thr Thr Arg Leu Tyr Ile His Ser Thr
1 5 10 15

<210> SEQ ID NO 461
<211> LENGTH: 15
<212> TYPE: PRT
<213> ORGANISM: artificial sequence
<220> FEATURE:
<223> OTHER INFORMATION: synthetic

<400> SEQUENCE: 461

```
Leu Leu Leu Gly Pro Glu Gly Thr Val Leu Tyr Asn Cys Ser Thr
1               5                   10                  15


<210> SEQ ID NO 462
<211> LENGTH: 15
<212> TYPE: PRT
<213> ORGANISM: artificial sequence
<220> FEATURE:
<223> OTHER INFORMATION: synthetic

<400> SEQUENCE: 462

Leu His Leu Glu Pro Glu Asp Thr Phe Leu Tyr Glu Gln Leu Cys
1               5                   10                  15


<210> SEQ ID NO 463
<211> LENGTH: 15
<212> TYPE: PRT
<213> ORGANISM: artificial sequence
<220> FEATURE:
<223> OTHER INFORMATION: synthetic

<400> SEQUENCE: 463

Cys His Leu Cys Pro Glu Thr Thr Arg Leu Tyr Ile His Ser Thr
1               5                   10                  15


<210> SEQ ID NO 464
<211> LENGTH: 15
<212> TYPE: PRT
<213> ORGANISM: artificial sequence
<220> FEATURE:
<223> OTHER INFORMATION: synthetic

<400> SEQUENCE: 464

Cys Cys Leu Cys Pro Glu Thr Thr Arg Leu Tyr Val Gln Ser Thr
1               5                   10                  15


<210> SEQ ID NO 465
<211> LENGTH: 15
<212> TYPE: PRT
<213> ORGANISM: artificial sequence
<220> FEATURE:
<223> OTHER INFORMATION: synthetic

<400> SEQUENCE: 465

Arg Cys Leu Lys Pro Glu Asp Thr Gly Leu Tyr Arg Asp Ile Val
1               5                   10                  15


<210> SEQ ID NO 466
<211> LENGTH: 97
<212> TYPE: PRT
<213> ORGANISM: artificial sequence
<220> FEATURE:
<223> OTHER INFORMATION: synthetic

<400> SEQUENCE: 466

Met Arg Gly His Lys Pro Thr Leu Lys Glu Tyr Val Leu Asp Leu Tyr
1               5                   10                  15

Pro Glu Pro Thr Asp Leu Tyr Cys Tyr Glu Gln Leu Ser Asp Ser Ser
            20                  25                  30

Asp Glu Asp Glu Gly Leu Asp Arg Pro Asp Gly Gln Ala Gln Pro Ala
        35                  40                  45

Thr Ala Asp Tyr Tyr Ile Val Thr Cys Cys His Thr Cys Asn Thr Thr
    50                  55                  60

Val Arg Leu Cys Val Asn Ser Thr Ala Ser Asp Leu Arg Thr Ile Gln
65                  70                  75                  80
```

```
Gln Leu Leu Met Gly Thr Val Asn Ile Val Cys Pro Thr Cys Ala Gln
                85                  90                  95

Gln
```

<210> SEQ ID NO 467
<211> LENGTH: 1611
<212> TYPE: DNA
<213> ORGANISM: artificial sequence
<220> FEATURE:
<223> OTHER INFORMATION: synthetic

<400> SEQUENCE: 467

```
atggccataa gtggagtccc tgtgctagga tttttcatca tagctgtgct gatgagcgct      60
caggaatcat gggctatcaa agaagaacat gtgatcatcc aggccgagtt ctatctgaat     120
cctgaccaat caggcgagtt tatgtttgac tttgatggtg atgagatttt ccatgtggat     180
atggcaaaga aggagacggt ctggcggctt gaagaatttg gacgatttgc cagctttgag     240
gctcaaggtg cattggccaa catagctgtg gacaaagcca acctggaaat catgacaaag     300
cgctccaact atactccgat caccaatgta cctccagagg taactgtgct cacgaacagc     360
cctgtggaac tgagagagcc caacgtcctc atctgtttca tcgacaagtt caccccacca     420
gtggtcaatg tcacgtggct tcgaaatgga aaacctgtca ccacaggagt gtcagagaca     480
gtcttcctgc ccagggaaga ccaccttttc cgcaagttcc actatctccc cttcctgccc     540
tcaactgagg acgtttacga ctgcagggtg gagcactggg gcttggatga gcctcttctc     600
aagcactggg agtttgatgt gtcgaccaag ggcccatcgg tcttccccct ggcaccctct     660
agcaagagca cctctggggg cacagcggcc ctgggctgcc tggtcaagga ctacttcccc     720
gaaccggtga cggtgtcgtg gaactcaggc gccctgacca gcggcgtgca caccttcccg     780
gctgtcctac agtcctcagg actctactcc ctcagcagcg tggtgaccgt gccctccagc     840
agcttgggca cccagaccta catctgcaac gtgaatcaca agcccagcaa caccaaggtg     900
gacaagagag ttgagcccaa atcttgtgac aaaactcaca catgcccacc gtgcccagca     960
cctgaactcc tggggggacc gtcagtcttc ctcttccccc caaaacccaa ggacaccctc    1020
atgatctccc ggacccctga ggtcacatgc gtggtggtgg acgtgagcca cgaagaccct    1080
gaggtcaagt tcaactggta cgtggacggc gtggaggtgc ataatgccaa gacaaagccg    1140
cgggaggagc agtacaacag cacgtaccgt gtggtcagcg tcctcaccgt cctgcaccag    1200
gactggctga atggcaagga gtacaagtgc aaggtctcca acaaagccct cccagccccc    1260
atcgagaaaa ccatctccaa agccaaaggg cagccccgag aaccacaggt gtacaccctg    1320
cccccatccc gggaggagat gaccaagaac caggtcagcc tgacctgcct ggtcaaaggc    1380
ttctatccca gcgacatcgc cgtggagtgg gagagcaatg ggcagccgga gaacaactac    1440
aagaccacgc ctcccgtgct ggactccgac ggctccttct tcctctatag caagctcacc    1500
gtggacaaga gcaggtggca gcaggggaac gtcttctcat gctccgtgat gcatgaggct    1560
ctgcacaacc actacacgca gaagagcctc tccctgtctc cgggtaaatg a             1611
```

<210> SEQ ID NO 468
<211> LENGTH: 536
<212> TYPE: PRT
<213> ORGANISM: artificial sequence
<220> FEATURE:
<223> OTHER INFORMATION: synthetic

<400> SEQUENCE: 468

```
Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Val Ser
        195                 200                 205

Thr Lys Gly Pro Ser Val Phe Pro Leu Ala Pro Ser Ser Lys Ser Thr
    210                 215                 220

Ser Gly Gly Thr Ala Ala Leu Gly Cys Leu Val Lys Asp Tyr Phe Pro
225                 230                 235                 240

Glu Pro Val Thr Val Ser Trp Asn Ser Gly Ala Leu Thr Ser Gly Val
                245                 250                 255

His Thr Phe Pro Ala Val Leu Gln Ser Ser Gly Leu Tyr Ser Leu Ser
            260                 265                 270

Ser Val Val Thr Val Pro Ser Ser Ser Leu Gly Thr Gln Thr Tyr Ile
        275                 280                 285

Cys Asn Val Asn His Lys Pro Ser Asn Thr Lys Val Asp Lys Arg Val
    290                 295                 300

Glu Pro Lys Ser Cys Asp Lys Thr His Thr Cys Pro Pro Cys Pro Ala
305                 310                 315                 320

Pro Glu Leu Leu Gly Gly Pro Ser Val Phe Leu Phe Pro Pro Lys Pro
                325                 330                 335

Lys Asp Thr Leu Met Ile Ser Arg Thr Pro Glu Val Thr Cys Val Val
            340                 345                 350

Val Asp Val Ser His Glu Asp Pro Glu Val Lys Phe Asn Trp Tyr Val
        355                 360                 365

Asp Gly Val Glu Val His Asn Ala Lys Thr Lys Pro Arg Glu Glu Gln
    370                 375                 380

Tyr Asn Ser Thr Tyr Arg Val Val Ser Val Leu Thr Val Leu His Gln
385                 390                 395                 400

Asp Trp Leu Asn Gly Lys Glu Tyr Lys Cys Lys Val Ser Asn Lys Ala
                405                 410                 415
```

```
Leu Pro Ala Pro Ile Glu Lys Thr Ile Ser Lys Ala Lys Gly Gln Pro
            420                 425                 430

Arg Glu Pro Gln Val Tyr Thr Leu Pro Pro Ser Arg Glu Glu Met Thr
        435                 440                 445

Lys Asn Gln Val Ser Leu Thr Cys Leu Val Lys Gly Phe Tyr Pro Ser
    450                 455                 460

Asp Ile Ala Val Glu Trp Glu Ser Asn Gly Gln Pro Glu Asn Asn Tyr
465                 470                 475                 480

Lys Thr Thr Pro Pro Val Leu Asp Ser Asp Gly Ser Phe Phe Leu Tyr
                485                 490                 495

Ser Lys Leu Thr Val Asp Lys Ser Arg Trp Gln Gln Gly Asn Val Phe
            500                 505                 510

Ser Cys Ser Val Met His Glu Ala Leu His Asn His Tyr Thr Gln Lys
        515                 520                 525

Ser Leu Ser Leu Ser Pro Gly Lys
    530                 535


<210> SEQ ID NO 469
<211> LENGTH: 5
<212> TYPE: PRT
<213> ORGANISM: artificial sequence
<220> FEATURE:
<223> OTHER INFORMATION: synthetic

<400> SEQUENCE: 469

Gly Ser Tyr Ala Asp
1               5


<210> SEQ ID NO 470
<211> LENGTH: 5
<212> TYPE: PRT
<213> ORGANISM: artificial sequence
<220> FEATURE:
<223> OTHER INFORMATION: synthetic

<400> SEQUENCE: 470

Ala Gly Gly Ile Ile
1               5


<210> SEQ ID NO 471
<211> LENGTH: 5
<212> TYPE: PRT
<213> ORGANISM: artificial sequence
<220> FEATURE:
<223> OTHER INFORMATION: synthetic

<400> SEQUENCE: 471

Asn Ala Ser Ile Ile
1               5


<210> SEQ ID NO 472
<211> LENGTH: 5
<212> TYPE: PRT
<213> ORGANISM: artificial sequence
<220> FEATURE:
<223> OTHER INFORMATION: synthetic

<400> SEQUENCE: 472

Ser Val Ser Val Ser
1               5


<210> SEQ ID NO 473
<211> LENGTH: 5
```

<212> TYPE: PRT
<213> ORGANISM: artificial sequence
<220> FEATURE:
<223> OTHER INFORMATION: synthetic

<400> SEQUENCE: 473

Pro Gly Gln Ala Pro
1               5

<210> SEQ ID NO 474
<211> LENGTH: 9
<212> TYPE: PRT
<213> ORGANISM: artificial sequence
<220> FEATURE:
<223> OTHER INFORMATION: synthetic

<400> SEQUENCE: 474

Ala Ala Gly Ile Gly Ile Leu Thr Val
1               5

<210> SEQ ID NO 475
<211> LENGTH: 15
<212> TYPE: PRT
<213> ORGANISM: artificial sequence
<220> FEATURE:
<223> OTHER INFORMATION: synthetic

<400> SEQUENCE: 475

Leu Gly Val Leu Leu Leu Ile Gly Cys Trp Tyr Cys Arg Arg Arg
1               5                   10                  15

<210> SEQ ID NO 476
<211> LENGTH: 7
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 476

Leu Leu Xaa Gly Xaa Trp Tyr
1               5

<210> SEQ ID NO 477
<211> LENGTH: 15
<212> TYPE: PRT
<213> ORGANISM: artificial sequence
<220> FEATURE:
<223> OTHER INFORMATION: synthetic

<400> SEQUENCE: 477

Leu Gly Val Leu Leu Leu Ile Gly Cys Trp Tyr Cys Arg Arg Arg
1               5                   10                  15

<210> SEQ ID NO 478
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 478

Val Xaa Xaa Leu Xaa Gly Xaa Trp Tyr
1               5

<210> SEQ ID NO 479
<211> LENGTH: 15
<212> TYPE: PRT
<213> ORGANISM: artificial sequence
<220> FEATURE:
<223> OTHER INFORMATION: synthetic

<400> SEQUENCE: 479

Val Ser Phe Gly Val Trp Ile Arg Thr Pro Pro Ala Tyr Arg Pro
1               5                   10                  15

<210> SEQ ID NO 480
<211> LENGTH: 5
<212> TYPE: PRT
<213> ORGANISM: artificial sequence
<220> FEATURE:
<223> OTHER INFORMATION: synthetic

<400> SEQUENCE: 480

Phe Trp Arg Pro Pro
1               5

<210> SEQ ID NO 481
<211> LENGTH: 5
<212> TYPE: PRT
<213> ORGANISM: artificial sequence
<220> FEATURE:
<223> OTHER INFORMATION: synthetic

<400> SEQUENCE: 481

Val Trp Arg Pro Pro
1               5

<210> SEQ ID NO 482
<211> LENGTH: 15
<212> TYPE: PRT
<213> ORGANISM: artificial sequence
<220> FEATURE:
<223> OTHER INFORMATION: synthetic

<400> SEQUENCE: 482

Val Ser Phe Gly Val Trp Ile Arg Thr Pro Pro Ala Tyr Arg Pro
1               5                   10                  15

<210> SEQ ID NO 483
<211> LENGTH: 5
<212> TYPE: PRT
<213> ORGANISM: artificial sequence
<220> FEATURE:
<223> OTHER INFORMATION: synthetic

<400> SEQUENCE: 483

Phe Trp Arg Pro Pro 1 5

<210> SEQ ID NO 484
<211> LENGTH: 5
<212> TYPE: PRT
<213> ORGANISM: artificial sequence
<220> FEATURE:
<223> OTHER INFORMATION: synthetic

<400> SEQUENCE: 484

Val Trp Arg Pro Pro
1 5

<210> SEQ ID NO 485
<211> LENGTH: 5
<212> TYPE: PRT
<213> ORGANISM: artificial sequence
<220> FEATURE:
<223> OTHER INFORMATION: synthetic

<400> SEQUENCE: 485

Val Gln Lys Asn Pro
1 5

<210> SEQ ID NO 486
<211> LENGTH: 5
<212> TYPE: PRT
<213> ORGANISM: artificial sequence
<220> FEATURE:
<223> OTHER INFORMATION: synthetic

<400> SEQUENCE: 486

Gly Gly Gly Gly Ser
1 5

<210> SEQ ID NO 487
<211> LENGTH: 5
<212> TYPE: PRT
<213> ORGANISM: artificial sequence
<220> FEATURE:
<223> OTHER INFORMATION: synthetic

<400> SEQUENCE: 487

Pro Glu Thr Leu Tyr
1 5

<210> SEQ ID NO 488
<211> LENGTH: 5
<212> TYPE: PRT
<213> ORGANISM: artificial sequence
<220> FEATURE:
<223> OTHER INFORMATION: synthetic

<400> SEQUENCE: 488

Leu Glu Thr Leu Tyr
1 5

<210> SEQ ID NO 489
<211> LENGTH: 15
<212> TYPE: PRT
<213> ORGANISM: artificial sequence
<220> FEATURE:
<223> OTHER INFORMATION: Synthetic

<400> SEQUENCE: 489

Thr Ala Val Arg Ala Gly Leu Gly Ser Ile Ile Pro Leu Gln Leu
1 5 10 15

<210> SEQ ID NO 490
<211> LENGTH: 15
<212> TYPE: PRT
<213> ORGANISM: artificial sequence
<220> FEATURE:
<223> OTHER INFORMATION: Synthetic

<400> SEQUENCE: 490

Ala Ser Glu Thr Ala Gly Ser Gly Tyr Ile Ile Asn Thr Arg Arg
1 5 10 15

<210> SEQ ID NO 491
<211> LENGTH: 15
<212> TYPE: PRT
<213> ORGANISM: artificial sequence
<220> FEATURE:
<223> OTHER INFORMATION: Synthetic

<400> SEQUENCE: 491

Leu Glu Ala Gln Ala Gly Thr Gly His Ile Ile Asp Pro Ala Thr
1 5 10 15

<210> SEQ ID NO 492
<211> LENGTH: 15
<212> TYPE: PRT
<213> ORGANISM: artificial sequence
<220> FEATURE:
<223> OTHER INFORMATION: Synthetic

<400> SEQUENCE: 492

Ser Ala Arg Pro Ala Gly Lys Gly Ala Ile Ile Gly Phe Ile Lys
1 5 10 15

<210> SEQ ID NO 493
<211> LENGTH: 15
<212> TYPE: PRT
<213> ORGANISM: artificial sequence
<220> FEATURE:
<223> OTHER INFORMATION: Synthetic

<400> SEQUENCE: 493

Pro Arg Asp Pro Ala Gly Cys Gly Asp Ile Ile Ala Asp Gln Glu
1 5 10 15

<210> SEQ ID NO 494
<211> LENGTH: 15
<212> TYPE: PRT
<213> ORGANISM: artificial sequence
<220> FEATURE:
<223> OTHER INFORMATION: Synthetic

<400> SEQUENCE: 494

Ile Leu Thr Leu Ala Gly Asn Gly Leu Ile Ile Ala Thr Val Trp
1 5 10 15

<210> SEQ ID NO 495
<211> LENGTH: 15
<212> TYPE: PRT
<213> ORGANISM: artificial sequence
<220> FEATURE:
<223> OTHER INFORMATION: Synthetic

<400> SEQUENCE: 495

Gln Tyr Met Arg Ala Gly Glu Gly Phe Ile Ile Cys Tyr Ser Ile
1 5 10 15

-continued

<210> SEQ ID NO 496
<211> LENGTH: 15
<212> TYPE: PRT
<213> ORGANISM: artificial sequence
<220> FEATURE:
<223> OTHER INFORMATION: Synthetic

<400> SEQUENCE: 496

Met Gly Ala Pro Asn Ala Trp Ser Thr Ile Ile Val Pro Gly Met
1 5 10 15

<210> SEQ ID NO 497
<211> LENGTH: 15
<212> TYPE: PRT
<213> ORGANISM: artificial sequence
<220> FEATURE:
<223> OTHER INFORMATION: Synthetic

<400> SEQUENCE: 497

Ser Ile Ile Ser Asn Ala Val Ser Asn Ile Ile Cys Ser Leu Cys
1 5 10 15

<210> SEQ ID NO 498
<211> LENGTH: 15
<212> TYPE: PRT
<213> ORGANISM: artificial sequence
<220> FEATURE:
<223> OTHER INFORMATION: Synthetic

<400> SEQUENCE: 498

Pro Gly Asp Glu Asn Ala Glu Ser Ser Ile Ile His Phe Glu Pro
1 5 10 15

<210> SEQ ID NO 499
<211> LENGTH: 15
<212> TYPE: PRT
<213> ORGANISM: artificial sequence
<220> FEATURE:
<223> OTHER INFORMATION: Synthetic

<400> SEQUENCE: 499

Gln Gln Gly Glu Asn Ala Thr Ser Asn Ile Ile Leu Thr Leu Ala
1 5 10 15

<210> SEQ ID NO 500
<211> LENGTH: 15
<212> TYPE: PRT
<213> ORGANISM: artificial sequence
<220> FEATURE:
<223> OTHER INFORMATION: Synthetic

<400> SEQUENCE: 500

Phe Lys Ile Asn Asn Ala Val Ser Asn Ile Ile Cys Ser Ile Thr
1 5 10 15

<210> SEQ ID NO 501
<211> LENGTH: 15
<212> TYPE: PRT
<213> ORGANISM: artificial sequence
<220> FEATURE:
<223> OTHER INFORMATION: Synthetic

<400> SEQUENCE: 501

Ala Gly Ser Gly Ile Ile Ile Ser Asp Thr Pro Val His Asp Cys
1 5 10 15

UNITED STATES PATENT AND TRADEMARK OFFICE
CERTIFICATE OF CORRECTION

PATENT NO. : 10,755,801 B2
APPLICATION NO. : 15/325655
DATED : August 25, 2020
INVENTOR(S) : Robert D. Bremel, Jane Homan and Michael Imboden It is certified that error appears in the above-identified patent and that said Letters Patent is hereby corrected as shown below:

In the Claims

In Claim 6, Column 366, Lines 25-32, should read:
6. The method of claim 1, further comprising determining the predicted MHC binding affinity of said peptide sequences comprising said T-cell-exposed motifs derived from said target protein by determining the MHC allele-specific binding of the groove exposed motifs corresponding to each T-cell-exposed motif and modifying the one or more peptide sequences to have an increased or decreased MHC binding affinity.

Signed and Sealed this
Twenty-ninth Day of September, 2020

Andrei Iancu
*Director of the United States Patent and Trademark Office*